(12) United States Patent
Vergne et al.

(10) Patent No.: US 7,122,565 B2
(45) Date of Patent: Oct. 17, 2006

(54) THIADIAZOLES AND OXADIAZOLES AND THEIR USE AS PHOSPHODIESTERASE-7 INHIBITORS

(75) Inventors: Fabrice Vergne, Gif-sur-Yvette (FR); Pierre Ducrot, Varrieres le buisson (FR); Charles Andrianjara, Fresnes (FR); Patrick Bernardelli, Fontenay Aux Roses (FR); Edwige Lorth Ois, Paris (FR)

(73) Assignee: Warner-Lambert LLC, Morris Plains, NJ (US)

( * ) Notice: Subject to any disclaimer, the term of this patent is extended or adjusted under 35 U.S.C. 154(b) by 676 days.

(21) Appl. No.: 09/968,371

(22) Filed: Oct. 1, 2001

(65) Prior Publication Data

US 2003/0045557 A1 Mar. 6, 2003

(30) Foreign Application Priority Data

Oct. 2, 2000 (EP) .............................................. 00402710

(51) Int. Cl.
*C07D 285/135* (2006.01)
*A61K 31/433* (2006.01)

(52) U.S. Cl. ......................... 514/363; 548/138; 548/143
(58) Field of Classification Search ................. 514/363, 514/364; 548/138, 143
See application file for complete search history.

(56) References Cited

FOREIGN PATENT DOCUMENTS

| DE | 0251979 | 12/1987 | ......... C07D/413/02 |
|---|---|---|---|
| DE | 3717232 | 12/1988 | |
| DE | 4418066 | 11/1995 | |
| EP | 0023766 | * 2/1981 | ................. 548/138 |
| FR | 7712352 | 4/1977 | |
| FR | 8015072 | 7/1980 | |
| WO | WO 9942089 | 8/1999 | .......... A61K/31/00 |
| WO | 9942089 | 8/1999 | |

OTHER PUBLICATIONS

Huigsen Chem. Ber. 97 1085 1964.*
Partial European Search Report, EP 00 40 2710.
Bellstein Registry No. 8230509 and 8229251.
Bellstein Registry No. 8431170.
Bellstein Registry No. 7836658.
Akiba et al., "Cycloaddition–elimination reactions of iminothiadiazolines with acetylenes: hypervalent sulfur intermediates", *Tetrabedrom Letters*, No. 22, pp. 1877–187, 1976.
Yamamoto et al., "A mechanistic Study on the Reaction of Iminothiadiazolines with Activated Acetylenes: Competitive Pathway through Hypervalent Sulfurane and Zwitterion", *Bull, Chem. Soc. Jpn.*, vol. 62, No. 1, pp. 211–218, 1989.
Bellstein Registry No. 4210220 and 4207808.

Chemical Abstracts, vol. 120, No. 25, 1994, abstract No. 323458w.
Databse Caplus, Database accession No. 1994:323458, pp. 1–3.
Ali et al., "Metal Chelates of Dithiocarbazic Acid and Its Derivatives. III, Complexes of the Tridentate Schiff Base $_\alpha N$–Methyl–$S$–methyl–$\beta$–$N$–(2–pyridyl)methylendithiocarbazate with Some 3d Metal Ions", *Inorganica Chimica Acta*, 1972, 6:11–16.
Molina et al., "Alkyl 2–Methyldithiocarbazates in Heterocyclic Synthesis: Preparation of 2–Alkylthio–1,3,4–thiadiazolium Cations and 2–Thioxo–2,3–dihydro–1,3,4–Oxadiazole Derivatives", *Synthesis*, 1988:690–693.
Molina et al., "2–Methyithio–1,3,4–thiadiazolium Cations as Useful Procursors for the Preparation of 2–Amino–1,3,4–thiadiazole Derivatives and as Dehydrating Reagents of Aldoximes", *Heterocycles*, vol. 29, No. 12, 1989, pp. 2301–2316.
Noto et al., "A Quantitative Study of Substituent Effects on Oxidative Cyclization of Some 2–Methylaubstituted Aldehydes. Thiosemicarbazones Induced by Ferric Chloride", *J. Heterocyclic Chem.*, vol. 33, 1996, pp. 863–872.

(Continued)

Primary Examiner—Joseph K. McKane
Assistant Examiner—Rebecca Anderson
(74) Attorney, Agent, or Firm—Peter C. Richardson; Gregg C. Benson; Robert T. Ronau

(57) ABSTRACT

The invention provides 1,3,4-thiadiazoles and 1,3,4-oxadiazoles having the following Formula I:

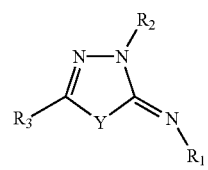

in which,

Y is S or O, $R_1$ is alkyl, alkenyl, alkynyl, cycloalkyl, heterocycloalkyl, cycloalkenyl, aryl, heteroaryl or a polycyclic group, optionally substituted, $R_2$ is alkyl, alkenyl, alkynyl, cycloalkyl, heterocycloalkyl, cycloalkenyl or aryl optionally substituted, $R_3$ is $X_2$—$R'_3$, in which $X_2$ is a binding group and $R'_3$ is cycloalkyl, heterocycloalkyl, cycloalkenyl, aryl, heteroaryl, or a polycyclic group; optionally substituted, or their pharmaceutically acceptable derivatives, a compound of Formula I, for their preparation, and processes for pharmaceutical compositions containing methods of using the compounds for the treatment of disorders for which a treatment by a PDE7 inhibitor is relevant.

23 Claims, No Drawings

OTHER PUBLICATIONS

Kane and Staeger, "An improved method for the synthesis of 5–aryl–3–methyl–2–methylimino–1,3,4–oxadiazoles", *Synthetic Communications*, 22(1); 1992, pp. 1–11.

Chemical Abstracts, vol. 120, No. 25, 1994, "Synthesis and biological activity of novel quinazollnones derived from 2–hydrazion–3–phenyl–4(3H)–quinazolinones".

L'Abbe G et al, Journal of Organic Chemistry, vol. 46, No. 22, pp. 4478–4481.

Chemical Abstracts, vol. 73, No. 11, 1970 2–amino–1,3, 4–oxadiazoles. XXXV. Synthesis and reaction of 1,3,4–oxadiazolo'3,2–alpyrimidinones, p. 322.

Awasthl A K and Al, "A new route to 2,3,5–trisubstituted 2,3–dihydro–1,3,4–oxadiazoles via stabilized sulfuranes", No 7, 1984, pp. 590–591.

* cited by examiner

THIADIAZOLES AND OXADIAZOLES AND THEIR USE AS PHOSPHODIESTERASE-7 INHIBITORS

FIELD OF THE INVENTION

The invention relates to novel thiadiazoles and oxadiazoles, processes for their preparation, and their use as phosphodiesterase 7 (PDE7) inhibitors.

BACKGROUND OF THE INVENTION

Phosphodiesterases (PDE) play an important role in various biological processes by hydrolyzing the key second messengers adenosine and guanosine 3',5'-cyclic monophosphates (cAMP and cGMP, respectively) into their corresponding 5'-monophosphate nucleotides. Therefore, inhibition of PDE activity produces an increase of cAMP and cGMP intracellular levels that activate specific protein phosphorylation pathways involved in a variety of functional responses.

At least 11 isoenzymes of mammalian cyclic nucleotide phosphodiesterases, numbered PDE1 through PDE11, have been identified on the basis of primary structure, substrate specificity, or sensitivity to cofactors or inhibitory drugs.

Among these phosphodiesterases, PDE 7 is a cAMP-specific PDE. The biochemical and pharmacological characterization showed a high-affinity cAMP-specific PDE (Km=0.2 µM), that was not affected by cGMP potent selective PDE isoenzyme inhibitors.

PDE 7 activity or protein has been detected in T-cell lines, B-cell lines, airway epithelial (AE) cell lines, and several fetal tissues.

Increasing cAMP levels by selective PDE7 inhibition appears to be a potentially promising approach to specifically block T-cell mediated immune responses. Further studies have demonstrated that elevation of intracellular cAMP levels can modulate inflammatory and immunological processes. This selective approach could presumably be devoid of the side effects associated with known selective inhibitors (eg, PDE3 or PDE4 selective inhibitors) and which limit their use.

A functional role of PDE7 in T-cell activation has also been disclosed; therefore selective PDE7 inhibitors would be candidates for the treatment of T-cell-related diseases.

AE cells actively participate in inflammatory airway diseases by liberating mediators such as arachidonate metabolites and cytokines. Selective inhibition of PDE7 may be a useful anti-inflammatory approach for treating AE cells related diseases.

Thus, there is a need for selective PDE7 inhibitors, which are active at very low concentrations, ie, micromolar inhibitor, preferably nanomolar inhibitors.

SUMMARY OF THE INVENTION

The invention provides pharmaceutical compositions comprising a compound having the following Formula I:

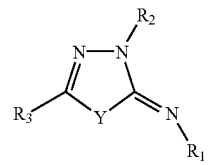

wherein:
Y is O or S;
$R_1$ is:
  $C_1$–$C_{10}$ alkyl,
  $C_2$–$C_{10}$ alkenyl,
  $C_2$–$C_{10}$ Calkynyl,
  cycloalkyl,
  cycloalkenyl,
  heterocycle,
  aryl,
  or a polycyclic group;
each optionally substituted with one or several groups $X_1$—$R_4$, identical or different, in which:
  $X_1$ is:
    a single bond, lower alkylene, $C_2$–$C_6$ alkenylene, cycloalkylene, arylene or divalent heterocycle, and,
  $R_4$ is:
    1) H, =O, $NO_2$, CN, halogen, lower haloalkyl, lower alkyl, carboxylic acid bioisostere,
    2) $COOR_5$, $C(=O)R_5$, $C(=S)R_5$, $SO_2R_5$, $SOR_5$, $SO_3R_5$, $SR_5$, $OR_5$,
    3) $C(=O)NR_7R_8$, $C(=S)NR_7R_8$, $C(=N-CN)NR_7R_8$, $C(=N-SO_2NH_2)NR_7R_8$, $C(=CH-NO_2)NR_7R_8$, $C(=NR_7)NHR_8$, $C(=NR_7)R_8$, $C(=NR_9)NHR_8$, $C(=NR_9)R_8$, $SO_2NR_7R_8$ or $NR_7R_8$ in which $R_7$ and $R_8$ are the same or different and are selected from OH, $R_5$, $R_6$, $C(=O)NR_5R_6$, $C(=O)R_5$, $SO_2R_5$, $C(=NR_9)NHR_{10}$, $C(=NR_9)R_{10}$, $C(=CH-NO_2)NR_9R_{10}$, $C(=N-SO_2NH_2)NR_9R_{10}$, $C(=N-CN)NR_9R_{10}$ or $C(=S)NR_9R_{10}$;

$R_2$ is:
  lower alkyl,
  $C_2$–$C_{10}$ alkenyl,
  $C_2$–$C_{10}$ alkynyl,
  cycloalkyl,
  cycloalkenyl,
  heterocycle,
  aryl;
each optionally substituted with one or several groups which are the same or different and which are selected from:
  1) H, carboxylic acid bioisostere, lower haloalkyl, halogen,
  2) $COOR_5$, $OR_5$, $SO_2R_5$,
  3) $SO_2NR_{11}R_{12}$, $C(=O)NR_{11}R_{12}$ or $NR_{11}R_{12}$ in which $R_{11}$ and $R_{12}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$;

$R_3$ is $X_2$—$R'_3$ wherein:
  $X_2$ is a single bond or,
    a group selected from $C_1$–$C_4$ alkylene, $C_2$–$C_6$ alkenylene, $C_2$–$C_6$ alkynylene, each optionally substituted with one or several groups which are the same or different and which are selected from:
1) H, $C_1$–$C_3$ alkyl, $C_3$–$C_4$ cycloalkyl, aryl, heterocycle, =O, CN,
2) $OR_5$, =$NR_5$ or,
3) $NR_{13}R_{14}$ in which $R_{13}$ and $R_{14}$ are the same or different and are selected from $R_5$, $R_6$, C(=O)$NR_5R_6$, C(=O)$R_5$, $SO_2R_5$, C(=S)$NR_9R_{10}$, C(=CH—$NO_2$)$NR_9R_{10}$, C(=$NR_9$)$NHR_{10}$, or C(=$NR_9$)$R_{10}$;

R'3 is:
cycloalkyl,
cycloalkenyl,
aryl,
heterocycle,
or a polycyclic group;
each optionally substituted with one or several groups $X_3$—$R_{17}$, identical or different, in which:
$X_3$ is:
a single bond, lower alkylene, $C_2$–$C_6$ alkenylene, $C_2$–$C_6$ alkynylene, cycloalkylene, arylene, divalent heterocycle, or a divalent polycyclic group, and,
$R_{17}$ is:
1) H, =O, $NO_2$, CN, lower haloalkyl, halogen, carboxylic acid bioisostere, cycloalkyl,
2) $COOR_5$, C(=O)$R_5$, C(=S)$R_5$, $SO_2R_5$, $SOR_5$, $SO_3R_5$, $SR_5$, $OR_5$,
3) C(=O)$NR_{15}R_{16}$, C(=S)$NR_{15}R_{16}$, C(=N—CN)$NR_{15}R_{16}$, C(=N—$SO_2NH_2$)$NR_{15}R_{16}$, C(=CH—$NO_2$)$NR_{15}R_{16}$, $SO_2NR_{15}R_{16}$, C(=$NR_{15}$)$NHR_{16}$, C(=$NR_{15}$)$R_{16}$, C(=$NR_9$)$NHR_{16}$, C(=$NR_9$)$R_{16}$ or $NR_{15}R_{16}$ in which $R_{15}$ and $R_{16}$ are the same or different and are selected from OH, $R_5$, $R_6$, C(=O)$NR_5R_6$, C(=O)$R_5$, $SO_2R_5$, C(=S)$NR_9R_{10}$, C(=CH—$NO_2$)$NR_9R_{10}$, C(=N—CN)$NR_9R_{10}$, C(=N—$SO_2NH_2$)$NR_9R_{10}$, C(=$NR_9$)$NHR_{10}$ or C(=$NR_9$)$R_{10}$,
4) heterocycle optionally substituted with one or several groups $R_5$;
wherein:
$R_5$ and $R_6$ are the same or different and are selected from:
H,
lower alkyl, $C_2$–$C_6$ alkenyl, $C_2$–$C_6$ alkynyl;
$X_4$-cycloalkyl, $X_4$-cycloalkenyl, $X_4$-aryl, $X_4$-heterocycle or $X_4$-polycyclic group, in which $X_4$ is a single bond, lower alkylene or $C_2$–$C_6$ alkenylene;
each optionally substituted with one or several groups which are the same or different and which are selected from:
halogen, =O, $COOR_{20}$, CN, $OR_{20}$, lower alkyl optionally substituted with $OR_{20}$, O-lower alkyl optionally substituted with $OR_{20}$, C(=O)-lower alkyl, lower haloalkyl,

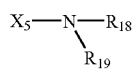

in which $X_5$ is a single bond or lower alkylene and $R_{18}$, $R_{19}$, and $R_{20}$ are the same or different and are selected from H or lower alkyl;
$X_6$-heterocycle, $X_6$-aryl, $X_6$-cycloalkyl, $X_6$-cycloalkenyl, $X_6$-polycyclic group in which $X_6$ is selected from a single bond or lower alkylene, these groups being optionally substituted with one or several groups, identical or different, selected from halogens, $COOR_{21}$, $OR_{21}$, or $(CH_2)_nNR_{21}R_{22}$ in which n is 0, 1, or 2 and $R_{21}$ and $R_{22}$ are the same or different and are selected from H or lower alkyl;
$R_9$ is selected from H, CN, OH, lower alkyl, O-lower alkyl, aryl, heterocycle, $SO_2NH_2$ or

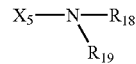

in which $X_5$ is a single bond or lower alkylene and $R_{18}$ and $R_{19}$ are the same or different and are selected from H or lower alkyl;
$R_{10}$ is selected from hydrogen, lower alkyl, cyclopropyl or heterocycle;
or a pharmaceutically acceptable derivative thereof,
together with a pharmaceutically acceptable carrier, with the proviso that the substituent group "=O" is not bonded to a single bond, a carbon atom of a carbon-carbon double bond or a carbon-carbon triple bond, a carbon atom of a trisubstituted carbon, an arylene, or a heteroatom of a divalent heterocycle, and
with the proviso that the compound of Formula I is not 4-[2-formylimino-5-(4-methoxy-phenyl)-[1,3,4]thiadiazol-3-yl]-butyric acid ethyl ester, 4-[5-(4-chloro-phenyl)-2-formylimino-[1,3,4]thiadiazol-3-yl]-butyric acid ethyl ester.

The invention also relates to novel compounds having the following Formula I above.

These compounds are selective PDE7 inhibitors. They can be used in the treatment of various diseases, such as T-cell-related diseases, autoimmune diseases, inflammatory diseases, respiratory diseases, central nervous system (CNS) diseases, allergic diseases, endocrine or exocrine pancreas diseases, gastrointestinal diseases, visceral pain, inflammatory bowel disease, osteoarthritis, multiple sclerosis, chronic obstructive pulmonary disease (COPD), asthma, cancer, acquired immune deficiency syndrome (AIDS), or graft rejection.

The invention also relates to a process for preparing the above compounds.

The invention further concerns the use of a compound of Formula I for the preparation of a medicament for the prevention or the treatment of disorders for which therapy by a PDE7 inhibitor is relevant.

The invention also provides a method for the treatment of a disorder for which therapy by a PDE7 inhibitor is relevant, comprising administering to a mammal in need thereof an effective amount of compound of Formula I.

The invention also concerns a pharmaceutical composition comprising a compound of Formula I together with a pharmaceutically acceptable carrier.

The invention also relates to a pharmaceutical composition for the treatment of a disorder for which therapy by a PDE7 inhibitor is relevant, comprising a compound of Formula I together with a pharmaceutically acceptable carrier.

DETAILED DESCRIPTION OF THE INVENTION

The present invention provides pharmaceutical compositions comprising compounds having Formula I,

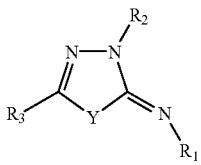

in which $R_1$, $R_2$, $R_3$, and Y are as defined above with the exclusion of the compounds recited above.

In the following and in the foregoing text:

aryl is understood to refer to an unsaturated carbocycle, exclusively comprising carbon atoms in the cyclic structure, the number of which is between 5 and 10, including phenyl, naphthyl, or tetrahydronaphthyl;

heterocycle is understood to refer to a nonsaturated or saturated monocycle containing between 1 and 7 carbon atoms in the cyclic structure and at least one heteroatom in the cyclic structure, such as nitrogen, oxygen, or sulfur, preferably from 1 to 4 heteroatoms, identical or different, selected from nitrogen, sulfur and oxygen atoms. Suitable heterocycles include morpholinyl, piperazinyl, pyrrolidinyl, piperidinyl, pyrimidinyl, 2- and 3-furanyl, 2- and 3-thienyl, 2-pyridyl, 2- and 3-pyranyl, hydroxypyridyl, pyrazolyl, isoxazolyl, tetrazole, imidazole, triazole, and the like;

polycyclic groups include at least two cycles, identical or different, selected from aryl, heterocycle, cycloalkyl, cycloalkenyl groups fused together to form said polycyclic group such as 2- and 3-benzothienyl, 2- and 3-benzofuranyl, 2-indolyl, 2- and 3-quinolinyl, acridinyl, quinazolinyl, indolyl benzo[1,3]dioxolyl, and 9-thioxantanyl.

Preferred polycyclic groups include 2 or 3 cycles as defined above.

More preferred polycyclic groups include 2 cycles (bicyclic substituents) as defined above.

bicyclic groups refer to two cycles, which are the same or different and which are chosen from aryl, heterocycle, cycloalkyl or cycloalkenyl, fused together to form said bicyclic groups;

halogen is understood to refer to fluorine, chlorine, bromine, or iodine;

lower alkyl is understood to mean that the alkyl is linear or branched and contains 1 to 6 carbon atoms; Examples of lower alkyl groups include methyl, ethyl, propyl, butyl, isopropyl, tert-butyl, isobutyl, n-butyl, pentyl, hexyl and the like.

alkenyl is understood to refer to a linear or branched unsaturated carbon atom chain, comprising one or several double bonds, preferably one or two double bonds. Preferred alkenyls comprise from 3 to 6 carbon atoms and one double bonds.

alkynyl is understood to refer to a linear or branched unsaturated carbon atom chain, comprising one or several triple bonds, preferably one or two triple bonds. Preferred alkynyls comprise from 3 to 6 carbon atoms and one triple bond.

lower haloalkyl are understood to refer to a lower alkyl substituted with one or several halogens; preferred lower haloalkyl groups include perhaloalkyl groups such as $CF_3$.

cycloalkyl is understood to refer to saturated monocarbocyle containing from 3 to 10 carbon atoms; preferred cycloalkyl groups comprise cyclopropyl, cyclobutyl, cyclopentyl, cyclohexyl, and cycloheptyl.

cycloalkenyl is understood to refer to unsaturated monocarbocyle containing from 3 to 10 carbon atoms. Preferred cyloalkenyl groups contain 1 or 2 double bonds. Examples of suitable cycloalkenyl are 3-cyclohexene, 3-cycloheptene or the like.

carboxylic acid bioisostere has the classical meaning; common carboxylic acid bioisostere are tetrazol-5-yl, $C(=O)N(H)OH$, isoxazol-3-yl, hydroxythiadiazolyl, sulfonamido, sulfonylcarboxamido, phosphonic acid, phosphonamido, phosphinic acid, sulfonic acids, acyl sulfonamido, mercaptoazole, acyl cyanamides. The term "mammal" includes human, cat, dog, sheep, horse, cow, and pig.

Preferred pharmaceutical composition are those containing a compound of Formula I in which $R_1$, $R_2$, $R_3$, and Y are as defined above, with the proviso that when $R_1$ is $C(=O)$—H, then $R_2$ does not represent $(CH_2)_3$—$C(=O)OCH_2CH_3$.

The present invention also relates to compounds of Formula I,

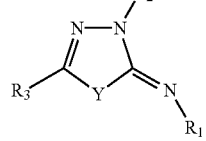

in which
Y is O or S;
$R_1$ is:
  $C_2$–$C_{10}$ alkenyl,
  $C_2$–$C_{10}$ alkynyl,
  cycloalkyl,
  cycloalkenyl,
  heterocycle,
  aryl,
  or a bicyclic group;
each optionally substituted with one or several groups $X_1$—$R_4$, identical or different, in which:
$X_1$ is:
  a single bond, lower alkylene, $C_2$–$C_6$ alkenylene, cycloalkylene, arylene or divalent heterocycle, and,
$R_4$ is:
  1) H, $=O$, $NO_2$, CN, halogen, lower haloalkyl, lower alkyl, carboxylic acid bioisostere,
  2) $COOR_5$, $C(=O)R_5$, $C(=S)R_5$, $SO_2R_5$, $SOR_5$, $SO_3R_5$, $SR_5$, $OR_5$,
  3) $C(=O)NR_7R_8$, $C(=S)NR_7R_8$, $C(=CH-NO_2)NR_7R_8$, $C(=N-CN)NR_7R_8$, $C(=N-SO_2NH_2)NR_7R_8$, $C(=NR_7)NHR_8$, $C(=NR_7)R_8$, $C(=NR_9)NHR_8$, $C(=NR_9)R_8$, $SO_2NR_7R_8$ or $NR_7R_8$ in which $R_7$ and $R_8$ are the same or different and are selected from OH, $R_5$, $R_6$, $C(=O)NR_5R_6$, $C(=O)R_5$, $SO_2R_5$, $C(=NR_9)NHR_{10}$, $C(=NR_9)R_{10}$, $C(=CH-NO_2)NR_9R_{10}$, $C(=N-SO_2NH_2)NR_9R_{10}$, $C(=N-CN)NR_9R_{10}$ or $C(=S)NR_9R_{10}$;
$R_2$ is:
  lower alkyl,
  $C_2$–$C_{10}$ alkenyl,
  $C_4$–$C_{10}$ alkynyl,
  cycloalkyl, cycloalkenyl,
heterocycle,
aryl;
each optionally substituted with one or several groups which are the same or different and which are selected from:
1) H, carboxylic acid bioisostere, lower haloalkyl, halogen,
2) $COOR_5$, $OR_5$, $SO_2R_5$,
3) $SO_2NR_{11}R_{12}$, $C(=O)NR_{11}R_{12}$, or $NR_{11}R_{12}$ in which $R_{11}$ and $R_{12}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$;

$R_3$ is $X_2-R'_3$ wherein:
$X_2$ is a single bond or,
a group selected from $C_1-C_4$ alkylene, $C_2-C_6$ alkenylene, $C_2-C_6$ alkynylene, each optionally substituted with one or several groups which are the same or different and which are selected from:
1) H, $C_1-C_3$ alkyl, $C_3-C_4$ cycloalkyl, aryl, heterocycle, =O, CN,
2) $OR_5$, $=NR_5$ or,
3) $NR_{13}R_{14}$ in which $R_{13}$ and $R_{14}$ are the same or different and are selected from $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, or $C(=NR_9)R_{10}$;

$R'_3$ is:
cycloalkyl,
cycloalkenyl,
aryl,
heterocycle,
or a polycyclic group;
each optionally substituted with one or several groups $X_3-R_{17}$, identical or different, in which:
$X_3$ is:
a single bond, lower alkylene, $C_2-C_6$ alkenylene, $C_2-C_6$ alkynylene, cycloalkylene, arylene, divalent heterocycle or a divalent polycyclic group, and,
$R_{17}$ is:
1) H, =O, $NO_2$, CN, lower haloalkyl, halogen, cycloalkyl,
2) $COOR_5$, $C(=O)R_5$, $C(=S)R_5$, $SO_2R_5$, $SOR_5$, $SO_3R_5$, $SR_5$, $OR_5$,
3) $C(=O)NR_{15}R_{16}$, $C(=S)NR_{15}R_{16}$, $C(=N-CN)NR_{15}R_{16}$, $C(=N-SO_2NH_2)NR_{15}R_{16}$, $C(=CH-NO_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ in which $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$;
4) heterocycle optionally substituted with one or several groups $R_5$;
wherein, $R_5$, $R_6$, $R_8$, and $R_{10}$ are as defined above,
with the proviso that,
the substituent group "=O" is not bonded to a single bond, a carbon atom of a carbon-carbon double bond or a carbon-carbon triple bond, a carbon atom of a trisubstituted carbon, an arylene, or a heteroatom of a divalent heterocycle,
when $R_1$ is phenyl, it bears at least one substituent other than H, when $X_2$ is a single bond and both $R_1$ and $R'_3$ are phenyl, each of R1 and $R'_3$ bear at least one substituent other than H,
when $X_2$ is a single bond and $R'_3$ is phenyl, $R'_3$ is not substituted by an ester or a carboxylic acid in the ortho position,
the atom of $R_3$ which is linked to the thiadiazole group is a carbon atom, with the exclusion of the following compounds:

1-Phenyl-1-[4-phenyl-5-(5-trifluoromethyl-2H-[1,2,4]triazol-3-ylimino)-4,5-dihydro-[1,3,4]thiadiazol-2-yl]-methanone, 1-[4-Phenyl-5-(5-trifluoromethyl-2H-[1,2,4]triazol-3-ylimino)-4,5-dihydro-[1,3,4]thiadiazol-2-yl]-1-thiophen-2-yl-methanone, 1-Phenyl-1-(4-phenyl-5-p-tolylimino-4,5-dihydro-[1,3,4]thiadiazol-2-yl)-methanone, Cyclohexyl-[3-(2,4,6-trichloro-phenyl)-5-(2,3,3-trimethyl-cyclopent-1-enylmethyl)-3H-[1,3,4]thiadiazol-2-ylidene]-amine, 2-(3,5-Diphenyl-3H-[1,3,4]thiadiazol-2-ylideneamino)-1,4-diphenyl-but-2-ene-1,4-dione, 2-[3-Phenyl-5-(1-phenyl-methanoyl)-3H-[1,3,4]thiadiazol-2-ylideneamino]-but-2-enedioic acid dimethyl ester, 2-[5-(1-Phenyl-methanoyl)-3-p-tolyl-3H-[1,3,4]thiadiazol-2-ylideneamino]-but-2-enedioic acid dimethyl ester, and 2-[3-(4-Chloro-phenyl)-5-(1-phenyl-methanoyl)-3H-[1,3,4]thiadiazol-2-ylideneamino]-but-2-enedioic acid dimethyl ester.

Preferred compounds of Formula I are those in which $R_1$, $R_2$, $R_3$, and Y are as defined above, with the proviso that, when $R_2$ is a phenyl, unsubstituted or substituted with 1 to 3 chlorine or with a methyl, then $R_3$ does not represent $C(=O)$-phenyl, $C(=O)$-thienyl, phenyl, or $CH_2$-(2,3,3-trimethyl-cyclopent-1-enyl).

Other preferred compounds of formula (I) are those in which:
$R_1$ is:
$C_4-C_6$ alkyl,
cycloalkyl,
cycloalkenyl,
heterocycle,
aryl,
or a bicyclic group;
each optionally substituted with one or several groups $X_1-R_4$, identical or different, in which:
$X_1$ is a single bond, a divalent heterocycle, or a lower alkylene, and
$R_4$ is selected from:
1) H, =O, halogen, CN, lower haloalkyl, preferably $CF_3$, lower alkyl, carboxylic acid bioisostere,
2) $COOR_5$, $SO_2R_5$, $OR_5$, $C(=O)R_5$
3) $C(=O)NR_7R_8$, $SO_2NR_7R_8$, or $NR_7R_8$ in which $R_7$ and $R_8$ are the same or different and are selected from $R_5$, $R_6$, $C(=O)NR_5R_6$, $C(=O)R_5$, $SO_2R_5$, $C(=NR_9)NHR_{10}$, $C(=NR_9)R_{10}$, or $C(=S)NR_9R_{10}$.

Other preferred compounds of Formula I are those in which $R_2$ is lower alkyl.

Further preferred compounds of Formula I are those in which $R_3$ is $X_2-R'_3$ wherein,
$X_2$ is a single bond, $C_1-C_4$ alkylene, $C_2-C_6$ alkenylene, or $C_2-C_6$ alkynylene and, R'3 is:
  cycloalkyl,
  cycloalkenyl,
  aryl,
  heterocycle,
  or a polycyclic group;
each optionally substituted with one or several groups $X_3$—$R_{17}$, identical or different, in which:
$X_3$ is a single bond or lower alkylene, and
$R_{17}$ is:
  1) H, $=$O, $NO_2$, CN, lower haloalkyl, halogen, cycloalkyl,
  2) $COOR_5$, $C(=O)R_5$, $C(=S)R_5$, $SO_2R_5$, $SOR_5$, $SO_3R_5$, $SR_5$, $OR_5$,
  3) $C(=O)NR_{15}R_{16}$, $C(=S)NR_{15}R_{16}$, $C(=N-CN)NR_{15}R_{16}$, $C(=CH-NO_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ in which $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=NR_9)NHR_{10}$, or $C(=NR_9)R_{10}$,
  4) heterocycle optionally substituted with one or several groups $R_5$.

Particularly preferred compounds of Formula I are those in which
$R_1$ is:
  cycloalkyl, preferably cyclohexane,
  cycloalkenyl,
  aryl, preferably phenyl,
  or a bicyclic group;
each optionally substituted with one or several groups $X_1$—$R_4$, identical or different, in which:
$X_1$ is a single bond or a divalent heterocycle, and
$R_4$ is selected from:
  1) H, halogen, $CF_3$, $=$O,
  2) $COOR_5$, $OR_5$,
  3) $C(=O)NR_5R_6$.

Other particularly preferred compounds of Formula I are those in which $R_2$ is $CH_3$.

Further particularly preferred compounds of Formula I are those in which $R_3$ is $X_2$—$R'_3$ wherein,
$X_3$ is a single bond or —$CH_2$—, and
$R_{17}$ is:
  1) H, CN, $CF_3$, halogen, $NO_2$,
  2) $COOR_5$, $SO_2R_5$, $OR_5$, $C(=O)R_5$,
  3) $C(=O)NR_{15}R_{16}$, $S_2NR_{15}R_{16}$, or $NR_{15}R_{16}$ in which $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, $C(=NR_9)R_{10}$, or $C(=N-CN)NR_9R_{10}$,
  4) heterocycle optionally substituted with one or several groups $R_5$.

More preferred compounds of Formula I are those in which
$R_1$ is:
  $C_4$–$C_6$ alkyl
  cycloalkyl,
  cycloalkenyl,
  heterocycle,
  aryl,
  or a bicyclic group;
each optionally substituted with one or several groups $X_1$—$R_4$, identical or different, in which:
  $X_1$ is a single bond, a divalent heterocycle, or a lower alkylene, and
  $R_4$ is selected from:
    1) H, $=$O, halogen, CN, lower haloalkyl, preferably $CF_3$, lower alkyl, carboxylic acid bioisostere,
    2) $COOR_5$, $SO_2R_5$, $OR_5$, $C(=O)R_5$,
    3) $C(=O)NR_7R_8$, $SO_2NR_7R_8$ or $NR_7R_8$ in which $R_7$ and $R_8$ are the same or different and are selected from $R_5$, $R_6$, $C(=O)NR_5R_6$, $C(=O)R_5$, $SO_2R_5$, $C(=NR_9)NHR_{10}$, $C(=NR_9)R_{10}$ or $C(=S)NR_9R_{10}$,
    4) heterocycle optionally substituted with one or several groups $R_5$.
$R_2$ is lower alkyl, and,
$R_3$ is $X_2$—$R'_3$ wherein,
  $X_2$ is a single bond, $C_1$–$C_4$ alkylene, $C_2$–$C_6$ alkenylene, or $C_2$–$C_6$ alkynylene, and
  $R'_3$ is:
    cycloalkyl,
    cycloalkenyl,
    aryl,
    heterocycle,
    or a polycyclic group;
each optionally substituted with one or several groups $X_3$—$R_{17}$, identical or different, in which:
  $X_3$ is a single bond or lower alkylene, and,
  $R_{17}$ is:
    1) H, $=$O, $NO_2$, CN, lower haloalkyl, halogen, cycloalkyl,
    2) $COOR_5$, $C(=O)R_5$, $C(=S)R_5$, $SO_2R_5$, $SOR_5$, $SO_3R_5$, $SR_5$, $OR_5$,
    3) $C(=O)NR_{15}R_{16}$, $C(=S)NR_{15}R_{16}$, $C(=N-CN)NR_{15}R_{16}$, $C(=CH-N_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ in which $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=NR_9)NHR_{10}$, or $C(=NR_9)R_{10}$,
    4) heterocycle optionally substituted with one or several groups $R_5$.

Other more preferred compounds of Formula I are those in which,
$R_1$ is:
  cycloalkyl, preferably cyclohexane,
  cycloalkenyl,
  aryl, preferably phenyl,
  or a bicyclic group;
each optionally substituted with one or several groups $X_1$—$R_4$, identical or different, in which:
$R_1$ is:
  cycloalkyl, preferably cyclohexane,
  cycloalkenyl,
  aryl, preferably phenyl,
  or a bicyclic group;
each optionally substituted with one or several groups $X_1$—$R_4$, identical or different, in which:
  $X_1$ is a single bond or a divalent heterocycle, and
  $R_4$ is selected from:
    1) H, halogen, $CF_3$, $=$O,
    2) $COOR_5$, $OR_5$,
    3) $C(=O)NR_5R_6$;
$R_2$ is $CH_3$, and $R_3$ is $X_2$—$R'_3$ wherein,
  $X_2$ is a single bond, $C_1$–$C_4$ alkylene or $C_2$–$C_6$ alkenylene, and
  $R'_3$ is:
    cycloalkyl,
    aryl, preferably phenyl,
    heterocycle,
    or a polycyclic group;
  each optionally substituted with one or several groups $X_3$—$R_{17}$, identical or different, in which:
    $X_3$ is a single bond or —$CH_2$—, and
    $R_{17}$ is:
      1) H, CN, $CF_3$, halogen, $NO_2$
      2) $COOR_5$, $SO_2R_5$, $OR_5$, $C(=O)R_5$,
      3) $C(=O)NR_{15}R_{16}$, $SO_2NR_{15}R_{16}$, or $NR_{15}R_{16}$ in which $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, $C(=NR_9)R_{10}$, or $C(=N-CN)NR_9R_{10}$,
      4) heterocycle optionally substituted with one or several groups $R_5$.

Other more preferred compounds of Formula I are those in which,
Y is O;
$R_1$ is:
  cycloalkyl, preferably cyclohexane,
  cycloalkenyl,
  aryl, preferably phenyl,
  or a bicyclic group;
  each optionally substituted with one or several groups $X_1$—$R_4$, identical or different, in which:
    $X_1$ is a single bond or a divalent heterocycle, and
    $R_4$ is selected from:
      1) H, halogen, $CF_3$, =O,
      2) $COOR_5$, $OR_5$,
      3) $C(=O)NR_5R_6$;
$R_2$ is $CH_3$, and
$R_3$ is $X_2$—$R'_3$ wherein,
  $X_2$ is a single bond, $C_1$–$C_4$ alkylene or $C_2$–$C_6$ alkenylene, and
  $R'_3$ is:
    cycloalkyl,
    aryl, preferably phenyl,
    heterocycle,
    or a polycyclic group;
  each optionally substituted with one or several groups $X_3$—$R_{17}$, identical or different, in which:
    $X_3$ is a single bond or —$CH_2$—, and
    $R_{17}$ is:
      1) H, CN, $CF_3$, halogen, $NO_2$
      2) $COOR_5$, $SO_2R_5$, $OR_5$, $C(=O)R_5$
      3) $C(=O)NR_{15}R_{16}$, $SO_2NR_{15}R_{16}$, or $NR_{15}R_{16}$ in which $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, $C(=NR_9)R_{10}$, or $C(=N-CN)NR_9R_{10}$,
      4) heterocycle optionally substituted with one or several groups $R_5$.

More specifically, a group of compounds of Formula I which has been found to be of particular interest are those in which,
R1 is:
  cyclohexane,
  phenyl
  or a bicyclic group;
  each optionally substituted with one or several groups $X_1$—$R_4$, identical or different, in which:
    $X_1$ is a single bond or a divalent heterocycle, and,
    $R_4$ is selected from:
      1) H, halogen, $CF_3$,
      2) COOH, OH,
      3) $C(=O)NR_7R_8$ in which $R_7$ and $R_8$ are the same or different and are selected from H or lower alkyl;
$R_2$ is $CH_3$, and
$R_3$ is $X_2$—$R'_3$ wherein,
  $X_2$ is a single bond, $C_1$–$C_4$ alkylene or $C_2$–$C_6$ alkenylene, and
  $R'_3$ is:
    phenyl
    heterocycle,
    or a polycyclic group;
  each optionally substituted with one or several groups $X_3$—$R_{17}$, identical or different, in which:
    $X_3$ is a single bond, and,
    $R_{17}$ is:
      1) CN, OH, $CF_3$, =O, $C_1$–$C_6$ alkoxy, halogen,
      2) $COOR_5$, $SO_2R_5$,
      3) $C(=O)NR_{15}R_{16}$, $SO_2NR_{15}R_{16}$, or $NR_{15}R_{16}$ in which $R_{15}$ and $R_{16}$ are the same or different and are selected from OH, $C(=O)R_5$, $C(=O)NR_5R_6$, $R_5$, or $R_6$,
      4) heterocycle optionally substituted with one or several groups $R_5$.

Most preferred compounds of Formula I are those in which Y is S. Preferably, in each of the above definition of $R_1$:
$R_5$ is selected from:
  H, or,
  lower alkyl, optionally substituted with OH, preferably $CH_3$.
$R_6$ is selected from
  H, or,
  lower alkyl, preferably $CH_3$.
$R_9$ and $R_{10}$ are selected from
  H, or,
  lower alkyl, preferably $CH_3$.
Preferably, in each of the above definition of $R_2$:
$R_5$ and $R_6$ are selected from
  H, or,
  lower alkyl, preferably $CH_3$.
$R_9$ and $R_{10}$ are selected from:
  H, or,
  lower alkyl, preferably $CH_3$.
Preferred compounds are:
I1 3-[5-(4-Chloro-phenyl)-3-methyl-3H-[1,3,4]thiadiazol-2-ylideneamino]-benzoic acid;
I1.1 (1R*,2R*)-2-[5-(4-Chloro-phenyl)-3-methyl-3H-[1,3,4]thiadiazol-2-ylideneamino]-cyclohexanecarboxylic acid;
I1.2 (S)-2-[5-(4-Chloro-phenyl)-3-methyl-3H-[1,3,4]thiadiazol-2-ylideneamino]-2-phenyl-ethanol;
I1.7 2-{2-[5-(4-Chloro-phenyl)-3-methyl-3H-[1,3,4]thiadiazol-2-ylideneamino]-phenyl}-ethanol;
I1.9 {1-[5-(4-Chloro-phenyl)-3-methyl-3H-[1,3,4]thiadiazol-2-ylideneamino]-cyclopentyl}-methanol;
I1.10 3-[5-(4-Chloro-phenyl)-3-methyl-3H-[1,3,4]thiadiazol-2-ylideneamino]-cyclohexanecarboxylic acid;

I2.1  5-[5-(4-Chloro-phenyl)-3-methyl-3H[1,3,4]thiadiazol-2-ylideneamino]-2-fluoro-benzoic acid;
I2.2  3-[5-(4-Chloro-phenyl)-3-methyl-3H-[1,3,4]thiadiazol-2-ylideneamino]-2,5,6-trifluoro-benzoic acid;
I3  [5-(4-Chloro-phenyl)-3-methyl-3H-[1,3,4]thiadiazol-2-ylidene]-propyl-amine;
I3.1  (S)-2-[5-(4-Chloro-phenyl)-3-methyl-3H-[1,3,4]thiadiazol-2-ylideneamino]-butan-1-ol;
I3.3  [5-(4-Chloro-phenyl)-3-methyl-3H-[1,3,4]thiadiazol-2-ylidene]-cyclobutyl-amine;
I3.4  3-[5-(4-Chloro-phenyl)-3-methyl-3H-[1,3,4]thiadiazol-2-ylideneamino]-azepan-2-one;
I3.7  [5-(4-Chloro-phenyl)-3-methyl-3H-[1,3,4]thiadiazol-2-ylidene]-cyclopentyl-amine;
I3.8  [5-(4-Chloro-phenyl)-3-methyl-3H-[1,3,4]thiadiazol-2-ylidene]-cycloheptyl-amine;
I3.10  (S)-2-[5-(4-Chloro-phenyl)-3-methyl-3H-[1,3,4]thiadiazol-2-ylideneamino]-3-methyl-butan-1-ol;
I3.11  2-[5-(4-Chloro-phenyl)-3-methyl-3H-[1,3,4]thiadiazol-2-ylideneamino]-2-methyl-propan-1-ol;
I3.13  tert-Butyl-[5-(4-chloro-phenyl)-3-methyl-3H-[1,3,4]thiadiazol-2-ylidene]-amine;
I3.14  [5-(4-Chloro-phenyl)-3-methyl-3H-[1,3,4]thiadiazol-2-ylidene]-isopropyl-amine;
I3.15  4-[5-(4-Chloro-phenyl)-3-methyl-3H-[1,3,4]thiadiazol-2-ylideneamino]-benzoic acid;
I3.16  [5-(4-Chloro-phenyl)-3-methyl-3H-[1,3,4]thiadiazol-2-ylidene]-(1-ethyl-propyl)-amine;
I3.17  4-[5-(4-Chloro-phenyl)-3-methyl-3H-[1,3,4]thiadiazol-2-ylideneamino]-phenol;
I3.18  N-[5-(4-Chloro-phenyl)-3-methyl-3H-[1,3,4]thiadiazol-2-ylidene]-cyclohexane-1,2-diamine;
I3.19  [5-(4-Chloro-phenyl)-3-methyl-3H-[1,3,4]thiadiazol-2-ylidene]-(4-fluoro-phenyl)-amine;
I3.20  N-[5-(4-Chloro-phenyl)-3-methyl-3H-[1,3,4]thiadiazol-2-ylidene]-cyclohexane-1,4-diamine;
I3.25  (1R*,2S*)-2-[5-(4-Chloro-phenyl)-3-methyl-3H-[1,3,4]thiadiazol-2-ylideneamino]-cyclohexanol;
I3.26  [5-(4-Chloro-phenyl)-3-methyl-3H-[1,3,4]thiadiazol-2-ylidene]-(4-trifluoromethyl-phenyl)-amine;
I4  3-[5-(4-Methanesulfonyl-phenyl)-3-methyl-3H-[1,3,4]thiadiazol-2-ylideneamino]-benzoic acid;
I5  3-[5-(4-Chloro-phenyl)-3-methyl-3H-[1,3,4]thiadiazol-2-ylideneamino]-phenol;
I6  5-[5-(4-Chloro-phenyl)-3-methyl-3H-[1,3,4]thiadiazol-2-ylideneamino]-2-hydroxy-benzoic acid;
I6.1  (1-Aza-bicyclo[2.2.2]oct-3-yl)-[5-(4-chloro-phenyl)-3-methyl-3H-[1,3,4]thiadiazol-2-ylidene]-amine;
I6.3  2-[5-(4-Chloro-phenyl)-3-methyl-3H-[1,3,4]thiadiazol-2-ylideneamino]-phenol;
I6.5  (R)-2-[5-(4-Chloro-phenyl)-3-methyl-3H-[1,3,4]thiadiazol-2-ylideneamino]-butan-1-ol;
I6.7  [5-(4-Chloro-phenyl)-3-methyl-3H-[1,3,4]thiadiazol-2-ylidene]-(3-fluoro-phenyl)-amine;
I6.8  (3-Chloro-phenyl)-[5-(4-chloro-phenyl)-3-methyl-3H-[1,3,4]thiadiazol-2-ylidene]-amine;
I6.9  {3-[5-(4-Chloro-phenyl)-3-methyl-3H-[1,3,4]thiadiazol-2-ylideneamino]-phenyl}-acetic acid;
I6.11  3-[5-(4-Chloro-phenyl)-3-methyl-3H-[1,3,4]thiadiazol-2-ylideneamino]-benzamide;
I7  Bicyclo[2.2.1]hept-2-yl-[5-(4-chloro-phenyl)-3-methyl-3H-[1,3,4]thiadiazol-2-ylidene]-amine;
I8  (1R*,2R*)-2-[5-(4-Chloro-phenyl)-3-methyl-3H-[1,3,4]thiadiazol-2-ylideneamino]-cyclohexanol;
I8.1  5-(5-Cyclohexyl-3-methyl-3H-[1,3,4]thiadiazol-2-ylideneamino)-2-methoxy-phenol;
I8.2  3-(5-Cyclohexyl-3-methyl-3H-[1,3,4]thiadiazol-2-ylideneamino)-benzoic acid;
I8.3  3-[5-(4-Chloro-phenyl)-3-methyl-3H-[1,3,4]thiadiazol-2-ylideneamino]-4-hydroxy-benzoic acid;
I8.4  (5-Cyclohexyl-3-methyl-3H-[1,3,4]thiadiazol-2-ylidene)-(3-methanesulfonyl-phenyl)-amine;
I9  (1R*,2R*)-2-[5-(4-Methanesulfonyl-phenyl)-3-methyl-3H-[1,3,4]thiadiazol-2-ylideneamino]-cyclohexanol;
I10  Cyclohexyl-[5-(2,4-dichloro-phenyl)-3-methyl-3H-[1,3,4]thiadiazol-2-ylidene]-amine;
I10.1  [5-(2-Chloro-phenyl)-3-methyl-3H-[1,3,4]thiadiazol-2-ylidene]-cyclohexyl-amine;
I11  Cyclohexyl-[3-methyl-5-(4-trifluoromethyl-phenyl)-3H-[1,3,4]thiadiazol-2-ylidene]-amine;
I12  Cyclohexyl-(3-methyl-5-pyridin-4-yl-3H-[1,3,4]thiadiazol-2-ylidene)-amine;
I13  [5-(3-Chloro-phenyl)-3-methyl-3H-[1,3,4]thiadiazol-2-ylidene]-cyclohexyl-amine;
I14  4-(5-Cyclohexylimino-4-methyl-4,5-dihydro-[1,3,4]thiadiazol-2-yl)-benzonitrile;
I15  Cyclohexyl-[5-(4-methanesulfonyl-phenyl)-3-methyl-3H-[1,3,4]thiadiazol-2-ylidene]-amine;
I15.1  [3-(5-Cyclohexylimino-4-methyl-4,5-dihydro-[1,3,4]thiadiazol-2-yl)-phenyl]-dimethyl-amine;
I15.2  Cyclohexyl-[5-(3-methoxy-4-nitro-phenyl)-3-methyl-3H-[1,3,4]thiadiazol-2-ylidene]-amine;
I16  2,4-Dichloro-5-(5-cyclohexylimino-4-methyl-4,5-dihydro-[1,3,4]thiadiazol-2-yl)-benzenesulfonamide;
I17  Cyclohexyl-(3-methyl-5-thiophen-3-yl-3H-[1,3,4]thiadiazol-2-ylidene)-amine;
I17.1  Cyclohexyl-[5-(3,5-dichloro-phenyl)-3-methyl-3H-[1,3,4]thiadiazol-2-ylidene]-amine;
I17.2  Cyclohexyl-[5-(2-ethyl-5-methyl-2H-pyrazol-3-yl)-3-methyl-3H-[1,3,4]thiadiazol-2-ylidene]-amine;
I18  [5-(3-Chloro-2,6-dimethoxy-phenyl)-3-methyl-3H-[1,3,4]thiadiazol-2-ylidene]-cyclohexyl-amine;
I18.1  Cyclohexyl-(5-isoxazol-5-yl-3-methyl-3H-[1,3,4]thiadiazol-2-ylidene)-amine;
I18.2  Cyclohexyl-[3-methyl-5-(5-pyridin-2-yl-thiophen-2-yl)-3H-[1,3,4]thiadiazol-2-ylidene]-amine;
I18.3  5-(5-Cyclohexylimino-4-methyl-4,5-dihydro[1,3,4]thiadiazol-2-yl)-2-methoxy-benzene-1,3-diol; compound with trifluoro-methanesulfonic acid;
I18.4  5-(5-Cyclohexylimino-4-methyl-4,5-dihydro[1,3,4]thiadiazol-2-yl)-2,3-dimethoxy-phenol; compound with trifluoro-methanesulfonic acid;
I18.5  [5-(4-Chloro-phenyl)-3-methyl-3H-[1,3,4]thiadiazol-2-ylidene]-cyclohexyl-amine;
I18.6  2-Chloro-4-(5-cyclohexylimino-4-methyl-4,5-dihydro-[1,3,4]thiadiazol-2-yl)-6-methoxy-phenol; compound with 1,1,1-trifluoro-methanesulfonic acid;
I19  2-Chloro-5-(5-cyclohexylimino-4-methyl-4,5-dihydro-[1,3,4]thiadiazol-2-yl)-benzenesulfonamide;
I19.1  2-Chloro-5-(5-cyclohexylimino-4-methyl-4,5-dihydro[1,3,4]thiadiazol-2-yl)-N,N-diethyl-benzenesulfonamide;
I19.2  {5-[4-Chloro-3-(4-methyl-piperazine-1-sulfonyl)-phenyl]-3-methyl-3H-[1,3,4]thiadiazol-2-ylidene}-cyclohexyl-amine;
I19.3  2-Chloro-5-(5-cyclohexylimino-4-methyl-4,5-dihydro-[1,3,4]thiadiazol-2-yl)-N-pyridin-4-ylmethyl-benzenesulfonamide;
I19.4  2-Chloro-5-(5-cyclohexylimino-4-methyl-4,5-dihydro-[1,3,4]thiadiazol-2-yl)-N-(2-morpholin-4-yl-ethyl)-benzenesulfonamide;
I19.5  2-Chloro-5-(5-cyclohexylimino-4-methyl-4,5-dihydro-[1,3,4]thiadiazol-2-yl)-N-ethyl-benzenesulfonamide;
I19.6  2-Chloro-5-(5-cyclohexylimino-4-methyl-4,5-dihydro-[1,3,4]thiadiazol-2-yl)-N-ethyl-N-(2-morpholin-4-yl-ethyl)-benzenesulfonamide;

I19.7 2-Chloro-5-(5-cyclohexylimino-4-methyl-4,5-dihydro-[1,3,4]thiadiazol-2-yl)-N-isopropyl-N-(2-morpholin-4-yl-ethyl)-benzenesulfonamide;

I19.8 2-Chloro-5-(5-cyclohexylimino-4-methyl-4,5-dihydro-[1,3,4]thiadiazol-2-yl)-N-ethyl-N-[2-(2-methoxy-ethoxy)-ethyl]-benzenesulfonamide;

I19.9 2-Chloro-(cyclohexylimino-methyl-4,5-dihydro-[1,3,4]thiadiazol-2-yl)-N-(3-dimethylamino-2-hydroxy-propyl)-N-ethyl-benzenesulfonamide;

I19.10 2-Chloro-5-(5-cyclohexylimino-4-methyl-4,5-dihydro-[1,3,4]thiadiazol-2-yl)-N-(2,3-dihydroxy-propyl)-N-ethyl-benzenesulfonamide;

I19.11 2-Chloro-5-(5-cyclohexylimino-4-methyl-4,5-dihydro-[1,3,4]thiadiazol-2-yl)-N-ethyl-N-(2-hydroxy-3-pyrrolidin-1-yl-propyl)-benzenesulfonamide;

I19.12 2-Chloro-5-(cyclohexylimino-methyl-4,5-dihydro-[1,3,4]thiadiazol-2-yl)-N-(2-diethylamino-ethyl)-N-ethyl-benzenesulfonamide;

I19.14 2-Chloro-5-(5-cyclohexylimino-4-methyl-4,5-dihydro-[1,3,4]thiadiazol-2-yl)-N-(2-dimethylamino-propyl)-N-ethyl-benzenesulfonamide;

I20 [5-(4-Chloro-phenyl)-2-cyclohexylimino-[1,3,4]thiadiazol-3-yl]-acetic acid methyl ester;

I21 3-(5-Cyclohexylimino-4-methyl-4,5-dihydro-[1,3,4]thiadiazol-2-yl)-benzoic acid methyl ester;

I21.1 3-(5-Cyclohexylimino-4-methyl-4,5-dihydro-[1,3,4]thiadiazol-2-yl)-benzoic acid;

I21.2 3-(5-Cyclohexylimino-4-methyl-4,5-dihydro-[1,3,4]thiadiazol-2-yl)-benzamide;

I21.3 3-(5-Cyclohexylimino-4-methyl-4,5-dihydro-[1,3,4]thiadiazol-2-yl)-N-(2-hydroxy-ethyl)-benzamide;

I21.4 3-(5-Cyclohexylimino-4-methyl-4,5-dihydro-[1,3,4]thiadiazol-2-yl)-N-methyl-benzamide;

I22 4-(5-Cyclohexylimino-4-methyl-4,5-dihydro-[1,3,4]thiadiazol-2-yl)-benzene-1,2-diol;

I23 4-(5-Cyclohexylimino-4-methyl-4,5-dihydro-[1,3,4]thiadiazol-2-yl)-2,6-dimethoxy-phenol;

I23.1 6-(5-Cyclohexylimino-4-methyl-4,5-dihydro-[1,3,4]thiadiazol-2-yl)-pyridin-2-ol;

I23.2 5-(5-Cyclohexylimino-4-methyl-4,5-dihydro-[1,3,4]thiadiazol-2-yl)-benzene-1,2,3-triol;

I24 2-(5-Cyclohexylimino-4-methyl-4,5-dihydro-[1,3,4]thiadiazol-2-yl)-quinolin-8-ol;

I25 Cyclohexyl-(3-methyl-5-pyrazin-2-yl-3H-[1,3,4]thiadiazol-2-ylidene)-amine;

I26 5-[(E)-2-(5-Cyclohexylimino-4-methyl-4,5-dihydro-[1,3,4]thiadiazol-2-yl)-vinyl]-2-methoxy-phenol;

I27 4-(5-Cyclohexylimino-4-methyl-4,5-dihydro-[1,3,4]thiadiazol-2-yl)-2-methoxy-phenol;

I28 Cyclohexyl-(3-methyl-5-quinolin-8-yl-3H-[1,3,4]thiadiazol-2-ylidene)-amine;

I29 [4-(5-Cyclohexylimino-4-methyl-4,5-dihydro-[1,3,4]thiadiazol-2-yl)-phenyl]-dimethyl-amine;

I30 4-(5-Cyclohexylimino-4-methyl-4,5-dihydro-[1,3,4]thiadiazol-2-yl)-benzenesulfonamide;

I31 [5-(5-Chloro-1H-indol-2-yl)-3-methyl-3H-[1,3,4]thiadiazol-2-ylidene]-cyclohexyl-amine; compound with trifluoro-methanesulfonic acid;

I31.1 2-(5-Cyclohexylimino-4-methyl-4,5-dihydro-[1,3,4]thiadiazol-2-yl)-phenol; compound with 1,1,1-trifluoro-methanesulfonic acid;

I32 5-(5-Cyclohexylimino-4-methyl-4,5-dihydro-[1,3,4]thiadiazol-2-yl)-2-methoxy-phenol; compound with 1,1,1-trifluoro-methanesulfonic acid;

I33 4-(5-Cyclohexylimino-4-methyl-4,5-dihydro-[1,3,4]thiadiazol-2-yl)-phenol; compound with 1,1,1-trifluoro-methanesulfonic acid I34 Cyclohexyl-[5-(3,4-dimethoxy-phenyl)-3-methyl-3H-[1,3,4]thiadiazol-2-ylidene]-amine I35 [5-(3-Bromo-4-methoxy-phenyl)-3-methyl-3H-[1,3,4]thiadiazol-2-ylidene]-cyclohexyl-amine;

I35.1 Cyclohexyl-[5-(4-methoxy-phenyl)-3-methyl-3H-[1,3,4]thiadiazol-2-ylidene]-amine;

I35.2 Cyclohexyl-(3-methyl-5-phenyl-3H-[1,3,4]thiadiazol-2-ylidene)-amine;

I36 3-(5-Cyclohexylimino-4-methyl-4,5-dihydro-[1,3,4]thiadiazol-2-yl)-phenol;

I37 4-(5-Cyclohexylimino-4-methyl-4,5-dihydro-[1,3,4]thiadiazol-2-yl)-benzoic acid methyl ester;

I37.1 4-(5-Cyclohexylimino-4-methyl-4,5-dihydro-[1,3,4]thiadiazol-2-yl)-benzoic acid;

I37.2 4-(5-Cyclohexylimino-4-methyl-4,5-dihydro-[1,3,4]thiadiazol-2-yl)-N-hydroxy-benzamide;

I37.3 4-(5-Cyclohexylimino-4-methyl-4,5-dihydro-[1,3,4]thiadiazol-2-yl)-benzamide;

I37.4 4-(5-Cyclohexylimino-4-methyl-4,5-dihydro-[1,3,4]thiadiazol-2-yl)-N-(2H-tetrazol-5-yl)-benzamide hydrochloride salt;

I37.5 4-(5-Cyclohexylimino-4-methyl-4,5-dihydro[1,3,4]thiadiazol-2-yl)-N-quinolin-8-yl-benzamide;

I37.6 4-(5-Cyclohexylimino-4-methyl-4,5-dihydro[1,3,4]thiadiazol-2-yl)-N-(2,6-dimethoxy-pyridin-3-yl)-benzamide;

I37.7 4-(5-Cyclohexylimino-4-methyl-4,5-dihydro[1,3,4]thiadiazol-2-yl)-N-isopropyl-benzamide;

I37.8 4-(5-Cyclohexylimino-4-methyl-4,5-dihydro[1,3,4]thiadiazol-2-yl)-N-ethyl-benzamide;

I37.8-1 Cyclohexyl-{5-[4-(1-ethyl-1H-tetrazol-5-yl)-phenyl]-3-methyl-3H-[1,3,4]thiadiazol-2-ylidene}-amine;

I37.9 4-(5-Cyclohexylimino-4-methyl-4,5-dihydro[1,3,4]thiadiazol-2-yl)-N-(2-dimethylamino-ethyl)-benzamide;

I37.10 4-(5-Cyclohexylimino-4-methyl-4,5-dihydro[1,3,4]thiadiazol-2-yl)-N-pyridin-4-ylmethyl-benzamide;

I37.11 4-(5-Cyclohexylimino-4-methyl-4,5-dihydro[1,3,4]thiadiazol-2-yl)-N-methyl-N-(1-methyl-piperidin-4-yl)-benzamide, I37.12 4-(5-Cyclohexylimino-4-methyl-4,5-dihydro-[1,3,4]thiadiazol-2-yl)-N-isobutyl-benzamide;

I37.13 4-(5-Cyclohexylimino-4-methyl-4,5-dihydro-[1,3,4]thiadiazol-2-yl)-N-methyl-benzamide;

I37.13-1 4-(Cyclohexylimino-methyl-4,5-dihydro-[1,3,4]thiadiazol-2-yl)-N-(2-dimethylamino-ethyl)-N-methyl-benzamide;

I37.14 [4-(5-Cyclohexylimino-4-methyl-4,5-dihydro-[1,3,4]thiadiazol-2-yl)-phenyl]-1-(3-hydroxymethyl-piperidin-1-yl)-methanone;

I37.15 2-[4-(5-Cyclohexylimino-4-methyl-4,5-dihydro-[1,3,4]thiadiazol-2-yl)-benzoylamino]-3-(4-hydroxy-phenyl)-propionic acid tert-butyl ester;

I37.15-a (S)-2-[4-(5-Cyclohexylimino-4-methyl-4,5-dihydro-[1,3,4]thiadiazol-2-yl)-benzoylamino]-3-(4-hydroxy-phenyl)-propionic acid; compound with 2,2,2-trifluoro-acetic acid;

I37.16 (S)-2-[4-(5-Cyclohexylimino-4-methyl-4,5-dihydro-[1,3,4]thiadiazol-2-yl)-benzoylamino]-propionic acid tert-butyl ester;

I37.16-a (S)-2-[4-(5-Cyclohexylimino-4-methyl-4,5-dihydro-[1,3,4]thiadiazol-2-yl)-benzoylamino]-propionic acid; compound with 2,2,2-trifluoro-acetic acid;

I37.17 [4-(5-Cyclohexylimino-4-methyl-4,5-dihydro-[1,3,4]thiadiazol-2-yl)-phenyl]-(4-pyridin-2-yl-piperazin-1-yl)-methanone;

I37.18 [4-(5-Cyclohexylimino-4-methyl-4,5-dihydro[1,3,4]thiadiazol-2-yl)-phenyl]-[4-(4-fluoro-phenyl)-piperazin-1-yl]-methanone;

I37.19 4-(5-Cyclohexylimino-4-methyl-4,5-dihydro-[1,3,4]thiadiazol-2-yl)-N-(3,4,5-trimethoxy-benzyl)-benzamide;

I37.20 [4-(5-Cyclohexylimino-4-methyl-4,5-dihydro-[1,3,4]thiadiazol-2-yl)-phenyl]-(4-pyrimidin-2-yl-piperazin-1-yl)-methanone;

I37.21 [4-(5-Cyclohexylimino-4-methyl-4,5-dihydro-[1,3,4]thiadiazol-2-yl)-phenyl]-(4-methyl-piperazin-1-yl)-methanone;

I37.22 4-(5-Cyclohexylimino-4-methyl-4,5-dihydro-[1,3,4]thiadiazol-2-yl)-N-[3-(4-methyl-piperazin-1-yl)-propyl]-benzamide;

I37.23 4-(5-Cyclohexylimino-4-methyl-4,5-dihydro-[1,3,4]thiadiazol-2-yl)-N-(1-ethyl-pyrrolidin-2-ylmethyl)-benzamide;

I37.24 4-(5-Cyclohexylimino-4-methyl-4,5-dihydro-[1,3,4]thiadiazol-2-yl)-N-pyridin-3-ylmethyl-benzamide;

I37.25 N-Benzyl-4-(5-cyclohexylimino-4-methyl-4,5-dihydro-[1,3,4]thiadiazol-2-yl)-benzamide;

I37.26 N-(1-Benzyl-piperidin-4-yl)-4-(5-cyclohexylimino-4-methyl-4,5-dihydro-[1,3,4]thiadiazol-2-yl)-benzamide;

I37.27 4-(5-Cyclohexylimino-4-methyl-4,5-dihydro-[1,3,4]thiadiazol-2-yl)-N-(2-ethyl-2H-pyrazol-3-yl)-benzamide;

I37.28 4-(5-Cyclohexylimino-4-methyl-4,5-dihydro-[1,3,4]thiadiazol-2-yl)-N-(2-morpholin-4-yl-ethyl)-benzamide;

I37.28-1 [5-(4-((N-cyano-N'-ethylmorpholine)-carboximidamide)-phenyl)-3-methyl-3H-[1,3,4]thiadiazol-2-ylidene]-cyclohexyl-amine;

I37.29 4-(5-Cyclohexylimino-4-methyl-4,5-dihydro-[1,3,4]thiadiazol-2-yl)-N-(2-pyrrolidin-1-yl-ethyl)-benzamide;

I38 Cyclohexyl-(3-methyl-5-pyridin-3-yl-3H-[1,3,4]thiadiazol-2-ylidene)-amine;

I39 3-(5-Cyclohexylimino-4-methyl-4,5-dihydro-[1,3,4]thiadiazol-2-yl)-benzenesulfonamide;

I40 (5-Benzo[1,3]dioxol-5-yl-3-methyl-3H-[1,3,4]thiadiazol-2-ylidene)-cyclohexyl-amine;

I41 Cyclohexyl-[3-methyl-5-(3,4,5-trimethoxy-phenyl)-3H-[1,3,4]thiadiazol-2-ylidene]-amine;

I42 4-(5-Cyclopentylimino-4-methyl-4,5-dihydro-[1,3,4]thiadiazol-2-yl)-benzonitrile;

I43 4-(5-Cycloheptylimino-4-methyl-4,5-dihydro-[1,3,4]thiadiazol-2-yl)-benzonitrile;

I44 4-[5-(4-Fluoro-phenylimino)-4-methyl-4,5-dihydro-[1,3,4]thiadiazol-2-yl]-benzonitrile;

I45 4-[5-(3-Hydroxy-phenylimino)-4-methyl-4,5-dihydro-[1,3,4]thiadiazol-2-yl]-benzonitrile;

I46 5-[5-(4-Cyano-phenyl)-3-methyl-3H-[1,3,4]thiadiazol-2-ylideneamino]-2-fluoro-benzoic acid;

I47-a 4-[4-Methyl-5-(cis-4-methyl-cyclohexylimino)-4,5-dihydro-[1,3,4]thiadiazol-2-yl]-benzonitrile;

I47-b 4-[4-Methyl-5-(trans-4-methyl-cyclohexylimino)-4,5-dihydro-[1,3,4]thiadiazol-2-yl]-benzonitrile;

I48 4-[5-(trans-4-Hydroxy-cyclohexylimino)-4-methyl-4,5-dihydro-[1,3,4]thiadiazol-2-yl]-benzonitrile;

I49 4-[5-(Bicyclo[2.2.1]hept-2-ylimino)-4-methyl-4,5-dihydro-[1,3,4]thiadiazol-2-yl]-benzonitrile;

I50 4-[5-((1R*,2R*)-2-Hydroxy-cyclohexylimino)-4-methyl-4,5-dihydro-[1,3,4]thiadiazol-2-yl]-benzonitrile;

I51 4-[5-((1R*,2S*)-2-Hydroxy-cyclohexylimino)-4-methyl-4,5-dihydro-[1,3,4]thiadiazol-2-yl]-benzonitrile;

I52-a 4-[5-((1R*,3R*)-3-Hydroxy-cyclohexylimino)-4-methyl-4,5-dihydro-[1,3,4]thiadiazol-2-yl]-benzonitrile;

I52-b 4-[5-((1R*,3S*)-3-Hydroxy-cyclohexylimino)-4-methyl-4,5-dihydro-[1,3,4]thiadiazol-2-yl]-benzonitrile;

I53 (1R*,3R*))-3-[5-(4-Methanesulfonyl-phenyl)-3-methyl-3H-[1,3,4]thiadiazol-2-ylideneamino]-cyclohexanol;

I54 4-[5-(1R*,3R*)-3-Hydroxy-cyclohexylimino)-4-methyl-4,5-dihydro-[1,3,4]thiadiazol-2-yl]-benzoic acid;

I55 4-[5-((1R*,3R*)-3-Hydroxy-cyclohexylimino)-4-methyl-4,5-dihydro-[1,3,4]thiadiazol-2-yl]-N-(2-morpholin-4-yl-ethyl)-benzamide;

I56 4-[5-(trans-4-Hydroxy-cyclohexylimino)-4-methyl-4,5-dihydro-[1,3,4]thiadiazol-2-yl]-benzoic acid;

I57 4-[5-(trans-4-Hydroxy-cyclohexylimino)-4-methyl-4,5-dihydro-[1,3,4]thiadiazol-2-yl]-N-(2-hydroxy-1,1-dimethyl-ethyl)-benzamide;

I58 4-[5-((1R*,3R*)-3-Hydroxy-cyclohexylimino)-4-methyl-4,5-dihydro-[1,3,4]thiadiazol-2-yl]-N-(2-hydroxy-1,1-dimethyl-ethyl)-benzamide;

I59 N-tert-Butyl-4-[5-((1R*,3R*)-3-hydroxy-cyclohexylimino)-4-methyl-4,5-dihydro-[1,3,4]thiadiazol-2-yl]-benzamide;

I60 N-(1,1-dimethyl-3-oxo-butyl)-4-[5-(1R*,3R*)-3-hydroxy-cyclohexylimino)-4-methyl-4,5-dihydro-[1,3,4]thiadiazol-2-yl]-benzamide;

I61 N-(2-Cyano-1,2,2-trimethyl-ethyl)-4-[5-((1R*,3R*)-3-hydroxy-cyclohexylimino)-4-methyl-4,5-dihydro-[1,3,4]thiadiazol-2-yl]-benzamide;

I62 1-{4-[5-((1R*,3R*)-3-Hydroxy-cyclohexylimino)-4-methyl-4,5-dihydro-[1,3,4]thiadiazol-2-yl]-benzoylamino}-cyclopropanecarboxylic acid methyl ester;

I63 4-(5-Cyclopentylimino-4-methyl-4,5-dihydro-[1,3,4]thiadiazol-2-yl)-benzamide;

I64 4-(5-Cycloheptylimino-4-methyl-4,5-dihydro-[1,3,4]thiadiazol-2-yl)-benzamide;

I65 4-[5-(4-Fluoro-phenylimino)-4-methyl-4,5-dihydro-[1,3,4]thiadiazol-2-yl]-benzamide;

I66 4-[5-(3-Hydroxy-phenylimino)-4-methyl-4,5-dihydro-[1,3,4]thiadiazol-2-yl]-benzamide;

I67 5-[5-(4-Carbamoyl-phenyl)-3-methyl-3H-[1,3,4]thiadiazol-2-ylideneamino]-2-fluoro-benzoic acid;

I68 4-[4-Methyl-5-(4-methyl-cyclohexylimino)-4,5-dihydro-[1,3,4]thiadiazol-2-yl]-benzamide;

I69 4-[5-(4-Hydroxy-cyclohexylimino)-4-methyl-4,5-dihydro-[1,3,4]thiadiazol-2-yl]-benzamide;

I70 4-[5-(Bicyclo[2.2.1]hept-2-ylimino)-4-methyl-4,5-dihydro-[1,3,4]thiadiazol-2-yl]-benzamide;

I71 4-[5-((1R*,2R*)-2-Hydroxy-cyclohexylimino)-4-methyl-4,5-dihydro-[1,3,4]thiadiazol-2-yl]-benzamide;

I72 4-[5-((1R*,2S*)-2-Hydroxy-cyclohexylimino)-4-methyl-4,5-dihydro-[1,3,4]thiadiazol-2-yl]-benzamide;

I73 4-[5-((1R*,3R*)-3-Hydroxy-cyclohexylimino)-4-methyl-4,5-dihydro-[1,3,4]thiadiazol-2-yl]-benzamide;

I74 4-[5-((1R*,3S*)-3-Hydroxy-cyclohexylimino)-4-methyl-4,5-dihydro-[1,3,4]thiadiazol-2-yl]-benzamide;

I74.1 4-[4-Methyl-5-(3-oxo-cyclohexylimino)-4,5-dihydro-[1,3,4]thiadiazol-2-yl]-benzamide;

I75 4-[5-(3,3-Difluoro-cyclohexylimino)-4-methyl-4,5-dihydro-[1,3,4]thiadiazol-2-yl]-benzamide;

I76 4-[5-((1R*,3R*)-3-Fluoro-cyclohexylimino)-4-methyl-4,5-dihydro-[1,3,4]thiadiazol-2-yl]-benzamide;

I77 4-[5-(Cyclohex-3-enylimino)-4-methyl-4,5-dihydro-[1,3,4]thiadiazol-2-yl]-benzamide;

I78 (1R*,3R*)-3-{3-Methyl-5-[4-(1H-tetrazol-5-yl)-phenyl]-3H-[1,3,4]thiadiazol-2-ylideneamino}-cyclohexanol;

I79 3-[5-(4-Chloro-phenyl)-3-methyl-3H-[1,3,4]thiadiazol-2-ylideneamino]-2-hydroxy-benzoic acid;

I80 3-[5-(4-Cyano-phenyl)-3-methyl-3H-[1,3,4]thiadiazol-2-ylideneamino]-benzoic acid;

I80.1 3-[5-(4-carbamoyl-phenyl)-3-methyl-3H-[1,3,4]thiadiazol-2-ylideneamino]-benzoic acid;

I81 2-Fluoro-5-[5-(4-methanesulfonyl-phenyl)-3-methyl-3H-[1,3,4]thiadiazol-2-ylideneamino]-benzoic acid;

I82 3-[5-(4-methanesulfonyl-phenyl)-3-methyl-3H-[1,3,4] thiadiazol-2-ylideneamino]-cyclohexanecarboxylic acid;

I83 [5-(4-methanesulfonyl-phenyl)-3-methyl-3H-[1,3,4] thiadiazol-2-ylidene]-piperidin-1-yl amine;

I84 [5-(4-Methanesulfonyl-phenyl)-3-methyl-3H-[1,3,4] thiadiazol-2-ylidene]-(tetrahydro-pyran-4-yl)-amine;

I85 3-[5-(4-Acetylamino-phenyl)-3-methyl-3H-[1,3,4] thiadiazol-2-ylideneamino]-benzoic acid;

I86 N-{4-[5-(trans-4-Hydroxy-cyclohexylimino)-4-methyl-4,5-dihydro-[1,3,4]thiadiazol-2-yl]-phenyl}-acetamide;

I87 N-{4-[5-((1R*,3S*)-3-Hydroxy-cyclohexylimino)-4-methyl-4,5-dihydro-[1,3,4]thiadiazol-2-yl]-phenyl}-acetamide;

I88 N-{4-[5-((1R*,3R*)-3-Hydroxy-cyclohexylimino)-4-methyl-4,5-dihydro-[1,3,4]thiadiazol-2-yl]-phenyl}-acetamide;

I89 N-{5-[5-((1R*,3R*)-3-Hydroxy-cyclohexylimino)-4-methyl-4,5-dihydro-[1,3,4]thiadiazol-2-yl]-pyridin-2-yl}-acetamide;

I90 3-[5-(4-Chloro-phenyl)-3-methyl-3H/-[1,3,4]thiadiazol-2-ylideneamino]-benzonitrile;

I90.1 [5-(4-Chloro-phenyl)-3-methyl-3H-[1,3,4]thiadiazol-2-ylidene]-[3-(1H-tetrazol-5-yl)-phenyl]-amine;

I90.2 3-[5-(4-Chloro-phenyl)-3-methyl-3H-[1,3,4]thiadiazol-2-ylideneamino]-N-hydroxy-benzamidine;

I90.3 3-{3-[5-(4-Chloro-phenyl)-3-methyl-3H-[1,3,4]thiadiazol-2-ylideneamino]-phenyl}-[1,2,4]oxadiazol-5-ol;

I91 [5-(4-Bromo-3-methyl-phenyl)-3-methyl-3H-[1,3,4]thiadiazol-2-ylidene]-cyclohexyl-amine;

I91.1 4-(5-Cyclohexylimino-4-methyl-4,5-dihydro-[1,3,4]thiadiazol-2-yl)-2-methyl-benzonitrile;

I91.2 4-(5-Cyclohexylimino-4-methyl-4,5-dihydro-[1,3,4]thiadiazol-2-yl)-2-methyl-benzamide;

I92 [5-(4-Bromo-3-methoxy-phenyl)-3-methyl-2,3-dihydro-[1,3,4]thiadiazol-2-yl]-cyclohexyl-amine;

I92.1 4-(5-Cyclohexylimino-4-methyl-4,5-dihydro-[1,3,4]thiadiazol-2-yl)-2-methoxy-benzamide;

I92.2 4-(5-Cyclohexylimino-4-methyl-4,5-dihydro-[1,3,4]thiadiazol-2-yl)-2-hydroxy-benzamide;

I93 4-(5-Cyclohexylimino-4-methyl-4,5-dihydro-[1,3,4]thiadiazol-2-yl)-2-nitro-benzoic acid methyl ester;

I93.1 2-Amino-4-(5-cyclohexylimino-4-methyl-4,5-dihydro-[1,3,4]thiadiazol-2-yl)-benzoic acid methyl ester;

I93.2 2-Acetylamino-4-(5-cyclohexylimino-4-methyl-4,5-dihydro-[1,3,4]thiadiazol-2-yl)-benzoic acid methyl ester;

I93.3 2-Amino-4-(5-cyclohexylimino-4-methyl-4,5-dihydro-[1,3,4]thiadiazol-2-yl)-benzamide;

I93.4 7-(5-Cyclohexylimino-4-methyl-4,5-dihydro-[1,3,4]thiadiazol-2-yl)-3H-quinazolin-4-one;

I93.5 7-(5-Cyclohexylimino-4-methyl-4,5-dihydro-[1,3,4]thiadiazol-2-yl)-quinazolin-4-ylamine;

I93.6 7-(5-Cyclohexylimino-4-methyl-4,5-dihydro-[1,3,4]thiadiazol-2-yl)-1H-quinazoline-2,4-dione;

I94 4-(5-Cyclohexylimino-4-methyl-4,5-dihydro-[1,3,4]thiadiazol-2-yl)-2-methoxy-benzenesulfonamide;

I95 5-(5-Cyclohexylimino-4-methyl-4,5-dihydro-[1,3,4]thiadiazol-2-yl)-2-methoxy-benzenesulfonamide;

I96 3-[5-(3-Cyano-phenyl)-3-methyl-3H-[1,3,4]thiadiazol-2-ylideneamino]-benzoic acid methyl ester;

I96.1 3-[5-(3-Cyano-phenyl)-3-methyl-3H-[1,3,4]thiadiazol-2-ylideneamino]-benzoic acid;

I97.1 3-[3-Methyl-5-pyridin-2-yl-3H-[1,3,4]thiadiazol-2-ylideneamino]-benzoic acid;

I98 3-[5-(4-Chloro-3-sulfamoyl-phenyl)-3-methyl-3H-[1,3,4]thiadiazol-2-ylideneamino]-benzoic acid;

I99 4-(5-Cyclohexylimino-4-methyl-4,5-dihydro-[1,3,4]thiadiazol-2-yl)-benzonitrile;

I99.1 Cyclohexyl-{3-methyl-5-[4-(1H-tetrazol-5-yl)-phenyl]-3H-[1,3,4]thiadiazol-2-ylidene}-amine;

I100 Cyclohexyl-[3-methyl-5-(4-nitro-phenyl)-3H-[1,3,4] thiadiazol-2-ylidene]-amine;

I100.1 4-(5-Cyclohexylimino-4-methyl-4,5-dihydro-[1,3,4] thiadiazol-2-yl)-phenylamine;

I100.2 [5-(4-(N-cyano-N'-(2-dimethylaminoethyl)-carboximidamide)-phenyl)-3-methyl-3H-[1,3,4]thiadiazol-2-ylidene]-cyclohexyl-amine;

I100.3 N-[4-(5-Cyclohexylimino-4-methyl-4,5-dihydro-[1,3,4]thiadiazol-2-yl)-phenyl]-acetamide;

I100.4 [5-(4-(bis-Ethylsulfonylamino)-phenyl)-3-methyl-3H-[1,3,4]thiadiazol-2-ylidene]-cyclohexyl-amine;

I100.5 [5-(4-(1-(2-dimethylaminoethyl)amino-2-nitro-vinylamino)-phenyl)-3-methyl-3H-[1,3,4]thiadiazol-2-ylidene]-cyclohexyl-amine;

I100.6 (E)-N$^1$-[4-(5-Cyclohexylimino-4-methyl-4,5-dihydro-[1,3,4]thiadiazol-2-yl)-phenyl]-2-nitro-ethene-1,1-diamine;

I100.7 [5-(N-cyano-N'-methyl-4-carboximidamide-phenyl)-3-methyl-3H-[1,3,4]thiadiazol-2-ylidene]-cyclohexyl-amine;

I100.8 [5-(4-(N-cyano-N'-amino-carboximidamide)-phenyl)-3-methyl-3H-[1,3,4]thiadiazol-2-ylidene]-cyclohexyl-amine I100.9 Ethanesulfonic acid [4-(5-cyclohexylimino-4-methyl-4,5-dihydro-[1,3,4]thiadiazol-2-yl)-phenyl]-amide I100.10 [4-(5-Cyclohexylimino-4-methyl-4,5-dihydro-[1,3,4]thiadiazol-2-yl)-phenyl]-urea I100.11 1-[4-(Cyclohexylimino-methyl-4,5-dihydro-[1,3,4]thiadiazol-2-yl)-phenyl]-3-(2-dimethylamino-ethyl)-urea I101 2-Chloro-4-(5-cyclohexylimino-4-methyl-4,5-dihydro-[1,3,4]thiadiazol-2-yl)-benzenesulfonamide I102 2-Chloro-4-(5-cyclohexylimino-4-methyl-4,5-dihydro-[1,3,4]thiadiazol-2-yl)-benzoic acid methyl ester I102.1 2-Chloro-4-(5-cyclohexylimino-4-methyl-4,5-dihydro-[1,3,4]thiadiazol-2-yl)-benzamide I103 2-Chloro-5-(5-cyclohexylimino-4-methyl-4,5-dihydro-[1,3,4]thiadiazol-2-yl)-benzamide I104 4-(5-Cyclohexylimino-4-methyl-4,5-dihydro-[1,3,4] oxadiazol-2-yl)-benzoic acid methyl ester I104.1 4-(5-Cyclohexylimino-4-methyl-4,5-dihydro-[1,3,4] oxadiazol-2-yl)-benzamide Other embodiments of the present invention include:
A compound selected from the group consisting of:
5-(5-Cyclohexylimino-4-methyl-4,5-dihydro[1,3,4] thiadiazol-2-yl)-2-methoxy-benzene-1,3-diol; compound with trifluoro-methanesulfonic acid, 5-(5-Cyclohexylimino-4-methyl-4,5-dihydro[1,3,4] thiadiazol-2-yl)-2,3-dimethoxy-phenol; compound with trifluoro-methanesulfonic acid, 2-Chloro-5-(5-cyclohexylimino-4-methyl-4,5-dihydro-[1,3,4]thiadiazol-2-yl)-benzenesulfonamide, 2-Chloro-5-(5-cyclohexylimino-4-methyl-4,5-dihydro[1,3,4]thiadiazol-2-yl)-N,N-diethyl-benzenesulfonamide, {5-[4-Chloro-3-(4-methyl-piperazine-1-sulfonyl)-phenyl]-3-methyl-3H-[1,3,4]thiadiazol-2-ylidene}-cyclohexyl-amine, 2-Chloro-5-(5-cyclohexylimino-4-methyl-4,5-dihydro-[1,3,4]thiadiazol-2-yl)-N-pyridin-4-ylmethyl-benzenesulfonamide, 2-Chloro-5-(5-cyclohexylimino-4-methyl-4,5-dihydro-[1,3,4]thiadiazol-2-yl)-N-(2-morpholin-4-yl-ethyl)-benzenesulfonamide, 2-Chloro-5-(5-cyclohexylimino-4-methyl-4,5-dihydro-[1,3,4]thiadiazol-2-yl)-N-ethyl-benzenesulfonamide, 2-Chloro-5-(5-cyclohexylimino-4-methyl-4,5-dihydro-[1,3,4]thiadiazol-2-yl)-N-ethyl-N-(2-morpholin-4-yl-ethyl)-benzenesulfonamide, 2-Chloro-5-(5-cyclohexylimino-4-methyl-4,5-dihydro-[1,3,4]thiadiazol-2-yl)-N-isopropyl-N-(2-morpholin-4-yl-ethyl)-benzenesulfonamide, 2-Chloro-5-(5-cyclohexylimino-4-methyl-4,5-dihydro-[1,3,4]thiadiazol-2-yl)-N-ethyl-N-[2-(2-methoxy-ethoxy)-ethyl]-benzenesulfonamide, C-Chloro-(cyclohexylimino-methyl-4,5-dihydro-[1,3,4]thiadiazol-2-yl)-N-(dimethylamino-hydroxy-propyl)-N-ethyl-benzenesulfonamide, 2-Chloro-5-(5-cyclohexylimino-4-methyl-4,5-dihydro-[1,3,4]thiadiazol-2-yl)-N-(2,3-dihydroxy-propyl)-N-ethyl-benzenesulfonamide, 2-Chloro-5-(5-cyclohexylimino-4-methyl-4,5-dihydro-[1,3,4]thiadiazol-2-yl)-N-ethyl-N-(2-hydroxy-3-pyrrolidin-1-yl-propyl)-benzenesulfonamide, 3-(5-Cyclohexylimino-4-methyl-4,5-dihydro-[1,3,4]thiadiazol-2-yl)-benzamide, 4-(5-Cyclohexylimino-4-methyl-4,5-dihydro-[1,3,4]thiadiazol-2-yl)-benzamide, 4-(5-Cyclohexylimino-4-methyl-4,5-dihydro[1,3,4]thiadiazol-2-yl)-N-quinolin-8-yl-benzamide, 4-(5-Cyclohexylimino-4-methyl-4,5-dihydro[1,3,4]thiadiazol-2-yl)-N-(2,6-dimethoxy-pyridin-3-yl)-benzamide, 4-(5-Cyclohexylimino-4-methyl-4,5-dihydro[1,3,4]thiadiazol-2-yl)-N-isopropyl-benzamide, 4-(5-Cyclohexylimino-4-methyl-4,5-dihydro[1,3,4]thiadiazol-2-yl)-N-ethyl-benzamide, 4-(5-Cyclohexylimino-4-methyl-4,5-dihydro[1,3,4]thiadiazol-2-yl)-N-(2-dimethylamino-ethyl)-benzamide, 4-(5-Cyclohexylimino-4-methyl-4,5-dihydro[1,3,4]thiadiazol-2-yl)-N-pyridin-4-ylmethyl-benzamide, 2-Chloro-5-(5-cyclohexylimino-4-methyl-4,5-dihydro[1,3,4]thiadiazol-2-yl)-N,N-diethyl-benzenesulfonamide, 4-(5-Cyclohexylimino-4-methyl-4,5-dihydro-[1,3,4]thiadiazol-2-yl)-N-methyl-benzamide, 2-[4-(5-Cyclohexylimino-4-methyl-4,5-dihydro-[1,3,4]thiadiazol-2-yl)-benzoylamino]-3-(4-hydroxy-phenyl)-propionic acid tert-butyl ester, (S)-2-[4-(5-Cyclohexylimino-4-methyl-4,5-dihydro-[1,3,4]thiadiazol-2-yl)-benzoylamino]-3-(4-hydroxy-phenyl)-propionic acid, compound with 2,2,2-trifluoro-acetic acid, 4-(5-Cyclohexylimino-4-methyl-4,5-dihydro-[1,3,4]thiadiazol-2-yl)-N-(3,4,5-trimethoxy-benzyl)-benzamide, 4-(5-Cyclohexylimino-4-methyl-4,5-dihydro-[1,3,4]thiadiazol-2-yl)-N-[3-(4-methyl-piperazin-1-yl)-propyl]-benzamide, 4-(5-Cyclohexylimino-4-methyl-4,5-dihydro-[1,3,4]thiadiazol-2-yl)-N-pyridin-3-ylmethyl-benzamide, N-(1-Benzyl-piperidin-4-yl)-4-(5-cyclohexylimino-4-methyl-4,5-dihydro-[1,3,4]thiadiazol-2-yl)-benzamide, 4-(5-Cyclohexylimino-4-methyl-4,5-dihydro-[1,3,4]thiadiazol-2-yl)-N-(2-ethyl-2H-pyrazol-3-yl)-benzamide, 4-(5-Cyclohexylimino-4-methyl-4,5-dihydro-[1,3,4]thiadiazol-2-yl)-N-(2-morpholin-4-yl-ethyl)-benzamide, 4-(5-Cyclohexylimino-4-methyl-4,5-dihydro-[1,3,4]thiadiazol-2-yl)-N-(2-pyrrolidin-1-yl-ethyl)-benzamide, 3-[5-(4-carbamoyl-phenyl)-3-methyl-3H-[1,3,4]thiadiazol-2-ylideneamino]-benzoic acid,

[5-(4-Chloro-phenyl)-3-methyl-3H-[1,3,4]thiadiazol-2-ylidene]-[3-(1H-tetrazol-5-yl)-phenyl]-amine, 2-Amino-4-(5-cyclohexylimino-4-methyl-4,5-dihydro-[1,3,4]thiadiazol-2-yl)-benzoic acid methyl ester, 2-Amino-4-(5-cyclohexylimino-4-methyl-4,5-dihydro-[1,3,4]thiadiazol-2-yl)-benzamide, 7-(5-Cyclohexylimino-4-methyl-4,5-dihydro-[1,3,4]thiadiazol-2-yl)-3H-quinazolin-4-one, 7-(5-Cyclohexylimino-4-methyl-4,5-dihydro-[1,3,4]thiadiazol-2-yl)-quinazolin-4-ylamine, N-[4-(5-Cyclohexylimino-4-methyl-4,5-dihydro-[1,3,4]thiadiazol-2-yl)-phenyl]-acetamide, and, 1-[4-(Cyclohexylimino-methyl-4,5-dihydro-[1,3,4]thiadiazol-2-yl)-phenyl]-3-(2-dimethylamino-ethyl)-urea;

A pharmaceutical composition according to Claim 19, comprising a compound of Formula I, in which $R_1$, $R_2$, $R_3$, and Y are as defined in Claim 19, with the proviso that when $R_1$ is C(=O)—H, then $R_2$ does not represent $(CH_2)_3$—C(=O)OCH$_2$CH$_3$;

Pharmaceutical composition comprising a compound of Formula I according to any one of Claims 1 to 14, or 17 or 18, together with a pharmaceutically acceptable carrier;

Pharmaceutical composition comprising a compound of Formula I according to Claim 15, together with a pharmaceutically acceptable carrier;

Pharmaceutical composition comprising a compound of Formula I according to Claim 16, together with a pharmaceutically acceptable carrier;

Method for the treatment of a disease for which treatment by a PDE7 inhibitor is relevant, comprising administering to a mammal in need thereof, an effective amount of compound of Formula I according to any one of Claims 1 to 14, or 17 or 18;

Method for the treatment of a disease for which treatment by a PDE7 inhibitor is relevant, comprising administering to a mammal in need thereof, an effective amount of compound of Formula I according to Claim 15;

Method for the treatment of a disease for which treatment by a PDE7 inhibitor is relevant, comprising administering to a mammal in need thereof, an effective amount of compound of Formula I according to Claim 16;

Method according to Claim 24, in which the disease being treated is selected from T-cell-related diseases, autoimmune diseases, inflammatory diseases, respiratory diseases, CNS diseases, allergic diseases, endocrine or exocrine pancreas diseases, or gastrointestinal diseases;

Method according to Claim 25 or 26, in which the disease being treated is selected from T-cell-related diseases, autoimmune diseases, inflammatory diseases, respiratory diseases, CNS diseases, allergic diseases, endocrine or exocrine pancreas diseases, or gastrointestinal diseases;

Method according to Claim 24, in which the disease being treated is selected from visceral pain, inflammatory bowel disease, osteoarthritis, multiple sclerosis, chronic obstructive pulmonary disease (COPD), asthma, cancer, acquired immune deficiency syndrome (AIDS), or graft rejection;

Method according to Claim 25 or 26, in which the disease being treated is selected from visceral pain, inflammatory bowel disease, osteoarthritis, multiple sclerosis, chronic obstructive pulmonary disease (COPD), asthma, cancer, acquired immune deficiency syndrome (AIDS), or graft rejection;

A process for the preparation of a compound of Formula I according to Claim 1 in which Y is S, comprising the following steps:

(a) reaction of a substituted hydrazine $R_2NHNH_2$ in which $R_2$ is as defined in Claim 1, with carbon disulphide and MeX where X is a leaving group to obtain a compound of formula 1

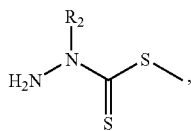

(b) reaction of the S-methyldithiocarbazate (1) with an acyl chloride $R_3COCl$ in which $R_3$ is as defined in Claim 1 to obtain an acylated methyldithiocarbazate (2)

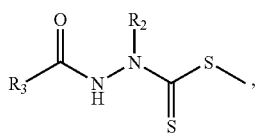

(c) cyclization of the acylated methyldithiocarbazate (2) into a 1,3,4-thiadiazole (3)

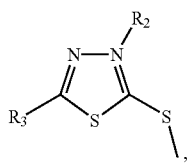

(d) reaction of the 1,3,4-thiadiazole (3) with an amine $R_1NH_2$ in which $R_1$ is as defined in Claim 1, to obtain the compound of Formula I in which Y is S, and (e) isolating the compound of Formula I;

Process for the preparation of a compound of Formula I according to Claim 1, in which Y is S, comprising the following steps:

(a) reaction of a substituted hydrazine $R_2NHNH_2$ in which $R_2$ is as defined in Claim 1, with a substituted isothiocyanate $SCNR_1$ in which $R_1$ is as defined in Claim 1, to obtain the substituted thiosemicarbazide (5)

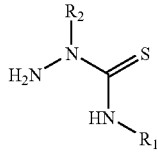

(b) reaction of the thiosemicarbazide (5) with an aldehyde $R_3CHO$ in which $R_3$ is as defined in Claim 1, to obtain the thiosemicarbazone (6)

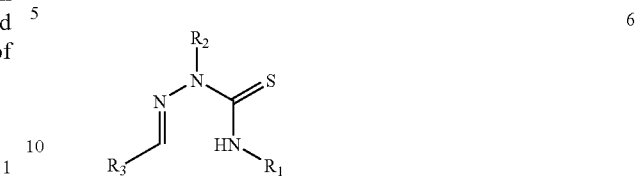

(c) cyclization of the thiosemicarbazone (6) into the compound of Formula I in which Y is S, and (d) isolating the compound of Formula I;

Process for the preparation of a compound of Formula I according to Claim 1, in which Y is S, comprising the following steps:

(a) reaction of a carboxylic acid $R_3COOH$ in which $R_3$ is as defined in Claim 1, with the following thiosemicarbazide (5')

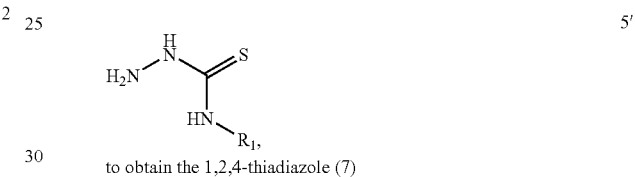

to obtain the 1,2,4-thiadiazole (7)

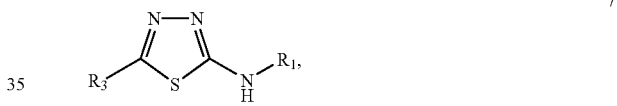

(b) reaction of the 1,3,4-thiadiazole (7) with $R_2X$, in which $R_2$ is as defined in Claim 1, and X is a leaving group to obtain the compound of Formula I in which Y is S, and (c) isolating the compound of Formula I;

Process for the preparation of a compound of Formula I according to Claim 1, in which Y is S, comprising the following steps:

(a) reaction of a carboxylic acid $R_3COOH$, in which $R_3$ is as defined in Claim 1, with the following thiosemicarbazide (5)

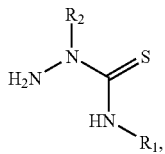

to obtain the final compound of Formula I in which Y is S, and (b) isolating the compound of Formula I; and Process for the preparation of a compound of Formula I according to Claim 1, in which Y is O, comprising the following steps:

(a) reaction of a substituted hydrazine $R_2NHNH_2$, in which $R_2$ is as defined is in Claim 1, with a substituted isothiocyanate $SCNR_1$, in which $R_1$ is as defined in Claim 1, to obtain the substituted thiosemicarbazide (5)

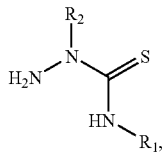

(b) reaction of the thiosemicarbazide (5) with $R_3$—C(=O)Cl, in which $R_3$ is as defined in Claim 1, to form the desired thiosemicarbazide (8)

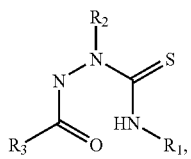

(c) cyclization of the thiosemicarbazide (8) into the final compound of Formula I in which Y is O, and (d) isolating the compound of Formula I.

The compounds utilized in the invention include pharmaceutically acceptable derivatives of compounds of Formula I such as solvates, hydrates, pharmaceutically acceptable salts and polymorphs (different crystalline lattice descriptors).

Pharmaceutically acceptable salts of a compound of Formula I include salts having a basic part and salts having an acidic part.

The expression pharmaceutically acceptable salt of a compound of Formula I having a basic part should be understood to refer to the addition salts of the compounds of Formula I which may be formed from nontoxic inorganic or organic acids such as, for example, hydrobromic, hydrochloric, sulfuric, phosphoric, nitric, acetic, succinic, tartaric, citric, maleic, hydroxymaleic, benzoic, fumaric, toluenesulfonic and isethionic acid salts, and the like. The various quaternary ammonium salts of the derivatives (1) are also included in this category of compounds of the invention. In addition, the expression pharmaceutically acceptable salt of a compound of Formula I having an acidic part is understood to refer to the usual salts of the compounds of Formula I which may be formed from nontoxic inorganic or organic bases such as, for example, the hydroxides of alkali metals and alkaline-earth metals (sodium, potassium, magnesium and calcium), amines (dibenzylethylenediamine, trimethylamine, piperidine, pyrrolidine, benzylamine and the like) or alternatively quaternary ammonium hydroxides such as tetramethylammonium hydroxide. (See also "Pharmaceutical salts: by Berge S. M. et al. *J. Pharm. Sci.,* 1997;66:1–19, which is incorporated herein by reference.)

Use of a prodrug of a compound of the invention such as would occur to one skilled in the art (see Bundgaard, et al., *Acta Pharm. Suec.,* 1987;24:233–246) is also contemplated.

Process for the Preparation

The compounds of this invention can be synthesized according to the general procedures of synthesis A–E, utilizing methodology described herein which is known to a person skilled in the art.

Protocol A:

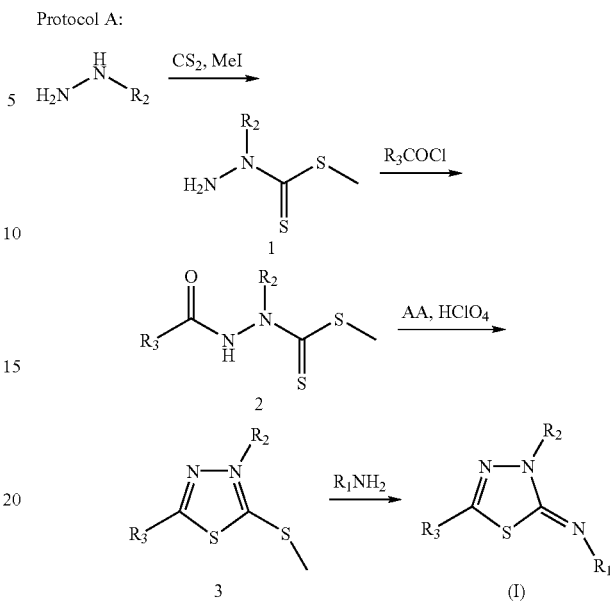

The starting compounds are either commercially available or can be prepared according to routes known to the skilled man. See M. Akbar Ali, S. E. Livingston, and D. J. Philipps, *Inorganica Chimica Acta,* 4 1972;6:11; P. Molina, A. Tarraga, A. Espinosa; *Synthesis,* 1988:690; P. Molina, A. Tarraga, A. Espinosa, *Heterocycles,* 1989;29(12).

In step 1, the substituted hydrazine is reacted with carbon disulphide and with an alkyl-iodide such as methyl-iodide to form the desired 2-substituted S-alkyldithiocarbazate (1). Various solvents, operating conditions, bases, can be used and will be easily determined by the skilled person. For example, and without any limitation, one can use for the reaction of the substituted hydrazine with carbon disulphide an alcoholic solution of potassium hydroxide with a temperature not exceeding 15° C. Methyl iodide can be added to this solution or to a diluted solution (e.g., with water).

In step 2, the substituted S-methyldithiocarbazate is reacted with an appropriate group $R_3CO$—X in which X is a leaving group such as halogen. Preferably, $R_3CO$—X is an acyl chloride ($R_3COCl$). The reaction can be carried out in e.g., toluene as the solvent at reflux. The corresponding acylated methyldithiocarbazate (2) is obtained.

In step 3, the acylated methyldithiocarbazate is cyclized into the desired 1,3,4-thiadiazole. The reaction can be carried out in the presence of acetic anhydride (AA) and perchlorate $HClO_4$ in ether, preferably, at a temperature comprised between –5° C. and 5° C., preferably 0° C., or in the presence of trimethylsilyl trifluoromethanesulfonate in dichloromethane, preferably, at a temperature comprised between 0° C. and 25° C. After stirring at room temperature several hours, an intermediate compound which is the 1,3,4-thiadiazolium perchlorate (3) is obtained.

In step 4, the 1,3,4-thiadiazole (or its perchlorate or sulfonate) is reacted with a suitable amine $R_1NH_2$, to form the final compound. The reaction can be carried out in alcohol such as ethanol as a solvent (the solvent may also be an aprotic solvent such as dioxane, dimethylformamide (DMF), or acetonitrile), in the presence of a base such as triethylamine, and preferably, at a temperature comprised between 40 C. and 110° C., preferably between 40 C. and 80° C.

Protocol B:

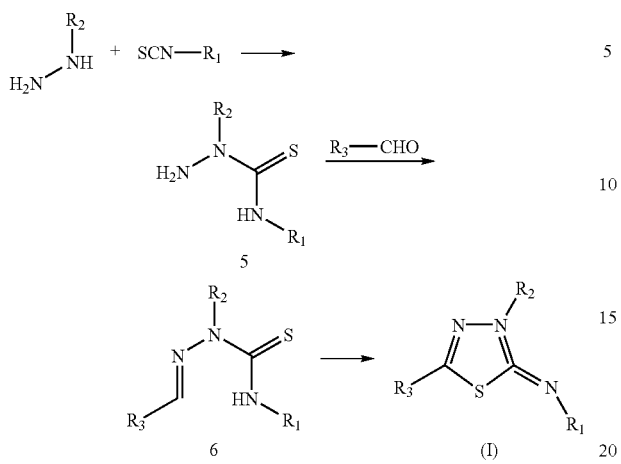

The starting compounds are either commercially available or can be prepared according to routes known to the skilled person. See R. Noto, P. Lo Meo, M. Gruttadauria, G. Werber. *J. Heterocyclic Chem.*, 1996;33:863.

In step 1, the substituted isothiocyanate is reacted with the substituted hydrazine to form the desired substituted thiosemicarbazide (5). The reaction can be carried out in alcohol, e.g., methanol and/or water at a temperature comprised between −5° C. and 15° C., preferably 0° C.

In step 2, the substituted thiosemicarbazide is reacted with an aldehyde $R_3CHO$ to form the desired thiosemicarbazone (6). The reaction can be carried out in alcohol e.g., methanol, at a temperature comprised between 50 C. and 90° C., preferably 75° C.

In step 3, the substituted thiosemicarbazone is cyclized to yield compound (I). The reaction can be carried out in alcohol, e.g., ethanol, at a temperature comprised between 20° C. and 110° C., preferably 75° C., in the presence of an oxidant such as $FeCl_3$.

Protocol C:

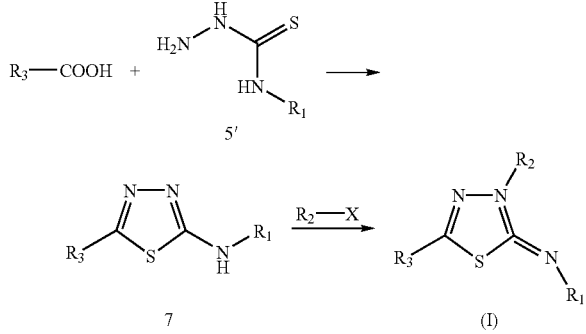

The starting compounds are either commercially available or can be prepared according to routes known to the skilled man. See FR-A-7712352, DE-A-4418066, and FR-A-8015072.

In the first step, the carboxylic acid is reacted with the thiosemicarbazide derivative (5') to yield the desired 1,3,4-thiadiazole (7). The reaction can be carried out in an aprotic solvent such as dioxane, at reflux, in the presence of a deshydrating agent, e.g., $POCl_3$.

In the second step, the desired 1,3,4-thiadiazole is reacted with $R_2X$, where X is a leaving group such as trifluoromethane sulfonate, iodide, or bromide. The reaction can be carried out in an aprotic solvent such as dioxane or DMF (if $R_2$—X is alkyl-iodide or bromide), preferably at room temperature (RT) or under heating to yield compound (I).

Protocol D: 1 step

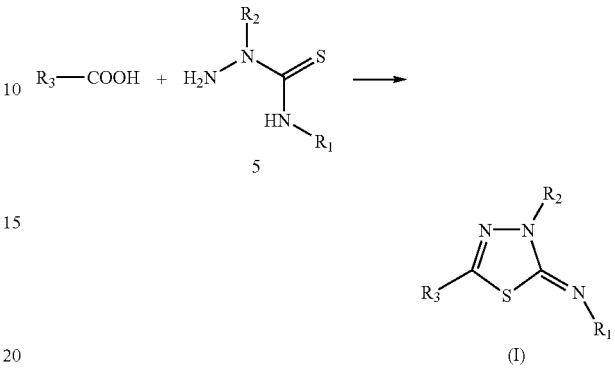

The starting compounds are either commercially available or can be prepared according to routes known to the skilled man.

In the first step, the carboxylic acid is reacted with the substituted thiosemicarbazide derivative (5) to yield the desired final 1,3,4-thiadiazole (I). The reaction can be carried out in an aprotic solvent such as dioxane, at reflux and at a temperature comprised between 75 C. and 120° C., in the presence of a deshydrating agent, e.g., $POCl_3$.

The solvent, reaction time, temperature, catalyst if any, can be varied in all steps described above for all routes, as the skilled man will appreciate.

Protocol E: 3 step

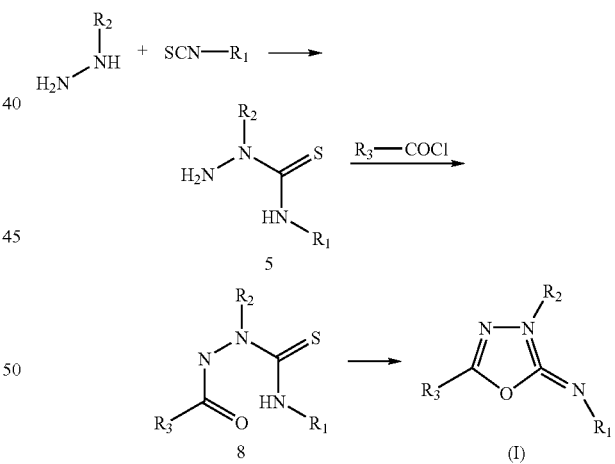

See J. M. Kane, M. A. Staeger, *Synthetic Communication*, 1992;22(1):1–11.

The starting compounds are either commercially available or can be prepared according to methods known to the skilled person. (See R. Noto, P. Lo Meo, M. Gruttadauria, G. Werber; *J. Heterocyclic Chem.*, 1996;33:863.)

In step 1, the substituted isothiocyanate is reacted with the substituted hydrazine to form the desired substituted thiosemicarbazide (5). The reaction can be carried out in alcohol, e.g., methanol and/or water at a temperature comprised between −5 C. and 15° C., preferably 0° C.

In step 2, the substituted thiosemicarbazide is reacted with the acid chloride to form the desired thiosemicarbazide (8).

The reaction can be carried out in a basic medium such as pyridine at room temperature, or in an aprotic solvent in the presence of a base such as pyridine or triethylamine.

In step 3, the substituted thiosemicarbazide is cyclized to yield compound (I). The reaction can be carried out in alcohol, e.g., methanol, at a temperature of, for example, 75° C. in the presence of Mercuric oxide (HgO).

Pharmaceutical Compositions

The products of the invention are administered in the form of compositions, which are appropriate depending on the nature, and severity of the condition to be treated. The daily dose in humans is usually between 2 mg and 1 g of the active ingredient, which may be taken in one or more individual doses. The compositions are prepared in forms which are compatible with the intended route of administration, such as, for example, tablets, coated tablets, capsules, mouthwashes, aerosols, powders for inhalation, suppositories, enemas, foams (such as rectal foams), gels, or suspensions. These compositions are prepared by methods which are familiar to those skilled in the art and comprise from 0.5% to 60% by weight of active ingredient (compound of the invention) and 40% to 99.5% by weight of a pharmaceutical vehicle or carrier which is appropriate and compatible with the active principle and the physical form of the intended composition.

Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid, which is in a mixture with the finely divided active component. In tablets, the active component is mixed with the carrier having the necessary binding properties in suitable proportions and compacted in the shape and size desired. The powders, tablets, cachets, or encapsulated forms for capsules preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration. The drug may be delivered as a spray (either in a pressurized container fitted with an appropriate valve or in a nonpressurized container fitted with a metering valve).

Liquid form preparations include solutions, suspensions, and emulsions.

Sterile water or water-propylene glycol solutions of the active compounds may be mentioned as an Example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify. Enemas are obtained according to known procedures to prepare solutions adapted for rectal administration. Foams are prepared according to known methods (these foams can notably be similar to those used to administer a drug such as 5-ASA for treating rectocolite).

Preferably the pharmaceutical preparation is in unit dosage form. In such form, the preparation is divided into unit doses containing appropriate quantities of drug. The unit dosage form can be a packaged preparation, the package containing discrete quantities of the preparation, for example, packaged tablets, capsules, and powders in vials or ampoules. The unit dosage form can also be a capsule, cachet, or tablet itself, or it can be the appropriate number of any of these packaged forms.

The following examples illustrate pharmaceutical compositions of the present invention. The examples are representative only, and are not to be construed as limiting the invention in any respect.

FORMULATION EXAMPLE 1

FORMULATION EXAMPLE 1
Tablet Formulation:

| Ingredient | Amount (mg) |
| --- | --- |
| The compound of Example I1 | 25 |
| Lactose | 50 |
| Cornstarch (for mix) | 10 |
| Cornstarch (paste) | 10 |
| Magnesium stearate (1%) | 5 |
| Total | 100 |

The compound of Example I1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 and screen and dried at 80° C. The dry granules are lubricated with the 1% magnesium stearate and pressed into a tablet. Such tablets can be administered to a human from 1 to 4 times a day for treatment of disease caused by overactivity of phosphodiesterase-7.

FORMULATION EXAMPLE 2

Coated Tablets

The tablets of Formulation Example 1 are coated in a customary manner with a coating of sucrose, potato starch, talc, tragacanth, and colorant.

FORMULATION EXAMPLE 3

Injection Vials

The pH of a solution of 500 g of the compound of Example I18.2 and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the compound of Example I18.2.

FORMULATION EXAMPLE 4

Suppositories

A mixture of 25 g of the compound of Example I37.8, 100 g of soya lecithin, and 1400 g of cocoa butter is fused, poured into molds, and allowed to cool. Each suppository contains 25 mg of the compound of Example I37.8.

FORMULATION EXAMPLE 5

Solution

A solution is prepared from 1 g of the compound of Example I37.10, 9.38 g of $NaH_2PO_4 \cdot 12H_2O$, 28.48 g of $Na_2HPO_4 \cdot 12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Example I37.10.

FORMULATION EXAMPLE 6

Ointment 500 mg of the compound of Example I19 is mixed with 99.5 g of petroleum jelly under aseptic conditions. A 5 g portion of the ointment contains 25 mg of the compound of Example I19.

FORMULATION EXAMPLE 7

Capsules 2 kg of the compound of Example I30 are filled into hard gelatin capsules in a customary manner such that each capsule contains 25 mg of the invention compound.

FORMULATION EXAMPLE 8

Ampoules

A solution of 2.5 kg of the compound of Example I4 is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Example I4.

Methods of Treatment

The compounds of the invention are selective PDE7 inhibitors. They can be used in the treatment of various diseases, as they can modulate inflammatory and immunological processes due to an increase of intracellular cAMP levels.

The diseases that can be successfully treated include namely T-cell-related diseases, autoimmune diseases, inflammatory diseases, respiratory diseases, CNS diseases, allergic diseases, endocrine or exocrine pancreas diseases, gastrointestinal diseases, visceral pain, inflammatory bowel disease, osteoarthritis, multiple sclerosis, chronic obstructive pulmonary disease (COPD), asthma, cancer, acquired immune deficiency syndrome (AIDS), or graft rejection.

The compounds of the invention have low $IC_{50}$ values, typically at most 5 µM, preferably below 1 µM, and even below 100 nM.

The invention finally relates to a method for the treatment of the above-mentioned diseases comprising administering to a mammal, particularly a human, in need thereof an effective amount of compound of the invention.

The following examples illustrate the invention without limiting it.

EXAMPLES

Compounds of the invention have been named with the software "AutoNom Version 4.0".

Protocol A:

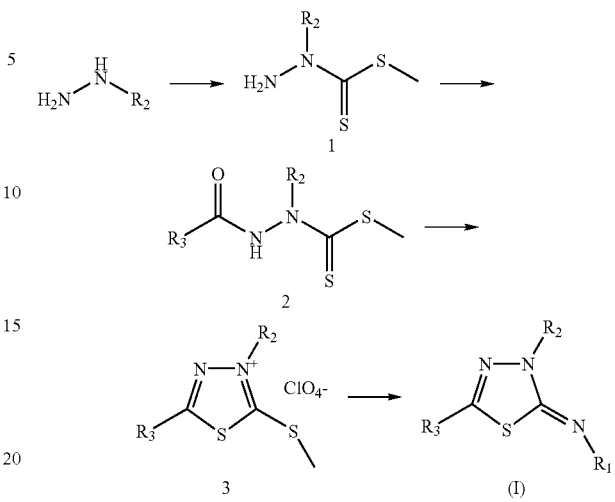

Intermediate 1: Protocol A
Intermediate 1a: $R_2$=methyl
N-Methyl-hydrazinecarbodithioic acid methyl ester Methylhydrazine (370 mmol, 19.43 mml) was added to a solution of potassium hydroxide (370 mmol, 20.7 g) in 90% aqueous alcohol (130 mL). The mixture was cooled to 5° C., then carbon disulphide (370 mmol, 22.2 mL) was added dropwise with vigorous stirring, over 1 hour, while the temperature of the mixture was not allowed to rise above 7° C. The resulting yellow solution was diluted with water (300 mL), and the methyl iodide (370 mmol, 23.34 mL) was added slowly while the mixture was stirred vigorously. After the stirring had been continued for 3 hours at 10° C. to 15° C., the white crystals of 2-methyl-S-methyldithiocarbazate (1a) were filtered off, washed with a mixture 1:1 of ethanol/petroleum ether to give 38 g of the desired compound. Yield: 84%.

$^1$H-NMR (400 MHz, DMSO) δ ppm: 2.32 (s, 3H), 3.60 (s, 3H), 5.55 (s, 2H).

Intermediate 2: Protocol A
Intermediate 2a: $R_2$=methyl, $R_3$=4-chloro-phenyl
N'-[1-(4-Chloro-phenyl)-methanoyl]-N-methyl-hydrazinecarbodithioic acid methyl ester The appropriate acyl chloride (73.39 mmol, 9.30 mL) ($R_3$COCl) was added to a suspension of 2-methyl-S-methyldithiocarbazate (73.39 mmol, 10 g) in toluene (80 mL). The mixture was stirred at reflux for 4 hours then allowed to cool down overnight. The solids were isolated by filtration, washed with water and then with ether to give 15 g of the expected 3-acyl-2-methyl-S-methyldithiocarbazate (2a). Yield: 74%.

$^1$H-NMR (400 MHz, DMSO) δ ppm: 2.45 (s, 3H), 3.65 (s, 3H), 7.65 (dd, 2H), 7.90 (dd, 2H), 11.68 (s, 1H).

Intermediate 2b: $R_2$=methyl, $R_3$=4-(methylsulfonyl)-phenyl
N'-[1-(4-Methanesulfonyl-phenyl)-methanoyl]-N-methyl-hydrazinecarbodithioic acid methyl ester The acid chloride was prepared from the corresponding benzoic acid. The appropriate acyl chloride (1.68 mmol, 0.39 g) was added to a suspension of 2-methyl-S-methyldithiocarbazate (1.77 mmol, 0.24 g) in toluene (2 mL). After 5 hours at reflux, the mixture was cooled down overnight, triturated in ether and stirred over 2 hours at RT to give 440 mg of the expected product (2b) as a white solid. Yield: 82%.

$^1$H-NMR (400 MHz, DMSO) δ ppm: 2.5 (s, 3H), 3.30 (s, 3H), 3.65 (s, 3H), 8.15 (m, 4H), 11.9 (s, 1H).

Intermediate 2c: $R_2$=methyl, $R_3$=4-cyano-phenyl
N'-[1-(4-Cyano-phenyl)-methanoyl]-N-methyl-hydrazinecarbodithioic acid methyl ester The appropriate acyl chloride (22.77 mmol, 3.77 g) ($R_3$COCl) was added to a suspension of 2-methyl-S-methyldithio carbazate (22.77 mmol, 3.10 g) in toluene (25 mL). The mixture was stirred at reflux for 3 hours to 3 hours 30 minutes, then allowed to cool down overnight. The solids were isolated by filtration, washed with water then with ether and dried to give 4.15 g of the expected 3-acyl-2-methyl-S-methyldithiocarbazate (2c). Yield: 68%.

$^1$H-NMR (400 MHz, DMSO) δ ppm: 2.45 (s, 3H), 3.65 (s, 3H), 8.05 (m, 4H), 11.85 (s, 1H).

Intermediate 2d: $R_2$=methyl, $R_3$=4-acetyamino-phenyl
N'-(4-Acetylamino-benzoyl)-N-methyl-hydrazinecarbodithioic acid methyl ester The acid chloride was prepared from the corresponding benzoic acid. To a suspension of the appropriate acyl chloride (10 mmol, 1.4 g) in toluene (30 mL) was added triethylamine (20 mmol, 2.8 mL) followed by 2-methyl-S-methyldithiocarbazate (12 mmol, 2.4 g). The mixture was maintained at 90° C. for 2 hours and was concentrated under reduced pressure. The residue was taken into dichloromethane, washed once with water, concentrated under reduced pressure, and washed with AcOEt to give 1.28 g of the title compound. Yield: 45%.

$^1$H-NMR (400 MHz, DMSO) δ ppm: 2.10 (s, 3H), 2.45 (s, 3H), 3.65 (s, 3H), 7.85 (d, 2H), 7.90 (d, 2H), 10.30 (s, 1H), 11.40 (s, 1H).

Intermediate 2e: $R_2$=methyl, $R_3$=4-acetylamino-3-pyridyl
N'-(6-Acetylamino-pyridine-3-carbonyl)-N-methyl-hydrazinecarbodithioic acid methyl ester The acid chloride was prepared from the corresponding benzoic acid. To a suspension of the appropriate acyl chloride (63 mmol, 11 g) in toluene (150 mL) was added triethylamine (130 mmol) followed by 2-methyl-S-methyldithiocarbazate (62 mmol, 9 g). After 3 hours at RT, the mixture was concentrated under reduced pressure. The residue was taken into dichloromethane, washed once with water, concentrated under reduced pressure, and purified by chromatography on silica gel (95:5 (dichloromethane (DCM)/MeOH) to give 9 g of the title compound. Yield: 50%.

$^1$H-NMR (400 MHz, DMSO) δ ppm: 2.15 (s, 3H), 2.45 (s, 3H), 3.65 (s, 3H), 8.25 (m, 2H), 8.80 (s, 1H), 10.90 (s, 1H).

MS (m/z)/M+1=298.99

Intermediate 3: Protocol A
Intermediate 3a: $R_2$=methyl, $R_3$=4-chloro-phenyl
1,3,4-Thiadiazolium, 5-(4-chlorophenyl)-3-methyl-2-(methylthio)-perchlorate To a suspension of the intermediate (2a) (54.4 mmol, 15 g) in ether (150 mL) at 0° C., acetic anhydride (30 mL) was added slowly and then HClO$_4$ 70% (65.33 mmol, 5.61 mL) was added dropwise at 0° C. for 1 hour. The resultant mixture was stirred at RT overnight and the precipitate separated by filtration, was washed with ether and then air dried to give 19 g of the title compound (3a) as white solid. Yield: 97%.

$^1$H-NMR (400 MHz, DMSO) δ ppm: 2.92 (s, 3H), 3.99 (s, 3H), 7.52 (dd, 2H), 7.82 (dd, 2H).

MS (m/z)/M+1=257/259.

Intermediate 3b: $R_2$=methyl, $R_3$=4-(methylsulfonyl)phenyl
1,3,4-Thiadiazolium, 5-(4-methanesulfonyl-phenyl)-3-methyl-2-(methylthio)-perchlorate To a suspension of the intermediate (2b) (0.69 mmol, 0.22 g) in ether (3 mL) at 0° C., acetic anhydride (0.4 mL) was added slowly and then HClO$_4$ 70% (0.90 mmol, 0.080 mL) was added dropwise at 0° C. for 1 hour. The resultant mixture was then allowed to rise to RT and stirred for 3 hours. The precipitate was isolated by filtration then air dried to give 220 mg of the expected 3-methyl-2-methylthio[1,3,4]thiadiazolium perchlorate (3b) as a white solid. Yield: 78%.

$^1$H-NMR (400 MHz, DMSO) δ ppm: 3.14 (s, 3H), 3.33 (s, 3H), 4.20 (s, 3H), 8.20 (dd, 2H), 8.25 (dd, 2H).

MS (m/z)/M+1=301/303.

Intermediate 3c: $R_2$=methyl, $R_3$=4-cyano-phenyl
1,3,4-Thiadiazolium, 5-(4-cyanophenyl)-3-methyl-2-(methylthio)-perchlorate To a suspension of intermediate (2c) (15.64 mmol, 4.15 g) in ether (50 mL) and acetic anhydride (13.3 mL), HClO$_4$ 70% (18.76 mmol, 1.6 mL) was added dropwise at 0° C. and stirred during 15 to 30 minutes at 0° C. The resultant mixture was stirred during 1 hour 30 minutes at RT and the precipitate, separated by filtration, was washed with ether and then air dried to give 5.22 g of the title compound (3c) as white solid. Yield: 96%.

$^1$H-NMR (400 MHz, DMSO) δ ppm: 3.15 (s, 3H), 4.21 (s, 3H), 8.15 (m, 4H).

Intermediate 3d: $R_2$=methyl, $R_3$=4-acetylamino-phenyl
1,3,4-Thiadiazolium, 5-(4-acetylaminophenyl)-3-methyl-2-(methylthio)-trifluoromethanesulfonic acid To a suspension of (2d) (4.3 mmol, 1.28 g) in dichloromethane (15 mL) was added trimethylsilyl trifluoromethane-sulfonate (12.9 mmol, 2.34 mL) dropwise. The resulting mixture was stirred overnight. The precipitate was isolated by filtration and then dried under reduced pressure to give 1.3 g of the expected 3-methyl-2-methylthio [1,3,4]thiadiazolium triflate (3d) as a white solid. Yield: 72%.

$^1$H-NMR (400 MHz, DMSO) δ ppm: 2.10 (s, 3H), 3.10 (s, 3H), 4.15 (s, 3H), 7.80 (dd, 2H), 7.95 (dd, 2H), 10.40 (s, 1H).

Intermediate 3e: $R_2$=methyl, $R_3$=4-acetylamino-3-pyridyl
1,3,4-Thiadiazolium, 5-(6-acetylamino-pyridin-3-yl)-3-methyl-2-(methylthio)-perchlorate To a suspension of (2e) (3.4 mmol, 1 g) in ether (11 mL) was slowly added acetic anhydride (2 mL) followed by HClO$_4$ 70% (4 mmol, 0.7 g) dropwise at 0° C. over 1 hour. The resulting mixture was then allowed to warm up to RT and stirred overnight. Additional HClO$_4$ 70% (0.7 mmol, 0.1 g) was added at 0° C., and the mixture was stirred for 2 hours. The precipitate was isolated by filtration washed with AcOEt then dried under reduced pressure to give 1 g of the expected (3e). Yield: 77%.

$^1$H-NMR (400 MHz, DMSO) δ ppm: 2.15 (s, 3H), 3.15 (s, 3H), 4.20 (s, 3H), 8.30 (dd, 1H), 8.40 (dd, 2H), 8.90 (d, H), 11.05 (s, 1H).

MS (m/z)/M+1=280.92.

Compound I: Protocol A

Example I1

$R_1$=3-benzoic acid, $R_2$=methyl, $R_3$=4-chloro-phenyl
3-[5-(4-Chloro-phenyl)-3-methyl-3H-[1,3,4]thiadiazol-2ylideneamino]-benzoic acid To a suspension of 1,3,4-thiadiazolium perchlorate (3a) (0.7 mmol, 0.25 g) in ethanol (3.5 mL), 3-aminobenzoic acid (1.05 mmol, 0.144 g), and triethylamine (0.7 mmol, 0.098 mL) were added, and the mixture was maintained at 70° C. for 7 hours. On cooling to RT overnight, the solid formed was isolated by filtration to give 0.180 g of the expected compound. Yield: 74.3%.

$^1$H-NMR (400 MHz, DMSO) δ ppm: 3.72 (s, 3H), 7.30 (dd, 1H), 7.5 (dd, 1H), 7.54 (dd, 2H), 7.60 (s, 1H), 7.54 (dd, 1H), 7.71 (dd, 2H), 12.91–13.04 (b, 1H).

MS (m/z)/M+1=346/348.

HPLC (UV purity, λ=214 nm): 99.03%.

The following compounds were prepared by the procedure described in Example I.1 using appropriate intermediates and reagents. The desired products were obtained after purification by chromatography on silica gel.

I1.1 (1R*,2R*)-2-[5-(4-Chloro-phenyl)-3-methyl-3H-[1,3,4]thiadiazol-2-ylideneamino]-cyclohexanecarboxylic acid I1.2 (S)-2-[5-(4-Chloro-phenyl)-3-methyl-3H-[1,3,4] thiadiazol-2-ylideneamino]-2-phenyl-ethanol I1.3 [5-(4-Chloro-phenyl)-3-methyl-3H-[1,3,4]thiadiazol-2-ylidene]-(3-ethyl-phenyl)-amine I1.4 [5-(4-Chloro-phenyl)-3-methyl-3H-[1,3,4]thiadiazol-2-ylidene]-pyrrolidin-3-yl-amine I1.5 N-[5-(4-Chloro-phenyl)-3-methyl-3H-[1,3,4]thiadiazol-2-ylidene]-N',N'-dimethyl-benzene-1,4-diamine I1.6 2-[5-(4-Chloro-phenyl)-3-methyl-3H-[1,3,4]thiadiazol-2-ylideneamino]-6-methyl-benzoic acid I1.7 2-{2-[5-(4-Chloro-phenyl)-3-methyl-3H-[1,3,4]thiadiazol-2-ylideneamino]-phenyl}-ethanol I1.8 [5-(4-Chloro-phenyl)-3-methyl-3H-[1,3,4]thiadiazol-2-ylidene]-(4-ethyl-phenyl)-amine I1.9 {1-[5-(4-Chloro-phenyl)-3-methyl-3H-[1,3,4]thiadiazol-2-ylideneamino]-cyclopentyl}-methanol

Example I1.10

$R_1$=3-carboxylic acid cyclohexyl, $R_2$=methyl, $R_3$=4-chloro-phenyl

3-[5-(4-Chloro-phenyl)-3-methyl-3H-[1,3,4]thiadiazol-2-ylideneamino]-cyclohexanecarboxylic acid Compound I1.10 was prepared by the procedure described in Example I1 (3 hours at 75° C.) using appropriate intermediates and reagents (Protocol A). The mixture was filtered, and the filtrate was evaporated to dryness. The residue was purified by silica gel chromatography eluting with dichloromethane containing from 0 to 5% of methanol and then isocratic elution with DCM/MeOH (90:10). Yield: 7.0%.

$^1$H-NMR (400 MHz, DMSO) δ ppm: 0.95–1.20 (m, 4H), 1.62–1.74 (m, 3H), 1.74–1.80 (m 1H), 2.10–2.13 (b, 1H), 2.39–2.48 (b, 1H), 2.84–2.90 (m, 1H), 3.10 (3H, s), 7.33 (dd, 2H), 7.44 (dd, 2H), 11.89–11.84 (b, 1H).

MS (m/z)/M+1=352/354.

HPLC (UV purity, λ=214 m): 97.61%.

Example I2

$R_1$=2-benzoic acid, $R_2$=methyl, $R_3$=4-chloro-phenyl

2-[5-(4-Chloro-phenyl)-3-methyl-3H-[1,3,4]thiadiazol-2-ylideneamino]-benzoic acid To a suspension of 1,3,4-thiadiazolium perchlorate (3a) (0.7 mmol, 0.25 g) in ethanol (3 mL), 2-aminobenzoic acid (0.84 mmol, 0.115 g), and triethylamine (0.7 mmol, 0.098 mL) were added, and the mixture was heated at 70° C. for 7 hours. On cooling, the solid formed was filtered off to give 210 mg of the expected compound. Yield: 87%.

$^1$H-NMR (400 MHz, DMSO) δ ppm: 3.8 (s, 3H), 7.20 (m, 1H), 7.2.8 (dd, 1H), 7.56–7.64 (m, 3H), 7.78 (dd, 2H), 7.95 (dd, 1H), 13.52–13.59 (b, 1H).

MS (m/z)/M+1=346/348.

HPLC (UV purity, λ=214 nm): 97.64%.

Example I2.1

$R_1$=(4-fluoro)-3 benzoic acid, $R_2$=methyl, $R_3$=4-chloro-phenyl

5-[5-(4-Chloro-phenyl)-3-methyl-3H[1,3,4]thiadiazol-2-ylideneamino]-2-fluoro-benzoic acid Compound I2.1 was prepared by the procedure described in Example I2 using appropriate intermediates and reagents (Protocol A). The precipitate obtained on cooling was washed with EtOH to give 0.250 g of the title compound. Yield: 60%.

$^1$H-NMR (400 MHz, DMSO) δ ppm: 3.71 (s, 3H), 7.29–7.33 (m, 3H), 7.48–7.51(m 1H), 7.54 (dd, 2H), 7.70 (dd, 2H), 13.27–13.29 (b, 1H).

MS (m/z)/M+1=364/366.

HPLC (UV purity, λ=214 nm): 95.77%.

Example I2.2

$R_1$=(2,4,5-fluoro)-3 benzoic acid, $R_2$=methyl, $R_3$=4-chloro-phenyl

3-[5-(4-Chloro-phenyl)-3-methyl-3H-[1,3,4]thiadiazol-2-ylideneamino]-2,5,6-trifluoro-benzoic acid Compound I2.2 was prepared by the procedure described in Example I2 using the appropriate intermediates and reagents. Acetonitrile was used as solvent and the reaction was warmed at 80° C. for 24 hours (Protocol A). The solid formed after cooling was filtered off and washed with MeOH to give 0.250 g of the title compound. Yield: 48.6%.

$^1$H-NMR (400 MHz, DMSO) δ ppm: 3.74 (s, 3H), 7.44–7.54 (m, 1H), 7.55 (dd, 2H), 7.73 (dd, 2H), 14.15–14.30 (b, 1H).

MS (m/z)/M+1=400/402.

HPLC (UV purity, λ=214 nm): 95.82%.

Example I3

$R_1$=propyl, $R_2$=methyl, $R_3$=4-chloro-phenyl

[5-(4-Chloro-phenyl)-3-methyl-3H-[1,3,4]thiadiazol-2-ylidene]-propyl-amine

To a suspension of 1,3,4-thiadiazolium perchlorate (3a) (0.28 mmol, 0.10 g) in methanol (4 mL), propylamine (1.35 mmol, 0.115 mL) and triethylamine (0.28 mmol, 0.038 mL) were added, and the reaction was heated at 55° C. for 5 hours. On cooling, the mixture was evaporated to dryness and the crude was chromatographed on silica gel (Alltech column, 2 g silica) with a mixture of cyclohexane/EtOAc (98:2) to give the expected compound. Yield: 0.03 g, 45.2%.

$^1$H-NMR (400 MHz, DMSO) δ ppm: 1.89 (t, 3H), 5.53–5.65 (m, 2H), 2.97 (t, 2H), 7.49 (dd, 2H), 7.62 (dd, 2H).

MS (m/z)/M+1=268/270.

HPLC (UV purity, λ=214 nm): 97.60%.

The following compounds were prepared by the procedure described in Example I3 using appropriate intermediates and reagents.

I3.1 (S)-2-[5-(4-Chloro-phenyl)-3-methyl-3H-[1,3,4]thiadiazol-2-ylideneamino]-butan-1-ol I3.2 [5-(4-Chloro-phenyl)-3-methyl-3H-[1,3,4]thiadiazol-2-ylidene]-[3-(4-methyl-piperazin-1-yl)-propyl]-amine I3.3 [5-(4-Chloro-phenyl)-3-methyl-3H-[1,3,4]thiadiazol-2-ylidene]-cyclobutyl-amine I3.4 3-[5-(4-Chloro-phenyl)-3-methyl-3H-[1,3,4]thiadiazol-2-ylideneamino]-azepan-2-one I3.5 (4-Chloro-benzyl)-[5-(4-chloro-phenyl)-3-methyl-3H-[1,3,4]thiadiazol-2-ylidene]-amine I3.6 Benzyl-[5-(4-chloro-phenyl)-3-methyl-3H-[1,3,4]thiadiazol-2-ylidene]-amine I3.7 [5-(4-Chloro-phenyl)-3-methyl-3H-[1,3,4]thiadiazol-2-ylidene]-cyclopentyl-amine I3.8 [5-(4-Chloro-phenyl)-3-methyl-3H-[1,3,4]thiadiazol-2-ylidene]-cycloheptyl-amine I3.9 (S)-2-[5-(4-Chloro-phenyl)-3-methyl-3H-[1,3,4]thiadiazol-2-ylideneamino]-3-phenyl-propan-1-ol I3.10 (S)-2-[5-(4-Chloro-phenyl)-3-methyl-3H-[1,3,4]thiadiazol-2-ylideneamino]-3-methyl-butan-1-ol The following compounds were prepared by the procedure described in Example 13 using appropriate intermediates and reagents and with isopropanol as solvent.

I3.11 2-[5-(4-Chloro-phenyl)-3-methyl-3H-[1,3,4]thiadiazol-2-ylideneamino]-2-methyl-propan-1-ol I3.12 2-[5-(4-Chloro-phenyl)-3-methyl-3H-[1,3,4]thiadiazol-2-ylideneamino]-2-hydroxymethyl-propane-1,3-diol I3.13 tert-Butyl-[5-(4-chloro-phenyl)-3-methyl-3H-[1,3,4]thiadiazol-2-ylidene]-amine I3.14 [5-(4-Chloro-phenyl)-3-methyl-3H-[1,3,4]thiadiazol-2-ylidene]-isopropyl-amine I3.15 4-[5-(4-Chloro-phenyl)-3-methyl-3H-[1,3,4]thiadiazol-2-ylideneamino]-benzoic acid I3.16 [5-(4-Chloro-phenyl)-3-methyl-3H-[1,3,4]thiadiazol-2-ylidene]-(1-ethyl-propyl)-amine I3.17 4-[5-(4-Chloro-phenyl)-3-methyl-3H-[1,3,4]thiadiazol-2-ylideneamino]-phenol I3.18 N-[5-(4-Chloro-phenyl)-3-methyl-3H-[1,3,4]thiadiazol-2-ylidene]-cyclohexane-1,2-diamine I3.19 [5-(4-Chloro-phenyl)-3-methyl-3H-[1,3,4]thiadiazol-2-ylidene]-(4-fluoro-phenyl)-amine I3.20 N-[5-(4-Chloro-phenyl)-3-methyl-3H-[1,3,4]thiadiazol-2-ylidene]-cyclohexane-1,4-diamine I3.21 [5-(4-Chloro-phenyl)-3-methyl-3H-[1,3,4]thiadiazol-2-ylidene]-(3,4-dichloro-phenyl)-amine I3.22 [5-(4-Chloro-phenyl)-3-methyl-3H-[1,3,4]thiadiazol-2-ylidene]-(4-methoxy-phenyl)-amine I3.23 (1R*,2S*)-2-[5-(4-Chloro-phenyl)-3-methyl-3H-[1,3,4]thiadiazol-2-ylideneamino]-cyclohexanecarboxylic acid I3.24 N'-[5-(4-Chloro-phenyl)-3-methyl-3H-[1,3,4]thiadiazol-2-ylidene]-N,N-dimethyl-ethane-1,2-diamine Example I3.25

$R_1$=(1R*,2S*)-cyclohexyl-2-ol, $R_2$=methyl, $R_3$=4-chloro-phenyl (1R*,2S*)-2-[5-(4-Chloro-phenyl)-3-methyl-3H-[1,3,4]thiadiazol-2-ylideneamino]-cyclohexanol The compound I3.25 was prepared by the procedure described in Example I3 (Protocol A) with isopropanol as solvent. The title product was isolated by chromatography on silica gel (Alltech, 2 g silica) eluting with dichloromethane containing from 0% to 1% methanol. Yield: 0.015 g, 12%.

$^1$H-NMR (400 MHz, DMSO) δ ppm: 1.20–1.30 (b, 2H), 1.40–1.50 (b, 2H), 1.50–1.72 (b, 4H), 2.80–2.83 (b, 1H), 3.50 (s, 3H), 3.55–3.60 (b, 1H), 4.02–4.04 (b, 1H), 7.45 (d, 2H), 7.60 (d, 2H).

MS (m/z)/M+1=324/3256.

HPLC (UV purity, λ=214 nm): 96.62%.

The following compound was prepared by the procedure described in Example I3 with isopropanol as solvent.

I3.26 [5-(4-Chloro-phenyl)-3-methyl-3H-[1,3,4]thiadiazol-2-ylidene]-(4-trifluoromethyl-phenyl)-amine Example I4

$R_1$=3-benzoic acid, $R_2$=methyl, $R_3$=4-(methanesulfonyl)-phenyl

3-[5-(4-Methanesulfonyl-phenyl)-3-methyl-3H-[1,3,4]thiadiazol-2-ylideneamino]-benzoic acid To a suspension of 1,3,4-thiadiazolium perchlorate (3b) (0.547 mmol, 0.22 g) in ethanol (2.5 mL), 3-aminobenzoic acid (0547 mmol, 0.075 g) and triethylamine (0.601 mmol, 0.084 mL) were added, and the reaction was maintained for 6 hours at 75° C. On cooling overnight, the precipitate was filtered off, washed with ethanol then purified on silica gel, eluted with a gradient of DCM then DCM/MeOH (95:5) to give 70 mg of the expected compound. Yield: 33%.

1H-NMR (400 MHz, DMSO) δ ppm: 3.78 (s, 3H), 7.31 (dd, 1H), 7.54 (dd, 1H), 7.60 (s, 1H), 7.65 (s, 1H), 7.97 (dd, 2H), 8.03 (dd, 2H), 12.92–12.03 (b, 1H).

MS (m/z)/M+1=390.

HPLC (UV purity, λ=214 nm): 95.14%.

The following compounds were prepared by the procedure described in Example I4 with an excess of triethylamine (10 eq.) and of the appropriate amine (10 eq.). The reaction was refluxed for 5 hours.

I4.1 [5-(4-Chloro-phenyl)-3-methyl-3H-[1,3,4]thiadiazol-2-ylidene]-cyclopropyl-amine I4.2 [5-(4-Chloro-phenyl)-3-methyl-3H-[1,3,4]thiadiazol-2-ylidene]-cyclohexylmethyl-amine Example I5

$R_1$=3-hydroxyphenyl, $R_2$=methyl, $R_3$=4-chlorophenyl

3-[5-(4-Chloro-phenyl)-3-methyl-3H-[1,3,4]thiadiazol-2-ylideneamino]-phenol

In this example, polystyrene morpholine resin was used to replace triethylamine and the isocyanate resin to remove the remaining amino derivative. The suspension of morpholine resin (0.70 mmol, 0.20 g) and 3-aminophenol (0.84 mmol, 0.09 g) in ethanol (3.5 mL) was stirred at RT for 5 minutes before the addition of 1,3,4-thiadiazolium perchlorate (3a) (0.70 mmol, 0.25 g). After 5 hours at 70° C., the mixture was allowed to cool down before the filtration of the resin. The crude obtained after the evaporation of the solvent was purified on chromatography gel (Alltech column, 2 g silica) and eluted with gradient of DCM and MeOH/DCM (99:1) to give a mixture (0.07 g) of the remained amino derivative and the expected compound. To this mixture in DCM (7 mL)/MeOH (0.5 mL), was added the isocyanate resin (2.44 mmol, 2.00 g), and the suspension was stirred at RT overnight. After filtration of the resin, the filtrate was evaporated to dryness to give 30 mg of the pure product. Yield: 13.5%.

$^1$H-NMR (400 MHz, DMSO) δ ppm: 3.68 (s, 3H), 6.45–6.51 (m, 3H), 7.13–7.19 (m, 1H), 7.55 (dd, 2H), 7.71 (dd, 2H), 9.40–9.48 (b, 1H).

MS (m/z)/M+1=318/320.

HPLC (UV purity, λ=214 nm): 98.44%.

Example I6

$R_1$=4-hydroxy-3-benzoic acid, $R_2$=methyl, $R_3$=4-chlorophenyl

5-[5-(4-Chloro-phenyl)-3-methyl-3H-[1,3,4]thiadiazol-2-ylideneamino]-2-hydroxy-benzoic acid The compound I6 was prepared by the procedure described in Example I2 (Protocol A). The precipitate obtained on cooling was washed with DCM then purified by chromatography on silica gel (Alltech column, 5 g silica) eluted with a mixture of DCM/MeOH from 100:0 to 85:15. Yield: 17.0%.

¹H-NMR (400 MHz, DMSO) δ ppm: 3.07 (s, 1H), 3.59 (s, 3H), 6.70 (d, 1H), 6.93–6.98 (m 1H), 7.30 (s, 1H), 7.38–7.41 (m, 2H), 7.57–7.62 (m, 2H).

MS (m/z)/M+1=362/364.

HPLC (UV purity, λ=214 nm): 95.89%.

The following compounds were prepared by the procedure described in Example I6, using appropriate intermediates and reagents. Either morpholine resin or pyridine was used to replace triethylamine.

I6.1 (1-Aza-bicyclo[2.2.2]oct-3-yl)-[5-(4-chloro-phenyl)-3-methyl-3H-[1,3,4]thiadiazol-2-ylidene]-amine I6.2 4-[5-(4-Chloro-phenyl)-3-methyl-3H-[1,3,4]thiadiazol-2-ylideneamino]-2-diethylaminomethyl-phenol I6.3 2-[5-(4-Chloro-phenyl)-3-methyl-3H-[1,3,4]thiadiazol-2-ylideneamino]-phenol I6.4 [5-(4-Chloro-phenyl)-3-methyl-3H-[1,3,4]thiadiazol-2-ylidene]-(2-ethyl-phenyl)-amine I6.5 (R)-2-[5-(4-Chloro-phenyl)-3-methyl-3H-[1,3,4]thiadiazol-2-ylideneamino]-butan-1-ol I6.6 [5-(4-Chloro-phenyl)-3-methyl-3H-[1,3,4]thiadiazol-2-ylidene]-(3-methoxy-phenyl)-amine I6.7 [5-(4-Chloro-phenyl)-3-methyl-3H-[1,3,4]thiadiazol-2-ylidene]-(3-fluoro-phenyl)-amine I6.8 (3-Chloro-phenyl)-[5-(4-chloro-phenyl)-3-methyl-3H-[1,3,4]thiadiazol-2-ylidene]-amine I6.9 {3-[5-(4-Chloro-phenyl)-3-methyl-3H-[1,3,4]thiadiazol-2-ylideneamino]-phenyl}-acetic acid I6.10 N-[5-(4-Chloro-phenyl)-3-methyl-3H-[1,3,4]thiadiazol-2-ylidene]-N',N'-dimethyl-benzene-1,3-diamine I6.11 3-[5-(4-Chloro-phenyl)-3-methyl-3H-[1,3,4]thiadiazol-2-ylideneamino]-benzamide Example I7

$R_1$=Exo-2-norbornyl, $R_2$=methyl, $R_3$=4-chloro-phenyl

Bicyclo[2.2.1]hept-2-yl-[5-(4-chloro-phenyl)-3-methyl-3H-[1,3,4]thiadiazol-2-ylidene]-amine The compound I7 was prepared by the procedure described in Example I3 using appropriate intermediates and reagents (Protocol A). The title product was isolated by chromatography on silica gel (Alltech, 2 g silica) with a gradient of cyclohexane/EtOAc from 100:0 to 97:3. Yield: 44.8%.

¹H-NMR (400 MHz, DMSO) δ ppm: 1.09–1.18 (b, 3H), 1.27–1.33 (b, 1H), 1.40–1.52 (b, 2H), 1.58–1.62 (m, 1H), 1.70–1.76 (m, 1H), 1.99–2.10 (b, 1H), 2.24–2.27 (b, 1H), 3.45 (s, 3H), 7.53 (d, 2H) 7.64 (d, 2H).

MS (m/z)/M+1=320/322.

HPLC (UV purity, λ=214 nm): 93.17%.

Example I8

$R_1$=(1R*,2R*)-cyclohexyl-2-ol, $R_2$=methyl, $R_3$=4-chloro-phenyl (1R*,2R*)-2-[5-(4-Chloro-phenyl)-3-methyl-3H-[1,3,4]thiadiazol-2-ylideneamino]-cyclohexanol The compound I8 was prepared by the procedure described in Example I3 using appropriate intermediates and reagents (Protocol A). Triethylamine was replaced by morpholine resin (2.1 mmol, 0.61 g, loading 3.47 mmol/g); the mixture of morpholine resin and trans-2-aminocyclohexanol hydrochloride (2.1 mmol, 0.318 g) was stirred in ethanol (3.5 mL) at RT for 5 minutes before the addition of 3-methyl-2-methylthio[1,3,4]thiadiazolium perchlorate (3a) (0.7 mmol, 0.25 g). The residue was subjected to silica gel chromatography (Alltech column, 2 g silica) eluting with dichloromethane containing from 0% to 1% methanol. Yield: 0.050 g, 22%.

¹H-NMR (400 MHz, DMSO) δ ppm: 1.10–1.25 (m, 4H), 1.50–1.66 (m, 3H), 1.71–1.79 (b, 1H), 2.28–2.33 (m, 1H), 3.21–3.27 (m, 1H), 3.40 (s, 3H), 4.38 (s, 1H), 7.42 (dd, 2H), 7.54 (dd, 2H).

MS (m/z)/M+1=324/326.

HPLC (UV purity, λ=214 nm): 99.9%.

The following compounds were prepared by the procedure described in Example I8 using appropriate intermediates and reagents.

I8.1 5-(5-Cyclohexyl-3-methyl-3H-[1,3,4]thiadiazol-2-ylideneamino)-2-methoxy-phenol I8.2 3-(5-Cyclohexyl-3-methyl-3H-[1,3,4]thiadiazol-2-ylideneamino)-benzoic acid I8.3 3-[5-(4-Chloro-phenyl)-3-methyl-3H-[1,3,4]thiadiazol-2-ylideneamino]-4-hydroxy-benzoic acid I8.4 (5-Cyclohexyl-3-methyl-3H-[1,3,4]thiadiazol-2-ylidene)-(3-methanesulfonyl-phenyl)-amine Example I9

$R_1$=(1R*,2R*)-cyclohexyl-2-ol, $R_2$=methyl, $R_3$=4-(methanesulfonyl)-phenyl (1R*,2R*)-2-[5-(4-Methanesulfonyl-phenyl)-3-methyl-3H-[1,3,4]thiadiazol-2-ylideneamino-cyclohexanol The compound I9 was prepared by the procedure described in Example I4 (Protocol A). 3-Methyl-2-methylthio[1,3,4]thiadiazolium perchlorate (3b) (0.372 mmol, 0.15 g), trans-2-aminocyclohexanol hydrochloride (0.410 mmol, 0.062 g), and triethylamine (0.7814 mmol, 0.109 mL) were reacted in ethanol (1.5 mL). The crude was twice chromatographed on silica gel with a mixture of DCM/MeOH (98:2) to give the title product. Yield: 0.030 g, 23%.

¹H-NMR (400 MHz, DMSO) δ ppm: 1.20–1.37 (m, 5H), 1.60–1.78 (b, 3H), 1.81–1.90 (b, 1H), 3.3 (s, 3H), 3.32–3.40 (b, 1H), 3.52 (s, 3H), 4.53 (s, 1H), 7.89 (d, 2H), 8.01 (d, 2H).

MS (m/z)/M+1=368/370.

HPLC (UV purity, λ=214 nm): 99.17%.

Protocol B

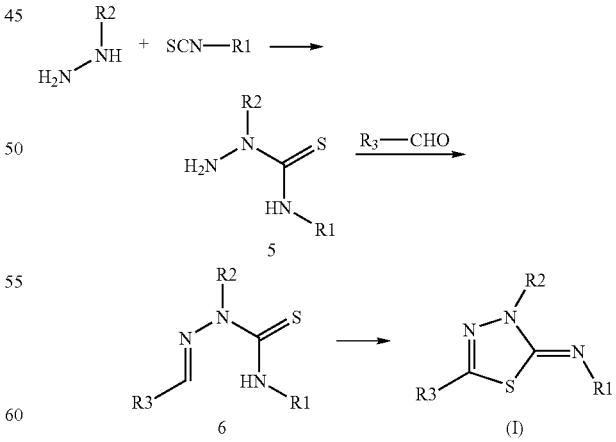

Intermediate 5: Protocol B

Intermediate 5a: $R_1$=cyclohexyl, $R_2$=methyl

Hydrazinecarbothioamide, N-(cyclohexyl)-1-methyl

The requisite cyclohexylisothiocyanate (70.8 mmol, 10 g) was dissolved in methanol (35 mL), and this solution was added dropwise (30 minutes) to a stirred solution of methylhydrazine (134.5 mmol, 7 mL) in water (35 mL) at 0° C. After mixing, the solution was allowed to stir at RT overnight. The precipitate was removed by filtration. The solid was washed with cold EtOH to give 11.7 g of the expected derivative 5a. Yield: 88.7%.

$^1$H-NMR (400 MHz, DMSO) δ ppm: 1.10–1.25 (m, 5H), 1.50–1.60 (m, 1H), 1.60–1.70 (m, 2H), 1.80–1.90(m, 2H), 3.40 (s, 3H), 3.90–4.00 (m, 1H), 4.80 (s, 2H), 7.85 (d, 1H).

MS (m/z)/M+1=188/33.

Intermediate 5b: $R_1$=cyclohexyl, $R_2$=H

Hydrazinecarbothioamide, N-cyclohexyl

The requisite cyclohexylisothiocyanate (141 mmol, 20 mL) was dissolved in methanol (30 mL), and this solution was added dropwise (35 minutes) to a stirred solution of hydrazinehydrate (423 mmol, 13.2 mL) in methanol (200 mL) at 0° C. After mixing, the solution was allowed to stir at RT overnight. The precipitate was removed by filtration. The solid was washed with cold EtOH to give 14.9 g of the expected derivative (5b). Yield: 61%.

$^1$H-NMR (400 MHz, DMSO) δ ppm: 1.10–1.35 (m, 5H), 1.50–1.60 (m, 1H), 1.60–1.75 (m, 2H), 1.75–1.90 (m, 2H), 4.00–4.10 (m, 1H), 4.40 (s, 2H), 7.50 (d, 1H), 8.50 (s, 1H).

MS (m/z)/M+1=174/25.

Intermediate 5c: $R_1$=3-benzoic-acid-methyl-ester, $R_2$=H

Hydrazinecarbothioamide, N-(3-benzoic-acid-methyl-ester)

3-Methoxycarbonylphenylisothiocyanate (77.6 mmol, 15 g) was added dropwise (30 minutes) to a stirred solution of hydrazine hydrate (97 mmol, 4.7 mL) in methanol (40 mL) at –10° C. After stirring at –10° C. for 5 hours, the solution was allowed to stir at room temperature overnight. The precipitate was filtered and washed with cold methanol to give 15.4 g of the expected compound. Yield: 88%.

$^1$H-NMR (400 MHz, DMSO) δ ppm: 3.85 (s, 3H), 4.85 (brs, 1H), 7.43 (t, 1H), 7.68 (d, 1H), 7.87 (d, 1H), 8.33 (s, 1H), 9.23 (s, 1H).

MS (m/z)/M+1=226.

Intermediate 6: Protocol B

Intermediate 6a: $R_1$=cyclohexyl, $R_2$=methyl, $R_3$=2,4-dichlorophenyl

Hydrazinecarbothioamide, N-cyclohexyl-2-[(2,4-chlorophenyl)methylene]

A suspension of 2-methylthiosemicarbazide (5a) (2.67 mmol, 500 mg) in ethanol (5 mL) and 2,4-dichlorobenzaldehyde (2.94 mmol, 515 mg) were heated at 75° C. for 18 hours. After cooling, the formed precipitate was filtered and washed with cold ethanol to give 876 mg of the title compound. Yield: 95.3%.

$^1$H-NMR (400 MHz, DMSO) δ ppm: 1.10–1.25 (m, 1H), 1.25–1.35 (m, 2H), 1.35–1.55 (m, 2H), 1.60–1.70 (m, 1H), 1.70–1.80 (m, 1H), 1.90–2.00 (m, 2H), 3.80 (s, 3H), 4.10–4.30 (m, 1H), 7.50 (d, 1H), 7.70 (s, 1H), 8.00 (s, 1H), 8.20 (d, 1H), 8.50 (d, 1H).

EXAMPLE I

Protocol B

Example I10

$R_1$=cyclohexyl, $R_2$=methyl, $R_3$=2,4-dichlorophenyl

Cyclohexyl-[5-(2,4-dichloro-phenyl)-3-methyl-3H-[1,3,4]thiadiazol-2-ylidene]-amine The appropriate thiosemicarbazone (prepared by the procedure described for intermediate 6a) (2.3 mmol, 800 mg) was suspended in ethanol (5 mL), and the oxidant FeCl$_3$, 6H$_2$O (5.06 mmol, 1.38 g) dissolved in ethanol (5 mL) was added. The mixture was heated at 75° C. during 1 hour (TLC control). The oxidant (1.15 mmol, 0.31 g) was added to allow reaction to completion. The mixture was concentrated by distillation of the solvent, and the crude material was solubilized in ethyl acetate. The inorganic salts were removed by extraction with water. The organic layer was washed with a solution of NaCl, dried under magnesium sulphate, filtered, and distilled to give a residue which was chromatographed on silica gel column (using a gradient of solvent ethyl acetate-cyclohexane starting with a ratio 5:95) to isolate 230 mg of the pure thiadiazoline. The byproduct mainly formed during this reaction is the 1,2,4-triazoline-5-thione. Yield: 35%.

$^1$H-NMR (400 MHz, DMSO) δ ppm: 1.10–1.40 (m, 5H), 1.50–1.60 (m, 1H), 1.65–1.80 (m, 4H), 2.55–2.70 (m, 1H), 3.50 (s, 3H), 7.50 (d, 1H), 7.70–7.80 (m, 2H).

MS (m/z)/M+1=344.1.

HPLC (UV purity, λ=214 nm): 99.9%.

Example I10.1

$R_1$=cyclohexyl, $R_2$=methyl, $R_3$=2-chloro-phenyl

[5-(2-Chloro-phenyl)-3-methyl-3H-[1,3,4]thiadiazol-2-ylidene]-cyclohexyl-amine

Compound I10.1 was prepared by the procedure described in I10 using appropriate intermediates and reagent. The residue was subjected to silica gel chromatography, eluting with cyclohexane containing from 0% to 6% AcOEt. Yield: 6%.

$^1$H-NMR (400 MHz, DMSO) δ ppm: 1.15–1.35 (m, 5H), 1.50–1.60 (m, 1H), 1.65–1.70 (m, 4H), 2.55–2.65 (m, 1H), 3.50 (s, 3H), 7.40–7.50 (m, 2H), 7.60 (d, 1H), 7.70 (d, 1H).

MS (m/z)/M+1=310.2.

HPLC (UV purity, λ=214 nm): 99.9%.

Example I11

$R_1$=cyclohexyl, $R_2$=methyl, $R_3$=4-(trifluoromethyl)-phenyl

Cyclohexyl-[3-methyl-5-(4-trifluoromethyl-phenyl)-3H-[1,3,4]thiadiazol-2-ylidene]-amine The appropriate thiosemicarbazone (prepared by the procedure described for intermediate 6a) (2 mmol, 700 mg) was suspended in ethanol (5 mL), and the oxidant FeCl$_3$, 6H$_2$O (4.4 mmol, 1.21 g) dissolved in ethanol (5 mL) was added. The mixture was heated at 75° C. during 19 hours. The mixture was concentrated by distillation of the solvent, and the crude material was solubilized in ethyl acetate. The inorganic salts were removed by extraction with water. The organic layer was washed with a solution of NaCl, dried under magnesium sulphate, filtered, and distilled to give a residue which was chromatographed on silica gel column (using a gradient of solvent ethyl acetate-cyclohexane as eluent with a rapport 5:95) to isolate 290 mg the pure thiadiazoline. Yield: 42%.

$^1$H-NMR (400 MHz, DMSO) δ ppm: 1.25–1.50 (m, 5H), 1.60–1.70 (m, 1H), 1.75–1.90 (m, 4H), 2.65–2.75 (m, 1H), 3.60 (s, 3H), 7.85–7.95 (m, 4H).

MS (m/z)/M+1=342.6.

HPLC (UV purity, λ=214 nm): 99.9%.

Example I12

$R_1$=cyclohexyl, $R_2$=methyl, $R_3$=4-pyridyl

Cyclohexyl-(3-methyl-5-pyridin-4-yl-3H-[1,3,4]thiadiazol-2-ylidene)-amine

Compound I12 was prepared by the procedure described in Example I11 using appropriate intermediates and reagents (Protocol B). The mixture was concentrated by distillation under reduced pressure, and the residue was dissolved in water. The aqueous mixture was then basified with saturated NaHCO₃ solution and extracted with ethyl acetate. The organic layer was washed with saturated solution of NaCl and dried over magnesium sulfate, filtered, and distilled to give a residue which was purified by silica gel chromatography (eluent: cyclohexane/ethyl acetate, 95:5). Yield: 80%.

¹H-NMR (400 MHz, DMSO) δ ppm: 1.15–1.40 (m, 5H), 1.55–1.65 (m, 1H), 1.70–1.85 (m, 4H), 2.55–2.70 (m, 1H), 3.55 (s, 3H), 7.60 (d, 2H), 8.65 (d, 2H).

MS (m/z)/M+1=275.2.

HPLC (UV purity, λ=214 nm): 99.9%.

Example I13

R₁=cyclohexyl, R₂=methyl, R₃=3-chloro-phenyl
[5-(3-Chloro-phenyl)-3-methyl-3H-[1,3,4]thiadiazol-2-ylidene]-cyclohexyl-amine Compound I13 was prepared by the procedure described in Example I10 using appropriate intermediates and reagents (Protocol B). The residue was subjected to silica gel chromatography, eluting with cyclohexane containing from 0% to 6% AcOEt. Yield: 23%.

¹H-NMR (400 MHz, DMSO) δ ppm: 1.15–1.40 (m, 5H), 1.55–1.65 (m, 1H), 1.70–1.85 (m, 4H), 2.55–2.70 (m, 1H), 3.50 (s, 3H), 7.45–7.55 (m, 2H), 7.55–7.65 (m, 1H), 7.70 (s, 1H).

MS (m/z)/M+1=308.

HPLC (UV purity, λ=214 nm): 99.9%.

Example I14

R₁=cyclohexyl, R₂=methyl, R₃=4-cyano-phenyl
4-(5-Cyclohexylimino-4-methyl-4,5-dihydro-[1,3,4]thiadiazol-2-yl)-benzonitrile Compounds I14 was prepared by the procedure described in Example I10 using appropriate intermediates and reagents (Protocol B). The residue was subjected to silica gel chromatography, eluting with cyclohexane containing from 0% to 8% AcOEt. Yield: 10%.

¹H-NMR (400 MHz, DMSO) δ ppm: 1.15–1.40 (m, 5H), 1.55–1.65 (m, 1H), 1.70–1.80 (m, 4H), 2.60–2.70 (m, 1H), 3.55 (s, 3H), 7.80 (d, 2H), 7.90 (d, 2H), MS (m/z)/M+1=299.2.

HPLC (UV purity, λ=214 nm): 99.3%.

Example I15

R₁=cyclohexyl, R₂=methyl, R₃=4-methylsulfonyl-phenyl
Cyclohexyl-[5-(4-methanesulfonyl-phenyl)-3-methyl-3H-[1,3,4]thiadiazol-2-ylidene]-amine Compounds I15 was prepared by the procedure described in Example I10 using appropriate intermediates and reagents (Protocol B). The residue was subjected to silica gel chromatography, eluting with cyclohexane containing from 0% to 10% AcOEt. Protocol D gave better yield to prepare I15. Yield: 3%.

¹H-NMR (400 MHz, DMSO) δ ppm: 1.15–1.35 (m, 5H), 1.45–1.55 (m, 1H), 1.60–1.75 (m, 4H), 2.50–2.60 (m, 1H), 3.20 (s, 3H), 3.45 (s, 3H), 7.80 (d, 2H), 7.90 (d, 2H).

MS (m/z)/M+1=352.5.

HPLC (UV purity, λ=214 nm): 87.3%.

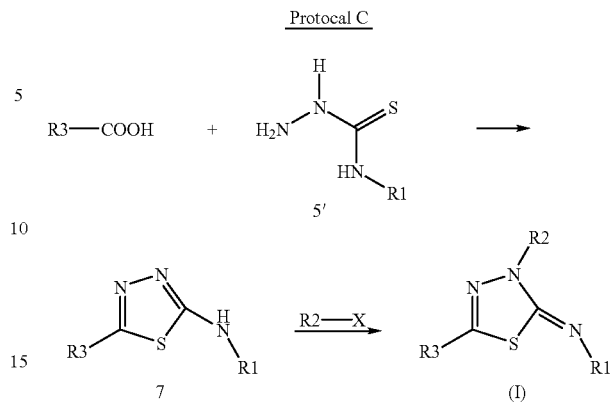

Intermediate 7: Protocol C

Intermediate 7a: R₁=cyclohexyl, R₃=4-chloro-3-sulfamoyl-phenyl
2-Chloro-5-(5-cyclohexylamino-[1,3,4]thiadiazol-2-yl)-benzenesulfonamide To a mixture of 4-chloro-3-sulfamoyl-benzoic acid (6.36 mmol, 1.5 g), thiosemicarbazide (5b) (6.36 mmol, 1.10 g) in dioxane (40 mL) at 60° C., POCl₃ (6.36 mmol, 600 µL) was added, and the mixture was warmed at reflux for 2 hours 30 minutes and 16 hours at RT. The solvent was removed by distillation under reduced pressure to give a crude material which was basified with a solution of diluted NH₄OH. The yellow precipitate obtained was collected by filtration, washed with water before drying under vacuum over P₂O₅ to give 2 g of the desired product. Yield: 84%.

¹H (400 MHz, DMSO) δ ppm: 1.10–1.37 (m, 5H), 1.55 (m, 1H), 1.70 (m, 2H), 1.98 (m, 2H), 3.55 (m, 1H), 7.66–7.82 (m, 3H), 7.90 (m, 1H), 8.25–8.37 (br, 2H).

MS (m/z)/M+1=373/375.

Intermediate 7b: R₁=cyclohexyl, R₃=2,4-dichloro-5-sulfamoyl-phenyl
2,4-Dichloro-5-(5-cyclohexylamino-[1,3,4]thiadiazol-2-yl)-benzenesulfonamide To a mixture of 2,4-dichlorobenzoic acid (1.85 mmol, 500 mg), thiosemicarbazide (5b) (1.85 mmol, 320 mg) in anhydrous dioxane (10 mL) at 70° C. to 80° C., POCl₃ (1.85 mmol, 173 µL) was added, and the mixture was warmed at 95° C. for 5 hours. The solvent was removed by distillation under reduced pressure to give a crude material which was basified at pH 8–7 with a saturated solution of NaHCO₃. The precipitate obtained was collected by filtration, washed with water and purified by silica gel chromatography using cyclohexane/ethyl acetate as eluent to give 351 mg of the title compound. Yield: 46.3%.

¹H-NMR (400 MHz, DMSO) δ ppm: 1.10–1.40 (m, 5H), 1.50–1.65 (m, 1H), 1.65–1.80 (m, 2H), 1.90–2.05 (m, 2H), 3.50–3.70 (m, 1H), 7.85 (d, 2H), 8.05 (s, 1H), 8.20–8.40 (m, 1H), 8.60 (s, 1H).

MS (m/z)/M+1=407.1.

HPLC (UV purity, λ=214 nm): 97.1%.

Intermediate 7c: R₁=cyclohexyl, R₃=3-thienyl
Cyclohexyl-(5-thiophen-3-yl-[1,3,4]thiadiazol-2-yl)-amine To a mixture of 3-thiophenecarboxylic acid (3.9 mmol, 500 mg), thiosemicarbazide (5b) (3.9 mmol, 675 mg) in anhydrous dioxane (10 mL) at 60° C. to 65° C., POCl₃ (5 mmol, 473 µL) was added, and the mixture was warmed at 95° C. for 5 hours. The solvent was removed by distillation under reduced pressure to give a crude material which was basified at pH 8–7 with a saturated solution of NaHCO₃. The precipitate obtained was collected by filtration and washed with water. The solid was then dried under vacuum to provide 965 mg of the desired compound (7c). Yield: 93%.

$^1$H-NMR (400 MHz, DMSO) δ ppm: 1.10–1.40 (m, 5H), 1.50–1.60 (m, 1H), 1.65–1.75 (m, 2H), 1.90–2.00 (m, 2H), 3.45–3.55 (m, 1H), 7.45 (d, 1H), 7.65 (d, 1H), 7.80 (d, 1H), 7.85 (s, 1H).

Intermediate 7d: $R_1$=cyclohexyl, $R_3$=3-chloro-2,6-dimethoxyphenyl

[5-(3-Chloro-2,6-dimethoxy-phenyl)-[1,3,4]thiadiazol-2-yl]-cyclohexyl-amine

To a mixture of 3-chloro-2,6-dimethoxybenzoic acid (2.3 mmol, 500 mg), thiosemicarbazide (5b) (2.3 mmol, 399 mg) in anhydrous dioxane (10 mL) at 70° C. to 80° C., POCl$_3$ (2.3 mmol, 215 μL) was added, and the mixture was warmed at 95° C. for 5 hours. The solvent was removed by distillation under reduced pressure to give a crude material which was basified at pH 8–7 with a saturated solution of NaHCO$_3$. The precipitate obtained was collected by filtration, washed with water, and dried under vacuum. The solid was subjected to flash chromatography eluting with ethyl acetate/cyclohexane to give 115 mg of the title compound. Yield: 14%.

$^1$H-NMR (400 MHz, DMSO) δ ppm: 1.15–1.40 (m, 5H), 1.55–1.65 (m, 1H), 1.70–1.80 (m, 2H), 1.95–2.05 (m, 2H), 3.50–3.60 (m, 1H), 3.70 (s, 3H), 3.80 (s, 3H), 7.00 (d, 1H), 7.55 (d, 1H), 7.75 (d, 1H).

MS (m/z)/M+1=354.1.

Intermediate 7e: $R_1$=cyclohexyl, $R_3$=3-bromo-4-methoxyphenyl

[5-(3-Bromo-4-methoxy-phenyl)-[1,3,4]thiadiazol-2-yl]-cyclohexyl-amine

To a mixture of 3-bromo-4-methoxybenzoic acid (2.16 mmol, 500 mg), thiosemicarbazide (5b) (2.16 mmol, 375 mg) in anhydrous dioxane (10 mL) at 60° C. to 65° C., POCl$_3$ (2.8 mmol, 262 μL) was added, and the mixture was warmed at 95° C. for 5 hours. The solvent was removed by distillation under reduced pressure to give a crude material which was basified at pH 8–7 with a saturated solution of NaHCO$_3$. The precipitate obtained was collected by filtration, washed with water, and dried under vacuum. The solid was solubilized in 50 mL of dichloromethane/methanol (7:3) to which was added a morpholine resin (13.88 mmol, 4 g). The mixture was stirred overnight to remove the excess of acid. The resin morpholine salt was filtered, and the organic layer was concentrated by distillation under reduced pressure to give 740 mg of the purified product (7e). Yield: 92.8%.

$^1$H-NMR (400 MHz, DMSO) δ ppm: 1.10–1.40 (m, 5H), 1.50–1.60 (m, 1H), 1.65–1.75 (m, 2H), 1.90–2.00 (m, 2H), 3.45–3.55 (m, 1H), 7.45 (dd, 1H), 7.65 (dd, 1H), 7.80 (dd, 1H), 7.85 (dd, 1H).

Intermediate 7f: $R_1$=cyclohexyl, $R_3$=2-pyrazinyl

Cyclohexyl-(5-pyrazin-2-yl-1,3,4]thiadiazol-2-yl)amine

To a mixture of 2-pyrazine carboxylic acid (2.885 mmol, 0.358 g), thiosemicarbazide (5b) (2.885 mmol, 0.5 g) in anhydrous dioxane (10 mL) was added phosphorus oxychloride (3.751 mmol, 0.350 mL) at 90° C., and the mixture was heated at 95° C. for 5 hours. The mixture was then basified to pH 7 with a saturated solution of sodium bicarbonate then extracted with EtOAc. The organic phase was dried over MgSO$_4$ and evaporated to dryness to give the expected product. Yield: 0.6 g, 79.6%.

$^1$H-NMR (400 MHz, DMSO) δ ppm: 1.20–1.44 (m, 5H), 1.56–1.63 (b, 1H), 1.70–1.77 (b, 2H), 2.00–2.05 (b, 2H), 3.60–3.68 (b, 1H), 8.22 (d, 1H), 8.67–8.69 (m, 2H), 9.28 (s, 1H).

Intermediate 7g: $R_1$=cyclohexyl, $R_3$=3,4-dihydroxyphenyl 4-(5-Cyclohexylamino-[1,3,4]thiadiazol-2-yl)-benzene-1,2-diol To a mixture of 3,4-dihydroxybenzoic acid (2.885 mmol, 0.445 g), thiosemicarbazide (5b) (2.885 mmol, 0.500 g) in anhydrous dioxane (10 mL) was added phosphorus oxychloride (3.751 mmol, 0.350 mL) at 90° C., and the mixture of sodium bicarbonate to pH 7 then stirred at RT overnight. The precipitate was filtered, washed with hexane, then dried to give the title compound. Yield: 71%.

$^1$H-NMR (400 MHz, DMSO) δ ppm: 1.15–1.39 (m, 5H), 1.55–1.62 (b, 1H), 1.70–1.78 (b, 2H), 1.95–2.00 (b, 2H), 3.48–3.53 (b, 1H), 6.80 (d, 1H), 6.98 (d, 1H), 7.19 (s, 1H), 7.68 (d, 1H), 9.20–9.40 (b, 2H).

Intermediate 7h: $R_1$=cyclohexyl, $R_3$=4-chloro-phenyl

[5-(4-Chloro-phenyl)-[1,3,4]thiadiazol-2-yl]-cyclohexyl-amine

Thiosemicarbazone (6b) (obtained from 5b following the protocol 6a) (10 mmol, 3 g) was suspended in ethanol (50 mL), and the oxidant FeCl$_3$, 6H$_2$O (23 mmol, 6.3 g) was added. The mixture was heated at reflux for 3 hours. The mixture was concentrated by distillation of the solvent, and the crude material was solubilized in ethyl acetate. The organic layer was washed with water, dried under magnesium sulphate, filtered, and distilled to give a residue submitted to another oxidative process with FeCl$_3$, 6H$_2$O (3 g) in ethanol (50 mL). The mixture was heated at reflux for 3 hours and 12 hours at RT. The mixture was concentrated by distillation of the solvent, and the crude material was solubilized in ethyl acetate. The inorganic salts were removed by extraction with water. The organic layer was washed with a solution of NaCl, dried under magnesium sulphate, filtered, and distilled to give a residue which was triturated and washed with cyclohexane to give 2.5 g of the title product. Yield: 85%.

$^1$H-NMR (400 MHz, DMSO) δ ppm: 0.95–1.22 (m, 5H), 1.35–1.45 (b, 1H), 1.50–1.60 (m, 2H), 1.80–1.87 (m, 2H), 3.32–3.42 (b, 1H), 7.35 (d, 2H), 7.55 (d, 2H), 7.75 (d, 1H).

MS (m/z)/M+1=294.1.

HPLC (UV purity, λ=214 nm): 97.21%.

Intermediate 7i: $R_1$=cyclohexyl, $R_3$=3-chloro-4-hydroxy-5-methoxyphenyl

2-Chloro-4-(5-cyclohexylamino-[1,3,4]thiadiazol-2-yl)-6-methoxy-phenol

To a mixture of 3-chloro-4-hydroxy-5-methoxybenzoic acid (2.468 mmol, 500 g), thiosemicarbazide (5b) (2.468 mmol, 427 mg) in dioxane (10 mL) at 65° C., POCl$_3$ (3.2 mmol, 300 μL) was added, and the mixture was warmed at 95° C. for 3 hours 30 minutes. The solvent was removed by distillation under reduced pressure to give a crude material which was basified with a solution of diluted NH$_4$OH. The precipitate obtained was collected by filtration, washed with water before drying under vacuum over P$_2$O$_5$ to give 675 mg of the desired product. Yield: 80%.

$^1$H-NMR (400 MHz, DMSO) δ ppm: 1.15–1.36 (m, 5H), 1.53–1.63 (m, 1H), 1.67–1.80 (m, 2H), 1.95–2.05 (m, 2H), 3.45–3.57 (m, 1H), 3.90 (s, 3H), 7.25 (s, 1H), 7.30 (s, 1H), 7.85 (d, 1H), 9.90 (s, 1H).

Intermediate 7j: $R_1$=3-benzoic-acid-methyl-ester, $R_3$=3-cyano-phenyl

3-[5-(3-Cyano-phenyl)-[1,3,4]thiadiazol-2-ylamino]-benzoic acid methyl ester

To a mixture of 3-cyanobenzoic acid (2.92 mmol, 0.43 g) (5c) (3 mmol, 0.7 g) in dioxane (10 mL) at 85° C., POCl$_3$ (3.8 mmol, 350 μL) was added, and the mixture was heated at 95° C. for 3 hours 30 minutes. The solvent was removed by distillation under reduced pressure to give a crude material which was basified with an aqueous saturated solution of NaHCO$_3$. The precipitate obtained was collected by filtration, washed successively with water and with ether before being dried under vacuum to give 0.5 g of the desired product. Yield: 49%.

$^1$H-NMR (400 MHz, DMSO) δ ppm: 3.88 (s, 3H), 7.53 (t, 1H), 7.63 (d, 1H), 7.72 (t, 1H), 7.86 (d, 1H), 7.96 (d, 1H), 8.23 (d, 1H), 8.32 (s, 1H), 8.43 (s, 1H), 10.89 (s, 1H).

MS (m/z)/M+1=337.

Intermediate 7k: R$_1$=3-benzoic-acid-methyl-ester, R$_3$=2-pyridyl 3-(5-Pyridin-2-yl-[1,3,4]thiadiazol-2-ylamino)-benzoic acid methyl ester To a mixture of picolinic acid (2.92 mmol, 0.36 g), (5c) (3 mmol, 0.7 g) in dioxane (10 mL) at 85° C., POCl$_3$ (3.8 mmol, 350 μL) was added, and the mixture was heated at 95° C. for 5 hours. The solvent was removed by distillation under reduced pressure to give a crude material. Methanol was added, and the precipitate obtained was collected by filtration, washed with methanol, and dried under vacuum to give 0.59 g (61%) of the desired product. The crude material was engaged in the next step without purification.

$^1$H-NMR (400 MHz, DMSO) δ ppm: 3.8 (s, 3H), 7.5 (m, 2H), 7.6 (d, 1H), 7.88 (d, 1H), 7.98 (t, 1H), 8.12 (d, 1H), 8.42 (s, 1H), 8.63 (d, 1H), 10.9 (s, 1H).

MS (m/z)/M+1=313/314/315.

Example I

Protocol C

Example I16

R$_1$=cyclohexyl, R$_2$=methyl, R$_3$=2,4-dichloro-5-sulfamoyl-phenyl 2,4-Dichloro-5-(5-cyclohexylimino-4-methyl-4,5-dihydro-[1,3,4]thiadiazol-2-yl)-benzenesulfonamide To a solution of 1,3,4-thiadiazole (7b) (0.195 mmol, 80 mg) in anhydrous dioxane (10 mL), methyltrifluoromethane sulfonate (0.23 mmol, 27 μL) was added. The resultant mixture was stirred for 24 hours. To this solution was added 0.527 mmol (64 μL) of methyltrifluoromethane sulfonate to allow reaction to completion and 0.585 mmol (82 μL) of triethylamine. The filtrate is concentrated by distillation under reduced pressure. The product was purified via column chromatography on silica gel (eluted with cyclohexane/ ethyl acetate, 80:20) to give 48 mg of the title product. Yield: 58%.

$^1$H-NMR (400 MHz, DMSO) δ ppm: 1.20–1.40 (m, 5H), 1.55–1.65 (m, 1H), 1.70–1.85 (m, 4H), 2.60–2.70 (m,1H), 3.55 (s, 3H), 7.80 (d, 2H), 8.0 (s, 1H), 8.35 (s, 1H).

MS (m/z)/M+1=421.3.

HPLC (UV purity, λ=214 nm): 99.4%.

Example I17

R$_1$=cyclohexyl, R$_2$=methyl, R$_3$=3-thienyl
Cyclohexyl-(3-methyl-5-thiophen-3-yl-3H-[1,3,4] thiadiazol-2-ylidene)-amine To a solution of 1,3,4-thiadiazole (7c) (0.75 mmol, 200 mg) in anhydrous dioxane (10 mL), methyltrifluoromethane sulfonate (1.13 mmol, 128 μL) was added. The resultant mixture was stirred for 24 hours. To this solution was added 0.225 mmol (26 μL) of methyltrifluoromethanesulfonate to allow reaction to completion, and 0.675 mmol (94 μL) of triethylamine. The mixture is concentrated by distillation under reduce pressure, and the residue was dissolved in water. The aqueous mixture was then basified (pH=5–6) with saturated NaHCO$_3$ solution with ethyl acetate. The organic layer was saturated with NaCl and dried over magnesium sulfate, filtered, and distilled to give a residue which was purified by silica gel chromatography, eluting with cyclohexane containing from 0% to 15% AcOEt to provide 80 mg of the desired product. Yield: 38%.

$^1$H-NMR (400 MHz, DMSO): δ ppm=1.15–1.40 (m, 5H), 1.55–1.65 (m, 1H), 1.7–1.8 (m, 4H), 2.55–2.65 (m, 1H), 3.45 (s, 3H), 7.40 (d, 1H), 7.70 (d, 1H), 7.85 (s, 1H).

MS (m/z)/M+1=280.23.

HPLC (UV purity, λ=214 nm): 99.9%.

Example I17.1

R$_1$=cyclohexyl, R$_2$=methyl, R$_3$=3,5-dichloro-phenyl
Cyclohexyl-[5-(3,5-dichloro-phenyl)-3-methyl-3H-[1,3,4] thiadiazol-2-ylidene]-amine Compound I17.1 was prepared by the procedure described in Example I17 using appropriate intermediates and reagents. Yield: 43%.

$^1$H-NMR (400 MHz, DMSO) δ ppm: 1.15–1.35 (m, 5H), 1.55–1.65 (m, 1H), 1.70–1.90 (m, 4H), 2.55–2.65 (m, 1H), 3.50 (s, 3H), 7.65 (s, 2H), 7.70 (s, 1H).

MS (m/z)/M+1=342.2.

HPLC (UV purity, λ=214 nm): 99.9%.

Compound I17.2 was prepared by the procedure described in Example I17 using appropriate intermediates and reagents:

I17.2 Cyclohexyl-[5-(2-ethyl-5-methyl-2H-pyrazol-3-yl)-3-methyl-3H-[1,3,4]thiadiazol-2-ylidene]-amine Example I18

R$_1$=cyclohexyl, R$_2$=methyl, R$_3$=3-chloro-2,6-dimethoxyphenyl

[5-(3-Chloro-2,6-dimethoxy-phenyl)-3-methyl-3H-[1,3,4] thiadiazol-2-ylidene]-cyclohexyl-amine To a solution of the 1,3,4-thiadiazole (7d) (0.226 mmol, 80 mg) in anhydrous dioxane (10 mL), methyltrifluoro methanesulfonate (0.27 mmol, 31 μL) was added. The resultant mixture was stirred for 24 hours. To this solution was added 0.068 mmol (7 μL) of methyltrifluoromethane-sulfonate to allow reaction to completion. The mixture was concentrated by distillation under reduced pressure, and the residue was dissolved in water. The aqueous mixture was then basified (pH=5–6) with saturated NaHCO$_3$ solution and extracted with ethyl acetate. The organic layer was washed with saturated solution of NaCl and dried over magnesium sulfate, filtered, and distilled to give a residue which was purified by silica gel chromatography (eluent: cyclohexane/ ethyl acetate, 80:20). 11 mg of desired product was obtained. Yield: 13%.

$^1$H-NMR (400 MHz, DMSO) δ ppm: 1.15–1.40 (m, 5H), 1.50–1.60 (m, 1H), 1.65–1.80 (m, 4H), 2.50–2.60 (m, 1H), 3.50 (s, 3H), 3.75 (s, 3H), 3.80 (s, 3H), 7.00 (d, 1H), 7.60 (d, 1H).

MS (m/z)/M+1=368.26.

HPLC (UV purity, λ=214 nm): 99.7%.

Compound I18.1 was prepared by the procedure described in Example I18 using appropriate intermediates and reagents:

I18.1 Cyclohexyl-(5-isoxazol-5-yl-3-methyl-3H-[1,3,4] thiadiazol-2-ylidene)-amine

Example I18.2

$R_1$=cyclohexyl, $R_2$=methyl, $R_3$=2-(5-pyridin-2-yl)-thienyl

Cyclohexyl-[3-methyl-5-(5-pyridin-2-yl-thiophen-2-yl)-3H-[1,3,4]thiadiazol-2-ylidene]-amine Compound I18.2 was prepared by the procedure described in Example I18 using appropriate intermediates and reagents. The residue was purified by silica gel chromatography eluting with a gradient of cyclohexane containing from 0% to 10% ethyl acetate. Yield: 57%.

$^1$H-NMR (400 MHz, DMSO) δ ppm: 1.15–1.35 (m, 5H), 1.50–1.60 (m, 1H), 1.65–1.80 (m, 4H), 2.55–2.65 (m, 1H), 3.45 (s, 3H), 7.30 (m, 1H), 7.35 (d, 1H), 7.80 (d, 1H), 7.85 (m, 1H), 7.95 (d, 1H), 8.55 (d, 1H).

MS (m/z)/M+1=3.57.3.

HPLC (UV purity, λ=214 nm): 99.5%.

Example I18.3

$R_1$=cyclohexyl, $R_2$=methyl, $R_3$=3,5-dihydroxy-4-methoxy-phenyl 5-(5-Cyclohexylimino-4-methyl-4,5-dihydro[1,3,4]thiadiazol-2yl)-2-methoxy-benzene-1,3-diol; compound with trifluoro-methanesulfonic acid Compound I18.3 was prepared from the appropriate 1,3,4-thiadiazole 7 prepared by the procedure described in Example I18. In this particular case, the mixture was concentrated, and the formed precipitate was filtered and washed with ethyl acetate to give the expected compound as a salt of trifluoromethansulfonic acid. Yield: 45%.

$^1$H-NMR (400 MHz, DMSO) δ ppm: 1–1.40 (m, 5H), 1.45–1.55 (m, 1H), 1.65–1.75 (m, 2H), 1.85–1.95 (m, 2H), 3.05–3.20 (m, 1H), 3.6 (s, 3H), 4.00 (bs, 3H), 6.65 (s, 2H), 9.60 (bs, 2H), 10.00 (bs, 1H).

MS (m/z)/M+1=336.4.

HPLC (UV purity, λ=214 nm): 99.7%.

Example I18.4

$R_1$=cyclohexyl, $R_2$=methyl, $R_3$=3-hydroxy-4,5-dimethoxy-phenyl 5-(5-Cyclohexylimino-4-methyl-4,5-dihydro[1,3,4]thiadiazol-2-yl)-2,3-dimethoxy-phenol;compound with trifluoro-methanesulfonic Acid Compound I18.4 was prepared from the appropriate 1,3,4-thiadiazole (7) prepared by the procedure described Example I18. In this particular case, the mixture was concentrated, and the formed precipitate was filtered and washed with ethyl acetate to give the expected compound as a salt of trifluoromethansulfonic acid. Yield: 11%.

1H-NMR (400 MHz, DMSO) δ ppm: 1.10–1.50 (m, 5H), 1.60–1.70 (m, 1H), 1.75–1.85 (m, 2H), 1.95–2.10 (m, 2H), 3.10–3.25 (m, 1H), 3.75 (s, 3H), 3.85 (s, 6H), 6.85 (s, 1H), 6.95 (s, 1H), 9.80 (bs, 1H), 9.90 (bs, 1H).

MS (m/z)/M+1=350.45.

HPLC (UV purity, λ=214 nm): 99.9%.

Example I18.5

$R_1$=cyclohexyl, $R_2$=methyl, $R_3$=4-chloro-phenyl

[5-(4-Chloro-phenyl)-3-methyl-3H-[1,3,4]thiadiazol-2-ylidene]-cyclohexyl-amine

Compound I18.5 was prepared by the procedure described in Example I18 using appropriate intermediates and reagents.

$^1$H-NMR (400 MHz, DMSO) δ ppm: 1.20–1.40 (m, 5H), 1.57–1.63 (m, 1H), 1.70–1.82 (m, 4H), 2.60 (br, 1H), 3.50 (s, 3H), 7.52 (d, 2H), 7.65 (d, 2H).

MS (m/z)/M+1=308/310.

HPLC (UV purity, λ=214 nm): 94.24%.

Example I18.6

$R_1$=cyclohexyl, $R_2$=methyl, $R_3$=3-chloro-4-hydroxy-5-methoxy-phenyl

2-Chloro-4-(5-cyclohexylimino-4-methyl-4,5-dihydro-[1,3,4]thiadiazol-2-yl)-6-methoxy-phenol, compound with 1,1,1-trifluoro-methanesulfonic acid Compound I18.6 was prepared from the appropriate 1,3,4-thiadiazole 7i. To a solution of intermediate 7i (2 mmol, 675 mg) in anhydrous dioxane (10 mL), methyltrifluoromethane sulfonate (3 mmol, 337 μL) was added. The resultant mixture was stirred for 48 hours to give a precipitate. The mixture was filtered and washed with ethyl acetate to give 400 mg of desired product as a salt of trifluoromethanesulfonic acid. Yield: 40%.

$^1$H-NMR (400 MHz, DMSO) δ ppm: 1.15–1.55 (m, 5H), 1.60–1.70 (m, 1H), 1.76–1.88 (m, 2H), 2.00–2.11 (m, 2H), 3.11–3.25 (m, 1H), 3.85 (s, 3H), 3.95 (s, 3H), 7.30 (s, 1H), 7.48 (s, 1H), 9.90 (s, 1H), 10.50 (s, 1H).

MS (m/z)/M+1=354/356.

HPLC (UV purity, λ=214 nm): 99.4%.

Example I19

$R_1$=cyclohexyl, $R_2$=methyl, $R_3$=4-chloro-3-sulfamoyl-phenyl

2-Chloro-5-(5-cyclohexylimino-4-methyl-4,5-dihydro-[1,3,4]thiadiazol-2-yl)-benzenesulfonamide To a solution of 1,3,4-thiadiazole (7a) (0.215 mmol, 80 mg) in anhydrous dioxane (10 mL), methyltrifluoromethane sulfonate (0.257 mmol, 29 μL) was added. The resultant mixture was stirred for 24 hours. To this solution was added (0.065 mmol, 7 μL) of methyltrifluoromethanesulfonate to allow reaction to completion. The filtrate is concentrated by distillation under reduced pressure, and the residue was dissolved in water. The aqueous mixture was then basified (pH=5–6) with saturated NaHCO$_3$ solution and extracted with ethyl acetate. The organic layer was washed with a saturated solution of NaCl and dried over magnesium sulfate, filtered, and distilled to give a residue which was purified by silica gel chromatography (eluted with a gradient of cyclohexane/ethyl acetate) to afford 59 mg of pure product. Yield: 71%.

$^1$H-NMR (400 MHz, DMSO) δ ppm: 1.25–1.55 (m, 5H), 1.65–1.75 (m, 1H), 1.75–1.95 (m, 4H), 2.70–2.80 (m, 1H), 3.65 (s, 3H), 7.80–7.95 (m, 4H), 8.30 (dd, 1H).

MS (m/z)/M+1: 387.3.

HPLC (UV purity, λ=214 nm): 99.7%.

Example I19.1

$R_1$=cyclohexyl, $R_2$=methyl, $R_3$=4-chloro-N,N-diethyl-3-sulfonamide-phenyl

2-Chloro-5-(5-cyclohexylimino-4-methyl-4,5-dihydro[1,3,4]thiadiazol-2-yl)-N,N-diethyl-benzenesulfonamide To a mixture of compound I19 (0.258 mmol, 0.100 g), tetra-n-butylammonium hydrogen sulphate (0.0258 mmol, 0.090 g), 50% aqueous sodium hydroxide (0.300 mL), and toluene (2.2 mL) was added ethylbromide (0.310 mmol, 0.023 mL). The reaction was stirred at RT for 2 hours and then heated to 90° C. for 1 hour 30 minutes before a second addition of ethylbromide (0.310 mmol, 0.023 mL). The mixture was heated at 90° C. for 2 hours 30 minutes, and the volatiles were removed by distillation. The crude material was solubilized with ethyl acetate and the organic layer was washed with brine, dried over MgSO₄, and concentrated under reduced pressure to give 0.1 g of the expected product as a white solid. Yield: 87.7%.

¹H-NMR (400 MHz, DMSO) δ ppm: 1.00 (t, 6H), 1.10–1.32 (b, 5H), 1.48–1.54 (m, 1H), 1.65–1.73 (b, 4H), 2.53–2.62 (b, 1H), 3.20–3.30 (m, 4H), 3.48 (s, 3H), 7.68–7.79 (m, 2H), 8.11 (s, 1H).

MS (m/z)/M+1=443/445.

HPLC (UV purity, λ=214 nm): 99.72%.

Example I19.2

$R_1$=cyclohexyl, $R_2$=methyl, $R_3$=4-Chloro-3-(4-methyl-piperazine-1-sulfonyl)-phenyl {5-[4-Chloro-3-(4-methyl-piperazine-1-sulfonyl)-phenyl]-3-methyl-3H-[1,3,4]thiadiazol-2-ylidene}-cyclohexyl-amine To a solution of I19 (0.516 mmol, 0.2 g) in DMF (13 mL) were added potassium carbonate (1.548 mmol, 0.214 g) and water (3 mL). The mixture was stirred at RT until obtaining a homogenous solution and then the bis-(2-chloro-ethyl) methyl-amine hydrochloride (0.516 mmol, 0.10 g) was added. After a day of stirring, the mixture was warmed at 80° C. for 15 hours. The solvents were then evaporated, and the crude material was solubilized in dichloromethane. The organic layer was washed with a saturated solution of bicarbonate of sodium, then with brine. After filtration, the filtrate was dried over MgSO₄ and concentrated by distillation. The crude material was chromatographed on silica gel, eluting with dichloromethane containing from 0% to 5% methanol. The solid product was then washed with ethyl acetate. Yield: 10%.

¹H-NMR (400 MHz, CDCl₃+D₂O) δ ppm: 1.20–1.48 (m, 5H), 1.62–1.68 (m, 1H), 1.79–1.89 (m, 4H), 2.45 (s, 3H), 2.45 (t, 4H), 2.55–2.65 (m, 1H), 3.33 (t, 4H), 3.60 (s, 3H), 7.52 (d, 1H), 7.72 (d, 1H), 8.24 (s, 1H).

MS (m/z)/M+1=470.

HPLC (UV purity, λ=214 nm): 99.53%.

Example I19.3

$R_1$=cyclohexyl, $R_2$=methyl, $R_3$=4-chloro-3-[(pyridin-4-ylmethyl)sulfamoyl]-phenyl 2-Chloro-5-(5-cyclohexylimino-4-methyl-4,5-dihydro-[1,3,4]thiadiazol-2-yl)N-pyridin-4-ylmethyl-benzenesulfonamide To a mixture of I19 (0.258 mmol, 0.1 g), triethylamine (0.516 mmol, 0.072 mL) and acetic acid (0.516 mmol, 0.03 mL) in 1,2-dichloroethane, 4-pyridine carboxaldehyde (0.387 mmol, 0.037 mL) was added. The mixture was cooled to 0° C., and sodium triacetoxyborohydride (0.516 mmol, 0.135 g) was added. After 24 hours of stirring at RT, the same quantities of borohydride and aldehyde were added, and the reaction was stirred for 15 hours. The mixture was then filtered, and the filtrate was diluted with dichloromethane, washed with water, brine, dried over MgSO₄, filtered, and then evaporated to dryness. The residue was purified on silica gel eluting with dichloromethane containing from 0% to 7% of methanol. The solid product was then washed with ether to give the title product. Yield: 40%.

¹H-NMR (400 MHz, DMSO) δ ppm: 1.15–1.39 (m, 5H), 1.54–1.60 (m, 1H), 1.70–1.80 (m, 4H), 2.60–2.67 (m, 1H), 3.50 (s, 3H), 4.18 (s, 2H), 7.22 (d, 2H), 7.67 (dd, 1H), 7.76 (dd, 1H), 8.06 (d, 1H), 8.39 (d, 2H), 8.73–8.78 (b, 1H).

MS (m/z)/M+1=478.

HPLC (UV purity, λ=214 nm): 99.99%.

Example I19.4

$R_1$=cyclohexyl, $R_2$=methyl, $R_3$=4-Chloro-3-(2-morpholin-4-yl-ethyl-sulfamoyl)-phenyl 2-Chloro-5-(5-cyclohexylimino-4-methyl-4,5-dihydro-[1,3,4]thiadiazol-2-yl)-N-(2-morpholin-4-yl-ethyl)-benzenesulfonamide 2-Chloro-N-(2-chloro-ethyl)-5-(5-cyclohexylimino-4-methyl-4,5-dihydro-[1,3,4]thiadiazol-2-yl)-benzenesulfonamide was prepared by the procedure described in Example I19.3 using an appropriate aldehyde and I19. The residue was purified by silica gel chromatography eluting with a gradient cyclohexane containing from 0% to 20% of ethyl acetate followed by an isocratic elution with ethyl acetate/cyclohexane (4:6). Yield: 84%.

To a mixture of this intermediate (0.866 mmol, 0.390 g), in presence of sodium iodide in ethanol (10 mL), morpholine (8.66 mmol, 0.756 mL) was added. After 15 hours at reflux, the mixture was evaporated to dryness, and the crude material was basified with a saturated solution of sodium bicarbonate. After extraction with ethyl acetate, the organic layer was washed with brine, dried over MgSO₄, filtered, and then evaporated to dryness. The residue was purified by chromatography on silica gel eluting with a gradient of cyclohexane containing from 0% to 50% of ethyl acetate. Yield: 65%.

¹H-NMR (400 MHz, CDCl₃) δ ppm: 1.20–1.50 (m, 5H), 1.61–1.69 (m, 1H), 1.80–1.89 (b, 4H), 2.30–2.39 (m, 4H), 2.41–2.49 (m, 2H), 2.59–2.68 (m, 1H), 3.00–3.09 (m, 2H), 3.60–3.73 (m, 7H), 5.81–5.89 (b, 1H), 7.54 (d, 1H), 7.73 (d, 1H), 8.32 (s, 1H).

MS (m/z)/M+1=500/501.

HPLC (UV purity, λ=214 nm): 97.76%.

Example I19.5

$R_1$=cyclohexyl, $R_2$=methyl, $R_3$=4-Chloro-3-ethylsulfamoyl-phenyl

2-Chloro-5-(5-cyclohexylimino-4-methyl-4,5-dihydro-[1,3,4]thiadiazol-2-yl)-N-ethyl-benzenesulfonamide The title compound was prepared as described in Example I19.3. In this particular case, a large excess of acetaldehyde (20 eq.) and triacetoxy borohydride (4 eq.) were used and added once. Yield: 50%.

¹H-NMR (400 MHz,CDCl₃) δ ppm: 1.13 (t, 3H), 1.22–1.50 (m, 5H), 1.61–1.68 (m, 1H), 1.78–1.87 (b, 4H), 2.57–2.64 (m, 1H), 2.97–3.04 (q, 2H), 3.60 (s, 3H), 4.90 (t, 1H), 7.53 (d, 1H), 7.77 (d, 1H), 8.30 (s, 1H).

MS (m/z)/M+1=415/416.

HPLC (UV purity, λ=214 nm): 99.36%.

Example I19.6

$R_1$=cyclohexyl, $R_2$=methyl, $R_3$=4-Chloro-3-[ethyl-(2-morpholin-4-yl-ethyl)-sulfamoyl]-phenyl 2-Chloro-5-(5-cyclohexylimino-4-methyl-4,5-dihydro-[1,3,4]thiadiazol-2-yl)-N-ethyl-N-(2-morpholin-4-yl-ethyl)-benzenesulfonamide To a mixture of I19.4 (0.100 mmol, 0.05 g), N-tetrabutyl ammonium hydrogen sulfate (0.02 mmol, 0.008 g), a solution of 50% of sodium hydroxide (1.25 mmol, 0.1 mL) in toluene (2 mL), ethylbromide (1 mmol, 0.075 mL) was added. The mixture was heated to 90° C. for 5 hours and then evaporated to dryness. The residue was solubilized in ethyl acetate, and the organic layer was washed with brine, dried over MgSO₄, filtered, and then distilled under vacuum. The crude material was purified on silica gel chromatography eluting with a mixture of ethyl acetate/cyclohexane in a ratio 1:9 then 2:8 to give the expected product. Yield: 60%.

$^1$H-NMR (400 MHz, CDCl$_3$) δ ppm: 1.13 (t, 3H), 1.22–1.45 (m, 5H), 1.61–1.68 (m, 1H), 1.78–1.84 (b, 4H), 2.38–2.43 (m, 4H), 2.50–2.53 (t, 2H), 2.57–2.64 (m, 1H), 3.40–3.50 (m, 4H), 3.60–3.65 (m, 7H), 7.50 (d, 1H), 7.70 (d, 1H), 8.30 (s, 1H).

MS (m/z)/M+1=528/529.

HPLC (UV purity, λ=214 nm): 98.57%.

Example I19.7

R$_1$=cyclohexyl, R$_2$=methyl, R$_3$=4-Chloro-3-isopropyl-(2-morpholin4-yl-ethyl)-sulfamoyl-phenyl 2-Chloro-5-(5-cyclohexylimino-4-methyl-4,5-dihydro-[1,3,4]thiadiazol-2-yl)N-isopropyl-N-(2-morpholin-4-yl-ethyl)-benzenesulfonamide The title compound was prepared as described in Example I19.6 with 13 equivalents of isopropylbromide. The residue was purified by silica gel chromatography eluting with a gradient of cyclohexane containing from 0% to 20% ethyl acetate. Yield: 74%.

$^1$H-NMR (400 MHz, CDCl$_3$) δ ppm: 1.50 (d, 6H), 1.22–1.47 (m, 5H), 1.61–1.68 (m, 1H), 1.78–1.83 (b, 4H), 2.44–2.50 (m, 4H), 2.57–2.63 (m, 3H), 2.47–2.51 (t, 2H), 3.60 (s, 3H), 3.68–3.70 (m, 4H), 3.98–4.04 (m, 1H), 7.50 (d, 1H), 7.70 (d, 1H), 8.30 (s, 1H).

MS (m/z)/M+1=542/543.

HPLC (UV purity, λ=214 nm): 96.86%.

Example I19.8

R$_1$=cyclohexyl, R$_2$=methyl, R$_3$=4-Chloro-3-{ethyl-[2-(2-methoxy-ethoxy)ethyl]-sulfamoyl}-phenyl 2-Chloro-5-(5-cyclohexylimino-4-methyl-4,5-dihydro-[1,3,4]thiadiazol-2-yl)N-ethyl-N-[2-(2-methoxy-ethoxy)-ethyl]-benzenesulfonamide To a solution of I19.5 (0.241 mmol, 0.1 g) in EtOH (4 mL), potassium carbonate (0.289 mmol, 0.040 g) was added, and then the reaction mixture was heated at reflux for 30 minutes before the addition of 1-bromo-2-(2-methoxyethoxy)ethane (0.289 mmol, 0.040 mL). After 3 hours at reflux, 2.4 equivalents of the bromo derivative were added, and the mixture was kept at reflux for additional 15 hours. The mixture was then evaporated to dryness, and the residue was diluted in water and extracted with dichloromethane. The organic layer was washed with water, brine, dried over MgSO$_4$, filtered, and evaporated to dryness. The crude material was purified by silica gel chromatography eluting with a gradient of cyclohexane containing from 10% to 60% ethyl acetate. Yield: 64%.

$^1$H-NMR (400 MHz, CDCl$_3$) δ ppm: 1.11 (t, 3H), 1.20–1.47 (m, 5H), 1.61–1.68 (m, 1H), 1.79–1.89 (b, 4H), 2.59–2.68 (m, 1H), 3.36 (s, 3H), 3.43–3.50 (m, 4H), 3.54–3.58 (m, 4H), 3.61–3.65 (m, 5H), 7.50 (d, 1H), 7.70 (d, 1H), 8.28 (s, 1H).

MS (m/z)/M+1=518/520.

HPLC (UV purity, λ=214 nm): 99.9%.

Example I19.9

R$_1$=cyclohexyl, R$_2$=methyl, R$_3$=4-Chloro-3-[(3-dimethylamino-2-hydroxy-propyl)-ethyl-sulfamoyl]-phenyl 2-Chloro-(cyclohexylimino-methyl-4,5-dihydro-[1,3,4]thiadiazol-2-yl)-N-(3-dimethylamino-2-hydroxy-propyl)-N-ethyl-benzenesulfonamide An excess of epibromohydrin (3 molar equivalents) was reacted with I19.5 following the procedure described in Example I19.8. The intermediate was isolated by chromatography on silica gel eluting with a mixture of cyclohexane/ethyl acetate in a ratio 1:9. To a solution of this intermediate (0.106 mmol, 0.05 g) in EtOH (2 mL) at 50° C., dimethylamine (0.318 mmol, 0.041 mL) was added, and the mixture was heated at 70° C. for 15 hours. The solvent was then removed under reduced pressure. The residue was diluted in water and extracted with dichloromethane. The organic layer was washed with water, brine, dried over MgSO$_4$, filtered, and the volatile was evaporated to give the desired product. Yield: 64%.

$^1$H-NMR (400 MHz, CDCl$_3$) δ ppm: 1.10 (t, 3H), 1.22–1.49 (m, 5H), 1.60–1.70 (m, 1H), 1.79–1.89 (b, 4H), 2.254–2.36 (m, 8H), 2.58–2.66 (m, 1H), 3.31–3.34 (dd, 1H), 3.42–3.60 (m, 6H), 3.79–3.87 (m, 1H), 7.50 (d, 1H), 7.70 (d, 1H), 8.30 (s, 1H).

MS (m/z)/M+1=516/517.

HPLC (UV purity, λ=214 nm): 96.60%.

Example I19.10

R$_1$=cyclohexyl, R$_2$=methyl, R$_3$=4-Chloro-3-[(2,3-dihydroxy-propyl)ethyl-sulfamoyl]-phenyl 2-Chloro-5-(5-cyclohexylimino-4-methyl-4,5-dihydro-[1,3,4]thiadiazol-2-yl)-N-(2,3-dihydroxy-propyl)-N-ethyl-benzenesulfonamide The title compound was prepared as described in Example I19.8 with 3 equivalents of 3-bromo-1,2-propane-diol, and the reaction mixture was heated at reflux for 12 hours. The desired product was obtained after purification of the crude material by silica gel chromatography eluting with a gradient of dichloromethane containing from 0 to 3% methanol. Yield: 38%.

$^1$H-NMR (400 MHz, CDCl$_3$) δ ppm: 1.10 (t, 3H), 1.22–1.49 (m, 5H), 1.62–1.68 (m, 1H), 1.79–1.89 (m, 4H), 2.17–2.22 (m, 1H), 2.59–2.66 (m, 2H), 3.40–3.48 (m, 3H), 3.51–3.57 (dd, 1H), 3.61 (s, 3H), 3.89–3.94 (m, 1H), 7.53 (d, 1H), 7.73 (d, 1H), 8.30 (s, 1H).

MS (m/z)/M+1=489/490.

HPLC (UV purity, λ=214 nm): 98.41%.

Example I19.11

R$_1$=cyclohexyl, R$_2$=methyl, R$_3$=4-Chloro-3-[ethyl-(2-hydroxy-3-pyrrolidin-1-yl-propyl)-sulfamoyl]-phenyl 2-Chloro-5-(5-cyclohexylimino-4-methyl-4,5-dihydro-[1,3,4]thiadiazol-2-yl)-N-ethyl-N-(2-hydroxy-3-pyrrolidin-1-yl-propyl)-benzenesulfonamide The title compound was prepared as described in Example I19.9 using the same intermediate and pyrrolidine (3 eq.) as nucleophile. The residue was purified by silica gel chromatography eluting with a gradient of dichloromethane containing from 2 to 3% of methanol. Yield: 27%.

$^1$H-NMR (400 MHz, CDCl$_3$) δ ppm: 1.10 (t, 3H), 1.19–1.47 (m, 5H), 1.64–1.70 (m, 1H), 1.77–1.90 (m, 4H), 2.48–2.51 (dd, 1H), 2.53–2.78 (m, 7H), 3.33–3.37 (dd, 1H), 3.45–3.54 (m, 2H), 3.56 (d, 2H), 3.61 (s, 3H), 3.87–3.95 (m, 1H), 7.51 (d, 1H), 7.72 (d, 1H), 8.30 (s, 1H).

MS (m/z)/M+1=542/543.

HPLC (UV purity, λ=214 nm): 95.50%.

Example I19.12

R$_1$=cyclohexyl, R$_2$=methyl, R$_3$=4-Chloro-3-[(2-diethylamino-ethyl)-ethyl-sulfamoyl]-phenyl 2-Chloro-5-(cyclohexylimino-methyl-4,5-dihydro-[1,3,4]thiadiazol-2-yl)-N-(2-diethylamino-ethyl)-N-ethyl-benzenesulfonamide The title compound was prepared as described in Example I19.8 using 3.3 equivalents of potassium carbonate and 2 equivalents of 2-diethylaminoethylchloride hydrochloride. The residue was purified by silica gel chromatography eluting with a mixture of MeOH/DCM (10:90). Yield: 32%.

$^1$H-NMR (400 MHz, CDCl3) δ ppm: 1.00 (t, 6H), 1.17 (t, 3H), 1.22–1.48 (m, 5H), 1.61–1.70 (b, 1H), 1.80–1.90 (m, 4H), 2.48–2.53 (q, 4H), 2.59–2.63 (m, 3H), 3.40–3.45 (m, 4H), 3.63 (s, 3H), 7.50 (d, 1H), 7.72 (d, 1H), 8.30 (s, 1H).

MS (m/z)/M+1=514/515.

HPLC (UV purity, λ=214 nm): 99.34%.

Example I19.13

R$_1$=cyclohexyl, R$_2$=methyl, R$_3$=4-Chloro-3-[(2-dimethylamino-1-methyl-ethyl)-ethyl-sulfamoyl]-phenyl 2-Chloro-5-(5-cyclohexylimino-4methyl-4,5-dihydro-[1,3,4]thiadiazol-2-yl)-N-(2-dimethylamino-methyl-ethyl)N-ethyl-benzenesulfonamide (minor isomer) and

Example I19.14

R$_1$=cyclohexyl, R$_2$=methyl, R$_3$=4-Chloro-3-[(2-dimethylamino-propyl)-ethyl-sulfamoyl]-phenyl 2-Chloro-5-(5-Cyclohexylimino-4-methyl-4,5-dihydro-[1,3,4]thiadiazol-2-yl)-N-(2-dimethylamino-propyl)-N-ethyl-benzenesulfonamide (major isomer)

The title compounds were prepared by the procedure described in Example I19.8 using 3.3 equivalents of potassium carbonate and 2 equivalents of the 2-dimethylaminoisopropylchloride hydrochloride. Two "isomers" were obtained from this reaction. The crude material was purified by silica gel chromatography eluting with dichloromethane/methanol (99:1) to afford two isomers.

The minor isomer: Yield: 10%.

$^1$H-NMR (400 MHz, CDCl$_3$) δ ppm: 1.20–1.47 (m, 1H), 1.64–1.72 (m, 1H), 1.77–1.86 (m, 4H), 2.10 (s, 6H), 2.23–2.36 (m, 2H), 2.54–2.66 (m, 1H), 3.31–3.39 (m, 1H), 3.42–3.52 (m, 1H), 3.59 (s, 3H), 3.88–3.93 (m, 1H), 7.50 (d, 1H), 7.70 (d, 1H), 8.30 (s, 1H).

MS (m/z)/M+1=500/501.

HPLC (UV purity, λ=214 nm): 98.67%.

The major isomer: Yield: 30%.

$^1$H-NMR (400 MHz, CDCl$_3$) δ ppm: 0.92 (d, 3H), 1.11 (t, 3H), 1.23–1.50 (m, 5H), 1.62–1.70 (m, 1H), 1.79–1.89 (m, 4H), 2.14 (s, 6H), 2.59–2.64 (m, 1H), 2.77–2.86 (m, 1H), 3.33–3.51 (m, 4H), 3.59 (s, 3H), 7.50 (d, 1H), 7.70 (d, H), 8.30 (s, 1H).

MS (m/z)/M+1=500/501.

HPLC (UV purity, λ=214 nm): 99.67%.

Example I20

R$_1$=cyclohexyl, R$_2$=methylacetate, R$_3$=4-chlorophenyl

[5-(4-Chloro-phenyl)-2-cyclohexylimino-[1,3,4]thiadiazol-3-yl]-acetic acid methyl ester To a solution of the appropriate 1,3,4-thiadiazole (7h) (0.34 mmol, 100 mg) in anhydrous dioxane (3 mL), an excess of methyl bromoacetate (3.4 mmol) was added. The resultant mixture was stirred for 48 hours at 90° C. The mixture was concentrated, and a saturated solution of K$_2$CO$_3$ was added. The solution was extracted with ethyl acetate, the organic layer was dried over MgSO$_4$, filtered, and concentrated to dryness. The residue was purified by chromatography on silica gel using a gradient of solvent cyclohexane/ethyl acetate to afford 66 mg of product. Yield: 52%.

$^1$H-NMR (400 MHz, DMSO) δ ppm: 1.20–1.35 (m, 5H), 1.55–1.60 (m, 1H), 1.65–1.75 (m, 4H), 2.65 (br, 1H), 3.65 (s, 3H), 4.77 (s, 2H), 7.53 (d, 2H), 7.67 (d, 2H).

MS (m/z)/M+1=366/368.

HPLC (UV purity, λ=214 nm): 99.70%.

The compounds of the following examples were prepared by the procedure described in Example I20 using appropriate intermediates and reagents:

I20.1 [5-(4-Chloro-phenyl)-3-cyclopropylmethyl-3H-[1,3,4]thiadiazol-2-ylidene]-cyclohexyl-amine I20.2 3-[5-(4-Chloro-phenyl)-2-cyclohexylimino-[1,3,4]thiadiazol-3-yl]-propane-1,2-diol I20.3 [5-(4-Chloro-phenyl)-3-(2-diethylamino-ethyl)-3H-[1,3,4]thiadiazol-2-ylidene]-cyclohexyl-amine

Example I21

R$_1$=cyclohexyl, R$_2$=methyl, R$_3$=3-benzoic acid methyl ester 3-(5-Cyclohexylimino-4-methyl-4,5-dihydro-[1,3,4]thiadiazol-2-yl)-benzoic acid methyl ester To a solution of the appropriate 1,3,4-thiadiazole 7 (1.86 mmol, 590 mg) prepared by the procedure described in Example 7g in anhydrous dioxane (20 mL), methyltrifluoromethane sulfonate (2.79 mmol, 316 μL) and triethylamine (2.23 mmol, 310 μL) were added. The mixture was stirred for 7 hours at RT. The mixture was filtered, and the precipitate was then poured into diluted NaHCO$_3$ solution and washed with dichloromethane. The organic layer was washed with saturated solution of NaCl and dried over magnesium sulfate, filtered, and concentrated under reduce pressure to give 200 mg of the title product. Yield: 37%.

$^1$H-NMR (400 MHz, DMSO) δ ppm: 1.10–1.35 (m, 5H), 1.45–1.55 (m, 1H), 1.60–1.75 (m, 4H), 2.50–2.60 (m, 1H), 3.45 (s, 3H), 3.80 (s, 3H), 7.55 (t, 1H), 7.80 (d, 2H), 7.95 (d, 2H), 8.10 (s, 1H).

MS (m/z)/M+1=332.3.

HPLC (UV purity, λ=214 nm): 99.9%.

Example I21.1

R$_1$=cyclohexyl, R$_2$=methyl, R$_3$=3-benzoic acid 3-(5-Cyclohexylimino-4-methyl-4,5-dihydro-[1,3,4]thiadiazol-2-yl)-benzoic acid To a solution of compound I21 (30 mg, 0.09 mmol) in methanol (10 mL) and water (2.5 mL), K$_2$CO$_3$ (163 mg, 1.17 mmol) was added. The mixture was heated at reflux for 3 hours, allowed to cool and concentrated in vacuo to give a crude material. This residue was poured into water and the suspension was carefully neutralized with a solution of HCl (0.1N), and the aqueous phase was extracted with ethyl acetate. The organic layer was washed with saturated solution of NaCl, dried over magnesium sulfate, filtered, and distilled to give 10 mg of the title product. Yield: 35%.

$^1$H-NMR (400 MHz, DMSO) δ ppm: 1.15–1.40 (m, 5H), 1.50–1.60 (m, 1H), 1.65–1.80 (m, 4H), 2.55–2.65 (m, 1H), 3.50 (s, 3H), 7.55 (t, 1H), 7.80 (d, 1H), 7.95 (d, 1H), 8.15 (s, 1H), 13.3 (bs, 1H).

MS (m/z)/M+1=318.3.

HPLC (UV purity, λ=214 nm): 99.6%.

Example I21.2

$R_1$=cyclohexyl, $R_2$=methyl, $R_3$=3-benzamide
3-(5-Cyclohexylimino-4-methyl-4,5-dihydro-[1,3,4]thiadiazol-2-yl)-benzamide To a solution of LiOH monohydrate (96 mg, 2.26 mmol) in 1.6 mL of water, a solution of I21 (500 mg, 1.51 mmol) in tetrahydrofuran (THF)/MeOH (50:50) (8 mL) was added. The mixture was stirred at RT for 24 hours and then concentrated under reduced pressure. The residue was dissolved in water and a solution of HCl (0.1N, 38 mL) was added. The resulting mixture was stirred for 2 hours. After distillation of water, the product was dried over $P_2O_5$ in vacuo. To a solution of this crude material (1.51 mmol) in toluene (10 mL), thionylchloride (10 mL) was added dropwise, and the mixture was heated at reflux for 5 hours. The mixture was concentrated under reduced pressure. A solution of ammonia (1 mL at 28%) was added to a solution of the residue (150 mg, 0.32 mmol) in THF (2 mL) cooled to 10° C. After 3 hours at RT, the mixture was concentrated to dryness, poured into water, and extracted with ethyl acetate. The combined organic extracts were washed with water and with a saturated solution of NaCl, dried over magnesium sulfate, filtered, and distilled under reduced pressure. The white solid material was purified by silica gel chromatography (eluted with dichloromethane/methanol at 99:1) to afford 14 mg of the title product. Yield: 14%.

$^1$H-NMR (400 MHz, DMSO) δ ppm: 1.20–1.45 (m, 5H), 1.60–1.70 (m, 1H), 1.75–1.90 (m, 4H), 2.65–2.75 (m, 1H), 3.60 (s, 3H), 7.52 (s, 1H), 7.60 (dd, 1H), 7.85 (d, 1H), 7.98 (d, 1H), 8.15 (s, 1H), 8.18 (s, 1H).

MS (m/z)/M+1=317.
HPLC (UV purity, λ=214 nm): 99.9%.

Example I21.3

$R_1$=cyclohexyl, $R_2$=methyl, $R_3$=3-[N-(2-hydroxy-ethyl)]-benzamide
3-(5-Cyclohexylimino-4-methyl-4,5-dihydro-[1,3,4]thiadiazol-2-yl)-N-(2-hydroxy-ethyl)-benzamide To a solution of LiOH monohydrate (96 mg, 2.26 mmol) in 1.6 mL of water, a solution of I21 (500 mg, 1.51 mmol) in THF/MeOH (50:50) (8 mL) was added. The mixture was stirred at RT for 24 hours and then concentrated under reduced pressure. The residue was dissolved in water, and a solution of HCl (0.1N, 38 mL) was added. The resulting mixture was stirred for 2 hours. After distillation of water, the product was dried over $P_2O_5$ in vacuo. To a solution of this crude material (1.51 mmol) in toluene (10 mL), thionylchloride (10 mL) was added dropwise, and the mixture was heated at reflux for 5 hours. The mixture was concentrated under reduced pressure. To a suspension of this residue (150 mg, 0.32 mmol) in THF (2 mL) with triethylamine (90 µL, 0.64 mmol) was added at 0° C. ethanolamine (20 µL, 0.32 mmol) and stirred at room temperature during 4 hours. Water was added in the mixture and extracted with ethyl acetate, washed with water and brine, dried with magnesium sulfate, filtered, and reduced under pressure vacuum. The residue was purified by silica gel chromatography with a gradient of dichloromethane containing from 0% to 2% methanol to afford 50 mg of the good product. Yield: 43%.

$^1$H-NMR (400 MHz, DMSO) δ ppm: 1.15–1.35 (m, 5H), 1.55–1.65 (m, 1H), 1.70–1.83 (m, 4H), 2.55–2.75 (m, 1H), 3.30–3.37 (m, 2H), 3.45–3.55 (m, 5H), 4.70 (t, 1H), 7.55 (dd, 1H), 7.80 (d, 1H), 7.90 (d, 1H), 8.05 (s, 1H), 8.60 (t, 1H).

MS (m/z)/M+1=361.
HPLC (UV purity, λ=214 nm): 99.7%.

Example I21.4

$R_1$=cyclohexyl, $R_2$=methyl, $R_3$=3-(N-methyl)-benzamide
3-(5-Cyclohexylimino-4-methyl-4,5-dihydro-[1,3,4]thiadiazol-2-yl)-N-methyl-benzamide To a solution of LiOH monohydrate (96 mg, 2.26 mmol) in 1.6 mL of water, a solution of I21 (500 mg, 1.51 mmol) in THF/MeOH (50:50) (8 mL) was added. The mixture was stirred at RT for 24 hours and then concentrated under reduced pressure. The residue was dissolved in water, and a solution of HCl (0.1N, 38 mL) was added. The resulting mixture was stirred for 2 hours. After distillation of water, the product was dried over $P_2O_5$ in vacuo. To a solution of this crude material (1.51 mmol) in toluene (10 mL), thionylchloride (10 mL) was added dropwise, and the mixture was heated at reflux for 5 hours. The mixture was concentrated under reduced pressure. To a suspension of this residue (150 mg, 0.32 mmol) in THF (4 mL) with triethylamine (90 µL, 0.64 mmol) was added at 0° C. methylamine hydrochloride (44 mg, 0.64 mmol) and stirred at room temperature during 4 hours. Water was added in the mixture and basified with a solution of $NaHCO_3$, extracted with ethyl acetate, washed with water and brine, dried with magnesium sulfate, filtered, and reduced under pressure vacuum. The residue was purified by silica gel chromatography with a gradient of dichloromethane containing from 0% to 2% methanol to afford the desired product. Yield: 9%.

$^1$H-NMR (400 MHz, DMSO) δ ppm: 1.15–1.40 (m, 5H), 1.55–1.65 (m, 1H), 1.70–1.85 (m, 4H), 2.60–2.70 (m, 1H), 2.82 (s, 3H), 3.55 (s, 3H), 7.60(t, 1H), 7.80 (d, 1H), 7.90 (d, 1H), 8.05 (s, 1H), 8.55–8.65 (m, 1H).

MS (m/z)/M+1=331.
HPLC (UV purity, λ=214 nm): 96.6%.

Example I22

$R_1$=cyclohexyl, $R_2$=methyl, $R_3$=3,4-dihydroxyphenyl
4-(5-Cyclohexylimino-4-methyl-4,5-dihydro-[1,3,4]thiadiazol-2-yl)-benzene-1,2-diol; compound with trifluoro methanesulfonic acid Compound I22 was prepared from 1,3,4-thiadiazole (7 g) by the procedure described in Example I18 using appropriate intermediates and reagents (Protocol C).

In this particular case, the mixture was filtered, and the precipitate was washed with dioxane and diethylether to give the expected compound as a trifluoromethanesulfonic acid salt. Yield: 54.1%.

$^1$H-NMR (400 MHz, DMSO) δ ppm: 1.10–1.53 (m, 5H), 1.64–1.69 (b, 1H), 1.78–1.84 (b, 1H), 2.03–2.10 (b, 2H), 3.19–3.27 (b, 1H), 3.84 (s, 3H), 6.90 (d, 1H), 7.13 (d, 1H), 7.20 (s, 1H), 9.55–9.63 (b, 1H), 9.75–9.81 (b, 1H), 9.96–10.3 (b, 1H).

MS (m/z)/M+1=306/307.
HPLC (UV purity, λ=214 nm): 97.35%.

Example I23

$R_1$=cyclohexyl, $R_2$=methyl, $R_3$=3,5-dimethoxy-4-hydroxy-phenyl
4-(5-Cyclohexylimino-4-methyl-4,5-dihydro-[1,3,4]thiadiazol-2-yl)-2,6-dimethoxy-phenol Compound I23 was prepared from the appropriate 1,3,4-thiadiazole 7 by the procedure described in Example I18 using appropriate intermediates and reagents (Protocol C).

In this particular case, the mixture was filtered, and the precipitate was washed with dioxane and diethylether to give the expected compound as a trifluoromethansulfonic acid salt. Yield: 13.9%.

$^1$H-NMR (400 MHz, DMSO) δ ppm: 1.12–1.27 (b, 1H), 1.27–1.41 (b, 2H), 1.41–1.54 (b, 2H), 1.63–1.70 (b, 1H), 1.80–1.87 (b, 2H), 2.03–2.11 (b, 2H), 3.17–3.26 (b, 1H), 3.88 (s, 9H), 7.06 (s, 2H), 9.38–9.47 (b, 1H), 9.80–9.88 (b, 1H), MS (m/z)/M+1=350/351.

HPLC (UV purity, λ=214 nm)=96.00%.

Compounds I23.1 and I23.2 were prepared by the procedure described in Example I18 using appropriate intermediates and reagents (Protocol C):

I23.1 6-(5-Cyclohexylimino-4-methyl-4,5-dihydro-[1,3,4]thiadiazol-2-yl)-pyridin-2-ol I23.2 5-(5-Cyclohexylimino-4-methyl-4,5-dihydro-[1,3,4]thiadiazol-2-yl)-benzene-1,2,3-triol Example I24

$R_1$=cyclohexyl, $R_2$=methyl, $R_3$=8-hydroxyquinolin-2-yl 2-(5-Cyclohexylimino-4-methyl-4,5-dihydro-[1,3,4]thiadiazol-2-yl)-quinolin-8-ol Compound I24 was prepared from the appropriate 1,3,4-thiadiazole (7) (procedure described in Example 7d) by the procedure described in Example I18.6. In this particular case, the mixture was filtered, and the precipitate was washed with dioxane and diethylether to give the expected compound as a trifluoromethansulfonic acid salt. Yield: 58.1%.

$^1$H-NMR (400 MHz, DMSO) δ ppm:1.25–1.36 (b, 1H), 1.45–1.67 (b, 4H), 1.74–1.81 (b, 1H), 1.90–1.96 (b, 2H), 2.18–2.22 (b, 2H), 3.40–3.50 (b, 1H), 4.02 (s, 3H), 7.35 (d, 1H), 7.63 (d, 1H), 7.69 (t, 1H), 8.21 (d, 1H), 8.64 (d, 1H), 10.08–10.13 (b, 1H), 10.21–10.28 (b, 1H).

MS (m/z)/M+1=341/342.

HPLC (UV purity, λ=214 nm)=94.88%.

Example I25

$R_1$=cyclohexyl, $R_2$=methyl, $R_3$=2-pyrazyl

Cyclohexyl-(3-methyl-5-pyrazin-2-yl-3H-[1,3,4]thiadiazol-2-ylidene)-amine

The 1,3,4-thiadiazole (7f) (0.770 mmol, 0.200 g) and methyltrifluoromethane sulfonate (0.924 mmol, 0.104 mL) were reacted in dioxane (7 mL). The residue, obtained after basification to pH 9–10 with a saturated solution of carbonate of potassium, was subjected to silica gel chromatography, eluting with dichloromethane containing from 0% to 10% methanol to give the expected product. Yield: 0.075 g, 35.37%.

$^1$H-NMR (400 MHz, DMSO) δ ppm: 1.20–1.43 (b, 5H), 1.56–1.65 (b, 1H), 1.90–2.00 (b, 4H), 2.63–2.70 (b, 1H), 3.56 (s, 3H), 8.67 (s, 2H), 9.12 (s, 1H).

MS (m/z)/M+1=276/277.

HPLC (UV purity, λ=214 nm): 98.32%.

Example I26

$R_1$=cyclohexyl, $R_2$=methyl, $R_3$=(E)-2-(3-hydroxy-4-methoxy-phenyl)-vinyl

5-[(E)-2-(5-Cyclohexylimino-4-methyl-4,5-dihydro-[1,3,4]thiadiazol-2-yl)-vinyl]-2-methoxy-phenol Compounds I26 was prepared by the procedure described in Example I18 using appropriate intermediate (1,3,4-thiadiazole (7)—procedure described for intermediate 7d) and reagents. The desired product was isolated by chromatography on silica gel eluting with dichloromethane containing from 0% to 7% methanol. Yield: 0.025 g, 24.1%.

$^1$H-NMR (400 MHz, DMSO) δ ppm: 1.10–1.36 (b, 6H), 1.52–1.59 (b, 1H), 1.66–1.78 (b, 4H), 3.39 (s, 3H), 3.76 (s, 3H), 6.70–6.80 (b, 1H), 6.85–6.97 (b, 2H), 6.97–7.07 (b, 2H), 9.04 (s, 1H).

MS (m/z)/M+1=346/347.

HPLC (UV purity, λ=214 nm): 98.64%.

Example I27

$R_1$=cyclohexyl, $R_2$=methyl, $R_3$=3-methoxy-4-hydroxy-phenyl 4-(5-Cyclohexylimino-4-methyl-4,5-dihydro-[1,3,4]thiadiazol-2-yl)-2-methoxy-phenol Compound I27 was prepared by the procedure described in Example I18 using appropriate intermediate (1,3,4-thiadiazole (7)—procedure described for intermediate 7d) and reagents. The desired product was isolated by chromatography on silica gel (Alltech, 2 g silice) eluting with cyclohexane containing from 0% to 4% ethyl acetate. Yield: 0.015 g, 14.2%.

$^1$H-NMR (400 MHz, DMSO) δ ppm: 1.01–1.20 (b, 5H), 1.39–1.44 (b, 1H), 1.53–1.63 (b, 4H), 2.4–2.48 (b, 1H), 3.30 (s, 3H), 3.65 (s, 3H), 6.64 (d, 1H), 6.87 (d, 1H), 7.00 (d, 1H), 9.38–9.43 (b, 1H).

MS (m/z)/M+1=320/321.

HPLC (UV purity, λ=214 nm): 99.08%.

Example I28

$R_1$=cyclohexyl, $R_2$=methyl, $R_3$=quinolin-8-yl

Cyclohexyl-(3-methyl-5-quinolin-8-yl-3H-[1,3,4]thiadiazol-2-ylidene)-amine

Compounds I28 was prepared by the procedure described in Example I18 using appropriate intermediate (1,3,4-thiadiazole (7)—procedure described for intermediate 7b) and reagents. The residue was subjected to silica gel chromatography, eluting with cyclohexane containing from 0% to 20% AcOEt. Yield: 41%.

$^1$H-NMR (400 MHz, DMSO) δ ppm: 1.10–1.35 (m, 5H), 1.50–1.60 (m, 1H), 1.65–1.80 (m, 4H), 2.70–2.80 (m, 1H), 3.45 (s, 3H), 7.55–7.60 (m, 1H), 7.60–7.70 (m, 1H), 7.95–8.05 (m, 1H), 8.35–8.40 (m, 1H), 8.40–8.45 (m, 1H), 8.20–8.80 (m, 1H).

MS (m/z)/M+1=325.3.

HPLC (UV purity, λ=214 nm): 99.9%.

Example I29

$R_1$=cyclohexyl, $R_2$=methyl, $R_3$=4-dimethylamino-phenyl

[4-(5-Cyclohexylimino-4-methyl-4,5-dihydro-[1,3,4]thiadiazol-2-yl)-phenyl]-dimethyl-amine Compound I29 was prepared by the procedure described in Example I18 using appropriate intermediate (1,3,4-thiadiazole (7)—procedure described for intermediate 7b) and reagents. The product was chromatographed on silica gel column using cyclohexane/ethyl acetate with a ratio 8:2 as solvent. Yield: 27%.

$^1$H-NMR (400 MHz, DMSO) δ ppm: 1.10–1.35 (m, 5H), 1.50–1.60 (m, 1H), 1.65–1.80 (m, 4H), 2.50–2.60 (m, 1H), 3.45 (s, 3H), 6.70 (d, 2H), 7.40 (d, 2H).

MS (m/z)/M+1=317.3.

HPLC (UV purity, λ=214 nm): 99.5%.

Example I30

R$_1$=cyclohexyl, R$_2$=methyl, R$_3$=4-sulfonamide-phenyl 4-(5-Cyclohexylimino-4-methyl-4,5-dihydro-[1,3,4]thiadiazol-2-yl)-benzenesulfonamide Compound I30 was prepared by the procedure described in Example I18 using appropriate intermediate (1,3,4-thiadiazole (7)—procedure described for intermediate 7b) and reagents. The residue was subjected to silica gel chromatography, eluting with cyclohexane containing from 0% to 20% AcOEt. Yield: 21%.

$^1$H-NMR (400 MHz, DMSO) δ ppm: 1.10–1.35 (m, 5H), 1.50–1.60 (m, 1H), 1.65–1.75 (m, 4H), 2.50–2.60 (m, 1H), 3.45 (s, 3H), 7.40 (s, 2H), 7.75 (d, 2H), 7.85 (d, 2H).

MS (m/z)/M+1=353.2.

HPLC (UV purity, λ=214 nm): 98.5%.

Example I31

R$_1$=cyclohexyl, R$_2$=methyl, R$_3$=5-chloroindol-2-yl

[5-(5-Chloro-1H-indol-2-yl)-3-methyl-3H-[1,3,4]thiadiazol-2-ylidene]-cyclohexyl-amine; compound with trifluoro-methanesulfonic acid Compound I31 was prepared by the procedure described in Example I18.6 using appropriate intermediate (1,3,4-thiadiazole (7)—procedure described for intermediate 7b) and reagents.

In this particular case, the mixture was filtered, and the precipitate was washed with ethyl acetate to give the expected compound as a salt of trifluoromethansulfonic acid. Yield: 88%.

$^1$H-NMR (400 MHz, DMSO) δ ppm: 1.15–1.55 (m, 5H), 1.60–1.70 (m, 1H), 1.75–1.85 (m, 2H), 1.95–2.10 (m, 2H), 3.10–3.30 (m, 1H), 3.85 (bs, 3H), 7.10–7.15 (m, 1H), 7.15–7.20 (m, 1H), 7.40–7.50 (m, 1H), 7.75 (bs, 1H), 10 (bs, 1H), 12.40 (bs, 1H).

MS (m/z)/M+1=347.3.

HPLC (UV purity, λ=214 nm): 95.2%.

Compound I31.1 was prepared by the procedure described in Example I31 using appropriate intermediates and reagents:

I31.1 2-(5-Cyclohexylimino-4-methyl-4,5-dihydro-[1,3,4]thiadiazol-2-yl)-phenol; compound with 1,1,1-trifluoro-methanesulfonic acid

Example I32

R$_1$=cyclohexyl, R$_2$=methyl, R$_3$=3-hydroxy-4-methoxy-phenyl 5-(5-Cyclohexylimino-4-methyl-4,5-dihydro-[1,3,4]thiadiazol-2-yl)-2-methoxy-phenol; compound with 1,1,1-trifluoro-methanesulfonic acid Compound I32 was prepared by the procedure described in Example I18.6 using appropriate intermediate (1,3,4-thiadiazole (7)—procedure described for intermediate 7b) and reagents.

In this particular case, the mixture was concentrated, filtered and the precipitate was washed with ethyl acetate to give the expected compound as a salt of trifluoromethansulfonic acid. Yield: 69%.

$^1$H-NMR (400 MHz, DMSO) δ ppm: 1.05–1.45 (m, 5H), 1.50–1.60 (m, 1H), 1.70–1.80 (m, 2H), 1.90–2.05 (m, 2H), 3.05–3.20 (m, 1H), 3.8 (2s, 6H), 7.00 (d, 1H), 7.15–7.20 (m, 2H), 9.60 (bs, 1H), 9.75 (bs, 1H).

MS (m/z)/M+1=320.3.

HPLC (UV purity, λ=214 nm): 98%.

Example I33

R$_1$=cyclohexyl, R$_2$=methyl, R$_3$=4-hydroxy-phenyl 4-(5-Cyclohexylimino-4-methyl-4,5-dihydro-[1,3,4]thiadiazol-2-yl)-phenol; compound with 1,1,1-trifluoro-methanesulfonic acid Compound I33 was prepared by the procedure described in Example I18.6 using appropriate intermediate (1,3,4-thiadiazole (7)—procedure described for intermediate 7b) and reagents.

In this particular case, the mixture was filtered, and the precipitate was washed with ethyl acetate to give the expected compound as a salt of trifluoromethansulfonic acid. Yield: 95%.

$^1$H-NMR (400 MHz, DMSO) δ ppm: 1.05–1.45 (m, 5H), 1.50–1.60 (m, 1H), 1.65–1.75 (m, 2H), 1.90–2.00 (m, 2H), 3.30–3.40 (m, 1H), 3.75 (s, 3H), 6.85 (d, 2H), 7.60 (d, 2H), 9.70 (bd, 1H), 10.25 (bd, 1H).

MS (m/z)/M+1=290.3.

HPLC (UV purity, λ=214 nm): 95.6%.

Example I34

R$_1$=cyclohexyl, R$_2$=methyl, R$_3$=3,4-dimethoxy-phenyl

Cyclohexyl-[5-(3,4-dimethoxy-phenyl)-3-methyl-3H-[1,3,4]thiadiazol-2-ylidene]-amine Compound I34 was prepared from the appropriate 1,3,4-thiadiazole (7) by the procedure described in Example I17 (Protocol C) using appropriate intermediates and reagents.

The desired product was isolated by chromatography on silica gel eluting with cyclohexane containing from 0% to 20% ethyl acetate. Yield: 28%.

$^1$H-NMR (400 MHz, DMSO) δ ppm: 1.15–1.30 (m, 5H), 1.45–1.55 (m, 1H), 1.60–1.75 (m, 4H), 2.45–2.60 (m, 1H), 3.40 (s, 3H), 3.70 (2s, 6H), 6.95 (d, 1H), 7.05 (d, 1H), 7.10 (s, 1H).

MS (m/z)/M+1=334.3.

HPLC (UV purity, λ=214 nm): 98.2%.

Example I35

R$_1$=cyclohexyl, R$_2$=methyl, R$_3$=3-bromo-4-methoxy-phenyl

[5-(3-Bromo-4-methoxy-phenyl)-3-methyl-3H-[1,3,4]thiadiazol-2-ylidene]-cyclohexyl-amine Compound I35 was prepared from 1,3,4-thiadiazole (7e), by the procedure described in Example I17 (Protocol C) using appropriate intermediates and reagents.

The desired product was isolated by chromatography on silica gel eluting with cyclohexane containing from 0% to 15% ethyl acetate. Yield: 13%.

$^1$H-NMR (400 MHz, DMSO) δ ppm: 1.15–1.35 (m, 5H), 1.55–1.65 (m, 1H), 1.70–1.85 (m, 4H), 2.55–2.65 (m, 1H), 3.50 (s, 3H), 3.90 (s, 3H), 7.20 (d, 1H), 7.60 (d, 1H), 7.85 (s, 1H).

MS (m/z)/M+1=384.2.

HPLC (UV purity, λ=214 nm): 95%.

The compounds of the following examples were prepared by the procedure described in Example I35 using appropriate intermediates and reagents:

I35.1 Cyclohexyl-[5-(4-methoxy-phenyl)-3-methyl-3H-[1,3,4]thiadiazol-2-ylidene]-amine I35.2 Cyclohexyl-(3-methyl-5-phenyl-3H-[1,3,4]thiadiazol-2-ylidene)-amine

Example I36

$R_1$=cyclohexyl, $R_2$=methyl, $R_3$=3-hydroxy-phenyl
3-(5-Cyclohexylimino-4-methyl-4,5-dihydro-[1,3,4]thiadiazol-2-yl)-phenol Compound I36 was prepared from the appropriate 1,3,4-thiadiazole (7) by the procedure described in Example I17 (Protocol C), using appropriate intermediates and reagents.

The product was chromatographed on silica gel column using a gradient of cyclohexane/ethyl acetate. Yield: 14%.

$^1$H-NMR (400 MHz, DMSO) δ ppm: 1.15–1.40 (m, 5H), 1.55–1.65 (m, 1H), 1.70–1.85 (m, 4H), 2.55–2.65 (m, 1H), 3.50 (s, 3H), 6.85 (d, 1H), 7.00–7.05 (m, 2H), 7.25 (t, 1H), 9.75 (s, 1H).

MS (m/z)/M+1=290.29.

HPLC (UV purity, λ=214 nm): 93.9%.

Example I37

$R_1$=cyclohexyl, $R_2$=methyl, $R_3$=4-benzoic acid methyl ester
4-(5-Cyclohexylimino-4-methyl-4,5-dihydro-[1,3,4]thiadiazol-2-yl)-benzoic acid methyl ester Compound I37 was prepared from the appropriate 1,3,4-thiadiazole (7) by the procedure described in Example I17 (Protocol C) using appropriate intermediates and reagents.

The product was chromatographed on silica gel column using a gradient of cyclohexane/ethyl acetate. Yield: 47%.

$^1$H-NMR (400 MHz, DMSO) δ ppm: 1.10–1.35 (m, 5H), 1.50–1.60 (m, 1H), 1.65–1.75 (m, 4H), 2.50–2.65 (m, 1H), 3.50 (s, 3H), 3.80 (s, 3H), 7.70 (d, 2H), 8.00 (d, 2H).

MS (m/z)/M+1=332.3.

HPLC (UV purity, λ=214 nm): 99.9%.

Example I37.1

$R_1$=cyclohexyl, $R_2$=methyl, $R_3$=4-benzoic acid
4-(5-Cyclohexylimino-4-methyl-4,5-dihydro-[1,3,4]thiadiazol-2-yl)-benzoic acid To a solution of 1,3,4-thiadiazole I37 (80 mg, 0.24 mmol) in methanol (10 mL) and water (2.5 mL), $K_2CO_3$ (434 mg, 3.14 mmol) was added. The mixture was heated at 65° C. during 3 hours then at RT overnight. The solvent was removed by distillation under reduced pressure to give a crude material. This residue was poured into water, the suspension was carefully neutralized with a solution of HCl (0.1N), and the aqueous phase was extracted with dichloromethane. The organic layer was washed with saturated solution of NaCl, dried over magnesium sulfate, filtered, and distilled to give 40 mg of the title product. Yield: 52%.

$^1$H-NMR (400 MHz, DMSO) δ ppm: 1.15–1.40 (m, 5H), 1.55–1.65 (m, 1H), 1.70–1.85 (m, 4H), 2.55–2.70 (m, 1H), 3.55 (s, 3H), 7.75 (d, 2H), 8.00 (d, 2H), 13.15 (bs, 1H).

MS (m/z)/M+1=318.4.

HPLC (UV purity, λ=214 nm): 99.9%.

Example I37.2

$R_1$=cyclohexyl, $R_2$=methyl, $R_3$=4-hydroxamic acid phenyl
4-(5-Cyclohexylimino-4-methyl-4,5-dihydro-[1,3,4]thiadiazol-2-yl)-N-hydroxy-benzamide To a solution of LiOH monohydrate (37 mg, 0.75 mmol) in 0.8 mL of water, a solution of compound I37 (250 mg, 0.75 mmol) in THF/MeOH (50:50) (4 mL) was added. The mixture was stirred at RT for 24 hours and then concentrated under reduced pressure. The residue was dissolved in water (2 mL), and a solution of HCl (0.1N, 15 mL) was added. The resulting mixture was stirred for 20 minutes. After distillation of water, the crude product was dried over $P_2O_5$ in vacuo. To a solution of 75 mg (0.19 mmol) of this crude material in toluene (1 mL), a drop of pyridine and thionylchloride (70 μL) were added and reacted at reflux during 4 hours. The volatiles were removed under reduced pressure. To a solution of this residue in anhydrous THF, O-(trimethylsilyl) hydroxylamine (230 μL, 0.47 mmol) was added with molecular sieves (3A), and the reaction mixture was stirred for 18 hours at RT. After filtration, the filtrate was concentrated under reduced pressure, and the residue was treated with a 1 M solution of HCl, stirred at RT, and then basified with a solution of $NaHCO_3$. The aqueous phase was extracted with dichloromethane. The organic layer was washed with brine, dried over magnesium sulfate, filtered, and concentrated in vacuo. The title product was isolated by preparative HPLC on inverse phase (HYPERSYL C18) eluting with water containing from 5% to 95% acetonitrile during 20 mn. Yield: 12 mg, 20%.

$^1$H-NMR (400 MHz, DMSO) δ ppm: 1.15–1.40 (m, 5H), 1.55–1.65 (m, 1H), 1.70–1.85 (m, 4H), 2.60–2.70 (m, 1H), 3.50 (s, 3H), 7.65 (d, 2H), 7.85 (d, 2H).

MS (m/z)/M+1=333.2.

HPLC (UV purity, λ=214 nm): 94.9%.

Example I37.3

$R_1$=cyclohexyl, $R_2$=methyl, $R_3$=4-benzamide
4-(5-Cyclohexylimino-4-methyl-4,5-dihydro-[1,3,4]thiadiazol-2-yl)-benzamide To a solution of LiOH monohydrate (126 mg, 3.0 mmol) in 0.8 mL of water, a solution of I37 (1.0 g, 3 mmol) in THF/MeOH (50:50) (4 mL) was added. The mixture was stirred at RT for 24 hours and then concentrated under reduced pressure. The residue was dissolved in water (8 mL), and a solution of HCl (0.1N, 60 mL) was added. The resulting mixture was stirred for 20 minutes. After distillation of water, the product was dried over $P_2O_5$ in vacuo. To a solution of 120 mg (0.3 mmol) of this crude material in 2 mL of toluene, thionylchloride (2 mL) was added dropwise, and the mixture was heated at reflux for 4 hours. The mixture was concentrated under reduced pressure. A solution of ammonia (1 mL at 28%) was added to a solution of the residue in THF (2 mL) cooled to 10° C. After allowing to stand 5 hours at RT, the mixture was concentrated to dryness, poured into water, and extracted with ethyl acetate. The combined organic extracts were washed with water and with a saturated solution of NaCl, dried over magnesium sulfate, filtered, and distilled under reduced pressure. The white solid material was purified by silica gel chromatography (eluted with dichloromethane) to afford 64 mg of the title product. Yield: 67%.

$^1$H-NMR (400 MHz, DMSO) δ ppm: 1.20–1.45 (m, 5H), 1.55–1.65 (m, 1H), 1.70–1.85 (m, 4H), 2.60–2.70 (m, 1H), 3.55 (s, 3H), 7.45 (bs, 1H), 7.75 (d, 2H), 7.95 (d, 2H), 8.05 (bs, 1H).

MS (m/z)/M+1=317.35.

HPLC (UV purity, λ=214 nm): 99.3%.

Example I37.4

$R_1$=cyclohexyl, $R_2$=methyl, $R_3$=4-N-(2H-tetrazol-5-yl)-benzamide
4-(5-Cyclohexylimino-4-methyl-4,5-dihydro-[1,3,4]thiadiazol-2-yl)-N-(2H-tetrazol-5-yl)-benzamide hydrochloride salt To a solution of LiOH monohydrate (187 mg, 4.5 mmol) in 0.8 mL of water, a solution of compound I37 (250 mg, 0.75 mmol) in THF/MeOH (50:50) (4 mL) was added. The mixture was stirred at RT for 24 hours and then concentrated under reduced pressure. The residue was dissolved in water (2 mL) and a 0.1 M solution of HCl was added to reach pH 6–7. After distillation of water, the crude material was dried over $P_2O_5$ in vacuo. Morpholine type resin (180 mg, 0.62 mmol) was added to a solution of 450 mg (0.62 mmol) of this crude material in 15 mL of THF cooled to −15° C. Then isobutylchloroformate (105 μL, 0.8 mmol) was added, and the mixture was stirred at −15° C. for 1 hour 30 minutes before addition of a suspension of amino-1H-tetrazole (80 mg, 0.74 mmol) in THF (10 mL). The reaction mixture was allowed to stand overnight at RT, and the mixture was filtered over a silica gel. The filtrate was concentrated to dryness, and purified by preparative HPLC on inverse phase C18 (HYPERSYL), eluting with water containing from 5% to 95% acetonitrile in 20 minutes to afford 10 mg of the title product. The compound was treated with a solution of ethanol/HCl to give the corresponding hydrochloride salt. Yield: 4%.

$^1$H-NMR (400 MHz, DMSO) δ ppm: 1.10–2.15 (m, 10H), 3.10–3.30 (m, 1H), 4.00 (bs, 3H), 8.10 (bd, 2H), 8.35 (bd, 2H), 12.70 (bs, 1H).

MS (m/z)/M+1=385.46.

HPLC (UV purity, λ=214 nm): 99.9%.

Example I37.5

$R_1$=cyclohexyl, $R_2$=methyl, $R_3$=4-(N-quinolin-8-yl)-benzamide 4-(5-Cyclohexylimino-4-methyl-4,5-dihydro[1,3,4]thiadiazol-2-yl)-N-quinolin-8-yl-benzamide To a solution of LiOH monohydrate (794 mg, 19 mmol) in 18 mL of water, a solution of I37 (5.7 g, 17.2 mmol) in THF/MeOH (50:50) (100 mL) was added. The mixture was stirred at RT for 24 hours and then concentrated under reduced pressure. The residue was dissolved in water and a solution of HCl (0.1N, 361 mL) was added. The resulting mixture was stirred for 3 hours 30 minutes. After distillation of water, the crude product was dried over $P_2O_5$ in vacuo. To a suspension of 200 mg (0.5 mmol) of this crude material in $CH_2Cl_2$/DMF (50:50) (6 mL) were added cyclocarbodiimide-N-methyl resin (1.03 g, 1.5 mmol), 1-hydroxy-7-azabenzotriazol (14 mg, 0.1 mmol), N,N-diisopropylethylamine (175 μL, 1 mmol), 8-aminoquinoline (145 mg, 1 mmol), molecular sieves (3A), and the reaction mixture was stirred 24 hours at RT. After filtration, methylisocyanate resin (1 g, 1 mmol) was added to the filtrate, and the mixture was stirred for another 24 hours at RT. The mixture was filtered, and the filtrate was concentrated under reduced pressure. The residue was purified by silica gel chromatography eluting with a gradient of cyclohexane containing from 0% to 20% ethyl acetate to afford 10 mg of the title product. Yield: 4.5%.

$^1$H-NMR (400 MHz, DMSO) δ ppm: 1.20–1.40 (m, 5H), 1.60–1.65 (m, 1H), 1.75–1.85 (m, 4H), 2.65–2.75 (m, 1H), 3.55 (s, 3H), 7.65–7.75 (m, 2H), 7.80 (d, 1H), 7.90 (d, 2H), 8.15 (d, 2H), 8.5 (d, 1H), 8.75 (d, 1H), 9.00 (d, 1H), 10.70 (s, 1H).

MS (m/z)/M+1=444.13.

HPLC (UV purity, λ=214 nm): 96.4%.

Example I37.6

$R_1$=cyclohexyl, $R_2$=methyl, $R_3$=4-N-(2,6-dimethoxy-pyridin-3-yl)-benzamide 4-(5-Cyclohexylimino-4-methyl-4,5-dihydro[1,3,4]thiadiazol-2-yl)-N-(2,6-dimethoxy-pyridin-3-yl)-benzamide To a solution of LiOH monohydrate (794 mg, 19 mmol) in 18 mL of water, a solution of I37 (5.7 g, 17.2 mmol) in THF/MeOH (50:50) (100 mL) was added. The mixture was stirred at RT for 24 hours and then concentrated under reduced pressure. The residue was dissolved in water and a solution of HCl (0.1N, 361 mL) was added. The resulting mixture was stirred for 3 hours 30 minutes. After distillation of water, the crude product was dried over $P_2O_5$ in vacuo. To a suspension of 200 mg (0.5 mmol) of this crude material in $CH_2Cl_2$/DMF (50:50) (6 mL) were added cyclocarbodiimide-N-methyl resin (1.03 g, 1.5 mmol), 1-hydroxy-7-azabenzotriazol (14 mg, 0.1 mmol), N,N-diisopropylethylamine (260 μL, 1.5 mmol), 3-amino-2,6-dimethoxypyridine monohydrochloride (190 mg, 1 mmol), molecular sieves (3A) and the reaction mixture was stirred 24 hours at RT. After filtration, methylisocyanate resin (1 g, 1 mmol) was added to the filtrate, and the mixture was stirred for another 24 hours at RT. The mixture was filtered, and the filtrate was concentrated under reduced pressure. The residue was purified by silica gel chromatography eluting with a gradient of cyclohexane containing from 0% to 10% ethyl acetate to afford 60 mg of the title product. Yield: 26%.

$^1$H-NMR (400 MHz, DMSO) δ ppm: 1.15–1.35 (m, 5H), 1.50–1.60 (m, 1H), 1.70–1.80 (m, 4H), 2.55–2.65 (m, 1H), 3.50 (s, 3H), 3.85 (s, 3H), 3.90 (s, 3H), 6.35 (d, 1H), 7.70–7.80 (m, 3H), 8.00 (d, 2H), 9.65 (s, 1H).

MS (m/z)/M+1=454.

HPLC (UV purity, λ=214 nm): 99.9%.

Example I37.7

$R_1$=cyclohexyl, $R_2$=methyl, $R_3$=4-N-isopropyl-benzamide 4-(5-Cyclohexylimino-4-methyl-4,5-dihydro[1,3,4]thiadiazol-2-yl)-N-isopropyl-benzamide To a solution of LiOH monohydrate (794 mg, 19 mmol) in 18 mL of water, a solution of I37 (5.7 g, 17.2 mmol) in THF/MeOH (50:50) (100 mL) was added. The mixture was stirred at RT for 24 hours and then concentrated under reduced pressure. The residue was dissolved in water and a solution of HCl (0.1N, 361 mL) was added. The resulting mixture was stirred for 3 hours 30 minutes. After distillation of water, the crude product was dried over $P_2O_5$ in vacuo. To a suspension of 200 mg (0.5 mmol) of this crude material in $CH_2Cl_2$/DMF (50:50) (6 mL) were added cyclocarbodiimide-N-methyl resin (1.03 g, 1.5 mmol), 1-hydroxy-7-azabenzotriazol (15 mg, 0.1 mmol), N,N-diisopropylethylamine (175 μL, 1 mmol), isopropylamine (85 μL, 1 mmol), molecular sieves (3A), and the reaction mixture was stirred 24 hours at RT. After filtration, methylisocyanate resin (1 g, 1 mmol) was added to the filtrate, and the mixture was stirred for another 24 hours at RT. The mixture was filtered, and the filtrate was concentrated under reduced pressure. The residue was purified by silica gel chromatography eluting with a gradient of cyclohexane containing from 0% to 20% ethyl acetate to afford 40 mg of the title product. Yield: 22%.

$^1$H-NMR (400 MHz, DMSO) δ ppm: 1.15–1.40 (m, 11H), 1.55–1.65 (m, 1H), 1.70–1.85 (m, 4H), 2.60–2.70 (m, 1H), 3.55 (s, 3H), 4.05–4.15 (m, 1H), 7.70 (d, 2H), 7.90 (d, 2H), 8.30 (d, 1H).

MS (m/z)/M+1=359.
HPLC (UV purity, λ=214 nm): 99.9%.

Example I37.8

$R_1$=cyclohexyl, $R_2$=methyl, $R_3$=4-N-ethyl-benzamide 4-(5-Cyclohexylimino-4-methyl-4,5-dihydro[1,3,4]thiadiazol-2-yl)-N-ethyl-benzamide To a solution of 2 M ethylamine (1.8 mL, 3.6 mmol) in dichloroethane (5 mL) under nitrogen at 0° C. was added 2 M trimethylaluminium (1.8 mL, 3.6 mmol), and the mixture was stirred at RT for 15 minutes. Then, a solution of compound I37 (180 mg, 0.54 mmol) in dichloroethane (5 mL) was added, and the reaction mixture was allowed to stir for 48 hours at RT. A solution of 2 M ethylamine (0.8 mL, 1.6 mmol) and of 2 M trimethylaluminium (0.8 mL, 1.6 mmol) were added to allow reaction to completion, and the mixture was stirred at RT for another 24 hours. The mixture was diluted with 50 mL of dichloromethane and 30 mL of water, stirred for 2 hours, and filtered through Celite. The filtrate was washed with water, brine, and the organic layer was dried over $MgSO_4$, filtered, and concentrated under reduced pressure. The residue was subjected to flash chromatography eluting with a gradient of cyclohexane containing from 0% to 20% ethyl acetate to afford 60 mg of the title product. Yield: 32%.

$^1$H-NMR (400 MHz, DMSO) δ ppm: 1.20 (t, 3H), 1.20–1.50 (m, 5H), 1.60–1.70 (m, 1H), 1.80–1.95 (m, 4H), 2.70–2.80 (m, 1H), 3.35–3.45 (m, 2H), 3.65 (s, 3H), 7.90 (d, 2H), 8.05 (d, 2H), 8.65 (m, 1H).
MS (m/z)/M+1=344.7.
HPLC (UV purity, λ=214 nm): 99.9%.

Example I37.8-1

$R_1$=cyclohexyl, $R_2$=methyl, $R_3$=4-(1-ethyl-1H-tetrazol-5-yl)-phenyl

Cyclohexyl-{5-[4-(1-ethyl-1H-tetrazol-5-yl)-phenyl]-3-methyl-3H-[1,3,4]thiadiazol-2-ylidene}-amine To a solution of I37.8 (0.29 mmol, 100 mg) in acetonitrile (3 mL) at 0° C. under a nitrogen atmosphere, sodium azide (0.44 mmol, 28 mg) and trifluoromethanesulfonic anhydride (0.44 mmol, 73 μL) were added. Then, the mixture was stirred overnight at RT, and a saturated solution of $NaHCO_3$ to pH 7 was added. The aqueous layer was extracted with dichloromethane, and the organic layer was washed with water, brine, dried over magnesium sulfate, filtered, and concentrated under reduced pressure. The residue was purified by silica gel chromatography, eluting with a gradient of dichloromethane/methanol, then by HPLC (C18-HYPERSYL column), eluting with water containing from 5% to 95% acetonitrile in 20 minutes to afford the title product. Yield: 9%.

$^1$H-NMR (400 MHz, DMSO) δ ppm: 1.20–1.40 (m, 5H), 1.47 (t, 3H), 1.55–1.65 (m, 1H), 1.70–1.82 (m, 4H), 2.50–2.55 (m, 1H), 3.55 (s, 3H), 4.52 (q, 2H), 7.85–7.90 (m, 4H).
MS (m/z)/M+1=370.
HPLC (UV purity, λ=214 nm)=96.8%.

Example I37.9

$R_1$=cyclohexyl, $R_2$=methyl, $R_3$=4-N-(2-dimethylamino-ethyl)-benzamide 4-(5-Cyclohexylimino-4-methyl-4,5-dihydro[1,3,4]thiadiazol-2-yl)-N-(2-dimethylamino-ethyl)-benzamide To a solution of N,N-dimethylethylenediamine (335 μL, 3 mmol) in dichloroethane (5 mL) under nitrogen atmosphere at 0° C. was added 2 M trimethylaluminium (1.5 mL, 3 mmol), and the mixture was stirred at RT for 1 hour 30 minutes. Then, a solution of compound I37 (180 mg, 0.54 mmol) in dichloroethane (5 mL) was added, and the reaction mixture was allowed to stir for 24 hours at RT and 24 hours at 45° C. The mixture was diluted with 10 mL of dichloromethane and 20 mL of water, stirred for 1 hour 30 minutes, and filtered through Celite. The filtrate was washed with water, brine, and the organic layer was dried over $MgSO_4$, filtered, and concentrated under reduced pressure. The residue was subjected to silica gel chromatography eluting with a gradient of dichloromethane containing 0% to 5% methanol to afford 140 mg of the title product. Yield: 60%.

$^1$H-NMR (400 MHz, DMSO) δ ppm: 1.15–1.40 (m, 5H), 1.55–1.65 (m, 1H), 1.70–1.85 (m, 4H), 2.25 (s, 6H), 2.60–2.70 (m, 1H), 3.55 (s, 3H), 7.75 (d, 2H), 7.90 (d, 2H), 8.50 (m, 1H).
MS (m/z)/M+1=388.
HPLC (UV purity, λ=214 nm): 99.4%.

Example I37.10

$R_1$=cyclohexyl, $R_2$=methyl, $R_3$=4-N-pyridin-4-ylmethyl-benzamide 4-(5-Cyclohexylimino-4-methyl-4,5-dihydro[1,3,4]thiadiazol-2-yl)-N-pyridin-4-ylmethyl-benzamide To a solution of LiOH monohydrate (794 mg, 19 mmol) in 18 mL of water, a solution of compound I37 (5.7 g, 17.2 mmol) in THF/MeOH (50:50) (100 mL) was added. The mixture was stirred at RT for 24 hours and then concentrated under reduced pressure. The residue was dissolved in water and a solution of HCl (0.1N, 361 mL) was added. The resulting mixture was stirred for 3 hours 30 minutes. After distillation of water, the crude product was dried over $P_2O_5$ in vacuo. To a suspension of 200 mg (0.5 mmol) of the crude material in $CH_2Cl_2$/DMF (50:50) (6 mL) were added cyclocarbodiimide-N-methyl resin (1.03 g, 1.5 mmol), O-(7-azabenzotriazol-1-yl)-N,N,N',N'-tetramethyl-uronium hexafluorophosphate (38 mg, 0.1 mmol), N,N-diisopropylethylamine (175 μL, 1 mmol), 4-picolylamine (105 μL, 1 mmol), molecular sieves (3A), and the reaction mixture was stirred 3 days at RT. This mixture was filtered, and in the organic layer was added methylisocyanate resin (1 g, 1 mmol) and stirred 3 days at RT. After filtration, the filtrate was concentrated under reduced pressure. The solid was poured into water and the mixture was stirred for 1 hour, before extraction with dichloromethane. The organic layer was dried over $MgSO_4$, filtered, and concentrated under reduced pressure. The residue was purified by silica gel chromatography eluting with a gradient of dichloromethane containing from 0% to 5% methanol to afford 30 mg of the title product. Yield: 15%.

$^1$H-NMR (400 MHz, DMSO) δ ppm: 1.15–1.40 (m, 5H), 1.55–1.65 (m, 1H), 1.70–1.85 (m, 4H), 2.60–2.75 (m, 1H), 3.55 (s, 3H), 4.50 (d, 2H), 7.35 (d, 2H), 7.75 (d, 2H), 8.00 (d, 2H), 8.50 (d, 2H), 9.25 (m, 1H).
MS (m/z)/M+1=408.
HPLC (UV purity, λ=214 nm): 99.7%.

Example I37.11

$R_1$=cyclohexyl, $R_2$=methyl, $R_3$=4-N-methyl-N-(1-methyl-piperidin-4-yl)-benzamide 4-(5-Cyclohexylimino-4-methyl-4,5-dihydro-[1,3,4]thiadiazol-2-yl)-N-methyl-N-(1-methyl-piperidin-4-yl)-benzamide To a solution of I37.1 (0.5 mmol, 200 mg) in DMF (2.5 mL), ethyl-diisopropyl-amine (1.6 mmol, 190 μL), benzotriazol-1-yloxytris(dimethylamino)phosphonium hexafluorophosphate (0.6 mmol, 265 mg), 1-hydroxy-7-azabenzotriazole (0.25 mmol, 34 mg) and 1-methyl-4-(methylamino)piperidine (0.6 mmol, 87 µL) were added, and the reaction mixture was stirred at RT overnight. The solvent was distilled under reduced pressure, and the residue was poured into water before extraction with dichloromethane. The organic layer was washed with brine and then with a saturated solution of $NaHCO_3$, dried over magnesium sulfate, filtered, and concentrated under vacuum. The residue was purified by silica gel chromatography using a gradient of dichloromethane containing 0% to 15% methanol, to give the desired product. Yield: 93.5%.

$^1$H-NMR (400 MHz, DMSO) δ ppm: 1.23–1.45 (m, 5H), 1.55–1.65 (m, 1H), 1.68–1.85 (m, 6H), 1.85–2.00 (m, 2H), 2.23–2.44 (m, 5H), 2.55–2.65 (m, 1H), 2.83 (s, 3H), 3.00–3.10 (m, 2H), 3.55 (s, 3H), 3.85–4.03 (m, 1H), 7.48 (dd, 2H), 7.70 (dd, 2H).

MS (m/z)/M+1=428.

HPLC (UV purity, λ=214 nm): 99.4%.

Example I37.12

$R_1$=cyclohexyl, $R_2$=methyl, $R_3$=4-N-isobutyl-benzamide 4-(5-Cyclohexylimino-4-methyl-4,5-dihydro-[1,3,4]thiadiazol-2-yl)-N-isobutyl-benzamide To a solution of I37.1 (0.5 mmol, 200 mg) in DMF (2.5 mL), ethyl-diisopropyl-amine (1.6 mmol, 190 µL), benzotriazol-1-yloxytris(dimethylamino)phosphonium hexafluorophosphate (0.6 mmol, 265 mg), 1-hydroxy-7-azabenzotriazole (0.25 mmol, 34 mg) and isobutylamine (2.3 mmol, 80 µL) were added, and the reaction mixture was stirred at RT overnight. The solvent was distilled, and the residue was poured into water before extraction with dichloromethane. The organic layer was washed with brine, a saturated solution of $NaHCO_3$, dried over magnesium sulfate, filtered, and concentrated under reduced pressure to give the desired product. Yield: 86%.

$^1$H-NMR (400 MHz, DMSO) δ ppm: 0.90 (d, 6H), 1.20–1.40 (m, 5H), 1.55–1.65 (m, 1H), 1.72–1.90 (m, 5H), 2.60–2.70 (m, 1H), 3.10 (t, 2H), 3.55 (s, 3H), 7.72 (dd, 2H), 7.92 (dd, 2H), 8.55 (t, 1H).

MS (m/z)/M+1=373.

HPLC (UV purity, λ=214 nm): 98.4%.

Example I37.13

$R_1$=cyclohexyl, $R_2$=methyl, $R_3$=4-N-methyl-benzamide 4-(5-Cyclohexylimino-4-methyl-4,5-dihydro-[1,3,4]thiadiazol-2-yl)-N-methyl-benzamide To a solution of I37.1 (4.25 mmol, 1.7 g) in DMF (20.5 mL) was added N-ethyldiisopropylamine-N,N-diisopropylethylamine (13.6 mmol, 1.615 mL), benzotriazol-1-yloxytris(dimethylamino)phosphonium hexafluorophosphate (5.1 mmol, 2.265 g), 1-hydroxy-7-azabenzotriazole (2.125 mmol, 290 mg), and a solution of methylamine at [2N] in methanol (5.1 mmol, 3.55 mL). The mixture was stirred at RT overnight. The mixture was reduced under pressure vacuum and extracted with dichloromethane in water. The organic layer was washed with brine, dried over magnesium sulfate, and reduced under pressure vacuum. The residue was purified by silica gel chromatography using a gradient of dichloromethane containing 0% to 4% methanol, to give a residue which was stirred in diethylether during 1 hour. The precipitate was filtered and dried under vacuum over $P_2O_5$ to give 550 mg of the desired product. Yield: 44%.

$^1$H-NMR (400 MHz, DMSO) δ ppm: 1.18–1.45 (m, 5H), 1.55–1.68 (m, 1H), 1.68–1.83 (m, 4H), 2.60–2.70 (m, 1H), 2.80 (d, 3H), 3.55 (s, 3H), 7.82 (dd, 2H), 7.92 (dd, 2H), 8.55 (q, 1H).

MS (m/z)/M+1=331.

HPLC (UV purity, λ=214 nm): 99.9%.

Example I37.13–1

$R_1$=cyclohexyl, $R_2$=methyl, $R_3$=4-N-(2-dimethylamino-ethyl)-N-methyl-benzamide 4-(Cyclohexylimino-methyl-4,5-dihydro-[1,3,4]thiadiazol-2-yl)-N-(2-dimethylamino-ethyl)-N-methyl-benzamide To a suspension of I37.13 (0.3 mmol, 100 mg) in dimethylformamide (1 mL), sodium hydride at 60% dispersion in mineral oil (0.6 mmol, 24 mg), 2-dimethylaminoethylchloride hydrochloride (0.36 mmol, 52 mg), and $K_2CO_3$ (0.36 mmol, 50 mg) were added. The mixture was stirred overnight at 40° C. Then, potassium tert-butoxyde (0.18 mmol, 20 mg) was added, and the mixture was stirred during 24 hours. 2-Dimethylaminoethylchloride hydrochloride (0.18 mmol, 26 mg) and $K_2CO_3$ (0.18 mmol, 25 mg) were added and warmed at 40° C. overnight. The mixture was reduced under pressure vacuum to give a residue which was purified by silica gel chromatography, eluting with a gradient of dichloromethane containing from 0% to 6% methanol to afford the title product. Yield: 16%.

$^1$H-NMR (400 MHz, DMSO) δ ppm: 1.20–1.42 (m, 5H), 1.55–1.65 (m, 1H), 1.70–1.85 (m, 4H), 2.00 (s, 3H), 2.25 (s, 3H), 2.30–2.40 (m, 1H), 2.60–2.70 (m, 1H), 2.88–3.02 (m, 3H), 3.55 (s, 3H), 7.45 (dd, 2H), 7.70 (dd, 2H).

MS (m/z)/M+1=402.

HPLC (UV purity, λ=214 nm): 98.8%.

Example I37.14

$R_1$=cyclohexyl, $R_2$=methyl, $R_3$=4-(3-hydroxy-methyl-piperidin-1-carbonyl)-phenyl

[4-(5-Cyclohexylimino-4-methyl-4,5-dihydro-[1,3,4]thiadiazol-2-yl)-phenyl]-1-(3-hydroxymethyl-piperidin-1-yl)-methanone Compound I37.14 was prepared by the procedure described in Example I37.11 using I37.1 as a starting material. The residue was purified by silica gel chromatography using a gradient of dichloromethane containing 0% to 5% methanol, to give the desired product. Yield: 34%.

$^1$H-NMR (350 K, 400 MHz, DMSO) δ ppm: 1.20–1.50 (m, 7H), 1.50–1.70 (m, 3H), 1.70–1.85 (m, 5H), 2.63–2.78 (m, 2H), 2.88–2.98 (m, 1H), 3.18–3.28 (m, 1H), 3.28–3.38 (m, 1H), 3.50 (s, 3H), 3.75–4.10 (m, 2H), 4.18–4.28 (m, 1H), 7.45 (dd, 2H), 7.68 (dd, 2H).

MS (m/z)/M+1=415.

HPLC (UV purity, λ=214 nm)=95.4%.

Example I37.15

$R_1$=cyclohexyl, $R_2$=methyl, $R_3$=4-{N-[(S)-1-tert-butoxycarbonyl-2-(4-hydroxy-phenyl)-ethyl]}benzamide 2-[4-(5-Cyclohexylimino-4-methyl-4,5-dihydro-[1,3,4]thiadiazol-2-yl)-benzoylamino]-3-(4-hydroxy-phenyl)-propionic acid tert-butyl ester Compound I37.15 was prepared by the procedure described in Example I37.11 using I37.1 as a starting material. The residue was purified by silica gel chromatography using a gradient of dichloromethane containing 0% to 2% methanol and then the product was washed with water, extracted with ethyl acetate, and the organic layer was washed with brine, dried over magnesium sulfate, and reduced under pressure vacuum to give the title product. Yield: 70%.

$^1$H-NMR (400 MHz, DMSO) δ ppm: 1.20–1.40 (m, 14H), 1.55–1.65 (m, 1H), 1.70–1.80 (m, 4H), 2.58–2.68 (m, 1H), 2.91–3.01 (m, 2H), 3.52 (s, 3H), 4.45–4.51 (m, 1H), 6.65 (dd, 2H), 7.08 (dd, 2H), 7.71 (dd, 2H), 7.90 (dd, 2H), 8.75 (d, 1H), 9.15 (s, 1H).

MS (m/z)/M+1=537.

HPLC (UV purity, λ=214 nm): 96.3%.

Example I37.15-a $R_1$=cyclohexyl, $R_2$=methyl, $R_3$=4-[N-((S)-1-carboxy-2-(4-hydroxy-phenyl)-ethyl)]benzamide (S)-2-[4-(5-Cyclohexylimino-4-methyl-4,5-dihydro-[1,3,4]thiadiazol-2-yl)-benzoylamino]-3-(4-hydroxy-phenyl)-propionic acid; compound with 2,2,2-trifluoro-acetic acid To a solution of I37.15 (0.186 mmol, 100 mg) in dichloromethane (1.5 mL), trifluoroacetic acid (4.4 mmol, 378 μL) was added, and the mixture was stirred at reflux during 2 hours. The mixture was purified by silica gel chromatography, eluting with a gradient of dichloromethane containing from 0% to 10% methanol to afford 60 mg of the title product. Yield: 54%.

$^1$H-NMR (400 MHz, DMSO) δ ppm: 1.12–1.52 (m, 5H), 1.58–1.68 (m, 1H), 1.73–1.85 (m, 2H), 1.85–2.05 (m, 2H), 2.88–3.11 (m, 3H), 3.75 (s, 3H), 4.48–4.60 (m, 1H), 6.62 (dd, 2H), 7.08 (dd, 2H), 7.85 (dd, 2H), 7.95 (dd, 2H), 9.15 (s, 1H), 12.75 (s, 1H).

MS (m/z)/M+1=481.

HPLC (UV purity, λ=214 nm): 98%.

Example I37.16

$R_1$=cyclohexyl, $R_2$=methyl, $R_3$=4-(N-((S)-1-tert-butoxycarbonyl)-ethyl)benzamide (S)-2-[4-(5-Cyclohexylimino-4-methyl-4,5-dihydro-[1,3,4]thiadiazol-2-yl)-benzoylamino]-propionic acid tert-butyl ester Compound I37.16 was prepared by the procedure described in Example I37.11 using I37.1 as a starting material. The residue was purified by silica gel chromatography using a gradient of dichloromethane containing 0% to 2% methanol, and the product was washed with water, filtered, and dried under pressure vacuum with $P_2O_5$ to give the title compound. Yield: 65%.

$^1$H-NMR (400 MHz, DMSO) δ ppm: 1.20–1.40 (m, 17H), 1.55–1.65 (m, 1H), 1.70–1.82 (m, 4H), 2.58–2.68 (m, 1H), 3.52 (s, 3H), 4.35 (q, 1H), 7.73 (dd, 2H), 7.95 (dd, 2H), 8.75 (d, 1H).

MS (m/z)/M+1=445.

HPLC (UV purity, λ=214 nm): 99.3%.

Example I37.16-a $R_1$=cyclohexyl, $R_2$=methyl, $R_3$=4-(N-((S)-1-carboxy)-ethyl)benzamide (S)-2-[4-(5-Cyclohexylimino-4-methyl-4,5-dihydro-[1,3,4]thiadiazol-2-yl)-benzoylamino]-propionic acid; compound with 2,2,2-trifluoro-acetic acid To a solution of I37.16 (0.225 mmol, 100 mg) in dichloromethane (1 mL) at 0° C., trifluoroacetic acid (5.85 mmol, 457 μL) was added, and the mixture was stirred at RT overnight. The mixture was purified by silica gel chromatography, eluting with a gradient of dichloromethane containing from 0% to 5% methanol to afford 40 mg of the title product. Yield: 35%.

$^1$H-NMR (400 MHz, DMSO) δ ppm: 1.10–1.48 (m, 8H), 1.55–1.65 (m, 1H), 1.70–1.81 (m, 2H), 1.81–2.00 (m, 2H), 2.89–3.05 (m, 1H), 3.71 (s, 3H), 4.44 (q, 1H), 7.87 (dd, 2H), 8.03 (dd, 2H), 8.82 (d, 1H), 12.57 (s, 1H).

MS (m/z)/M+1=388/389.

HPLC (UV purity, λ=214 nm): 97.9%.

Example I37.17

$R_1$=cyclohexyl, $R_2$=methyl, $R_3$=4-(4-pyridin-2-yl-piperazine-1-carbonyl)-phenyl

[4-(5-Cyclohexylimino-4-methyl-4,5-dihydro-[1,3,4]thiadiazol-2-yl)-phenyl]-(4-pyridin-2-yl-piperazin-1-yl)-methanone Compound I37.17 was prepared by the procedure described in Example I37.11 using I37.1 as a starting material. The residue was purified by silica gel chromatography using a gradient of dichloromethane containing 0% to 5% methanol, and then the product was washed with water, filtered, and dried under reduced pressure over $P_2O_5$ to give the desired product. Yield: 82%.

$^1$H-NMR (400 MHz, DMSO) δ ppm: 1.15–1.48 (m, 5H), 1.55–1.65 (m, 1H), 1.70–2.00 (m, 4H), 2.62–2.92 (m, 1H), 3.35–3.87 (m, 1H), 6.67 (dd, 1H), 6.88 (d, 1H), 7.45–7.63 (m, 3H), 7.78 (dd, 2H), 8.12 (d, 1H).

MS (m/z)/M+1=463.

HPLC (UV purity, λ=214 nm): 99.9%.

Example I37.18

$R_1$=cyclohexyl, $R_2$=methyl, $R_3$=4-[4-(4-fluoro-phenyl)-piperazine-1-carbonyl]-phenyl

[4-(5-Cyclohexylimino-4-methyl-4,5-dihydro-[1,3,4]thiadiazol-2-yl)-phenyl]-[4-(4-fluoro-phenyl)-piperazin-1-yl]-methanone Compound I37.18 was prepared by the procedure described in Example I37.11 using I37.1 as a starting material. The residue was purified by silica gel chromatography using a gradient of dichloromethane containing 0% to 5% methanol, and then the product was washed with water, filtered, and dried under reduced pressure over $P_2O_5$ to give the desired product. Yield: 31%.

$^1$H-NMR (400 MHz, DMSO) δ ppm: 1.15–1.40 (m, 5H), 1.55–1.65 (m, 1H), 1.65–1.86 (m, 4H), 2.56–2.70 (m, 1H), 2.96–3.10 (m, 4H), 3.37–3.85 (m, 7H), 6.67 (dd, 1H), 6.92–7.12 (m, 4H), 7.51 (dd, 2H), 7.71 (dd, 2H).

MS (m/z)/M+1=480.

HPLC (UV purity, λ=214 nm): 98.6%.

Example I37.19

$R_1$=cyclohexyl, $R_2$=methyl, $R_3$=4-[N-(3,4,5-trimethoxy-benzyl)]-benzamide 4-(5-Cyclohexylimino-4-methyl-4,5-dihydro-[1,3,4]thiadiazol-2-yl)-N-(3,4,5-trimethoxy-benzyl)-benzamide Compound I37.19 was prepared by the procedure described in Example I37.11 using I37.1 as a starting material. The residue was purified by silica gel chromatography using a gradient of cyclohexane containing 0% to 30% ethyl acetate, to give a product which was washed with water, filtered, and dried under reduced pressure over $P_2O_5$ to give the desired product. Yield: 52%.

$^1$H-NMR (400 MHz, DMSO) δ ppm: 1.19–1.42 (m, 5H), 1.55–1.65 (m, 1H), 1.71–1.88 (m, 4H), 2.60–2.70 (m, 1H), 3.50–3.55 (m, 3H), 3.55 (s, 3H), 3.75 (s, 6H), 4.42 (d, 2H), 6.65 (s, 4H), 7.70–7.80 (m, 1H), 8.00 (d, 1H), 9.10 (t, 1H).

MS (m/z)/M+1=497.

HPLC (UV purity, λ=214 nm): 99.5%.

Example I37.20

$R_1$=cyclohexyl, $R_2$=methyl, $R_3$=4-(4-pyrimidin-2-yl-piperazin-1-carbonyl)-phenyl

[4-(5-Cyclohexylimino-4-methyl-4,5-dihydro-[1,3,4]thiadiazol-2-yl)-phenyl]-(4-pyrimidin-2-yl-piperazin-1-yl)-methanone Compound I37.20 was prepared by the procedure described in Example I37.11 using I37.1 as a starting material. The residue was purified by silica gel chromatography using a gradient of dichloromethane containing 0% to 1% methanol, to give a product which was washed with water, filtered, and dried under reduced pressure over $P_2O_5$ to give the desired product. Yield: 4%.

$^1$H-NMR (400 MHz, DMSO) δ ppm: 1.15–1.41 (m, 5H), 1.55–1.65 (m, 1H), 1.68–1.75 (m, 4H), 2.55–2.70 (m, 1H), 3.00–3.90 (m, 11H), 6.65 (t, 1H), 6.88 (d, 1H), 7.50 (dd, 2H), 7.70 (dd, 2H), 8.38 (d, 2H).

MS (m/z)/M+1=464.

HPLC (UV purity, λ=214 nm): 97%.

Example I37.21

$R_1$=cyclohexyl, $R_2$=methyl, $R_3$=4-(4-methyl-piperazine-1-carbonyl)-phenyl

[4-(5-Cyclohexylimino-4-methyl-4,5-dihydro-[1,3,4]thiadiazol-2-yl)-phenyl]-(4-methyl-piperazin-1-yl)-methanone Compound I37.21 was prepared by the procedure described in Example I37.11 using I37.1 as a starting material. The residue was purified by silica gel chromatography using a gradient of dichloromethane containing 0% to 10% methanol, to give a product which was washed with water, filtered, and dried under reduced pressure over $P_2O_5$ to give the desired product. Yield: 55%.

$^1$H-NMR (400 MHz, DMSO) δ ppm: 1.18–1.40 (m, 5H), 1.55–1.65 (m, 1H), 1.69–1.81 (m, 4H), 2.25 (s, 3H), 2.33–2.52 (m, 4H), 2.59–2.69 (m, 1H), 3.25–3.45 (m, 2H), 3.52 (s, 3H), 3.55–3.70 (m, 2H), 7.78 (dd, 2H), 7.71 (dd, 2H).

MS (m/z)/M+1=400.

HPLC (UV purity, λ=214 nm): 99.6%.

Example I37.22

$R_1$=cyclohexyl, $R_2$=methyl, $R_3$=4-[N-(3-(4-methyl-piperazin-1-yl)-propyl)]benzamide 4-(5-Cyclohexylimino-4-methyl-4,5-dihydro-[1,3,4]thiadiazol-2-yl)-N-[3-(4-methyl-piperazin-1-yl)-propyl]-benzamide Compound I37.22 was prepared by the procedure described in Example I37.11 using I37.1 as a starting material. The residue was purified by silica gel chromatography using a gradient of dichloromethane containing 0% to 10% methanol, to give a product which was stirred in diethylether, filtered, and dried under reduced pressure over $P_2O_5$ to give the desired product. Yield: 3.5%.

$^1$H-NMR (400 MHz, CDCl$^3$) δ ppm: 1.20–1.50 (m, 5H), 1.60–2.05 (m, 7H), 2.35 (s, 3H), 2.48–2.85 (m, 11H), 3.52–3.64 (m, 2H), 3.50 (s, 3H), 7.68 (dd, 2H), 7.87 (dd, 2H), 8.00–8.08 (m, 1H).

MS (m/z)/M+1=457.

HPLC (UV purity, λ=214 nm): 97.2%.

Example I37.23

$R_1$=cyclohexyl, $R_2$=methyl, $R_3$=4-N-[(1-ethyl-pyrrolidin-2-ylmethyl)-benzamide 4-(5-Cyclohexylimino-4-methyl-4,5-dihydro-[1,3,4]thiadiazol-2-yl)-N-(1-ethyl-pyrrolidin-2-ylmethyl)-benzamide To a solution of 2-(aminomethyl)-1-ethylpyrrolidine (7.5 mmol, 967 mg) in dichloroethane (10 mL) under nitrogen atmosphere was added dropwise trimethylaluminium [2N] in toluene (7.5 mmol, 3.8 mL), and the mixture was stirred at RT during 2 hours. A solution of compound I37 (1.5 mmol, 500 mg) in dichloroethane (10 mL) was then added, and the stirring was pursued at 65° C. overnight. At RT, dichloromethane (30 mL) and water (50 mL) were added, and the mixture was stirred several hours. The mixture was filtered through Celite, extracted with dichloromethane, washed with water and brine, dried over magnesium sulfate, filtered, and concentrated under reduced pressure. The residue purified by silica gel chromatography eluting with a gradient of dichloromethane containing from 0% to 10% methanol to afford the desired product. Yield: 79%.

$^1$H-NMR (400 MHz, DMSO) δ ppm: 1.05 (t, 3H), 1.20–1.42 (m, 5H), 1.55–1.70 (m, 4H), 1.70–1.85 (m, 5H), 2.10–2.18 (m, 1H), 2.25–2.35 (m, 1H), 2.55–2.70 (m, 2H), 2.80–2.90 (m, 1H), 3.00–3.12 (m, 2H), 3.39–3.49 (m, 1H), 3.55 (s, 3H), 7.71 (dd, 2H), 7.92 (dd, 2H), 8.49 (t, 1H).

MS (m/z)/M+1=428.

HPLC (UV purity, λ=214 nm): 99.2%.

Example I37.24

$R_1$=cyclohexyl, $R_2$=methyl, $R_3$=4-N-[(pyridin-3-ylmethyl)-benzamide 4-(5-Cyclohexylimino-4-methyl-4,5-dihydro-[1,3,4]thiadiazol-2-yl)-N-pyridin-3-ylmethyl-benzamide Compound I37.24 was prepared by the procedure described in Example I37.23 using appropriate intermediates and reagents (I37 and 2-(aminoethyl)pyridine). The residue was purified by silica gel chromatography eluting with a gradient of dichloromethane containing from 0 to 8% methanol to afford the desired product. Yield: 34%.

$^1$H-NMR (400 MHz, DMSO) δ ppm: 1.20–1.42 (m, 5H), 1.55–1.65 (m, 1H), 1.70–1.85 (m, 4H), 2.60–2.70 (m, 1H), 3.55 (s, 3H), 4.50 (d, 2H), 7.35–7.40 (m, 1H), 7.70–7.80 (m, 3H), 8.00 (dd, 2H), 8.45–8.50 (m, 1H), 8.57 (s, 1H), 9.30 (t, 1H).

MS (m/z)/M+1=408.

HPLC (UV purity, λ=214 nm): 98.6%.

Example I37.25

$R_1$=cyclohexyl, $R_2$=methyl, $R_3$=4-(N-benzyl)-benzamide

N-Benzyl-4-(5-cyclohexylimino-4-methyl-4,5-dihydro-[1,3,4]thiadiazol-2-yl)-benzamide Compound I37.25 was prepared by the procedure described in Example I37.23 using appropriate intermediates and reagents (I37 and benzylamine). The residue was purified by silica gel chromatography eluting with a gradient of dichloromethane containing from 0 to 2% methanol to afford the desired product. Yield: 34%.

$^1$H-NMR (400 MHz, DMSO) δ ppm: 1.15–1.40 (m, 5H), 1.55–1.65 (m, 1H), 1.65–1.85 (m, 4H), 2.55–2.70 (m, 1H), 3.52 (s, 3H), 4.48 (d, 2H), 7.19–7.39 (m, 5H), 7.72 (dd, 2H), 7.98 (dd, 2H), 9.13 (t, 1H).

MS (m/z)/M+1=407.

HPLC (UV purity, λ=214 nm): 99.2%.

Example I37.26

R₁=cyclohexyl, R₂=methyl, R₃=4-[N-(1-benzyl-piperidin-4-yl)]-benzamide

N-(1-Benzyl-piperidin-4-yl)-4-(5-cyclohexylimino-4-methyl-4,5-dihydro-[1,3,4]thiadiazol-2-yl)-benzamide Compound I37.26 was prepared by the procedure described in Example I37.23 using appropriate intermediates and reagents (I37 and 4-amino-1-benzylpiperidine). The residue was purified by silica gel chromatography eluting with a gradient of dichloromethane containing from 0% to 8% methanol to afford the desired product. Yield: 50%.

$^1$H-NMR (400 MHz, DMSO) δ ppm: 1.15–1.40 (m, 5H), 1.53–1.65 (m, 3H), 1.70–1.83 (m, 6H), 1.97–2.07 (m, 2H), 2.70–2.80 (m, 1H), 2.77–2.87 (m, 2H), 3.47 (s, 2H), 3.55 (s, 3H), 3.70–3.85 (m, 1H), 7.22–7.35 (m, 5H), 7.70 (dd, 2H), 7.93 (dd, 2H), 8.35 (d, 1H).

MS (m/z)/M+1=490.

HPLC (UV purity, λ=214 nm): 96.4%.

Example I37.27

R₁=cyclohexyl, R₂=methyl, R₃=4-[N-(2-ethyl-2H-pyrazol-3-yl)]-benzamide 4-(5-Cyclohexylimino-4-methyl-4,5-dihydro-[1,3,4]thiadiazol-2-yl)-N-(2-ethyl-2H-pyrazol-3-yl)-benzamide Compound I37.27 was prepared by the procedure described in Example I37.23 using appropriate intermediates and reagents (I37 and 5-amino-1-ethylpyrazole). The residue was purified by silica gel chromatography eluting with a gradient of dichloromethane containing from 0% to 6% methanol, and then the solid was stirred in diethylether during 15 minutes, filtered, and dried under reduced pressure to give the title product. Yield: 26%.

$^1$H-NMR (400 MHz, DMSO) δ ppm: 1.20–1.45 (m, 8H), 1.60–1.70 (m, 1H), 1.75–1.87 (m, 4H), 2.63–2.73 (m, 1H), 3.55 (s, 3H), 4.05 (q, 2H), 6.25 (d, 1H), 7.45 (d, 1H), 7.83 (dd, 2H), 8.10 (dd, 2H), 10.40 (s, 1H).

MS (m/z)/M+1=411.

HPLC (UV purity, λ=214 nm): 99.7%.

Example I37.28

R₁=cyclohexyl, R₂=methyl, R₃=4-(2-morpholin-4-yl-ethyl)-benzamide 4-(5-Cyclohexylimino-4-methyl-4,5-dihydro-[1,3,4]thiadiazol-2-yl)-N-(2-morpholin-4-yl-ethyl)-benzamide Compound I37.28 was prepared by the procedure described in Example I37.23 using appropriate intermediates and reagents (I37 and N-(2-aminoethyl)morpholine). The residue was purified by silica gel chromatography eluting with a gradient of dichloromethane containing from 0% to 6% methanol, and then the solid was stirred in diethylether during 15 minutes, filtered, and dried under reduced pressure to give the title product. Yield: 21%.

$^1$H-NMR (400 MHz, DMSO) δ ppm: 1.15–1.40 (m, 5H), 1.55–1.63 (m, 1H), 1.70–1.83 (m, 5H), 2.35–2.50 (m, 6H), 2.57–2.67 (m, 1H), 3.38 (q, 2H), 3.50 (s, 3H), 3.52–3.57 (m, 4H), 7.80 (dd, 2H), 7.90 (dd, 2H), 8.50 (t, 1H).

MS (m/z)/M+1=430.

HPLC (UV purity, λ=214 nm): 99.9%.

Example I37.28-1

R₁=cyclohexyl, R₂=methyl, R₃=4-[(N-cyano-N'-ethylmorpholine)-carboxyimidamine]-phenyl

[5-(4-((N-cyano-N'-ethylmorpholine)-carboximidamide)-phenyl)-3-methyl-3H-[1,3,4]thiadiazol-2-ylidene]-cyclohexyl-amine To a solution of I37.28 (2.33 mmol, 1 g) in toluene (15 mL), Lawesson's reagent (4.65 mmol, 1.88 g) was added, and the mixture was stirred overnight at reflux. After cooling at RT, the mixture was acidified with a solution of HCl at 5% (3.5 mL) then basified with a solution of NaHCO₃. The aqueous layer was extracted with ethyl acetate, and the combined organic layers were washed with water, brine, dried over magnesium sulfate, filtered, and concentrated under reduced pressure. The residue was purified by silica gel chromatography to give 4-(5-cyclohexylimino-4-methyl-4,5-dihydro-[1,3,4]thiadiazol-2-yl)-N(2-morpholin-4-yl-ethyl)thiobenzamide. Yield: 56%.

$^1$H-NMR (400 MHz, DMSO) δ ppm: 1.15–1.40 (m, 5H), 1.55–1.65 (m, 1H), 1.70–1.83 (m, 4H), 2.60–2.75 (m, 3H), 3.52 (s, 3H), 3.55–3.63 (m, 4H), 3.78 (t, 2H), 3.80–3.90 (m, 2H), 7.70 (dd, 2H), 7.82 (dd, 2H), 10.28 (t, 1H).

To a solution of 4-(5-cyclohexylimino-4-methyl-4,5-dihydro-[1,3,4]thiadiazol-2-yl)-N(2-morpholin-4-yl-ethyl) thiobenzamide (1.12 mmol, 500 mg) in THF (20 mL), sodium hydride (60% dispersion in mineral oil, 1.12 mmol, 44 mg) was added, and the mixture was warmed at reflux during 1 hour. After cooling at RT, methyl iodide (1.35 mmol, 84 μL) was added, and the mixture was warmed 4 hours at reflux and then overnight at RT. The mixture was concentrated under reduced pressure to give a crude material which was solubilized in ethanol (50 mL). To this solution, cyanamide (1.8 mmol, 75 mg) and triethylamine (0.9 mmol, 125 μL) were added, and the mixture was stirred 2 days at reflux. Mercury(II)chloride (1.68 mmol, 457 mg) and cyanamide (2.35 mmol, 100 mg) were added, and the reaction was allowed to stir 3 days at RT. The mixture was concentrated under reduced pressure, and the residue was diluted in ethyl acetate and filtered through Celite. The filtrate was concentrated under vacuum. The residue was chromatographed on silica gel using a gradient of dichloromethane containing from 0% to 5% methanol to afford the title compound. Yield: 17%.

$^1$H-NMR (400 MHz, DMSO) δ ppm: 1.18–1.42 (m, 5H), 1.55–1.65 (m, 1H), 1.70–1.85 (m, 4H), 2.40–2.50 (m, 4H), 2.50–2.60 (m, 2H), 2.60–2.70 (m, 1H), 3.45–3.55 (m, 2H), 3.55 (s, 3H), 3.55–3.65 (m, 4H), 7.68 (dd, 2H), 7.52 (dd, 2H), 9.15 (t, 1H).

MS (m/z)/M+1=454.

HPLC (UV purity, λ=214 nm): 95%.

Example I37.29

R₁=cyclohexyl, R₂=methyl, R₃=4-N-(2-pyrrolidin-1-yl-ethyl)-benzamide 4-(5-Cyclohexylimino-4-methyl-4,5-dihydro-[1,3,4]thiadiazol-2-yl)-N-(2-pyrrolidin-1-yl-ethyl)-benzamide Compound I37.29 was prepared by the procedure described in Example I37.23 using appropriate intermediates and reagents (I37 and 1-(2-aminoethyl)pyrolidine). The residue was purified by silica gel chromatography eluting with a gradient of dichloromethane containing from 0% to 14% methanol to afford the desired product. Yield: 26%.

$^1$H-NMR (400 MHz, DMSO) δ ppm: 1.20–1.45 (m, 5H), 1.60–1.87 (m, 9H), 2.45–2.70 (m, 7H), 3.35–3.45 (m, 2H), 3.60 (s, 3H), 7.73 (dd, 2H), 7.95 (dd, 2H), 8.55 (t, 1H).

MS (m/z)/M+1=414.

HPLC (UV purity, λ=214 nm): 99.9%.

Protocal D

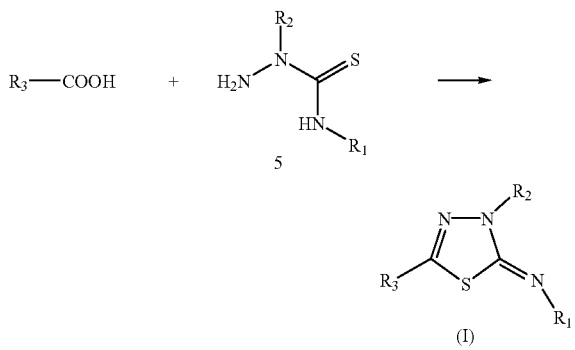

Example I

Protocol D

Example I15

R₁=cyclohexyl, R₂=methyl, R₃=4-methylsulfonyl-phenyl
Cyclohexyl-[5-(4-methanesulfonyl-phenyl)-3-methyl-3H-[1,3,4]thiadiazol-2-ylidene]-amine To a mixture of 4-methylsulfonyl-benzoic acid (2.5 mmol, 500 mg), 2-methylthiosemicarbazide (5a) (2.5 mmol, 468 mg) in anhydrous dioxane (5 mL) at 65° C., POCl₃ (3 mmol, 280 μL) was added, and the mixture was warmed at 95° C. for 5 hours. The solvent was removed by distillation under reduced pressure to give a crude material which was basified at pH 8–7 with a saturated solution of NaHCO₃. The aqueous phase was extracted with dichloromethane. The organic layer was washed with saturated solution of NaCl, dried over magnesium sulfate, filtered, and distilled to give a residue which was purified by silica gel chromatography (eluted with a gradient of cyclohexane/ethyl acetate finishing with the ratio 80:20) to afford 230 mg of the title compound. Yield: 26%.

¹H-NMR (400 MHz, DMSO) δ ppm: 1.25–1.45 (m, 5H), 1.65–1.75 (m, 1H), 1.75–1.95 (m, 4H), 1.70–1.80 (m, 1H), 3.35 (s, 3H), 3.65 (s, 3H), 8.05 (dd, 4H).

MS (m/z)/M+1=352.5.
HPLC (UV purity, λ=214 nm): 95.3%.

The compounds of the following examples were prepared by the procedure described in Example I15 using appropriate intermediates and reagents:

I15.1 [3-(5-Cyclohexylimino-4-methyl-4,5-dihydro-[1,3,4]thiadiazol-2-yl)-phenyl]-dimethyl-amine
I15.2 Cyclohexyl-[5-(3-methoxy-4-nitro-phenyl)-3-methyl-3H-[1,3,4]thiadiazol-2-ylidene]-amine Example I38

R₁=cyclohexyl, R₂=Me, R₃=3-pyridyl
Cyclohexyl-(3-methyl-5-pyridin-3-yl-3H-[1,3,4]thiadiazol-2-ylidene)-amine Compound I38 was prepared by the procedure described in Example I15 (Protocol D) using appropriate intermediates and reagents. The title product was isolated by chromatography on silica gel eluting with cyclohexane containing from 0 to 10% ethyl acetate. Yield: 0.06 g, 13.5%.

¹H-NMR (400 MHz, DMSO) δ ppm: 1.20–1.44 (m, 5H), 1.59–1.64 (m, 1H), 1.73–1.83 (b, 4H), 2.61–2.70 (b, 1H), 3.54 (s, 3H), 7.50–7.53 (m, 1H), 8.04 (d, 1H), 8.63–8.67 (m, 1H), 8.85 (s, 1H).

MS (m/z)/M+1=275/276.
HPLC (UV purity, λ=214 nm): 95.87%.

Example I39

R₁=cyclohexyl, R₂=methyl, R₃=3-sulfamoyl-phenyl
3-(5-Cyclohexylimino-4-methyl-4,5-dihydro-[1,3,4]thiadiazol-2-yl)-benzenesulfonamide Compound I39 was prepared by the procedure described in Example I15 (Protocol D) using appropriate intermediates and reagents. The title product was isolated by chromatography on silica gel eluting with dichloromethane containing from 0% to 5% methanol. Yield: 8.0%.

¹H-NMR (400 MHz, DMSO) δ ppm: 1.18–1.41 (m, 5H), 1.58–1.63 (m, 1H), 1.73–1.84 (m, 4H), 2.60–2.67 (m, 1H), 3.56 (s, 3H), 7.48 (s, 2H), 7.67 (t, 1H), 7.82–7.90 (m, 2H), 8.12 (s, 1H).

MS (m/z)/M+1=353/354.
HPLC (UV purity, λ=214 nm): 97.55%.

Example I40

R₁=cyclohexyl, R₂=methyl, R₃=benzo[1,3]dioxol-5-yl
(5-Benzo[1,3]dioxol-5-yl-3-methyl-3H-[1,3,4]thiadiazol-2-ylidene)-cyclohexyl-amine Compound I40 was prepared by the procedure described in Example I15 (Protocol D) using appropriate intermediates and reagents. The title product was isolated by chromatography on silica gel eluting with cyclohexane containing from 0% to 15% ethyl acetate. Yield: 27%.

¹H-NMR (400 MHz, DMSO) δ ppm: 1.20–1.45 (m, 5H), 1.60–1.70 (m, 1H), 1.70–1.85 (m, 4H), 2.60–2.70 (m, 1H), 3.50 (s, 3H), 6.15 (s, 2H), 7.00 (d, 1H), 7.15 (d, 1H), 7.25 (s, 1H).

MS (m/z)/M+1=318.
HPLC (UV purity, λ=214 nm): 99.9%.

Example I41

R₁=cyclohexyl, R₂=methyl, R₃=3,4,5-trimethoxyphenyl
Cyclohexyl-[3-methyl-5-(3,4,5-trimethoxy-phenyl)-3H-[1,3,4]thiadiazol-2-ylidene]-amine Compound I41 was prepared by the procedure described in Example I15 (Protocol D) using appropriate intermediates and reagents. The title product was isolated by chromatography on silica gel eluting with heptane containing from 0% to 20% diethylether. Yield: 26%.

¹H-NMR (400 MHz, DMSO) δ ppm: 1.15–1.50 (m, 5H), 1.55–1.65 (m, 1H), 1.70–1.85 (m, 4H), 2.65–2.70 (m, 1H), 3.50 (s, 3H), 3.70 (s, 3H), 3.85 (s, 6H), 6.90 (s, 2H).

MS (m/z)/M+1=364.49.
HPLC (UV purity, λ=214 nm): 99.9%.

Example I

Protocol A

Example I42

R₁=cyclopentyl, R₂=methyl, R₃=4-cyano-phenyl
4-(5-Cyclopentylimino-4-methyl-4,5-dihydro-[1,3,4]thiadiazol-2-yl)-benzonitrile To a suspension of 1,3,4-thiadiazolium perchlorate (3c) (0.86 mmol, 300 mg) in ethanol (20 mL), cyclopentylamine (1.03 mmol, 102 μL), and triethylamine (1.03 mmol, 264 μL) were added, and the mixture was stirred at reflux overnight. The mixture was concentrated by distillation of the solvent, and the crude material was solubilized in ethyl acetate. The inorganic salts were removed by extraction with water. The organic layer was washed with water and a solution of NaCl, dried under magnesium sulphate, filtered, and distilled to give a residue which was chromatographed on silica gel column (using a gradient of solvent ethyl acetate-cyclohexane starting with a ratio 0:100 to 20:80) to isolate 210 mg of the pure product. Yield: 85.7%.

$^1$H-NMR (400 MHz, DMSO) δ ppm: 1.40–1.95 (m, 8H), 3.15–3.25 (m, 1H), 3.50 (s, 3H), 7.80 (dd, 2H), 7.92 (dd, 2H).

MS (m/z)/M+1=285.

Example I43

$R_1$=cycloheptyl, $R_2$=methyl, $R_3$=4-cyanophenyl 4-(5-Cycloheptylimino-4-methyl-4,5-dihydro-[1,3,4] thiadiazol-2-yl)-benzonitrile The compound I43 was prepared by the procedure described in Example I42 using the appropriate intermediates and reagents (Protocol A). The residue was purified by chromatography on silica gel eluting with a gradient of cyclohexane containing from 0% to 20% ethyl acetate. Yield: 70.6%.

$^1$H-NMR (400 MHz, DMSO) δ ppm: 1.40–1.85 (m, 12H), 2.75–2.85 (m, 1H), 3.50 (s, 3H), 7.80 (dd, 2H), 7.90 (dd, 2H).

MS (m/z)/M+1=313.

Example I44

$R_1$=4-fluorophenyl, $R_2$=methyl, $R_3$=4-cyano-phenyl

4-[5-(4-Fluoro-phenylimino)-4-methyl-4,5-dihydro-[1,3,4] thiadiazol-2-yl]-benzonitrile The compound I44 was prepared by the procedure described in Example I42 using the appropriate intermediates and reagents (Protocol A). The residue was purified by chromatography on silica gel eluting with a gradient of cyclohexane containing from 0% to 20% ethyl acetate. Yield: 71.1%.

$^1$H-NMR (400 MHz, DMSO) δ ppm: 3.72 (s, 3H), 7.03–7.10 (m, 2H), 7.16–7.25 (m, 2H), 7.83 (dd, 2H), 7.93 (dd,2H).

MS (m/z)/M+1=311.

Example I45

$R_1$=3-phenol, $R_2$=methyl, $R_3$=4-cyano-phenyl

4-[5-(3-Hydroxy-phenylimino)-4-methyl-4,5-dihydro-[1,3,4]thiadiazol-2-yl]-benzonitrile The compound I45 was prepared by the procedure described in Example I42 using the appropriate intermediates and reagents (Protocol A). The residue was purified by chromatography on silica gel eluting with a gradient of dichloromethane containing from 0% to 20% methanol. Yield: 99%.

$^1$H-NMR (400 MHz, DMSO) δ ppm: 3.70 (s, 3H), 6.41–6.55 (m, 3H), 7.15 (t, 1H), 7.82 (dd, 2H), 7.91 (dd, 2H), 9.42 (s, 1H).

MS (m/z)/M+1=309.

Example I46

$R_1$=4-fluoro-3-benzoic acid, $R_2$=methyl, $R_3$=4-cyano-phenyl

5-[5-(4-Cyano-phenyl)-3-methyl-3H-[1,3,4]thiadiazol-2-ylideneamino]-2-fluoro-benzoic acid The compound I46 was prepared by the procedure described in Example I42 using the appropriate intermediates and reagents (Protocol A). In this particular case, the residue was precipitated in ethyl acetate to afford the pure product. Yield: 65.5%.

$^1$H-NMR (400 MHz, DMSO) δ ppm: 3.74 (s, 3H), 7.24–7.37 (m, 3H), 7.44–7.51 (m, 1H), 7.85 (dd, 2H), 7.94 (dd, 2H), 13.31 (b, 1H).

MS (m/z)/M+1=355.

Example I47

$R_1$=4-methyl-cyclohexyl, $R_2$=methyl, $R_3$=4-cyano-phenyl

I47a: 4-[4-Methyl-5-(cis-4-methyl-cyclohexylimino)-4,5-dihydro-[1,3,4]thiadiazol-2-yl]-benzonitrile I47b: 4-[4-Methyl-5-(trans-4-methyl-cyclohexylimino)-4,5-dihydro-[1,3,4]thiadiazol-2-yl]-benzonitrile The compound I47 was prepared by the procedure described in Example I42 using the appropriate intermediates and reagents (Protocol A). The residue was purified by chromatography on silica gel eluting with a gradient of cyclohexane containing from 0% to 20% ethyl acetate to give the cis and trans isomers. Yield: 68.6%.

Compound cis: I47a $^1$H-NMR (400 MHz, DMSO) δ ppm: 0.92 (d, 3H), 1.38–1.68 (m, 9H), 2.85–2.92 (m, 1H), 3.55 (s, 3H), 7.80 (dd, 2H), 7.92 (dd, 2H).

MS (m/z)/M+1=313.

Compound trans: I47b $^1$H-NMR (400 MHz, DMSO) δ ppm: 0.88 (d, 3H), 0.94–1.09 (m, 2H), 1.30–1.45 (m, 3H), 1.64–1.83 (m, 4H), 2.48–2.60 (m, 1H), 3.52 (s, 3H), 7.80 (dd, 2H), 7.92 (dd, 2H).

MS (m/z)/M+1=313.

Example I48

$R_1$=trans-4-hydroxycyclohexyl, $R_2$=methyl, $R_3$=4-cyano-phenyl

4-[5-(trans-4-Hydroxy-cyclohexylimino)-4-methyl-4,5-dihydro-[1,3,4]thiadiazol-2-yl]-benzonitrile The compound I48 was prepared by the procedure described in Example I42 using the appropriate intermediates and reagents (Protocol A). Using 0.86 mmol of thiadiazolium, an excess of trans-4-aminocyclohexanol hydrochloride (7.7 mmoL) and 8.6 mmol of triethylamine. The residue was purified by chromatography on silica gel eluting with a gradient of cyclohexane containing from 0% to 30% ethyl acetate. Yield: 74%.

$^1$H-NMR (400 MHz, DMSO) δ ppm: 1.18–1.42 (m, 4H), 1.73–1.89 (m, 4H), 2.52–2.62 (m, 1H), 3.40–3.50 (m, 1H), 3.53 (s, 3H), 4.50 (s, 1H), 7.80 (dd, 2H), 7.92 (dd, 2H).

MS (m/z)/M+1=315.

HPLC (UV purity, λ=214 nm): 99.9%.

Example I49

R₁=exo-2-norbornyl, R₂=methyl, R₃=4-cyano-phenyl

4-[5-(Bicyclo[2.2.1]hept-2-ylimino)-4-methyl-4,5-dihydro-[1,3,4]thiadiazol-2-yl]-benzonitrile The compound I49 was prepared by the procedure described in Example I48 using the appropriate intermediates and reagents (Protocol A). The residue was purified by chromatography on silica gel eluting with a gradient of cyclohexane containing from 0% to 8% ethyl acetate. Yield: 64%

$^1$H-NMR (400 MHz, DMSO) δ ppm: 1.10–1.20 (m, 3H), 1.26–1.35 (m, 1H), 1.40–1.53 (m, 2H), 1.56–1.61 (m, 1H), 1.70–1.79 (m, 1H), 2.09–2.14 (m, 1H), 2.24–2.29 (m, 1H), 2.71–2.78 (m, 1H), 3.52 (s, 3H), 7.80 (dd, 2H), 7.91 (dd, 2H).

MS (m/z)/M+1=311.

HPLC (UV purity, λ=214 nm): 99.2%.

Example I50

R₁=(1R*,2R*)-2-hydroxy-cyclohexyl, R₂=methyl, R₃=4-cyano-phenyl

4-[5-((1R*,2R*)-2-Hydroxy-cyclohexylimino)-4-methyl-4,5-dihydro-[1,3,4]thiadiazol-2-yl]-benzonitrile The compound I50 was prepared by the procedure described in Example I48 using the appropriate intermediates and reagents (Protocol A). The residue was purified by chromatography on silica gel eluting with a gradient of cyclohexane containing from 0% to 50% ethyl acetate. Yield: 74%.

$^1$H-NMR (400 MHz, DMSO) δ ppm: 1.15–1.40 (m, 5H), 1.58–1.75 (m, 3H), 1.80–1.90 (m, 1H), 2.38–2.49 (m, 1H), 3.30–3.40 (m, 1H), 3.55 (s, 3H), 4.50 (s, 1H), 7.80 (dd, 2H), 7.92 (dd, 2H).

MS (m/z)/M+1=315.

HPLC (UV purity, λ=214 nm): 99.9%.

Example I51

R₁=(1R*,2S*)-2-hydroxycyclohexyl, R₂=methyl, R₃=4-cyano-phenyl

4-[5-((1R*,2S*)-2-Hydroxy-cyclohexylimino)-4-methyl-4,5-dihydro-[1,3,4]thiadiazol-2-yl]-benzonitrile Compound I51 was prepared by the procedure described in Example I42 using the appropriate intermediates and reagents (Protocol A). 1,3,4-Thiadiazolium perchlorate (0.287 mmol, 100 mg) in ethanol (6 mL), cis-2-aminocyclohexanol hydrochloride (2.58 mmol, 390 mg), and triethylamine (2.87 mmol, 400 μL) were added. The residue was purified by chromatography on silica gel eluting with a gradient of cyclohexane containing from 0% to 30% ethyl acetate. Yield: 72%.

$^1$H-NMR (400 MHz, DMSO) δ ppm: 1.15–1.80 (m, 8H), 2.83–2.97 (m, 1H), 3.52–3.70 (m, 4H), 4.10–4.20 (m, 1H), 7.80 (dd, 2H), 7.94 (dd, 2H).

MS (m/z)/M+1=315.

HPLC (UV purity, λ=214 nm): 98.7%.

Examples I52-a and I52-b

R₁=3-hydroxycyclohexyl, R₂=methyl, R₃=4-cyano-phenyl

I52-a: 4-[5-((1R*,3R*)-3-Hydroxy-cyclohexylimino)-4-methyl-4,5-dihydro-[1,3,4]thiadiazol-2-yl]-benzonitrile
I52-b: 4-[5-((1R*,3S*)-3-Hydroxy-cyclohexylimino)-4-methyl-4,5-dihydro-[1,3,4]thiadiazol-2-yl]-benzonitrile The compounds I52-a and I52-b were prepared by the procedure described in Example I42 using the appropriate intermediates and reagents (Protocol A). A mixture of 1,3,4-thiadiazolium perchlorate (3c) (3.5 mmol, 1.22 g) in ethanol (80 mL), racemic-3-aminocyclohexanol (4.2 mmol, 485 mg), and triethylamine (4.2 mmol, 587 μL) was stirred at reflux during 4 hours. The residue was purified by chromatography on silica gel eluting with a gradient of cyclohexane containing from 0% to 60% ethyl acetate to give 120 mg of the trans isomer and 260 mg cis isomer. Yield: 11%.

1R*,3R* isomer (I52a)

$^1$H-NMR (400 MHz, DMSO) δ ppm: 1.35–1.50 (m, 2H), 1.50–1.70 (m, 6H), 3.04–3.12 (m, 1H), 3.54 (s, 3H), 3.88–3.96 (m, 1H), 4.44 (d, 1H), 7.80 (dd, 2H), 7.94 (dd, 2H).

1R*,3S* isomer (I52b)

$^1$H (400 MHz, DMSO) δ ppm: 1.03–1.30 (m, 4H), 1.64–1.78 (m, 2H), 1.78–1.87 (m, 1H), 1.98–2.04 (m, 1H), 2.58–2.70 (m, 1H), 3.40–3.58 (m, 4H), 4.61 (s, 1H), 7.44 (s, 1H), 7.70 (dd, 2H), 7.95 (dd, 2H), 8.07 (s, 1H).

Example I53

R₁=(1R*,3R*)-3-hydroxy-cyclohexyl, R₂=methyl, R₃=4-(methylsulfonyl)phenyl (1R*,3R*)-3-[5-(4-Methanesulfonyl-phenyl)-3-methyl-3H-[1,3,4]thiadiazol-2-ylideneamino]-cyclohexanol The compound I53 was prepared by the procedure described in Example I42 using the appropriate intermediates and reagents (Protocol A). A mixture of 1,3,4-thiadiazolium perchlorate (3b) (1 mmol, 400 mg), ethanol (25 mL), 3-aminocyclohexanol (1.2 mmol, 140 mg), and triethylamine (2.5 mmol, 350 μL) was stirred at reflux during 3 hours. The residue was purified by chromatography on silica gel eluting with a gradient of cyclohexane containing from 0% to 50% ethyl acetate. The product was then purified by HPLC on Kromasil C18 column with a gradient of acetonitrile/water 95:5 to 5:95 to give the pure product. Yield: 10%.

$^1$H-NMR (400 MHz, DMSO) δ ppm: 1.30–1.69 (m, 8H), 3.00–3.10 (m, 1H), 3.21 (s, 3H), 3.52 (s, 3H), 3.82–3.95 (m, 1H), 4.35 (d, 1H), 7.85 (dd, 2H), 7.98 (dd, 2H).

MS (m/z)/M+1=367/369.

HPLC (UV purity, λ=214 nm): 98.9%.

Example I54

R₁=(1R*,3R*)-3-hydroxy-cyclohexyl, R₂=methyl, R₃=4-benzoic acid

4-[5-(1R*,3R*)-3-Hydroxy-cyclohexylimino)-4-methyl-4,5-dihydro-[1,3,4]thiadiazol-2-yl]-benzoic acid To a solution of I52a (3.18 mmol, 1 g) in isopropanol (20 mL), a solution of KOH [6N] (15.9 mmol, 2.6 mL) was added, and the mixture was stirred at reflux during 4 days. The mixture was acidified to pH 6–7 with a solution of HCl and concentrated under reduced pressure to give the carboxylic acid derivative I54.

$^1$H (400 MHz, DMSO) δ ppm: 1.32–1.70 (m, 8H), 3.03–3.12 (m, 1H), 3.50 (s, 3H), 3.85–3.95 (m, 1H), 4.35–4.50 (m, 1H), 7.75 (dd, 2H), 8.00 (dd, 2H), 13.15 (s, 1H).

Example I55

R₁=(1R*,3R*)-3-hydroxycyclohexyl, R₂=methyl,
R₃=4-[N-(2-morpholin-4-yl-ethyl)]benzamide
4-[5-((1R*,3R*)-3-Hydroxy-cyclohexylimino)-4-methyl-4,5-dihydro-[1,3,4]thiadiazol-2-yl]-N-(2-morpholin-4-yl-ethyl)-benzamide Compound I55 was prepared by the procedure described in Example I37.11 using I54 as a starting material. The residue was purified by silica gel chromatography using a gradient of dichloromethane containing 0% to 4% methanol, to give the desired product. Yield: 14%.

¹H-NMR (400 MHz, DMSO) δ ppm: 1.35–1.70 (m, 8H), 2.35–2.52 (m, 6H), 3.02–3.12 (m, 1H), 3.32–3.45 (m, 2H), 3.50–3.62 (m, 7H), 3.88–3.95 (m, 1H), 4.40 (d, 1H), 7.72 (dd, 2H), 7.92 (dd, 2H), 8.50 (s, 1H).
MS (m/z)/M+1=446.
HPLC (UV purity, λ=214 nm): 96.6%.

Example I56

R₁=trans-4-hydroxycyclohexyl, R₂=methyl, R₃=4-benzoic acid
4-[5-(trans-4-Hydroxy-cyclohexylimino)-4-methyl-4,5-dihydro-[1,3,4]thiadiazol-2-yl]-benzoic acid To a solution of I48 (1.9 mmol, 600 mg) in ethanol (15 mL) and isopropanol (15 mL), a solution of KOH [6N] (5.7 mmol, 960 µL) was added and stirred at reflux during 7 hours. The mixture was acidified to pH 6–7 with a solution of HCl and then concentrated under reduced to give the carboxylic acid derivative (I56).

¹H-RMN (400 MHz, DMSO) δ ppm: 1.22–1.32 (m, 2H), 1.60–1.80 (b, 2H), 1.90–2.04 (m, 4H), 3.41–3.50 (m, 1H), 4.00 (s, 3H), 7.80–7.90 (m, 2H), 8.00–8.10 (m, 2H), 11.00 (s, 1H).

Example I57

R₁=trans-4-hydroxy-cyclohexyl, R₂=methyl, R₃=4-(N-2-hydroxy-1,1-dimethyl-ethyl)benzamide
4-[5-(trans-4-Hydroxy-cyclohexylimino)-4-methyl-4,5-dihydro-[1,3,4]thiadiazol-2-yl]-N-(2-hydroxy-1,1-dimethyl-ethyl)-benzamide Compound I57 was prepared by the procedure described in Example I37.11 using I56 as a starting material. The residue was purified by silica gel chromatography using a gradient of dichloromethane containing 0% to 9% methanol, to give the expected product. Yield: 20%.

¹H-NMR (400 MHz, DMSO) δ ppm: 1.15–1.45 (m, 10H), 1.70–1.90 (m, 4H), 2.50–2.60 (m, 1H), 3.40–3.55 (m, 6H), 4.50 (d, 1H) 4.85 (d, 1H), 7.60 (s, 1H), 7.70 (dd, 2H), 7.89 (dd, 2H).
MS (m/z)/M+1=405.
HPLC (UV purity, λ=214 nm): 99.9%.

Example I58

R₁=(1R*,3R*)-3-hydroxy-cyclohexyl, R₂=methyl,
R₃=4-(N-2-hydroxy-1,1-dimethyl-ethyl)benzamide
4-[5-((1R*,3R*)-3-Hydroxy-cyclohexylimino)-4-methyl-4,5-dihydro-[1,3,4]thiadiazol-2-yl]-N-(2-hydroxy-1,1-dimethyl-ethyl)-benzamide Compound I58 was prepared by the procedure described in Example I55 using appropriate intermediates and reagents (I54 and 1,1-dimethyl-2-ethanolamine). The residue was purified by silica gel chromatography using a gradient of dichloromethane containing 0% to 5% methanol, to give the desired product. Yield: 58%.

¹H-NMR (400 MHz, DMSO) δ ppm: 1.20–1.70 (m, 14H), 3.02–3.12 (m, 1H), 3.40–3.60 (m, 5H), 3.85–3.95 (m, 1H), 4.40 (d, 1H), 4.85 (d, 1H), 7.60 (s, 1H), 7.68 (dd, 2H), 7.85 (dd, 2H).
MS (m/z)/M+1=405.
HPLC (UV purity, λ=214 nm): 94.4%.

Example I59

R₁=(1R*,3R*)-3-hydroxycyclohexyl, R₂=methyl,
R₃=4-(N-tert-butyl)-benzamide
N-tert-Butyl-4-[5-((1R*,3R*)-3-hydroxy-cyclohexylimino)-4-methyl-4,5-dihydro-[1,3,4]thiadiazol-2-yl]-benzamide Compound I59 was prepared by the procedure described in Example I55 using appropriate intermediates and reagents (I54 and isobutylamine). The residue was purified by silica gel chromatography using a gradient of dichloromethane containing 0% to 10%. Yield: 33%.

¹H-NMR (400 MHz, DMSO) δ ppm: 1.30–1.70 (m, 17H), 3.02–3.12 (m, 1H), 3.50 (s, 3H), 3.85–3.95 (m, 1H), 4.40 (d, 1H), 7.68 (dd, 2H), 7.80–7.90 (m, 3H).
MS (m/z)/M+1=389.
HPLC (UV purity, λ=214 nm): 94.1%.

Example I60

R₁=(1R*,3R*)-3-hydroxy-cyclohexyl, R₂=methyl,
R₃=4-[N-(1,1-dimethyl-3-oxo-butyl)]-benzamide
N-(1,1-Dimethyl-3-oxo-butyl)-4-[5-(1R*,3R*)-3-hydroxy-cyclohexylimino)-4-methyl-4,5-dihydro-1,3,4]thiadiazol-2-yl]-benzamide To a suspension of diacetoamine hydrogenoxalate (3 mmol, 616 mg) in DMF (6 mL) under nitrogen atmosphere, morpholine resin [3.47 mmol/g] (7 mmol, 2 g) was added, and the mixture was stirred at RT during 30 minutes and then filtered. A mixture of acid I54 (0.6 mmol), the filtrate, N,N-diisopropylethylamine (1.32 mmol, 227 µL), benzotriazol-1-yloxytris(dimethylamino)phosphonium hexafluorophosphate (0.72 mmol, 318 mg), 1-hydroxy-7-azabenzotriazole (0.3 mmol, 82 mg) was stirred at RT during 4 hours. The mixture was concentrated and then diluted in dichloromethane. The organic layer was washed with a saturated solution of ammonium chloride, a saturated solution of NaHCO₃, with water, brine, dried over magnesium sulfate, filtered, and concentrated under reduced pressure. The residue was purified by silica gel chromatography using a gradient of dichloromethane containing 0% to 8% methanol. The compound was purified by HPLC (Kromasil C18 column) eluting with acetonitrile/water 95:5 to 5:95 to give the desired product. Yield: 10%.

¹H-NMR (400 MHz, DMSO) δ ppm: 1.30–1.70 (m, 14H), 2.05 (s, 3H), 2.92–3.10 (m, 3H), 3.50 (s, 3H), 3.85–3.95 (m, 1H), 4.40 (d, 1H), 7.68 (dd, 2H), 7.85 (dd, 2H), 7.95 (s, 1H).
MS (m/z)/M+1=431.
HPLC (UV purity, λ=214 nm): 99.3%.

Example I61

R₁=(1R*,3R*)-3-hydroxycyclohexyl, R₂=methyl,
R₃=4-[N-(2-cyano-1,2,2-trimethyl-ethyl)]-benzamide
N-(2-Cyano-1,2,2-trimethyl-ethyl)-4-[5-((1R*,3R*)-3-hydroxy-cyclohexylimino)-4-methyl-4,5-dihydro-[1,3,4]thiadiazol-2-yl]-benzamide Compound I61 was prepared by the procedure described in Example I55 using appropriate intermediates and reagents (I54 and 2-amino-2,3-dimethylbutanenitrile). The residue was purified by silica gel chromatography using a gradient of cyclohexane containing 0% to 70% ethyl acetate, to give the title product. Yield: 8%.

$^1$H-NMR (400 MHz, DMSO) δ ppm: 0.95 (d, 3H), 1.10 (d, 3H), 1.30–1.70 (m, 11H), 2.45–2.65 (m, 1H), 3.00–3.10 (m, 1H), 3.50 (s, 3H), 3.85–3.95 (m, 1H), 4.40 (d, 1H), 7.70 (dd, 2H), 7.90 (d, 2H), 8.65 (s, 1H).

MS (m/z)/M+1=428.

HPLC (UV purity, λ=214 nm): 99.4%.

Example I62

$R_1$=(1R*,3R*)-3-hydroxy-cyclohexyl, $R_2$=methyl, $R_3$=4-(N-1-methoxycarbonyl-cyclopropyl)-benzamide 1-{4-[5-((1R*,3R*)-3-Hydroxy-cyclohexylimino)-4-methyl-4,5-dihydro-[1,3,4]thiadiazol-2-yl]-benzoylamino}-cyclopropanecarboxylic acid methyl ester Compound I62 was prepared by the procedure described in Example I37.24 using appropriate intermediates and reagents (I55 and 1-aminocyclopropane-1-carboxylic acid, methylester hydrochloride). The residue was purified once by silica gel chromatography using a gradient of dichloromethane containing 0% to 10% methanol and by HPLC (HYPERSIL Column) with a gradient acetonitrile/water 95:5 to 5:95 to afford the desired product. Yield: 32%.

$^1$H-NMR (400 MHz, DMSO) δ ppm: 1.12–1.20 (m, 2H), 1.33–1.50 (m, 4H), 1.50–1.70 (m, 6H), 3.03–3.12 (m, 1H), 3.52 (s, 3H), 3.60 (s, 1H), 3.89–3.98 (m, 1H), 4.40 (d, 1H), 7.72 (dd, 2H), 7.94 (d, 2H), 9.17 (s, 1H).

MS (m/z)/M+1=431.

HPLC (UV purity, λ=214 nm): 97.9%.

Example I63

$R_1$=cyclopentyl, $R_2$=methyl, $R_3$=4-benzamide 4-(5-Cyclopentylimino-4-methyl-4,5-dihydro-[1,3,4]thiadiazol-2-yl)-benzamide To a solution of compound I42 (0.53 mmol, 150 mg) in ethanol (17 mL), a solution of Na$_2$CO$_3$ [3N] (5.6 mmol, 1.88 mL) and a solution of H$_2$O$_2$ at 30% in water (1.54 mL) were added. The solution was stirred overnight at RT. To the mixture, was added a solution of H$_2$O$_2$ at 30% in water (770 μL), and the solution was allowed to stir at RT during 2 days (reaction to completion). The resultant mixture was concentrated by distillation of the solvent, and the crude material was precipitated in water. The precipitate was filtered off, washed several times with water, and dried to give the pure product. Yield: 53.4%.

$^1$H-NMR (400 MHz, DMSO) δ ppm: 1.43–1.95 (m, 8H), 3.18–3.28 (m, 1H), 3.52 (s, 3H), 7.44 (s, 1H), 7.70 (dd, 2H), 7.95 (dd, 2H), 8.05 (s, 1H).

MS (m/z)/M+1=303.

HPLC (UV purity, λ=214 nm): 98.04%.

Example I64

$R_1$=cycloheptyl, $R_2$=methyl, $R_3$=4-benzamide 4-(5-Cycloheptylimino-4-methyl-4,5-dihydro-[1,3,4]thiadiazol-2-yl)-benzamide Compound I64 was prepared by the procedure described in Example I63 using appropriate intermediates (I43) and reagents. The precipitate was filtered, washed several times with water, and dried to give the pure product. Yield: 59.88%.

$^1$H-NMR (400 MHz, DMSO) δ ppm: 1.40–1.83 (m, 12H), 2.78–2.85 (m, 1H), 3.52 (s, 3H), 7.44 (s, 1H), 7.72 (dd, 2H), 7.97 (dd, 2H), 8.07 (s, 1H).

MS (m/z)/M+1=331.

HPLC (UV purity, λ=214 nm): 98.98%.

Example I65

$R_1$=4-fluoro-phenyl, $R_2$=methyl, $R_3$=4-benzamide

4-[5-(4-Fluoro-phenylimino)-4-methyl-4,5-dihydro-[1,3,4]thiadiazol-2-yl]-benzamide Compound I65 was prepared by the procedure described in Example I63 using appropriate intermediates I44 and reagents. The precipitate was filtered, washed several times with water, and dried to give the pure product. Yield: 72.43%.

$^1$H-NMR (400 MHz, DMSO) δ ppm: 3.72 (s, 3H), 7.02–7.40 (m, 2H), 7.15–7.24 (m, 2H), 7.44 (s, 1H), 7.72 (dd, 2H), 7.95 (dd, 2H), 8.05 (s, 1H).

MS (m/z)/M+1=329.

HPLC (UV purity, λ=214 nm): 97.7%.

Example I66

$R_1$=3-hydroxy-phenyl, $R_2$=methyl, $R_3$=4-benzamide

4-[5-(3-Hydroxy-phenylimino)-4-methyl-4,5-dihydro-[1,3,4]thiadiazol-2-yl]-benzamide Compound I66 was prepared by the procedure described in Example I63 using appropriate intermediates (I45) and reagents. The precipitate was filtered, washed several times with water, and dried to give the pure product. Yield: 59.84%.

$^1$H-NMR (400 MHz, DMSO) δ ppm: 3.70 (s, 3H), 6.44–6.52 (m, 3H), 7.18 (t, 1H), 7.44 (s, 1H), 7.75 (dd, 2H), 7.97 (dd, 2H), 8.06 (s, 1H), 9.40 (s, 1H).

MS (m/z)/M+1=327.

HPLC (UV purity, λ=214 nm): 99.68%.

Example I67

$R_1$=4-fluoro-3-benzoic acid, $R_2$=methyl, $R_3$=4-benzamide

5-[5-(4-Carbamoyl-phenyl)-3-methyl-3H-[1,3,4]thiadiazol-2-ylideneamino]-2-fluoro-benzoic acid Compound I67 was prepared by the procedure described in Example I63 using appropriate intermediate (I46) and reagents. The precipitate was filtered, washed several times with water, and dried to give the pure product. Yield: 44.41%.

$^1$H-NMR (400 MHz, DMSO) δ ppm: 3.72 (s, 3H), 7.25–7.32 (m, 2H), 7.43–7.50 (m, 2H), 7.78 (dd, 2H), 7.95 (dd, 2H), 8.05 (s, 1H), 13.30 (b, 1H).

MS (m/z)/M+1=373.

HPLC (UV purity, λ=214 nm): 90.52%.

Example I68

$R_1$=trans-4-methyl-cyclohexyl, $R_2$=methyl, $R_3$=4-benzamide

4-[4-Methyl-5-(trans-4-methyl-cyclohexylimino)-4,5-dihydro-[1,3,4]thiadiazol-2-yl]-benzamide Compound I68 was prepared by the procedure described in Example I63 using appropriate intermediates (I47b) and reagents. The precipitate was filtered, washed several times with water, and dried to give the pure product. Yield: 52.53%.

$^1$H-NMR (400 MHz, DMSO) δ ppm: 0.90 (d, 3H), 0.95–1.08 (m, 2H), 1.30–1.45 (m, 3H), 1.67–1.85 (m, 4H), 2.50–2.60 (m, 1H), 3.52 (s, 3H), 7.44 (s, 1H), 7.72 (dd, 2H), 7.95 (dd, 2H), 8.05 (s, 1H).

MS (m/z)/M+1=331.

HPLC (UV purity, λ=214 nm): 99.7%.

Example I69

R$_1$=trans-4-hydroxy-cyclohexyl, R$_2$=methyl, R$_3$=4-benzamide

4-[5-(trans-4-Hydroxy-cyclohexylimino)-4-methyl-4,5-dihydro-[1,3,4]thiadiazol-2-yl]-benzamide To a suspension of I48 (0.477 mmol, 150 mg) in ethanol (17 mL), a solution of Na$_2$CO$_3$ [3N] (5.1 mmol, 1.7 mL) and a solution of H$_2$O$_2$ at 30% in water (1.4 mL) were added, and the mixture was stirred overnight at RT. This mixture was poured into water before extraction with ethyl acetate. The organic layer was washed with water and with a saturated solution of NaCl, dried over magnesium sulfate, filtered, and distilled to give a residue which was purified by silica gel chromatography (eluted with a gradient of dichloromethane/methanol 100:0 to 98:2) to afford the pure product. Yield: 31%.

$^1$H-NMR (400 MHz, DMSO) δ ppm: 1.20–1.42 (m, 4H), 1.75–1.90 (m, 4H), 2.50–2.63 (m, 1H), 3.40–3.52 (m, 1H), 3.50 (s, 3H), 4.55 (s, 1H), 7.44 (s, 1H), 7.72 (dd, 2H), 7.98 (dd, 2H), 8.07 (s, 1H).

MS (m/z)/M+1=332/333.

HPLC (UV purity, λ=214 nm): 97.3%.

Example I70

R$_1$=bicyclo[2.2.1]hept-2-yl, R$_2$=methyl, R$_3$=4-benzamide

4-[5-(Bicyclo[2.2.1]hept-2-ylimino)-4-methyl-4,5-dihydro-[1,3,4]thiadiazol-2-yl]-benzamide Compound I70 was prepared by the procedure described in Example I69 using appropriate intermediates (I49) and reagents. The residue was purified by silica gel chromatography (eluted with a gradient of dichloromethane/methanol 100:0 to 90:10) to afford the desired product. Yield: 66%.

$^1$H-NMR (400 MHz, DMSO) δ ppm: 1.10–1.25 (m, 3H), 1.28–1.40 (m, 1H), 1.40–1.67 (m, 4H), 2.10–2.18 (m, 1H), 2.25–2.32 (m, 1H), (2.70–2.80 (m, 1H), 3.52 (s, 3H), 7.50 (s, 1H), 7.72 (dd, 2H), 7.97 (dd, 2H), 8.10 (s, 1H).

MS (m/z)/M+1=329.

HPLC (UV purity, λ=214 nm): 99.9%.

Example I71

R$_1$=(1R*,2R*)-2-hydroxy-cyclohexyl, R$_2$=methyl, R$_3$=4-benzamide

4-[5-((1R*,2R*)-2-hydroxy-cyclohexylimino)-4-methyl-4,5-dihydro-[1,3,4]thiadiazol-2-yl]-benzamide Compound I71 was prepared by the procedure described in Example I69 using appropriate intermediates (I50) and reagents. The residue was purified by silica gel chromatography (eluted with a gradient of dichloromethane/methanol 100:0 to 90:10) to afford the pure product. Yield: 44%.

$^1$H-NMR (400 MHz, DMSO) δ ppm: 1.20–1.39 (m, 4H), 1.60–1.75 (m, 3H), 1.80–1.90 (m, 1H), 2.35–2.45 (m, 1H), 3.50 (s, 3H), 4.55 (s, 1H), 7.50 (s, 1H), 7.72 (dd, 2H), 7.96 (dd, 2H), 8.05 (s, 1H).

MS (m/z)/M+1=333.

HPLC (UV purity, λ=214 nm): 97.4%.

Example I72

R$_1$=(1R*,2S*)-2-hydroxy-cyclohexyl, R$_2$=methyl, R$_3$=4-benzamide

4-[5-((1R*,3S*)-3-Hydroxy-cyclohexylimino)-4-methyl-4,5-dihydro-[1,3,4]thiadiazol-2-yl]-benzamide To a suspension of I51 (0.16 mmol, 50 mg) in DMSO (100 μL), K$_2$CO$_3$ (0.022 mmol, 3 mg), a solution of H$_2$O$_2$ at 30% in water (20 μL) was added, and the mixture was stirred overnight at RT. To this mixture, water was added, and the solution was allowed to stir 15 minutes. The precipitate was filtered off and dried under reduced pressure to give the desired product. Yield: 68%.

$^1$H-NMR (400 MHz, DMSO) δ ppm: 1.25–1.38 (m, 2H), 1.40–1.80 (m, 6H), 2.85–2.90 (m, 1H), 3.57 (s, 3H), 3.60–3.68 (m, 1H), 4.10 (d, 1H), 7.40 (s, 1H), 7.70 (dd, 2H), 7.95 (dd, 2H), 8.05 (s, 1H).

MS (m/z)/M+1=333.

HPLC (UV purity, λ=214 nm): 98.8%.

Example I73

R$_1$=(1R*,3R*)-3-hydroxy-cyclohexyl, R$_2$=methyl, R$_3$=4-benzamide

4-[5-((1R*,3R*)-3-Hydroxy-cyclohexylimino)-4-methyl-4,5-dihydro-[1,3,4]thiadiazol-2-yl]-benzamide Compound I73 was prepared by the procedure described in Example I69 using appropriate intermediates (I52-a) and reagents. The mixture was concentrated under reduced pressure and stirred in water several hours, filtered, and dried under vacuum to afford the desired product. Yield: 70%.

$^1$H-NMR (400 MHz, DMSO) δ ppm: 1.30–1.70 (m, 8H), 3.10 (s, 1H), 3.52 (s, 3H), 3.93 (s, 1H), 4.42 (d, 1H), 7.43 (s, 1H), 7.70 (dd, 2H), 7.96 (dd, 2H), 8.05 (s, 1H).

MS (m/z)/M+1=333.

HPLC (UV purity, λ=214 nm): 98.3%.

Example I74

R$_1$=(1R*,3S*)-3-hydroxy-cyclohexyl, R$_2$=methyl, R$_3$=4-benzamide

4-[5-((1R*,3S*)-3-Hydroxy-cyclohexylimino)-4-methyl-4,5-dihydro-[1,3,4]thiadiazol-2-yl]-benzamide Compound I74 was prepared by the procedure described in Example I69 using appropriate intermediates (I52-b) and reagents. The mixture was concentrated under reduced pressure and stirred in water several hours, filtered, and dried under vacuum to afford the desired product. Yield: 83%.

$^1$H-NMR (400 MHz, DMSO) δ ppm: 1.05–1.30 (m, 4H), 1.65–1.78 (m, 2H), 1.78–1.88 (m, 1H), 1.95–2.05 (m, 1H), 3.40–3.58 (m, 4H), 4.60 (s, 1H), 7.45 (s, 1H), 7.70 (dd, 2H), 7.95 (dd, 2H), 8.05 (s, 1H).

MS (m/z)/M+1=333.

HPLC (UV purity, λ=214 nm): 99.4%.

Example I74.1

R$_1$=3-oxo-cyclohexyl, R$_2$=methyl, R$_3$=4-benzamide

4-[4-Methyl-5-(3-oxo-cyclohexylimino)-4,5-dihydro-[1,3,4]thiadiazol-2-yl]-benzamide To a solution of I74 (0.15 mmol, 50 mg) in dichloromethane (0.5 mL), tetrapropylammoniumperruthenate (0.5% mol, 3 mg), 4-methylmorpholine-N-oxide (0.22 mmol, 28 mg) and molecular sieve (500 mg/mol, 75 mg) were added, and the mixture was stirred at RT overnight. The mixture was filtered through a pad of silica gel (eluted with dichloromethane/methanol 100:0 to 95:5), the filtrate was concentrated under reduced pressure and washed with diethylether to afford the pure product. Yield: 18%.

$^1$H-NMR (400 MHz, DMSO) δ ppm: 1.63–1.82 (m, 2H), 1.89–2.10 (m, 2H), 2.21–2.50 (m, 4H), 3.15–3.30 (m, 1H), 3.52 (s, 3H), 7.45 (s, 1H), 7.70 (dd, 2H), 7.98 (dd, 2H), 8.08 (s, 1H).

MS (m/z)/M+1=331.

HPLC (UV purity, λ=214 nm): 98.7%.

Example I75

$R_1$=3,3-difluoro-cyclohexyl, $R_2$=methyl, $R_3$=4-benzamide
4-[5-(3,3-Difluoro-cyclohexylimino)-4-methyl-4,5-dihydro-[1,3,4]thiadiazol-2-yl]-benzamide To a solution of I52b (0.318 mmol, 100 mg) in dichloromethane (1 mL) was added tetrapropylammonium perruthenate (0.5% mol, 6 mg), 4-methylmorpholine-N-oxide (0.477 mmol, 56 mg), and molecular sieve (500 mg/mol, 160 mg). The mixture was stirred at RT for 3 hours, filtered through silica gel (eluted with cyclohexane/ethyl acetate 100:0 to 60:40), and concentrated under reduced pressure to afford 4-[4-methyl-5-(3-oxo-cyclohexylimino)-4,5-dihydro-[1,3,4]thiadiazol-2-yl]-benzonitrile. Yield: 90%.

$^1$H-NMR (400 MHz, DMSO) δ ppm: 1.60–1.80 (m, 2H), 1.87–2.10 (m, 2H), 2.21–2.30 (m, 3H), 2.55–2.60 (m, 1H), 3.15 (s, 1H), 3.52 (s, 3H), 7.82 (dd, 2H), 7.92 (dd, 2H).

To a solution of this ketone (0.288 mmol, 90 mg) in dichloromethane (0.5 mL), a solution of deoxo-fluoro (0.49 mmol, 90 μL) in dichloromethane (1 mL) and ethanol (0.346 mmol, 5 μL) was added, and the mixture was stirred overnight at RT. The mixture was poured into a saturated solution of NaHCO$_3$ (pH 7), and the aqueous layer was extracted with dichloromethane. The organic layer was washed with water and brine, dried with magnesium sulfate, filtered, and concentrated under reduced pressure to give a residue which was purified by silica gel chromatography (eluted with a gradient of cyclohexane/ethyl acetate 100:0 to 80:20) to afford the pure di-fluoro compound: 4-[5-(3,3-difluoro-cyclohexylimino)-4-methyl-4,5-dihydro-[1,3,4]thiadiazol-2-yl]-benzonitrile. Yield: 12%.

$^1$H-NMR (400 MHz, DMSO) δ ppm: 1.40–1.55 (m, 2H), 1.78–1.90 (m, 4H), 1.95–2.09 (m, 1H), 2.15–2.28 (m, 1H), 2.80–2.90 (m, 1H), 3.55 (s, 3H), 7.82 (dd, 2H), 7.92 (dd, 2H).

To a solution of this di-fluoro derivative (0.036 mmol, 12 mg) in ethanol (1.6 mL), a solution of Na$_2$CO$_3$ [3N] (0.6 mmol, 200 μL), and a solution of H$_2$O$_2$ at 30% in water (150 μL) were added, and the mixture was stirred at 40° C. overnight. Then, a solution of H$_2$O$_2$ at 30% in water (130 μL) was added, and the solution was allowed to stir 12 hours at 40° C. The mixture was concentrated under reduced pressure. The residue was stirred in water several hours, filtered, washed with ether, and dried under vacuum to give the desired compound. Yield: 40%.

$^1$H-NMR (400 MHz, DMSO) δ ppm: 1.33–1.53 (m, 2H), 1.70–1.90 (m, 4H), 1.90–2.05 (m, 1H), 2.15–2.28 (m, 1H), 2.80–2.90 (m, 1H), 3.55 (s, 3H), 7.48 (s, 1H), 7.72 (dd, 2H), 7.96 (dd, 2H), 8.08 (s, 1H).

MS (m/z)/M+1=353.

HPLC (UV purity, λ=214 nm): 98.7%.

Example I76

$R_1$=(1R*,3R*)-3-fluoro-cyclohexyl, $R_2$=methyl, $R_3$=4-benzamide
4-[5-((1R*,3R*)-3-Fluoro-cyclohexylimino)-4-methyl-4,5-dihydro-[1,3,4]thiadiazol-2-yl]-benzamide To a solution of I52-b (1.59 mmol, 500 mg) in dichloromethane (4 mL), 4-morpholinisulfurtrifluoride (3.18 mmol, 390 μL) was added at −15° C. dropwise under nitrogen atmosphere. The mixture was warmed at RT during 30 minutes and poured into a saturated solution of NaHCO$_3$ (pH 7). The aqueous phase was extracted with dichloromethane. The organic layer was washed with water and brine, dried over magnesium sulfate, filtered, and concentrated under reduce pressure to give a residue which was purified by silica gel chromatography (eluted with a gradient of cyclohexane/ethyl acetate 100:0 to 70:30) to afford 4-[5-(cyclohex-3-enylimino)-4-methyl-4,5-dihydro-[1,3,4]thiadiazol-2-yl]-benzonitrile and a mono-fluoro intermediate (4-[5-((trans)-3-fluoro-cyclohexylimino)-4-methyl-4,5-dihydro-[1,3,4]thiadiazol-2-yl]-benzonitrile). Yield: 14%.

$^1$H-NMR (400 MHz, DMSO) δ ppm: 1.40–1.50 (m, 1H), 1.58–1.85 (m, 6H), 1.92–2.05 (m, 1H), 2.95–3.05 (m, 1H), 3.55 (s, 3H), 4.95 (d, 1H), 7.83 (dd, 2H), 7.95 (dd, 2H).

To a solution of this fluoro intermediate (0.2 mmol, 65 mg) in ethanol (8.7 mL), a solution of Na$_2$CO$_3$ [3N] (2.61 mmol, 870 μL) and a solution of H$_2$O$_2$ at 30% in water (705 μL) were added, and the mixture was stirred overnight at 40° C. A solution of H$_2$O$_2$ at 30% in water (705 μL) was added, and the reaction was allowed to stir for 10 hours at 40° C. The mixture was concentrated under reduced pressure. The residue was stirred in water several hours, filtered, washed with ether, and dried under vacuum to give the title product (176). Yield: 58%.

$^1$H-NMR (400 MHz, DMSO) δ ppm: 1.35–1.52 (m, 1H), 1.52–1.90 (m, 6H), 1.90–2.08 (m, 1H), 2.93–3.08 (m, 1H), 3.55 (s, 3H), 5.00 (d, 1H), 7.50 (s, 1H), 7.78 (dd, 2H), 7.99 (dd, 2H), 8.10 (s, 1H).

MS (m/z)/M+1=335.

HPLC (UV purity, λ=214 nm): 96.6%.

Example I77

$R_1$=3-cyclohexene, $R_2$=methyl, $R_3$=4-benzamide
4-[5-(Cyclohex-3-enylimino)-4-methyl-4,5-dihydro-[1,3,4]thiadiazol-2-yl]-benzamide To a solution of 4-[5-(cyclohex-3-enylimino)-4-methyl-4,5-dihydro-[1,3,4]thiadiazol-2-yl]-benzonitrile from protocol I76 (0.94 mmol, 280 mg) in ethanol (41 mL), a solution of Na$_2$CO$_3$ [3N] (12.3 mmol, 4.1 mL), and a solution of H$_2$O$_2$ at 30% in water (3.33 mL) were added. The mixture was stirred overnight at RT and concentrated under reduced pressure. The residue was stirred in water several hours, filtered, and dried under vacuum to afford the pure product. Yield: 64%.

$^1$H-NMR (400 MHz, DMSO) δ ppm: 1.48–1.65 (m, 1H), 1.72–2.35 (m, 5H), 2.82–2.92 (m, 1H), 3.55 (s, 3H), 5.65 (t, 2H), 7.50 (s, 1H), 7.71 (dd, 2H), 7.95 (dd, 2H), 8.09 (s, 1H).

MS (m/z)/M+1=315.

HPLC (UV purity, λ=214 nm): 96.1%.

Example I78

$R_1$=(1R*,3R*)-3-hydroxy-cyclohexyl, $R_2$=methyl, $R_3$=4-(1H-tetrazol-5-yl)-phenyl
(1R*,3R*)-3-{3-Methyl-5-[4-(1H-tetrazol-5-yl)-phenyl]-3H-[1,3,4]thiadiazol-2-ylideneamino}-cyclohexanol To a solution of I52-a (1.27 mmol, 400 mg) in toluene (3 mL), sodium azide (1.65 mmol, 108 mg) and triethylamine hydrochloride (1.65 mmol, 228 mg) were added, and the mixture was warmed at reflux during 24 hours. The reaction mixture was cooled at RT, acidified with a solution of HCl [0.1N], and then basified at pH 6–7 with a saturated solution of NaHCO$_3$. The aqueous phase was extracted with dichloromethane, and the organic layer was washed with a saturated solution of NaCl, dried over magnesium sulfate, filtered, and concentrated under reduced pressure. The residue was chromatographed on silica gel column using a gradient of dichloromethane containing from 0% to 20% methanol to afford the title compound. Yield: 50%.

$^1$H-NMR (400 MHz, DMSO) δ ppm: 1.30–1.70 (m, 8H), 3.00–3.15 (m, 1H), 3.50 (s, 3H), 3.85–3.98 (m, 1H), 4.40 (s, 1H), 7.75 (dd, 2H), 8.10 (d, 2H).

MS (m/z)/M+1=358.

HPLC (UV purity, λ=214 nm): 99.9%.

Example I79

$R_1$=3-(2-hydroxy)-benzoic acid, $R_2$=methyl, $R_3$=4-chloro-phenyl

3-[5-(4-Chloro-phenyl)-3-methyl-3H-[1,3,4]thiadiazol-2-ylideneamino]-2-hydroxy-benzoic acid The title compound was prepared by the procedure described in Example I3 using ethanol as solvent and appropriate intermediates and reagents. The residue was twice chromatographed on silica gel eluting with dichloromethane containing from 0% to 7% of methanol. The isolated product was washed with water to afford the desired product. Yield: 9.7%.

$^1$H-NMR (400 MHz, DMSO) δ ppm: 3.62 (s, 3H), 6.80 (t, 1H), 7.12 (d, 1H), 7.40–7.46 (m, 3H), 7.59 (d, 2H).

MS (m/z)/M+1=362/364.

HPLC (UV purity, λ=214 nm): 98.36%.

Example I80

$R_1$=3-benzoic acid, $R_2$=methyl, $R_3$=4-cyano-phenyl

3-[5-(4-Cyano-phenyl)-3-methyl-3H-[1,3,4]thiadiazol-2-ylideneamino]-benzoic acid A suspension of 1,3,4-thiadiazolium perchlorate (3c) (4.873 mmol, 1.70 g), 3-aminobenzoic acid (4.87 mmol, 0.668 g), and triethylamine (4.873 mmol, 0.679 mL) in ethanol (20 mL) was refluxed for 3.5 hours. On cooling, the solid formed was filtered off and washed with cold EtOH and ether. The solid was dried under reduced pressure to give 1.25 g of the expected compound. Yield: 76.2%.

$^1$H-NMR (400 MHz, DMSO) δ ppm: 3.87 (s, 3H), 7.39–7.42 (m, 1H), 7.60–7.65 (m, 1H), 7.70 (s, 1H), 7.78–7.82 (m, 1H), 7.96–8.00 (d, 2H), 8.00–8.04 (d, 2H).

MS (m/z)/M+1=337/338.

HPLC (UV purity, λ=214 nm): 93.22%.

Example I80.1

$R_1$=3-benzoic acid, $R_2$=methyl, $R_3$=4-benzamide

3-[5-(4-Carbamoyl-phenyl)-3-methyl-3H-[1,3,4]thiadiazol-2-ylideneamino]-benzoic acid Concentrated sulfuric acid (19.8 mmol, 1.06 mL) and water (0.13 mL) were respectively added, at 0° C., to I80 (0.595 mmol, 0.200 g), and the reaction mixture was heated at 80° C. for 1 hour 30 minutes. Then ice was added to the mixture, and the formed precipitate was filtered off and purified by chromatography on silica gel, eluting with a mixture of acetic acid/dichloromethane/methanol (1.5:85:13.5). The isolated product was triturated in methanol, and the solid was filtered off and dried under vacuum to give the title product. Yield: 34%.

$^1$H-NMR (400 MHz, DMSO) δ ppm: 3.76 (s, 3H), 7.30 (d, 1H), 7.46–7.55 (m, 2H), 7.62 (s, 1H), 7.67 (d, 1H), 7.80 (d, 2H), 7.99 (d, 2H), 8.09 (s, 1H), 12.90–13.02 (d, 1H).

MS (m/z)/M+1=355/356.

HPLC (UV purity, λ=214 nm): 96.37%.

Example I81

$R_1$=4-fluoro-3-benzoic acid, $R_2$=methyl, $R_3$=4-(methyl-sulfonyl)-phenyl

2-Fluoro-5-[5-(4-methanesulfonyl-phenyl)-3-methyl-3H-[1,3,4]thiadiazol-2-ylideneamino]-benzoic acid Compound I81 was prepared by the procedure described in Example I4 (Protocol A) with the appropriate reagents and using 1.0 equivalents of triethylamine. The reaction mixture was concentrated, and the residue was purified by silica gel chromatography eluting with dichloromethane and then a mixture of dichloromethane/MeOH/AcOH (98:1.8:0.2). Yield: 13%.

$^1$H-NMR (400 MHz, DMSO) δ ppm: 3.19 (s, 3H), 3.57 (s, 3H), 7.11–7.19 (m, 2H), 7.31–7.34 (m, 1H), 3.50–7.79 (d, 2H), 7.85 (d, 2H), 13.08–13.14 (b, 1H).

MS (m/z)/M+1=408/409.

HPLC (UV purity, λ=214 nm): 98.3%.

Example I82

$R_1$=3-carboxylic acid cyclohexyl, $R_2$=methyl, $R_3$=4-(methyl-sulfonyl)-phenyl 3-[5-(4-Methanesulfonyl-phenyl)-3-methyl-3H-[1,3,4]thiadiazol-2-ylideneamino]-cyclohexanecarboxylic acid Compound I82 was prepared by the procedure described in Example I4 with the appropriate reagents and using 1.0 equivalents of triethylamine. The mixture was filtered, and the filtrate was evaporated to dryness. The residue was purified by silica gel chromatography eluting with $CHCl_3$/MeOH (93:7) to afford 15 mg of the desired product. Yield: 1.52%.

$^1$H-NMR (400 MHz, DMSO) δ ppm: 1.02–1.24 (m, 4H), 1.58–1.70 (m, 3H), 1.80–1.86 (m, 1H), 2.12–2.19 (m, 1H), 2.44–2.52 (m, 1H), 3.06 (s, 3H), 3.36 (s, 3H), 7.70 (d, 2H), 7.82 (d, 2H), 11.82–11.90 (b, 1H).

MS (m/z)/M+1=395/396.

HPLC (UV purity, λ=214 nm): 98.76%.

Example I83

$R_1$=piperidin-1-yl, $R_2$=methyl, $R_3$=4-(methylsulfonyl)-phenyl

[5-(4-Methanesulfonyl-phenyl)-3-methyl-3H-[1,3,4]thiadiazol-2-ylidene]-piperidin-1-yl amine To a suspension of 1,3,4-thiadiazolium perchlorate (3b) (1.26 mmol, 0.5 g) in ethanol (6 mL) were added 1-aminopiperidine (2.5 mmol, 0.3 mL) then triethylamine (2.5 mmol, 0.4 mL), and the mixture was maintained at 70° C. for 3 hours. The mixture was concentrated under reduced pressure. The residue was taken into dichloromethane, washed twice with water, concentrated under reduced pressure, and purified by chromatography on silica gel (DCM/MeOH 99:1) to give 0.2 g of the title compound. Yield: 45%.

$^1$H-NMR (400 MHz, $CDCl_3$) δ ppm: 1.46 (s, 2H), 1.68–1.71 (m, 4H), 2.77 (s, 4H), 3.07 (s, 3H), 3.65 (s, 3H), 7.81–7.83 (dd, 2H), 7.95–7.97 (dd, 2H).

MS (m/z)/M+1=353.46.

HPLC (UV purity, λ=214 nm): 97.4%.

Example I84

$R_1$=tetrahydro-pyran-4-yl, $R_2$=methyl, $R_3$=4-(methyl-sulfonyl)-phenyl

[5-(4-Methanesulfonyl-phenyl)-3-methyl-3H-[1,3,4]thiadiazol-2-ylidene]-(tetrahydro-pyran-4-yl)-amine To a suspension of 1,3,4-thiadiazolium perchlorate (3b) (0.7 mmol, 0.3 g) in ethanol (4 mL) were added 4-aminotetrahydropyran (1.4 mmol, 0.3 g) and triethylamine (3 mmol, 0.4 mL). The mixture was maintained for 3 hours at 70° C., concentrated under reduced pressure. The residue was taken into dichloromethane, washed once with water, concentrated under reduced pressure, and purified by chromatography on silica gel (DCM/MeOH 99:1) and washed with ethyl acetate and heptane to give 23 mg of the expected compound. Yield: 30%.

$^1$H-NMR (400 MHz, CDCl$_3$) δ ppm: 1.68–1.85 (m, 4H), 2.88–2.95 (m, 1H), 3.07 (s, 3H), 3.47–3.57 (m, 2H), 3.65 (s, 3H), 4.01–4.06 (m, 2H), 7.81 (d, 2H), 7.97 (d, 2H).

MS (m/z)/M+1=354.03.

HPLC (UV purity, λ=214 nm): 100%.

Example I85

R$_1$=3-benzoic acid, R$_2$=methyl, R$_3$=4-acetylamino-phenyl

3-[5-(4-Acetylamino-phenyl)-3-methyl-3H-[1,3,4]thiadiazol-2-ylideneamino]-benzoic acid A suspension of 1,3,4-thiadiazolium triflate (3d) (0.7 mmol, 0.3 g), triethylamine (2.1 mmol, 0.3 mL), and 3-acetamidobenzoic acid (0.6 mmol, 0.077 g) in ethanol (20 mL) was refluxed overnight. The mixture was concentrated under reduced pressure, purified by chromatography on silica gel (DCM/MeOH 95:5) and washed with MeOH to give 0.01 g of a white solid. Yield: 5%.

$^1$H-NMR (400 MHz, DMSO) δ ppm: 2.06 (s, 3H), 2.71 (s, 3H), 7.26 (d, 1H), 7.47 (t, 1H), 7.60–7.70 (m, 6H), 10.18 (s, 1H).

MS (m/z)/M+1=368.95.

HPLC (UV purity, λ=214 nm): 98%.

Example I86

R$_1$=trans-4-hydroxy-cyclohexyl, R$_2$=methyl, R$_3$=4-acetylamino-phenyl

N-{4-[5-(trans-4-Hydroxy-cyclohexylimino)-4-methyl-4,5-dihydro-[1,3,4]thiadiazol-2-yl]-phenyl}-acetamide A mixture of trans-4-aminocyclohexanol (0.28 mmol, 0.04 g), triethylamine (0.39 mmol, 0.06 mL), and 3-methyl-2-methylthio[1,3,4]-thiadiazolium triflate (3d) (0.14 mmol, 0.05 g) were refluxed in ethanol (1 mL) overnight. The mixture was concentrated under reduced pressure. The residue was taken into dichloromethane, washed once with water, concentrated under reduced pressure, and purified by chromatography on silica gel (DCM/MeOH 95:5) to give 0.014 g of a white solid. Yield: 30%.

$^1$H-NMR (400 MHz, DMSO) δ ppm: 1.23–1.38 (m, 4H), 1.76–1.86 (m, 4H), 2.06 (s, 3H), 2.45–2.60 (m, 1H), 4.52 (d, 1H), 3.38–3.44 (m, 1H), 3.47 (m, 3H), 7.58 (d, 2H), 7.68 (d, 2H), 10.15 (s, 1H).

MS (m/z)/M+1=346.87.

HPLC (UV purity, λ=214 nm): 98.5%.

Example I87

R$_1$=(1R*,3S*)-3-hydroxy-cyclohexyl, R$_2$=methyl, R$_3$=4-acetylamino-phenyl

N-{4-[5-((1R*,3S*)-3-Hydroxy-cyclohexylimino)-4-methyl-4,5-dihydro-[1,3,4]thiadiazol-2-yl]-phenyl}-acetamide Compound I87 was prepared by the procedure described in Example I86 (Protocol A). Compound I87 was purified by chromatography on silica gel with AcOEt/Cyclohexane (80:20) and washed with MeOH to give 0.15 g of the expected compound. Yield: 20%.

$^1$H-NMR (400 MHz, DMSO) δ ppm: 1.10–1.30 (m, 4H), 1.55–2.00 (m, 4H), 2.10 (s, 3H), 2.60 (m, 1H), 3.50 (m, 1H), 3.50 (s, 3H), 4.6 (d, 1H), 7.60 (dd, 2H), 7.60 (dd, 2H), 10.15 (s,1H).

M+1=347.1.

Example I88

R$_1$=(1R*,3R*)-3-hydroxy-cyclohexyl, R$_2$=methyl, R$_3$=4-acetylamino-phenyl

N-{4-[5-((1R*,3R*)-3-Hydroxy-cyclohexylimino)-4-methyl-4,5-dihydro-[1,3,4]thiadiazol-2-yl]-phenyl}-acetamide To a suspension of I87 (0.4 mmol, 0.15 g) in DCM (2 mL) containing 4 Å molecular sieves (0.216 g), N-methyl morpholine oxide (0.65 mmol, 0.76 g) under nitrogen atmosphere was added tetrapropylammonium perruthenate (10% mol eq., 15 mg). The resulting mixture was stirred overnight, filtered, washed with methanol, and concentrated under reduced pressure. The residue was purified by chromatography on silica gel with DCM/MeOH (95:5) to give 0.1 g of a ketone intermediate: N-{4-[4-methyl-5-(3-oxo-cyclohexylimino)-4,5-dihydro-[1,3,4]thiadiazol-2-yl]-phenyl}-acetamide. Yield: 71%.

$^1$H-NMR (400 MHz, DMSO) δ ppm: 1.25 (m, 1H), 1.60–1.75 (m, 2H), 1.85–2 (m, 2H), 2.05 (s, 3H), 2.3 (m, 3H), 3.15 (m, 1H), 3.5 (s, 3H), 7.55 (dd, 2H), 7.70 (dd, 2H), 10.15 (s, 1H).

To a solution of this ketone intermediate (0.15 mmol, 0.05 g) in THF (2 mL) at −70° C. under nitrogen atmosphere was added a 1 M solution of L-Selectride in THF (0.2 mmol, 0.2 mL). The resulting mixture was allowed to warm up to RT over 1 hour, diluted with dichloromethane, washed with water, and concentrated under reduced pressure. The residue was purified by chromatography on silica gel with AcOEt/cyclohexane (80:20) to give 30 mg of the expected product. Yield: 60%.

$^1$H-NMR (400 MHz, CDCl$_3$) δ ppm: 1.25–1.30 (m, 3H), 1.72–1.78 (m, 5H), 2.20 (s, 3H), 3.11–3.14 (m, 1H), 3.58 (s, 3H), 4.13 (m, 1H), 7.20 (s, 1H), 7.52–7.60 (m, 4H).

MS (m/z)/M+1=347.21.

HPLC (UV purity, λ=214 nm): 98%.

Example I89

R$_1$=(1R*,3R*)-3-hydroxy-cyclohexyl, R$_2$=methyl, R$_3$=4-acetylamino-pyridin-3-yl N-{5-[5-((1R*,3R*)-3-Hydroxy-cyclohexylimino)-4-methyl-4,5-dihydro-[1,3,4]thiadiazol-2-yl]-pyridin-2-yl}-acetamide The compound I89 was prepared by the procedure described in Example I4 (Protocol A).

To a suspension of 1,3,4-thiadiazolium perchlorate (3e) (0.5 mmol, 2 g) in ethanol (20 mL) were added triethylamine (1.5 mmol, 2 mL) followed by 3-aminocyclohexanol (0.8 mmol, 0.9 mL), and the mixture was maintained at 70° C. overnight, concentrated under reduced pressure. The residue was taken into dichloromethane, washed twice with water, concentrated under reduced pressure, and purified by chromatography on silica gel (cyclohexane/EtOAc 20:80) to give 0.03 g of a white solid. Yield: 17%.

$^1$H-NMR (400 MHz, DMSO) δ ppm: 1.37–1.65 (m, 8H), 2.11 (s, 3H), 3.03–308 (m, 1H), 3.50 (s, 3H), 3.91–3.92 (m, 1H), 4.41 (d, 1H), 8.01–8.03 (dd, 1H), 8.17 (d, 1H), 8.55 (d, 1H), 10.75 (s, 1H).

MS (m/z)/M+1=348.3.

HPLC (UV purity, λ=214 nm): 99.2%.

Example I90

R$_1$=3-cyano-phenyl, R$_2$=methyl, R$_3$=4-chloro-phenyl

3-[5-(4-Chloro-phenyl)-3-methyl-3H-[1,3,4]thiadiazol-2-ylideneamino]-benzonitrile To a suspension of I6.11 (4.14 mmol, 1.43 g) in pyridine (20 mL) was added benzoyl chloride (8.28 mmol, 964 μL). The mixture was heated at reflux for 2 days.

The solvent was concentrated under reduced pressure, the reaction mixture was retaken in an aqueous solution of NaHCO$_3$, and the crude product was extracted with dichloromethane. The compound was purified by chromatography on silica gel (eluted with cyclohexane/ethyl acetate: 80:20 to 70:30) to give 1.25 g of the expected compound. Yield: 92%.

$^1$H-NMR (400 MHz, DMSO) δ ppm: 3.8 (s, 3H), 7.40 (d, 1H), 7.48 (s, 1H), 7.52-7.60 (m, 4H), 7.73 (d, 2H).

MS (m/z)/M+1=327/329.

HPLC (UV purity, λ=245 nm): 99.4%.

Example I90.1

R$_1$=3-(1H-Tetrazol-5-yl)-phenyl, R$_2$=methyl, R$_3$=4-chloro-phenyl

[5-(4-Chloro-phenyl)-3-methyl-3H-[1,3,4]thiadiazol-2-ylidene]-[3-(1H-tetrazol-5-yl)-phenyl]-amine A mixture of I90 (1.22 mmol, 0.4 g), sodium azide (1.59 mmol, 0.1 g), and triethylamine hydrochloride (1.59 mmol, 0.22 g) in toluene (7 mL) was heated at 90° C. with stirring under nitrogen atmosphere. After cooling, the reaction mixture was poured in water and extracted with dichloromethane. To the aqueous layer, aqueous HCl 0.1N was added until the pH is acidic (CAUTION! This has to be done under a well-ventilated hood). The precipitate was filtered, washed with ether, and the resulting compound was crystallized in dichloromethane containing few drops of methanol to give 0.1 g of the desired compound. Yield: 24%.

$^1$H-NMR (400 MHz, DMSO) δ ppm: 3.8 (s, 3H), 7.28 (d, 1H), 7.55 (d, 2H), 7.60 (t, 1H), 7.70-7.77 (m, 4H).

MS (m/z)/M+1=370/372.

HPLC (UV purity, λ=245 nm): 99.7%.

Example I90.2

R$_1$=3-(N-Hydroxycarbamimidoyl)-phenyl, R$_2$=methyl, R$_3$=4-chloro-phenyl

3-[5-(4-Chloro-phenyl)-3-methyl-3H-[1,3,4]thiadiazol-2-ylideneamino]-N-hydroxy-benzamidine To a mixture of I90 (1.53 mmol, 0.5 g) and hydroxylamine hydrochloride (2.29 mmol, 0.156 g) in ethanol (13 mL) was added sodium hydroxide (2.29 mmol, 0.09 g) dissolved in the minimum of water. The reaction mixture was heated at reflux for 24 hours with stirring. After cooling, the precipitate is filtered, washed with ethanol, and dried under vacuum at 45° C. to give 0.54 g of the desired compound. Yield: 98%.

$^1$H-NMR (400 MHz, DMSO) δ ppm: 3.8 (s, 3H), 5.76 (bs, 2H), 7.05 (dd, 1H), 7.34-7.4 (m, 3H), 7.54 (d, 2H), 7.70 (d, 2H), 9.6 (s, 1H).

MS (m/z)/M+1=360/362.

HPLC (UV purity, λ=245 nm): 97.3%.

Example I90.3

R$_1$=3-(5-hydroxy-[1,2,4]oxadiazol-3-yl)-phenyl, R$_2$=methyl, R$_3$=4-chloro-phenyl 3-{3-[5-(4-Chloro-phenyl)-3-methyl-3H-[1,3,4]thiadiazol-2-ylideneamino]-phenyl}-[1,2,4]oxadiazol-5-ol A mixture of I90.2 (2.78 mmol, 0.1 g) and 1,1'-carbonyldiimidazole (5.56 mmol, 0.9 g) in anhydrous THF (2 mL) was heated at reflux for 5 hours. After cooling, the reaction mixture was concentrated and poured in water. Dichloromethane was added, and the precipitate was filtered and washed with methanol. The resulting mixture was purified by chromatography on silica gel (eluent dichloromethane/methanol: 98:2+1% acetic acid) to give 0.03 g of the desired product. Yield: 28%.

$^1$H-NMR (400 MHz, DMSO) δ ppm: 3.8 (s, 3H), 7.20 (dt, 1H), 7.50–7.55 (m, 5H), 7.70 (d, 2H).

MS (m/z)/M+1=386/388.

HPLC (UV purity, λ=245 nm): 98.2%.

Example I

Protocol C

Example I91

R$_1$=cyclohexyl, R$_2$=methyl, R$_3$=3-methyl-4-bromo-phenyl

[5-(4-Bromo-3-methyl-phenyl)-3-methyl-3H-[1,3,4]thiadiazol-2-ylidene]-cyclohexyl-amine Compound I91 was prepared by the procedure described in Example I18 (Protocol C) using appropriate intermediates and reagents. Yield: 50.4%.

$^1$H-NMR (400 MHz, CDCl$_3$) δ ppm: 1.21–1.51 (m, 5H), 1.64–1.70 (m, 1H), 1.78–1.89 (m, 4H), 2.38 (s, 3H), 2.56–2.64 (m, 1H), 3.55 (s, 3H), 7.28 (d, 1H), 7.47 (s, 1H), 7.54 (d, 1H).

MS (m/z)/M+1=366/368.

Example I91.1

R$_1$=cyclohexyl, R$_2$=methyl, R$_3$=3-methyl-4-cyano-phenyl 4-(5-Cyclohexylimino-4-methyl-4,5-dihydro-[1,3,4]thiadiazol-2-yl)-2-methyl-benzonitrile To a solution of I91 (7.370 mmol, 2.7 g) in N-methyl-2-pyrrolidone (17 mL), copper cyanide (13.267 mmol, 1.19 g) was added, and the mixture was heated at reflux for 3 hours. The mixture was cooled at RT, basified with a solution of aqueous ammonia (2N), and stirred 10 hours at RT. The suspension was then filtered through Celite, and the aqueous layer was extracted with ethyl acetate, washed with water and brine, dried (MgSO$_4$), filtered, and then concentrated under reduced pressure. The residue was purified by chromatography on silica gel, eluting with a gradient of dichloromethane containing from 0% to 1% of methanol. Yield: 54.8%.

$^1$H-NMR (400 MHz, CDCl$_3$) δ ppm: 1.22–1.59 (m, 5H), 1.64–1.67 (m, 1H), 1.77–1.87 (m, 4H), 2.57–2.67 (m, 4H), 3.60 (s, 3H), 7.52 (d, 1H), 7.56 (s, 1H), 7.63 (d, 1H).

Example I91.2

R$_1$=cyclohexyl, R$_2$=methyl, R$_3$=3-methyl-4-benzamide 4-(5-Cyclohexylimino-4-methyl-4,5-dihydro-[1,3,4]thiadiazol-2-yl)-2-methyl-benzamide To a solution of I91.1 (0.320 mmol, 0.1 g) in ethanol (17 mL), an aqueous solution of sodium carbonate 3N (3.424 mmol, 1.14 mL) then a solution of hydrogen peroxide (5.60 mL) were added. The suspension was stirred for 2 days at RT, then heated at 40° C. for 8 hours. The mixture was poured into a solution of $Na_2S_2O_5$ and evaporated to dryness, then the crude material was diluted with water and extracted with dichloromethane. The organic layer was washed with water and brine, dried over $MgSO_4$, filtered, and concentrated under reduced pressure. Yield: 70%.

$^1$H-NMR (400 MHz, $CDCl_3$) δ ppm: 1.22–1.51 (m, 5H), 1.60–1.68 (m, 1H), 1.81–1.91 (m, 4H), 2.52 (s, 3H), 2.59–2.69 (m, 1H), 3.60 (m, 3H), 5.64–5.83 (b, 2H), 7.49 (s, 2H), 7.48 (s, 1H).

MS (m/z)/M+1=331/332.

HPLC (UV purity, λ=214 nm): 97.28%.

Example I92

$R_1$=cyclohexyl, $R_2$=methyl, $R_3$=4-bromo-3-methoxy-phenyl

[5-(4-Bromo-3-methoxy-phenyl)-3-methyl-2,3-dihydro-[1,3,4]thiadiazol-2-yl]-cyclohexyl-amine To a mixture of 3-hydroxybenzoic acid (14.480 mmol, 2 g) in acetic acid (14.5 mL) and sulfuric acid (1.5 mL) at 50° C., a solution of bromine (15.204 mmol, 0.780 mL) in acetic acid (7.2 mL) was added and stirred 30 minutes at 100° C. The reaction was allowed to cool to RT and diluted with water. The aqueous layer was extracted with ethyl acetate, washed with water and brine, dried ($MgSO_4$), filtered, and concentrated under reduced pressure to give the 4-bromo-2-hydroxy-benzoic acid. Yield: 100%.

To a solution of 4-bromo-3-hydroxybenzoic acid (14.480 mmol, 2.600 g) in acetone (180 mL), potassium carbonate (62.988 mmol, 8.710 g) and dimethylsulfate (31.422 mmol, 2.970 mL) were added. The reaction was stirred at RT for 30 minutes and evaporated to dryness. The residue was then diluted with water and extracted with ethyl acetate. The collected organic layer was washed with water and brine, dried ($MgSO_4$), filtered, and concentrated under reduced pressure. 4-Bromo-3-methoxy-benzoic acid methyl ester was isolated by chromatography on silica gel eluting with cyclohexane containing from 0% to 20% ethyl acetate. Yield: 47%.

To a solution of 4-bromo-3-methoxy-benzoic acid methyl ester (6.875 mmol, 1.676 mL) in a mixture 1:1 of THF/MeOH (15 mL), lithium hydroxide (7.553 mmol, 0.180 g) was added, and the reaction was stirred at RT overnight before distillation of volatiles. The residue was diluted with water, acidified with a solution of HCl (1N), and stirred for 1 hour. The formed precipitate was filtered off, and washed with water and petroleum ether to give 4-bromo-3-methoxy-benzoic acid. Yield: 56%.

The title compound was prepared by procedure as described in Example I17 (Protocol C) starting from 4-bromo-3-methoxy-benzoic acid. In this particular case, methyltrifluoromethanesulfonate (1.2 eq.) was added once, and the basic aqueous layer was extracted with DCM. The crude was chromatographed on silica gel eluting with cyclohexane containing from 0% to 10% ethyl acetate. The oil obtained was triturated in diethylether, and the formed white solid was isolated by filtration. Yield: 26% (overall, the 2 steps).

$^1$H-NMR (400 MHz, $CDCl_3$) δ ppm: 1.20–1.46 (m, 5H), 1.60–1.68 (m, 1H), 1.77–1.88 (m, 4H), 2.58–2.68 (m, 1H), 3.59 (s, 3H), 3.96 (s, 3H), 7.02 (d, 1H), 7.22 (s, 1H), 7.53 (d, 1H).

Example I92.1

$R_1$=cyclohexyl, $R_2$=methyl, $R_3$=3-methoxy-4-benzamide 4-(5-Cyclohexylimino-4-methyl-4,5-dihydro-[1,3,4]thiadiazol-2-yl)-2-methoxy-benzamide Compound I92 was reacted with copper cyanide by the procedure described in Example I91.1, and the formed intermediate was transformed to I92.1 following the following protocol:

To a heterogeneous solution of this material (0.9134 mmol, 0.300 g) in ethanol (50 mL), a solution of sodium carbonate (3N) (9.773 mmol, 3.258 mL) and hydrogen peroxide (13.3 mL) was added, and the reaction was heated at 40° C. for 1.5 days. The mixture was poured into a saturated solution of $Na_2S_2O_5$, and the solution was concentrated under reduced pressure. The residue was diluted with water, extracted with dichloromethane, and the organic layer was washed with water and brine, dried over $MgSO_4$, filtered, and then evaporated to dryness. The crude material was purified by chromatography on silica gel eluting with dichloromethane containing from 0% to 4% methanol. Yield: 25%.

$^1$H-NMR (400 MHz, $CDCl_3$) δ ppm: 1.20–1.50 (m, 5H), 1.76–1.88 (m, 4H), 2.59–2.69 (m, 1H), 3.60 (s, 3H), 4.02 (s, 3H), 5.80–5.90 (b, 1H), 7.25 (d, 1H), 7.34 (s, 1H), 7.62–7.67 (b, 1H), 8.23 (d, 1H).

MS (m/z)/M+1=347/348.

HPLC (UV purity, λ=214 nm): 97.61%.

Example I92.2

$R_1$=cyclohexyl, $R_2$=methyl, $R_3$=3-hydroxy-4-benzamide 4-(5-Cyclohexylimino-4-methyl-4,5-dihydro-[1,3,4]thiadiazol-2-yl)-2-hydroxy-benzamide To a mixture of I92.1 and n-tetrabutylammonium iodide (0.433 mmol, 0.160 g) in anhydrous dichloromethane (2 mL) under nitrogen atmosphere at −78° C., a solution of $BCl_3$ 1N in dichloromethane (0.433 mmol, 0433 mL) was added, and the reaction mixture was allowed to stir at −78° C. for 10 minutes followed by 2 hours at 0° C. and 1 hour and 30 minutes at RT. Then, a solution of $BCl_3$ 1N in dichloromethane (0.433 mmol, 0433 mL) was added. After an additional 1 hour and 30 minutes of stirring at RT, the reaction was quenched with water and basified with a saturated solution of sodium bicarbonate before extraction with dichloromethane. The organic layer was washed with brine, dried over $MgSO_4$, filtered, and evaporated to dryness. The residue was chromatographed on silica gel eluting with dichloromethane containing from 0% to 4% of methanol to give the desired product. Yield: 26%.

$^1$H-NMR (400 MHz, $CDCl_3$) δ ppm: 1.21–1.50 (m, 5H), 1.63–1.70 (m, 1H), 1.80–1.90 (m, 4H), 2.58–2.68 (m, 1H), 3.60 (s, 3H), 5.70–6.20 (b, 2H), 7.18 (s, 1H), 7.24 (d, 1H), 7.38 (d, 1H), 12.25 (s, 1H).

MS (m/z)/M+1=333/334.

HPLC (UV purity, λ=214 nm): 96.54%.

Example I93

$R_1$=cyclohexyl, $R_2$=methyl, $R_3$=3-nitro-4-methoxycarbonyl-phenyl 4-(5-Cyclohexylimino-4-methyl-4,5-dihydro-[1,3,4]thiadiazol-2-yl)-2-nitro-benzoic acid methyl ester Compound I93 was prepared by the procedure described in Example I21 (Protocol C) using the appropriate intermediates and reagents. In this particular case, triethylamine was not used, and the expected product was isolated by filtration after treatment with a saturated solution of $NaHCO_3$. Yield: 77%.

$^1$H-NMR (400 MHz, $CDCl_3$) δ ppm: 1.20–1.48 (m, 5H), 1.64–1.70 (m, 1H), 1.80–1.90 (m, 4H), 5.58–5.66 (m, 1H), 3.63 (s, 3H), 3.82 (s, 3H), 7.80–7.84 (m, 2H), 8.11 (s, 1H).

Example I93.1

$R_1$=cyclohexyl, $R_2$=methyl, $R_3$=3-amino-4-methoxycarbonyl-phenyl

2-Amino-4-(5-cyclohexylimino-4-methyl-4,5-dihydro-[1,3,4]thiadiazol-2-yl)-benzoic acid methyl ester To a solution of I93 (1.328 mmol, 0.500 g) in ethanol (20 mL), tin chloride dihydrate (6.641 mmol, 1.495 g) was added, and the mixture was heated at reflux for 5 hours then allowed to stand at RT overnight. The mixture was evaporated to dryness, and the crude material was basified with a saturated solution of sodium carbonate before extraction with dichloromethane. The organic layer was washed with brine, dried over $MgSO_4$, filtered, and concentrated under vacuum. The residue was chromatographed on silica gel eluting with dichloromethane containing from 0% to 2% of methanol to afford the desired compound. Yield: 65%.

$^1$H-NMR (400 MHz, $CDCl_3$) δ ppm: 1.21–1.49 (m, 5H), 1.60–1.69 (m, 1H), 1.80–1.90 (m, 4H), 2.58–2.67 (m, 1H), 3.60 (s, 3H), 3.89 (s, 3H), 5.77–5.83 (b, 2H), 7.88–7.92 (m, 2H), 7.89 (d, 1H).

MS (m/z)/M+1=347/349.

HPLC (UV purity, λ=214 nm): 98.31%.

Example I93.2

$R_1$=cyclohexyl, $R_2$=methyl, $R_3$=3-acetylamino-4-methoxycarbonyl-phenyl

2-Acetylamino-4-(5-cyclohexylimino-4-methyl-4,5-dihydro-[1,3,4]thiadiazol-2-yl)-benzoic acid methyl ester To a suspension of I93.1 (0.144 mmol, 0.05 g) in anhydrous toluene (2 mL) at 0° C., triethylamine (0.150 mmol, 0.015 mL) and acetic anhydride (0.160 mmol, 0.015 mL) were added. The reaction was allowed to stir at RT for 3 days, and 5.4 more equivalents of acetic anhydride and triethylamine were added. After 2 days of stirring at RT, the mixture was evaporated to dryness, and the residue was chromatographed on silica gel eluting with dichloromethane containing from 0% to 1% of methanol. Yield: 89%.

$^1$H-NMR (400 MHz, $CDCl_3$) δ ppm: 1.21–1.49 (m, 5H), 1.60–1.67 (m, 1H), 1.76–1.88 (m, 4H), 2.28 (s, 3H), 2.60–2.70 (m, 1H), 3.60 (s, 3H), 3.93 (s, 3H), 7.45 (d, 1H), 8.03 (d, 1H), 8.98 (s, 1H), 11.10 (s, 1H).

MS (m/z)/M+=389/390.

HPLC (UV purity, λ=214 nm): 96.93%.

Example I93.3

$R_1$=cyclohexyl, $R_2$=methyl, $R_3$=3-amino-4-benzamide

2-Amino-4-(5-cyclohexylimino-4-methyl-4,5-dihydro-[1,3,4]thiadiazol-2-yl)-benzamide Compound I93 was modified following the procedure described in Example I37.3 to afford the amide derivative with an overall yield 84%. The reduction of the nitro group to give Example I93.3 was performed as described in Example I93.1. In this particular case, the reactional mixture was basified with a saturated solution of sodium carbonate, then distilled. The crude was diluted in water and extracted with dichloromethane. The aqueous phase, saturated with brine, was then extracted with ethyl acetate, and the organic layer was dried over $MgSO_4$, filtered, and evaporated to dryness to give a residue which was purified by two consecutive chromatographies on silica gel, eluting first with dichloromethane/methanol (93:7), and the second purification made eluting with a gradient of cyclohexane containing from 0% to 40% ethyl acetate. Yield: 10%.

$^1$H-NMR (400 MHz, DMSO) δ ppm: 1.27–1.40 (m, 5H), 1.56–1.62 (m, 1H), 1.70–1.80 (m, 4H), 2.58–2.65 (m, 1H), 3.50 (s, 3H), 6.73–6.78 (m, 3H), 7.00 (s, 1H), 7.10–7.20 (b, 1H), 7.61 (d, 1H), 7.75–7.85 (b, 1H).

MS (m/z)/M+1=332/333.

HPLC (UV purity, λ=214 nm): 95.83%.

Example I93.4

$R_1$=cyclohexyl, $R_2$=methyl, $R_3$=4-oxo-3,4-dihydro-quinazoline-7-yl 7-(5-Cyclohexylimino-4-methyl-4,5-dihydro-[1,3,4]thiadiazol-2-yl)-3H-quinazolin-4-one A mixture of I93.1 (1.443 mmol, 0.500 g) and formamide (4 mL) was stirred and heated at reflux for 2 hours before cooling at RT. The mixture was diluted with water, and the precipitate was collected by filtration. The precipitate was washed with water and petroleum ether and purified by chromatography on silica gel, eluting with dichloromethane containing from 0% to 3% of methanol followed by an isocratic elution with dichloromethane/methanol (93:7). Yield: 20%.

$^1$H-NMR (400 MHz, DMSO) δ ppm: 1.20–1.40 (m, 5H), 1.55–1.64 (m, 1H), 1.70–1.83 (m, 4H), 2.63–2.71 (m, 1H), 3.56 (s, 3H), 7.73 (s, 1H), 7.00 (s, 1H), 7.80 (d, 1H), 8.12–8.19 (m, 3H), 12.30–12.40 (b, 1H).

MS (m/z)/M+1=342/343.

HPLC (UV purity, λ=214 nm): 95.19%.

Example I93.5

$R_1$=cyclohexyl, $R_2$=methyl, $R_3$=4-amino-quinazoline-7-yl 7-(5-Cyclohexylimino-4-methyl-4,5-dihydro-[1,3,4]thiadiazol-2-yl)-quinazolin-4-ylamine A mixture of I93.4 (0.264 mmol, 0.090 g), thionyl chloride (2 mL) and a catalytic amount of dimethylformamide was refluxed for 2 hours before distillation of solvents under reduced pressure. To the residue, a solution of $NH_3$ (0.5N) in dioxane (4 mL) was added, and the mixture was heated in a sealed tube at 80° C. for 4 days. The mixture was then evaporated to dryness, and the crude was diluted in a solution of acetic acid (0.1 mL AcOH in 10 mmL $H_2O$), and extracted with dichloromethane to remove the impurities. The aqueous phase was then basified with a solution NaOH (0.1N) and then extracted with dichloromethane. The organic layer was washed with water, brine, dried over $MgSO_4$, filtered, and concentrated under reduced pressure to give the desired product. Yield: 7.5%.

$^1$H-NMR (400 MHz, $CDCl_3$) δ ppm: 1.29–1.50 (m, 5H), 1.60–1.69 (m, 1H), 1.79–1.90 (m, 4H), 2.65–2.72 (m, 1H), 3.65 (s, 3H), 5.60–5.70 (b, 2H), 7.75 (d, 1H), 7.90 (s, 1H), 7.98 (d, 1H), 8.67 (s, 1H).

MS (m/z)/M+1=341/343.

HPLC (UV purity, λ=214 nm): 99.99%.

Example I93.6

$R_1$=cyclohexyl, $R_2$=methyl, $R_3$=2,4-Dioxo-1,2,3,4-tetrahydro-quinazoline-7-yl 7-(5-Cyclohexylimino-4-methyl-4,5-dihydro-[1,3,4]thiadiazol-2-yl)-1H-quinazoline-2,4-dione To a solution of 193.3 in THF (4 mL), carbonyldiimidazole (0.464 mmol, 0.080 g) was added, and the reaction was heated at reflux overnight. Carbonyldiimidazole (0.464 mmol, 0.080 g) was added, and the mixture was kept at reflux for 24 hours. Then, the solvent was distilled, and the residue was purified by chromatography on silica gel, eluting with a gradient of cyclohexane containing from 15% to 30%. The chromatographed product was solubilized in ethyl acetate, and the organic layer was washed with water. The collected organic layer was washed with brine, dried over $MgSO_4$, filtered, and evaporated to dryness to give the title product. Yield: 13.3%.

$^1$H-NMR (400 MHz, DMSO) δ ppm: 1.28–1.39 (m, 5H), 1.56–1.64 (m, 1H), 1.72–1.82 (m, 4H), 2.62–2.67 (m, 1H), 3.54 (s, 3H), 7.41–7.43 (m, 2H), 7.94 (d, 1H), 11.17 (s, 1H), 11.36 (s, 1H).

MS (m/z)/M+1=358/359.

HPLC (UV purity, λ=214 nm): 96.70%.

Example I94

$R_1$=cyclohexyl, $R_2$=methyl, $R_3$=3-methoxy-4-sulfamoyl-phenyl 4-(5-Cyclohexylimino-4-methyl-4,5-dihydro-[1,3,4]thiadiazol-2-yl)-2-methoxy-benzenesulfonamide The title compound was prepared by the procedure described in Example I19 (Protocol C) using the appropriate intermediates and reagents. The residue was purified by chromatography on silica gel, eluting with dichloromethane containing from 0% to 2% of methanol. Yield: 59%.

$^1$H-NMR (400 MHz, $CDCl_3$) δ ppm: 1.21–1.49 (m, 5H), 1.63–1.69 (m, 1H), 1.77–1.87 (m, 4H), 2.59–2.67 (m, 1H), 3.60 (s, 3H), 4.06 (s, 3H), 5.02 (s, 2H), 7.20 (d, 1H), 7.40 (s, 1H), 7.90 (d, 1H).

MS (m/z)/M+1=384/386.

HPLC (UV purity, λ=214 nm): 99.99%.

Example I95

$R_1$=cyclohexyl, $R_2$=methyl, $R_3$=4-methoxy-3-sulfamoyl-phenyl 5-(5-Cyclohexylimino-4-methyl-4,5-dihydro-[1,3,4]thiadiazol-2-yl)-2-methoxy-benzenesulfonamide The title compound was prepared by procedure as described in Example I18 (Protocol C) using the appropriate intermediates and reagents.

In this particular case, the residue obtained after extraction and distillation was triturated with methanol, and the precipitate was filtered off and purified by silica gel chromatography, eluting with a mixture of cyclohexane/ethyl acetate (1:1). Yield: 9%.

$^1$H-NMR (400 MHz, $CDCl_3$) δ ppm: 1.30–1.50 (m, 5H), 1.62–1.70 (m, 1H), 1.80–1.90 (m, 4H), 2.58–2.65 (m, 1H), 3.58 (s, 3H), 4.02 (s, 3H), 5.10 (s, 2H), 7.09 (d, 1H), 7.80 (d, 1H), 8.12 (s, 1H).

MS (m/z)/M+1=383/384.

HPLC (UV purity, λ=214 nm): 99.38%.

Example I96

$R_1$=3-methoxycarbonyl-phenyl, $R_2$=methyl, $R_3$=3-cyano-phenyl

3-[5-(3-Cyano-phenyl)-3-methyl-3H-[1,3,4]thiadiazol-2-ylideneamino]-benzoic acid methyl ester To a solution of 7j (1.25 mmol, 0.42 g) in anhydrous dioxane (14 mL) was added methyltrifluoromethane sulfonate (1.5 mmol, 142 μL). The resultant mixture was stirred for 24 hours at RT. To this solution was added methyltrifluoromethane sulfonate (0.45 mmol, 43 μL) to ensure completion of the reaction. The solvent was removed by distillation under reduced pressure to give a crude material which was basified with an aqueous saturated solution of $NaHCO_3$ and extracted with dichloromethane. The organic layer was dried over $Na_2SO_4$, filtered, and concentrated. The crude material was purified by two successive flash chromatographies (eluent: dichloromethane/methanol 95:5 and cyclohexane/ethyl acetate 90:10) to give the desired compound 0.23 g. Yield: 53%.

$^1$H-NMR (400 MHz, DMSO) δ ppm: 3.75 (s, 3H), 3.86 (s, 3H), 7.34 (d, 1H), 7.54 (t, 1H), 7.61 (s, 1H), 7.67–7.70 (m, 2H), 7.94 (d, 1H), 8.02 (d, 1H), 8.12 (s, 1H).

MS (m/z)/M+1: 351/353.

Example I96.1

$R_1$=3-benzoic-acid, $R_2$=methyl, $R_3$=3-cyano-phenyl

3-[5-(3-Cyano-phenyl)-3-methyl-3H-[1,3,4]thiadiazol-2-ylideneamino]-benzoic acid A mixture of I96 (3 mg, 8.56 mmol) and potassium hydroxide (1N in water, 12.8 mmol, 12.8 mL) in tetrahydrofuran (90 mL) was stirred at RT overnight. The reaction mixture was heated at reflux for 1 hour. After cooling, the reaction mixture was concentrated, water was added (2 mL), and a solution of HCl (1N in water, 12.8 mmol, 12.8 mL) was added. The precipitate was collected by filtration and washed successively with water and with ether before being dried under vacuum at 45° C. The compound was purified by flash chromatography (eluent: dichloromethane/methanol 99:1+1% acetic acid) to give 2.38 g of the title product. Yield: 83%.

$^1$H-NMR (400 MHz, DMSO) δ ppm: 3.8 (s, 3H), 7.31 (d, 1H), 7.51 (t, 1H), 7.61 (s, 1H), 7.65–7.69 (m, 2H), 7.93 (d, 1H), 8.01 (d, 1H), 8.11 (s, 1H), 13.06 (s, 1H).

MS (m/z)/M+1=337/338.

HPLC (UV purity, λ=245 nm): 99.6%.

Example I97

$R_1$=3-methoxycarbonyl-phenyl, $R_2$=methyl, $R_3$=2-pyridyl

3-[3-Methyl-5-pyridin-2-yl-3H-[1,3,4]thiadiazol-2-ylideneamino]-benzoic acid methyl ester To a solution of 7k (1.76 mmol, 0.55 g) in anhydrous dioxane (14 mL) and triethylamine (1.76 mmol, 264 μL), methyltrifluoromethane sulfonate (1.76 mmol, 199 μL) was added. The resultant mixture was stirred for 24 hours. To this solution was added methyltrifluoromethane sulfonate (0.53 mmol, 60 μL) and triethylamine (0.53 mmol, 79.2 μL) to allow reaction to completion. The solvent was removed by distillation under reduced pressure to give a crude material which was basified with an aqueous saturated solution of $NaHCO_3$ and extracted with dichloromethane. The organic layer was dried over $Na_2SO_4$, filtered, and concentrated. The crude material was purified by filtration on silica gel (eluent: dichloromethane) to give the desired compound. Yield: 28%.

$^1$H-NMR (400 MHz, DMSO) δ ppm: 3.76 (s, 3H), 3.86 (s, 3H), 7.35 (dd, 1H), 7.48–7.54 (m, 2H), 7.64–7.68 (m, 2H), 7.96–8.00 (m, 2H), 8.58 (d, 1H).

MS (m/z)/M+1: 327/329.

Example I97.1

$R_1$=3-benzoic-acid, $R_2$=methyl, $R_3$=2-pyridyl

3-[3-Methyl-5-pyridin-2-yl-3H-[1,3,4]thiadiazol-2-ylideneamino]-benzoic acid

A mixture of I97 (16 g, 0.49 mmol) and potassium hydroxide (1N in water, 0.58 mmol, 0.58 mL) in tetrahydrofuran (3 mL) was stirred at RT for 48 hours. The reaction mixture was heated at reflux for 2 hours. After cooling, the reaction mixture was concentrated, water was added (5 mL), the aqueous layer was extracted with dichloromethane and neutralized with a solution of HCl (0.1N in water). The precipitate was collected by filtration and washed successively with water and with ether before being dried under vacuum at 45° C. to give 0.08 g of the title product. Yield: 54%.

$^1$H-NMR (400 MHz, DMSO) δ ppm: 3.8 (s, 3H), 7.31 (d, 1H), 7.47–7.49 (m, 2H), 7.64–7.66 (m, 2H), 7.96–7.98 (m, 2H), 8.58 (d, 1H).

MS (m/z)/M+1=313/314/315.

HPLC (UV purity, λ=245 nm): 97.6%.

Example I98

$R_1$=3-benzoic-acid, $R_2$=methyl, $R_3$=4-Chloro-3-sulfamoyl-phenyl

3-[5-(4-Chloro-3-sulfamoyl-phenyl)-3-methyl-3H-[1,3,4] thiadiazol-2-ylideneamino]-benzoic acid Compound I98 was prepared by the procedure described in Example I96.1 using the appropriate intermediates and reagents. In this particular case, the ester intermediate was basified with triethylamine. The title product was isolated by chromatography on silica gel, eluting with ethyl acetate/cyclohexane (15:85). Yield: 19% (2 steps).

$^1$H-NMR (400 MHz, DMSO) δ ppm: 3.73 (s, 3H), 3.85 (s, 3H), 7.35 (d, 1H), 7.54 (t, 1H), 7.62 (s, 1H), 7.70–7.80 (m, 4H), 7.86 (d, 1H), 8.24 (s, 1H).

MS (m/z)/M+1=439/441.

Then, a solution (1N) of potassium hydroxide (1.139 mmol, 1.14 mL) was added to a solution of the ester derivative (0.456 mmol, 0.2 g) in THF (5 mL), and the mixture was stirred overnight. The reaction mixture was evaporated to dryness, and the residue was diluted in ethanol and acidified with a solution (6.9N) of HCl in ethanol (0.165 mL). The mixture was stirred at RT for 5 hours, and the solvent was distilled under reduced pressure. The crude material was chromatographed on silica gel, eluting with a gradient of dichloromethane containing from 5% to 25% methanol. The isolated product was solubilized in THF and filtered through a pad of silica gel, and the filtrate was evaporated to dryness to afford the desired product. Yield: 37%.

$^1$H-NMR (400 MHz, CDCl3) δ ppm: 3.74 (s, 3H), 7.24 (d, 1H), 7.45 (t, 1H), 7.62 (s, 1H), 7.66 (d, 1H), 7.73–7.80 (m, 3H), 7.84 (d, 1H), 8.23 (s, 1H).

MS (m/z)/M+1=425/427.

HPLC (UV purity, λ=214 nm): 94.86%.

Example I

Protocol D

Example I99

$R_1$=cyclohexyl, $R_2$=methyl, $R_3$=4-cyano-phenyl 4-(5-Cyclohexylimino-4-methyl-4,5-dihydro-[1,3,4] thiadiazol-2-yl)-benzonitrile Compound I99 was prepared by the procedure described in Example I15 (Protocol D).

To a mixture of 4-cyanobenzoic acid (74.8 mmol, 11 g), 2-methylthiosemicarbazide (5a) (74.8 mmol, 13.42 g) in anhydrous dioxane (110 mL) at 70° C., POCl$_3$ (89.65 mmol, 76.76 mL) was added, and the mixture was warmed at 95° C. for 4 hours. The solvent was removed by distillation under reduced pressure to give a crude material which was basified at pH 8–7 with a saturated solution of NaHCO$_3$. The aqueous phase was extracted with dichloromethane. The organic layer was washed with water and saturated solution of NaCl, dried over magnesium sulfate, filtered, and distilled to give a residue which was purified by silica gel chromatography (eluted with a gradient of cyclohexane/ethyl acetate finishing with the ratio 90:10) to afford 8.5 g of the title compound. Yield: 42%.

$^1$H-NMR (400 MHz, DMSO) δ ppm: 1.15–1.40 (m, 5H), 1.55–1.65 (m, 1H), 1.70–1.83 (m, 4H), 2.57–2.70 (m, 1H), 3.55 (s, 3H), 7.82 (dd, 2H), 7.93 (dd, 2H).

Example I99.1

$R_1$=cyclohexyl, $R_2$=methyl, $R_3$=4-(1H-tetrazol-5-yl)-phenyl

Cyclohexyl-{3-methyl-5-[4-(1H-tetrazol-5yl)-phenyl]-3H-[1,3,4]thiadiazol-2-ylidene}-amine To a solution of I99 (1.67 mmol, 500 mg) in toluene (2 mL), sodium azide (2.18 mmol, 142 mg), triethylamine hydrochloride (2.18 mmol, 300 mg) were added, and the mixture was warmed at reflux during 24 hours. The reaction mixture was cooled at RT, acidified with a solution of HCl [0.1N], and then basified at pH 6–7 with a saturated solution of NaHCO$_3$. The aqueous phase was extracted with ethyl acetate, and the organic layer was washed with a saturated solution of NaCl, dried over magnesium sulfate, filtered, and concentrated under reduced pressure. The residue was chromatographed on silica gel column using a gradient of dichloromethane containing from 0% to 20% methanol to afford the title compound. Yield: 61%.

$^1$H-NMR (400 MHz, DMSO) δ ppm: 1.20–1.42 (m, 5H), 1.55–1.65 (m, 1H), 1.70–1.85 (m, 4H), 2.60–2.72 (m, 1H), 3.55 (s, 3H), 7.85 (dd, 2H), 8.13 (dd, 2H).

MS (m/z)/M+1=341/342.

HPLC (UV purity, λ=214 nm): 99.9%.

Example I100

$R_1$=cyclohexyl, $R_2$=methyl, $R_3$=4-nitro-phenyl

Cyclohexyl-[3-methyl-5-(4-nitro-phenyl)-3H-[1,3,4] thiadiazol-2-ylidene]-amine

Compound I100 was prepared as described in Example I15 (Protocol D) using the appropriate reagents. The crude material was purified by silica gel chromatography eluting with a gradient of cyclohexane containing from 0% to 10% ethyl acetate. Yield: 40%.

$^1$H-NMR (400 MHz, DMSO) δ ppm: 1.20–1.40 (m, 5H), 1.57–1.64 (m, 1H), 1.72–1.83 (m, 4H), 2.61–2.91 (m, 1H), 3.56 (s, 3H), 7.89 (d, 2H), 8.29 (d, 2H).

MS (m/z)/M+1=319/320.

Example I100.1

$R_1$=cyclohexyl, $R_2$=methyl, $R_3$=4-amino-phenyl
4-(5-Cyclohexylimino-4-methyl-4,5-dihydro-[1,3,4]thiadiazol-2-yl)-phenylamine Tin chloride dihydrate (93.278 mmol, 20.987 g) was added to a solution (I100) (18.656 mmol, 5.940 g) in ethanol at 70° C., and the mixture was refluxed for 1 hour and 30 minutes. The mixture was then filtered on Celite, and the filtrate was evaporated to dryness. The crude material was basified with a saturated solution of sodium bicarbonate then extracted with ethyl acetate. The organic layer was washed with water and brine, dried over $MgSO_4$, filtered, and then evaporated to dryness. The residue was filtered through a pad of silica gel with a mixture of dichloromethane/methanol (95:5). Yield: 62%.

$^1$H-NMR (400 MHz, $CDCl_3$) δ ppm: 1.19–1.37 (m, 5H), 1.56–1.63 (m, 1H), 1.70–1.80 (b, 4H), 2.56–2.74 (m, 1H), 3.44 (s, 3H), 5.60 (s, 2H), 6.58 (d, 2H), 7.29 (d, 2H).

MS (m/z)/M+1=289/290.

HPLC (UV purity, λ=214 nm): 97.61%.

Example I100.2

$R_1$=cyclohexyl, $R_2$=methyl, $R_3$=4-(N-cyano-N'-(2-dimethylaminoethyl)carboximidamide)-phenyl
[5-(4-(N-Cyano-N'-(2-dimethylaminoethyl)-carboximidamide)-phenyl)-3-methyl-3H-[1,3,4]thiadiazol-2-ylidene]-cyclohexyl-amine To a solution of diphenylcyanocarbonimidate (0.364 mmol, 0.087 mmol) in acetonitrile (1 mL) at 70° C., I100.1 (0.347 mmol, 0.1 g) was added, and the reaction mixture was heated at 80° C. for 15 hours. One equivalent of carbonimidate was added, and the mixture was kept at 80° C. for an additional 5 hours before evaporation of volatiles. The residue was mixed with ethanol (2 mL) and N,N-dimethylethylene diamine (0.34 mmol, 0.038 mg). The mixture was stirred at RT for 15 hours and heated at reflux for 5 hours. On cooling to RT, the precipitate formed was filtered off and purified by silica gel chromatography eluting with a gradient of dichloromethane containing from 2% to 5% methanol. Yield: 32%.

$^1$H-NMR (400 MHz, $CDCl_3$) δ ppm: 1.16–1.41 (m, 5H), 1.50–1.70 (m, 1H), 1.80–1.91 (m, 4H), 2.35 (s, 6H), 2.50–2.60 (m, 3H), 3.31–3.38 (m, 2H), 3.55 (s, 3H), 6.00–6.10 (b, 1H), 7.30 (d, 2H), 7.52 (d, 2H).

MS (m/z)/M+1=427/428.

HPLC (UV purity, λ=214 nm): 97.23%.

Example I100.3

$R_1$=cyclohexyl, $R_2$=methyl, $R_3$=4-acetamide-phenyl
N-[4-(5-Cyclohexylimino-4-methyl-4,5-dihydro-[1,3,4]thiadiazol-2-yl)-phenyl]-acetamide To a solution of I100.1 (0.347 mmol, 0.1 g) in presence of triethylamine (0.361 mmol, 0.051 mL) in anhydrous toluene (3 mL) at 0° C., acetic anhydride (0.382 mmol, 0.036 mL) was added, and the reaction mixture was stirred at RT for 20 hours and then concentrated to dryness. The residue was mixed with a saturated solution of sodium bicarbonate, and then the aqueous mixture was extracted with dichloromethane. The organic layer was washed with water, brine, dried over $MgSO_4$, filtered, and evaporated to dryness. The residue was purified by silica gel chromatography eluting with a mixture of methanol/dichloromethane (2:98). Yield: 22%.

$^1$H-NMR (400 MHz, $CDCl_3$) δ ppm: 1.22–1.45 (m, 5H), 1.58–1.68 (m, 1H), 1.80–1.88 (m, 4H), 2.21 (s, 3H), 2.58–2.64 (m, 1H), 3.60 (s, 3H), 7.20 (s, 1H), 7.52–7.62 (m, 4H).

MS (m/z)/M+1=331/332.

HPLC (UV purity, λ=214 nm): 95.24%.

Example I100.4

$R_1$=cyclohexyl, $R_2$=methyl, $R_3$=4-(bis-ethylsulfonyl-amino)-phenyl
[5-(4-(bis-ethylsulfonylamino)-phenyl)-3-methyl-3H-[1,3,4]thiadiazol-2-ylidene]-cyclohexyl-amine To a solution of I100.1 (0.347 mmol, 0.1 g) in dichloromethane (5 mL) with triethylamine (0.520 mmol, 0.072 mL), chlorosulfonyl chloride (0.590 mmol, 0.057 mL) was added at 0° C., and the mixture was stirred at RT for 4 hours and 30 minutes before evaporation to dryness under reduced pressure. The crude material was purified by silica gel chromatography eluting with a gradient of dichloromethane containing from 0% to 5% methanol. Yield: 76%.

$^1$H-NMR (400 MHz, $CDCl_3$) δ ppm: 1.20–1.52 (m, 11H), 1.61–1.68 (m, 1H), 1.80–1.89 (m, 4H), 2.59–2.68 (m, 1H), 3.58–3.64 (m, 7H), 7.40 (d, 2H), 7.70 (d, 2H).

MS (m/z)/M+1=473/475.

HPLC (UV purity, λ=214 nm): 98.68%.

Example I100.5

$R_1$=cyclohexyl, $R_2$=methyl, $R_3$=4-(1-(2-dimethylaminoethyl)amino-2-nitro-vinylamino)-phenyl
[5-(4-(1-(2-Dimethylaminoethyl)amino-2-nitro-vinylamino)-phenyl)-3-methyl-3H-[1,3,4]thiadiazol-2-ylidene]-cyclohexyl-amine To a solution of 1,1-bis(methylthio)-2-nitroethylene (1.041 mmol, 0.172 g) in acetonitrile (1 mL), at 75° C., I100.1 (0.347 mmol, 0.1 g) was added, and the reaction was heated at reflux for 7 hours. The reaction mixture was then evaporated to dryness, and the crude material was purified by silica gel chromatography eluting with a gradient of dichloromethane containing from 0% to 5% of methanol to give the desired intermediate (0.09 g, Yield: 64%).

A mixture of ethylenediamine (0.133 mmol, 0.017 mL) and this intermediate (0.111 mmol, 0.045 g) in ethanol (2 mL) was heated at reflux for 3 hours. The mixture was concentrated under reduce pressure to give a residue which was purified by silica gel chromatography eluting with dichloromethane containing 2% methanol. Yield: 90%.

$^1$H-NMR (400 MHz, $CDCl_3$) δ ppm: 1.23–1.49 (m, 5H), 1.65–1.70 (m, 1H), 1.78–1.88 (m, 4H), 2.45 (s, 6H), 2.57–2.71 (m, 3H), 3.51–3.61 (m, 5H), 6.66 (s, 1H), 7.09 (d, 2H), 7.60 (d, 2H), 10.55–10.62 (b, 1H), 12.28–12.40 (b, 1H).

MS (m/z)/M+1=446/447.

HPLC (UV purity, λ=214 nm): 99.34%.

Example I100.6

$R_1$=cyclohexyl, $R_2$=methyl, $R_3$=4-(1-amino-2-nitro-vinylamino)-phenyl
(E)-$N^1$-[4-(5-Cyclohexylimino-4-methyl-4,5-dihydro-[1,3,4]thiadiazol-2-yl)-phenyl]-2-nitro-ethene-1,1-diamine The title product was prepared by the procedure described in Example I100.5 using a solution of ammonia (2N) in methanol (80 eq.) instead of ethylenediamine.

The desired product was isolated by chromatography on silica gel, eluting with a gradient of dichloromethane containing from 2% to 4% methanol. Yield: 83%.

$^1$H-NMR (400 MHz, $CDCl_3$) δ ppm: 1.20–1.47 (m, 5H), 1.62–1.67 (m, 1H), 1.76–1.87 (m, 4H), 2.60–2.66 (m, 1H), 3.60 (m, 3H), 6.70 (s, 1H), 7.24 (d, 2H), 7.67 (d, 2H).

MS (m/z)/M+1=375/376.
HPLC (UV purity, λ=214 nm): 94.09%.

Example I100.7

$R_1$=cyclohexyl, $R_2$=methyl, $R_3$=4-(N-cyano-N'-methyl-carboximidamide)-phenyl
[5-(N-cyano-N'-methyl-4-carboximidamide-phenyl)-3-methyl-3H-[1,3,4]thiadiazol-2-ylidene]-cyclohexyl-amine To a solution of diphenylcyanocarbonimidate (0.364 mmol, 0.087 g) in acetonitrile (1 mL) at 70° C., I100-1 (0.347 mmol, 0.1 g) was added, and the mixture was heated at 80° C. for 15 hours. One equivalent of diphenylcyanocarbonimidate was added, and the mixture was stirred for 5 hours. The mixture was concentrated under reduced pressure to give the intermediate which was used without further purification. The intermediate (0.416 mmol, 0.300 g) in a solution (2N) of methylamine in MeOH (32.890 mmol, 16.64 mL) was refluxed for 8 hours then allowed to stand at RT for 2 days. The mixture was evaporated to dryness, and the residue was purified by chromatography on silica gel, eluting with a gradient of dichloromethane containing from 0% to 4% of methanol to give the desired product. Yield: 29%.

$^1$H-NMR (400 MHz, CDCl$_3$) δ ppm: 1.20–1.45 (m, 5H), 1.62–1.67 (m, 1H), 1.76–1.87 (m, 4H), 2.57–2.67 (m, 1H), 2.90 (d, 3H), 3.60 (m, 3H), 4.90–5.01 (b, 1H), 7.17–7.28 (m, 3H), 7.69 (d, 2H).
MS (m/z)/M+1=370/371.
HPLC (UV purity, λ=214 nm): 99.99%.

Example I100.8

$R_1$=cyclohexyl, $R_2$=methyl, $R_3$=4-(N-cyano-N'-amino-carboximidamide)-phenyl
[5-(4-(N-cyano-N'-amino-carboximidamide)-phenyl)-3-methyl-3H-[1,3,4]thiadiazol-2-ylidene]-cyclohexyl-amine The title product was prepared by the procedure described in Example I116 using the same intermediate (0.416 mmol, 0.300 g) and a solution (2N) of ammonia in methanol (32.89 mmol, 16.64 mL). The desired product was purified by chromatography on silica gel eluting with a gradient of dichloromethane containing from 0% to 7% methanol. Yield: 67%.

$^1$H-NMR (400 MHz, CDCl$_3$) δ ppm: 1.20–1.46 (m, 5H), 1.60–1.66 (m, 1H), 1.78–1.88 (m, 4H), 2.55–2.65 (m, 1H), 3.58 (m, 3H), 6.10 (s, 2H), 7.42 (d, 2H), 7.55 (d, 2H), 8.71 (s, 1H).
MS (m/z)/M+1=356/357.
HPLC (UV purity, λ=214 nm): 97.39%.

Example I100.9

$R_1$=cyclohexyl, $R_2$=methyl, $R_3$=4-ethylsulfonylamino-phenyl
Ethanesulfonic acid [4-(5-cyclohexylimino-4-methyl-4,5-dihydro-[1,3,4]thiadiazol-2-yl)-phenyl]-amide Ethylsulfonyl chloride (0.416 mmol, 0.040 mL) was added to a solution of I100.1 (0.347 mmol, 0.10 g) in dichloromethane at 0° C. The mixture was stirred for 12 hours at RT, then basified with a saturated solution of sodium bicarbonate. The organic layer was collected and concentrated under reduce pressure. The crude material was reacted with 1,1-bis(methylthio)-2-nitroethlene (2.690 mmol, 0.445 g, 10 eq.) at reflux in acetonitrile (5 mL) for 24 hours. The solvent was then distilled under reduced pressure, and the residue was purified by silica gel chromatography eluting with dichloromethane containing a gradient from 0% to 10% methanol. Yield: 15%.

$^1$H-NMR (400 MHz, CDCl$_3$) δ ppm: 1.24–1.44 (m, 8H), 1.62–1.68 (m, 1H), 1.78–1.87 (m, 4H), 2.59–2.65 (m, 1H), 3.14–3.19 (q, 2H), 3.60 (s, 3H), 6.44 (s, 2H), 7.23 (dd, 2H), 7.61 (dd, 2H).
MS (m/z)/M+1=381/383.
HPLC (UV purity, λ=214 nm): 99.22%.

Example I100.10

$R_1$=cyclohexyl, $R_2$=methyl, $R_3$=4-Ureido-phenyl
[4-(5-Cyclohexylimino-4-methyl-4,5-dihydro-[1,3,4]thiadiazol-2-yl)-phenyl]-urea To a solution of I100.1 (0.348 mmol, 0.100 g) in THF (1 mL), trimethylsilyl isocyanate (0.416 mmol, 0.488 mL) was added, and the mixture was stirred at RT for 10 hours, and water was added. The organic layer was extracted with ethyl acetate, washed with water, brine, dried over MgSO$_4$, filtered, and then evaporated to dryness. The crude product was purified by chromatography on silica gel, eluting with a gradient of dichloromethane containing from 0% to 4% of methanol. Yield: 13%.

$^1$H-NMR (400 MHz, DMSO) δ ppm: 1.24–1.39 (m, 5H), 1.53–1.57 (m, 1H), 1.69–1.80 (m, 4H), 2.57–2.65 (m, 1H), 3.47 (s, 3H), 5.92 (s, 2H), 7.50 (s, 4H), 8.79 (s, 1H).
MS (m/z)/M+1=332/333.
HPLC (UV purity, λ=214 nm): 92.50%.

Example I100.11

$R_1$=cyclohexyl, $R_2$=methyl, $R_3$=4-[3-(2-dimethylamino-ethyl)-ureido]-phenyl
1-[4-(Cyclohexylimino-methyl-4,5-dihydro-[1,3,4]thiadiazol-2-yl)-phenyl]-3-(2-dimethylamino-ethyl)-urea To a solution of I100.1 (0.347 mmol, 0.100 g) with triethylamine (1.041 mmol, 0.145 mL) in dichloromethane anhydrous (5 mL) was added a solution of phosgene (20% in toluene) (1.024 mmol, 0.487 mL) at 0° C. The mixture was stirred at 0° C. for 10 minutes, then allowed to raise to RT for 1 hour, and N,N-dimethyl-ethylene diamine (0.694 mmol, 0.076 mL) was added. After 20 hours of stirring at RT, the mixture was basified with a saturated solution of sodium bicarbonate then extracted with dichloromethane. The organic phase was washed with water, brine, dried over MgSO$_4$, and evaporated under reduced pressure. The residue was chromatographed on silica gel eluting with a mixture dichloromethane/methanol (95:5) to afford the tittle product. Yield: 11%.

$^1$H-NMR (400 MHz, CDCl$_3$) δ ppm: 1.20–1.50 (m, 5H), 1.70–1.75 (m, 1H), 1.78–1.90 (m, 4H), 2.33 (s, 6H), 2.58–2.68 (m, 3H), 3.30–3.40 (b, 2H), 3.60 (s, 3H), 5.37–5.47 (b, 1H), 7.40 (d, 2H), 7.55 (d, 2H).
MS (m/z)/M+1=403/404.
HPLC (UV purity, λ=214 nm): 99.99%.

Example I101

$R_1$=cyclohexyl, $R_2$=methyl, $R_3$=3-chloro-4-sulfamoyl-phenyl
2-Chloro-4-(5-cyclohexylimino-4-methyl-4,5-dihydro-[1,3,4]thiadiazol-2-yl)-benzenesulfonamide The title compound was prepared by the procedure described in Example I15 (Protocol D) using the appropriate intermediates and reagents.

The desired product was isolated by chromatography on silica gel, eluting with a gradient of cyclohexane containing from 0% to 30% ethyl acetate. Yield: 23%.

$^1$H-NMR (400 MHz, CDCl$_3$) δ ppm: 1.21–1.49 (m, 5H), 1.60–1.69 (m, 1H), 1.79–1.87 (m, 4H), 2.59–2.69 (m, 1H), 3.60 (m, 3H), 5.10 (s, 2H), 7.58 (d, 1H), 7.80 (s, 1H), 8.10 (d, 1H).

MS (m/z)/M+1=388/389.
HPLC (UV purity, λ=214 nm): 98.32%.

Example I102

R$_1$=cyclohexyl, R$_2$=methyl, R$_3$=3-chloro-4-methoxycarbonyl-phenyl

2-Chloro-4-(5-cyclohexylimino-4-methyl-4,5-dihydro-[1,3,4]thiadiazol-2-yl)-benzoic acid methyl ester Compound I102 was prepared by procedure as described in Example I15 (Protocol D) using the appropriate intermediates and reagents. The desired product was isolated by chromatography on silica gel eluting with a gradient of cyclohexane containing from 0% to 7% ethyl acetate. Yield: 12%.

$^1$H-NMR (400 MHz, CDCl$_3$) δ ppm: 1.21–1.48 (m, 5H), 1.60–1.67 (m, 1H), 1.78–1.87 (m, 4H), 2.58–2.66 (m, 1H), 3.60 (s, 3H), 4.93 (s, 3H), 7.55 (d, 1H), 7.71 (s, 1H), 7.86 (d, 1H).

Example I102.1

R$_1$=cyclohexyl, R$_2$=methyl, R$_3$=3-chloro-4-benzamide

2-Chloro-4-(5-cyclohexylimino-4-methyl-4,5-dihydro-[1,3,4]thiadiazol-2-yl)-benzamide To a solution of I102 (0.391 mmol, 0.147 g) in a mixture of THF/MeOH (2 mL) (1:1), lithium hydroxide (0.430 mmol, 0.010 g) was added, and the reaction mixture was allowed to stir for 15 hours at RT. Lithium hydroxide (0.430 mmol, 0.010 g) was added, and the reaction was stirred for 24 hours before evaporation to dryness. The crude material was acidified with a solution of HCl (1N), stirred at RT for 3 hours, and the mixture was then concentrated to dryness.

Toluene (5 mL) was added to the residue (0.273 mmol, 0.120 g) followed by an addition of thionyl chloride (0.820 mmol, 0.598 mL), and the mixture was heated at reflux overnight before distillation of volatiles under reduced pressure. The residue was poured into THF (5 mL) and cooled to 0° C., then a solution of concentrated ammonia (6.833 mmol, 0.448 mL) was added. The reaction was allowed to stir at RT for 3 hours, and then the solvent was distilled. The residue was purified by chromatography on silica gel, eluting with dichloromethane containing from 0% to 1% methanol. Yield: 63% (overall).

$^1$H-NMR (400 MHz, CDCl$_3$) δ ppm: 1.20–1.48 (m, 5H), 1.62–1.69 (m, 1H), 1.79–1.88 (b, 4H), 2.58–2.67 (m, 1H), 3.60 (m, 3H), 5.86–5.93 (b, 1H), 6.38–6.48 (b, 1H), 7.57 (d, 1H), 7.70 (s, 1H), 7.87 (d, 1H).

MS (m/z)/M+1=351/353.
HPLC (UV purity, λ=214 nm): 96.60%.

Example I103

R$_1$=cyclohexyl, R$_2$=methyl, R$_3$=4-chloro-3-benzamide

2-Chloro-5-(5-cyclohexylimino-4-methyl-4,5-dihydro-[1,3,4]thiadiazol-2-yl)-benzamide The title compound was prepared by the procedure described in Example I102.1 using the appropriate intermediates and reagents (Protocol D). Yield: 47%.

$^1$H-NMR (400 MHz, CDCl$_3$) δ ppm: 1.20–1.42 (m, 5H), 1.60–1.69 (m, 1H), 1.77–1.89 (b, 4H), 2.55–2.65 (m, 1H), 3.60 (m, 3H), 5.89–6.00 (b, 1H), 6.30–6.40 (b, 1H), 7.46 (d, 1H), 7.68 (d, 1H), 8.00 (s, 1H).

MS (m/z)/M+1=351/353.
HPLC (UV purity, λ=214 nm): 98.70%.

Protocol E: Intermediate 8

R$_1$=cyclohexyl, R$_2$=methyl, R$_3$=4-methoxycarbonyl-phenyl 1-(4-Methoxycarbonyl-benzoyl)-2-methyl-4-cyclohexyl-thiosemicarbazide To a stirred solution of 5a (2.517 mmol, 0.456 g) in pyridine (6 mL), methyl-4-chloro carbonyl benzoate (2.517 mmol, 0.500 g) was added. The mixture was stirred 24 hours at RT, and then the pyridine was distilled under reduced pressure. The residue was poured into water and extracted with dichloromethane. The organic layer was washed with water, brine, dried over MgSO$_4$, and concentrated to dryness to afford 1.10 g of product.

1H-NMR (400 MHz, DMSO) δ ppm: 1.15–1.25 (m, 5H), 1.51–1.61 (m, 1H), 1.61–1.71 (m, 2H), 1.71–1.87 (m, 2H), 3.28 (s, 3H), 3.9 (s, 3H), 4.10–4.21 (m, 1H), 8.00–8.10 (m, 4H), 8.59 (d, 1H), 10.79 (s, 1H).

Example I

Protocol E

Example I104

R$_1$=cyclohexyl, R$_2$=methyl, R$_3$=4-methoxycarbonyl-phenyl 4-(5-Cyclohexylimino-4-methyl-4,5-dihydro-[1,3,4]oxadiazol-2-yl)-benzoic acid methyl ester A stirred mixture of the previous intermediate 8 (2.517 mmol, 1.10 g) and methanol (50 mL) was warmed until a homogeneous solution was obtained, then mercury oxide (10.068 mmol, 2.18 g) was added. After 18 hours at reflux, three more equivalents of HgO were added, and the reaction was kept at reflux for an additional 6 hours then allowed to cool down to RT. The reaction was filtered through a pad of Celite, and the filtrate was evaporated under reduced pressure. The crude material was purified by chromatography on silica gel eluting with cyclohexane containing from 10% to 20% ethyl acetate. Yield: 44%.

$^1$H-NMR (400 MHz, DMSO) δ ppm: 1.1–1.4 (m, 5H), 1.53–1.61 (m, 1H), 1.69–1.80 (m, 1H), 3.30 (s, 3H), 3.40–3.48 (m, 1H), 3.88 (s, 3H), 3.85 (d, 2H), 7.96 (d, 2H), 8.08 (d, 2H).

MS (m/z)/M+1=316/318.

Example 104.1

R$_1$=cyclohexyl, R$_2$=methyl, R$_3$=4-benzamide 4-(5-Cyclohexylimino-4-methyl-4,5-dihydro-[1,3,4]oxadiazol-2-yl)-benzamide The title compound was prepared by procedure described in Example I137.3. The desired product was isolated by chromatography on silica gel eluting with dichloromethane containing from 1% to 2% methanol. Yield: 26% (overall).

$^1$H-NMR (400 MHz, DMSO) δ ppm: 1.17–1.40 (m, 5H), 1.58–1.64 (m, 1H), 1.70–1.80 (m, 4H), 3.30 (s, 3H), 3.41–3.51 (m, 1H), 7.50–7.55 (b, 1H), 7.80 (d, 2H), 8.00 (d, 2H), 8.10–8.18 (b, 1H).

MS (m/z)/M+1=301/302.

HPLC (UV purity, λ=214 nm): 99.9%.

The compounds of Formula I disclosed in the examples are summarized in the following table:
| Example | Structure |
| --- | --- |
| I1 | 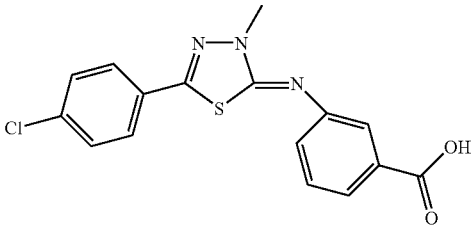 |
| I1,1 | 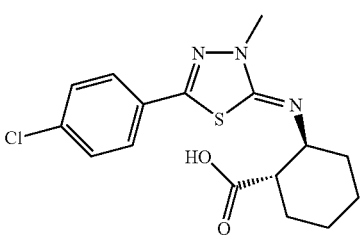 |
| I1,2 | 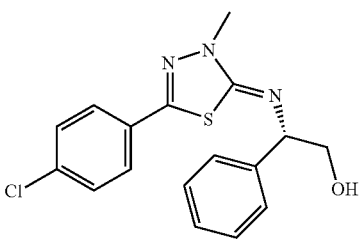 |
| I1,3 | 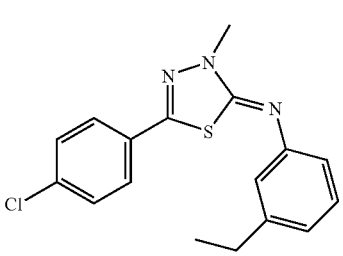 |
| I1,4 | 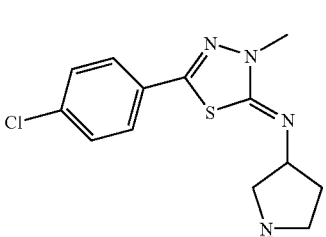 |
| I1,5 | 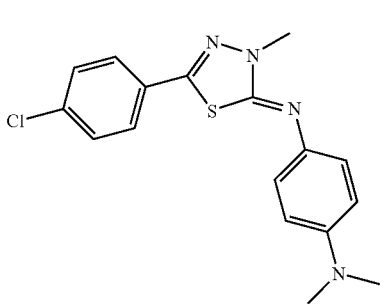 |

-continued
| Example | Structure |
|---|---|
| I1,6 | 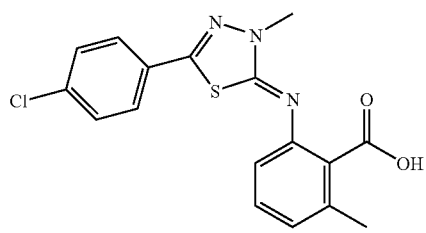 |
| I1,7 | 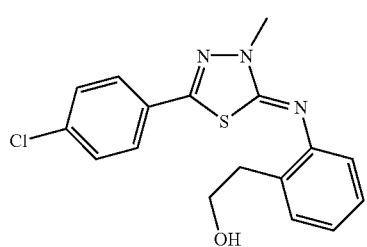 |
| I1,8 | 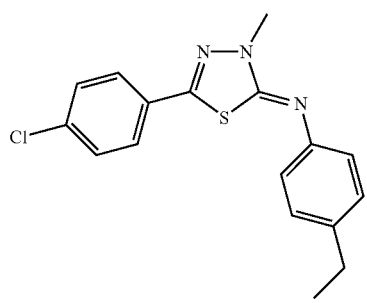 |
| I1,9 | 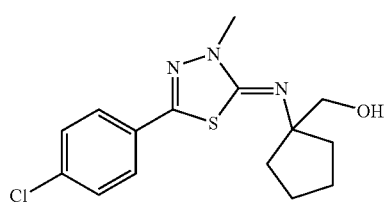 |
| I1,10 | 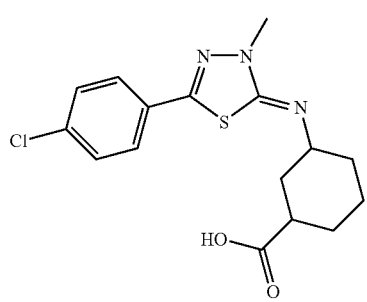 |
| I2 | 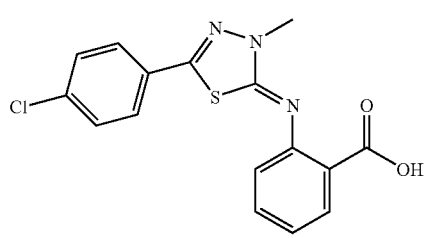 |

-continued
| Example | Structure |
|---|---|
| I2,1 | 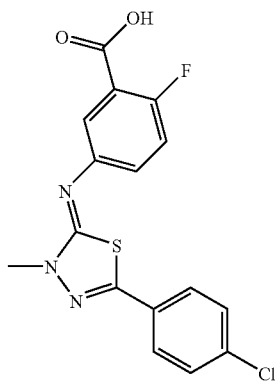 |
| I2,2 | 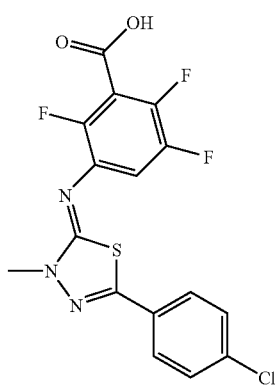 |
| I3 | 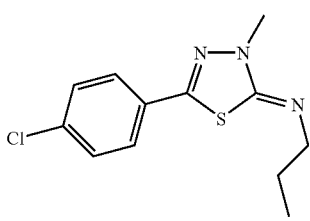 |
| I3,1 | 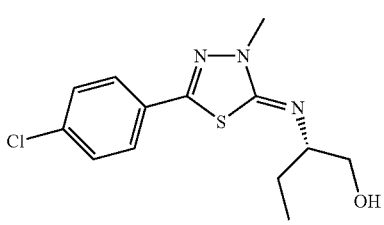 |
| I3,2 | 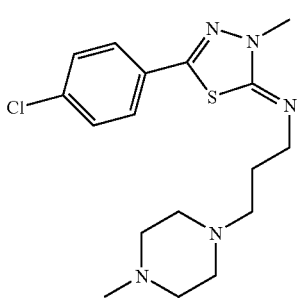 |

-continued
| Example | Structure |
|---------|-----------|
| I3,3 | 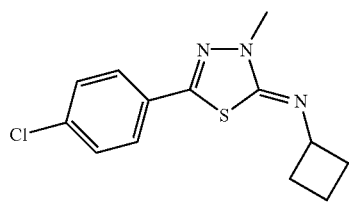 |
| I3,4 | 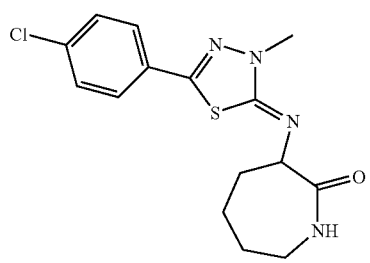 |
| I3,5 | 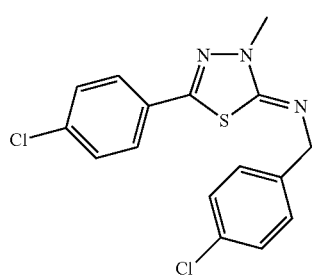 |
| I3,6 | 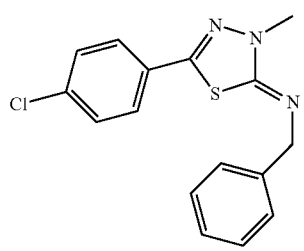 |
| I3,7 | 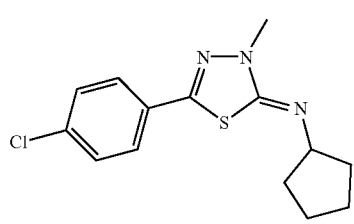 |
| I3,8 | 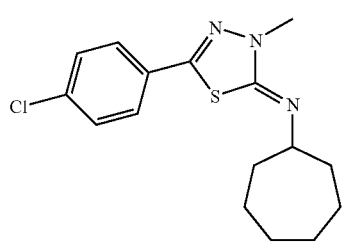 |

-continued
| Example | Structure |
|---|---|
| I3,9 | 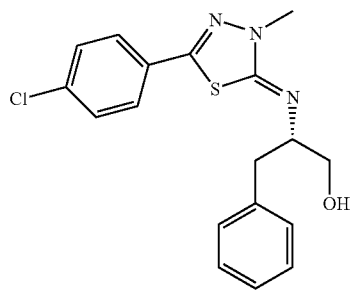 |
| I3,10 | 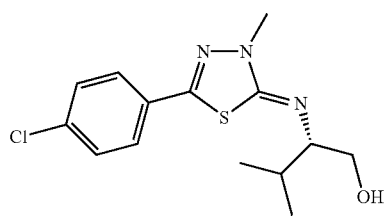 |
| I3,11 | 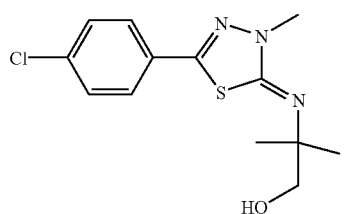 |
| I3,12 | 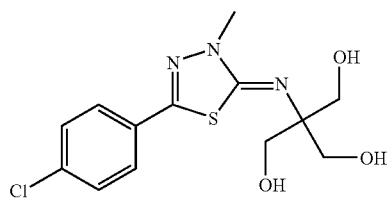 |
| I3,13 | 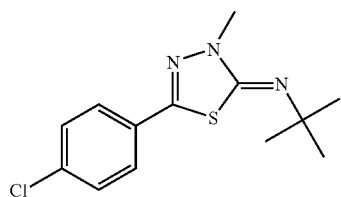 |
| I3,14 | 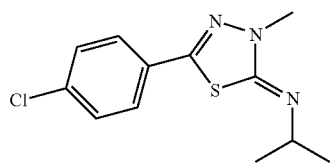 |

-continued
| Example | Structure |
|---|---|
| I3,15 | 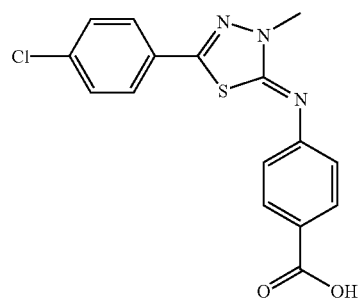 |
| I3,16 | 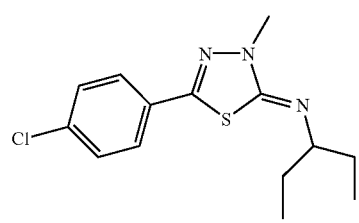 |
| I3,17 | 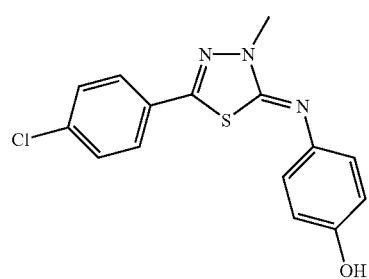 |
| I3.18 | 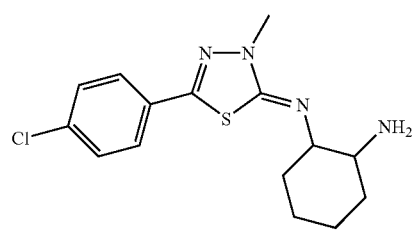 |
| I3,19 | 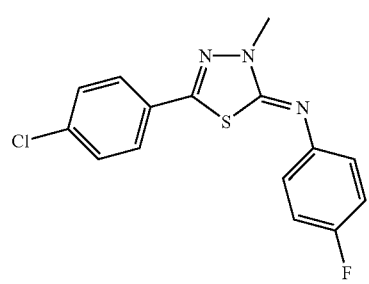 |

-continued

| Example | Structure |
|---|---|
| I3,20 | (structure) |
| I3,21 | (structure) |
| I3,22 | (structure) |
| I3,23 | (structure) |
| I3,24 | (structure) |
| I3,25 | (structure) |

-continued
| Example | Structure |
|---|---|
| I3,26 | 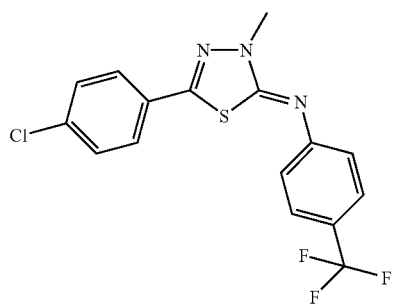 |
| I4 | 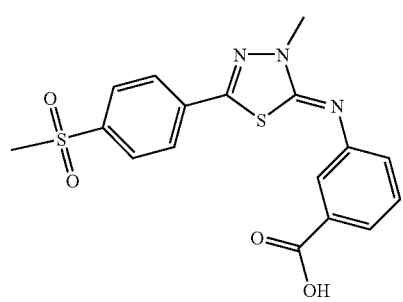 |
| I4,1 | 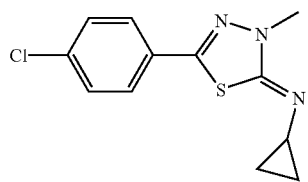 |
| I4,2 | 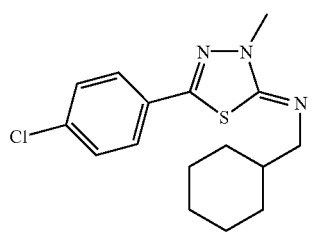 |
| I5 | 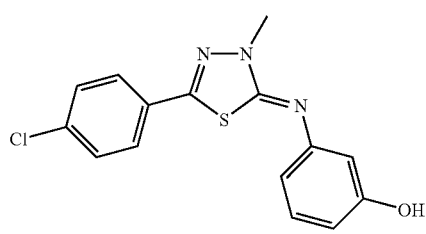 |
| I6 | 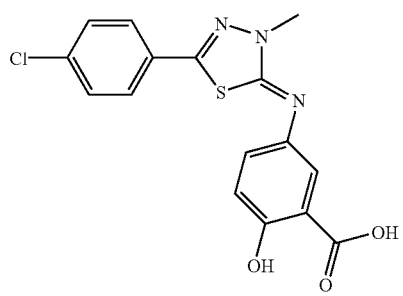 |

-continued
| Example | Structure |
|---|---|
| I6,1 | 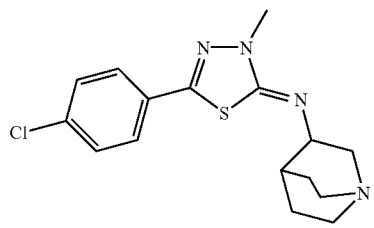 |
| I6,2 | 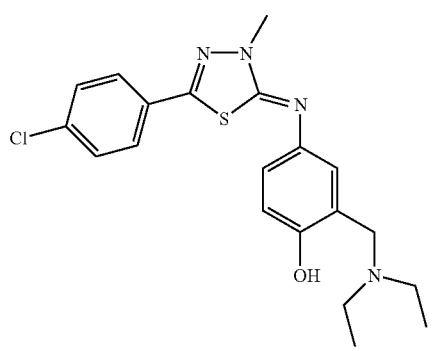 |
| I6,3 | 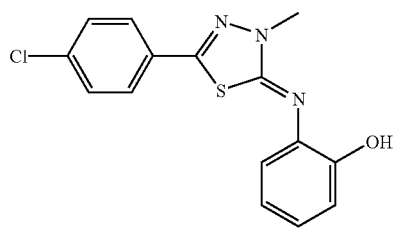 |
| I6,4 | 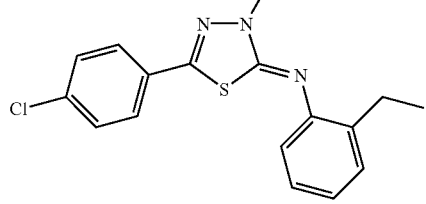 |
| I6,5 | 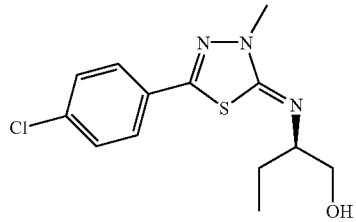 |

-continued
| Example | Structure |
|---------|-----------|
| I6,6 | 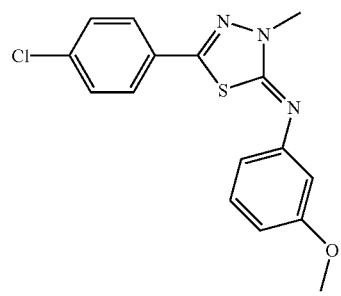 |
| I6,7 | 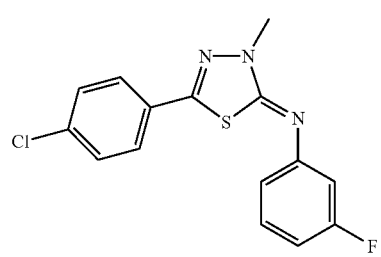 |
| I6,8 | 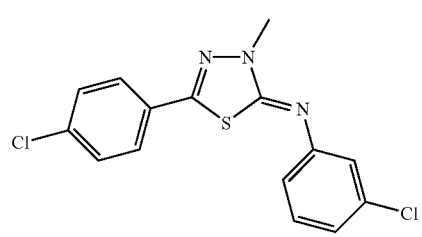 |
| I6,9 | 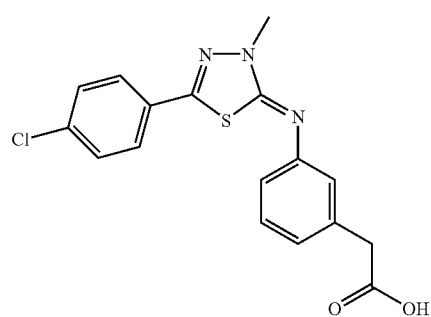 |
| I6,10 | 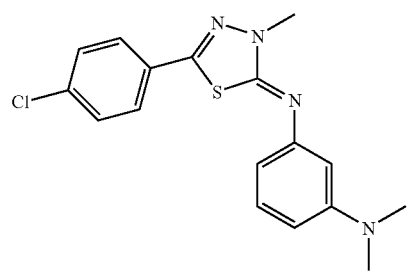 |

-continued
| Example | Structure |
|---|---|
| I6,11 | 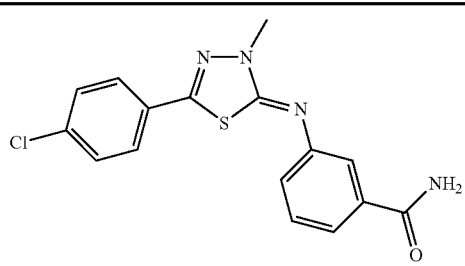 |
| I7 | 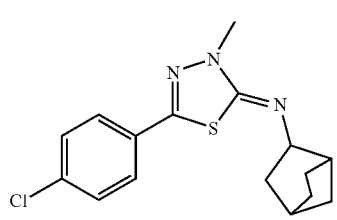 |
| I8 | 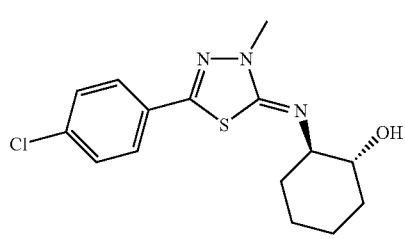 |
| I8,1 | 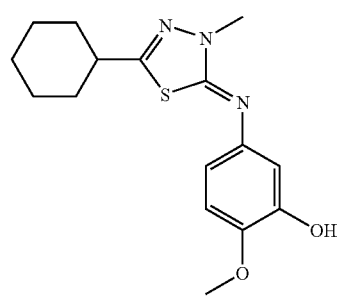 |
| I8,2 | 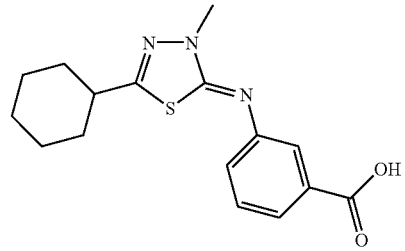 |
| I8,3 | 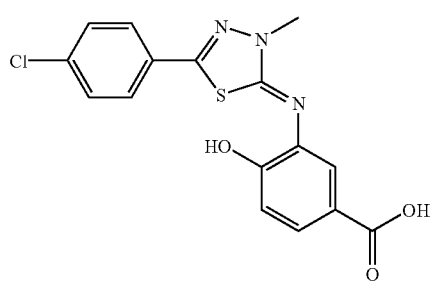 |

-continued
| Example | Structure |
|---|---|
| I8,4 | 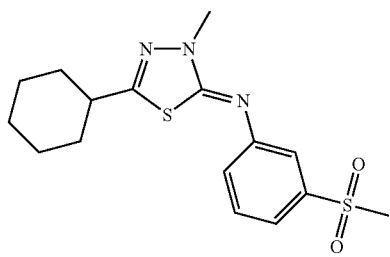 |
| I9 | 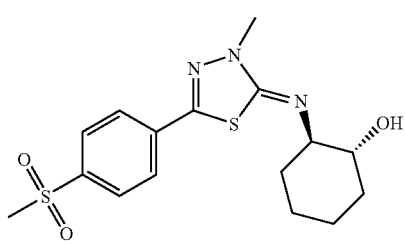 |
| I10 | 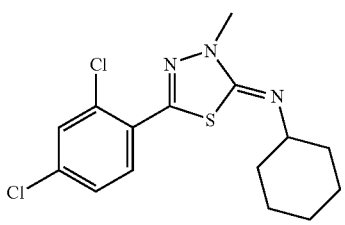 |
| I10,1 | 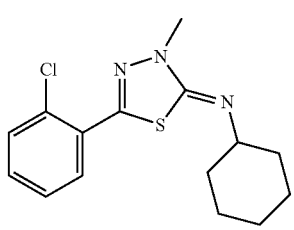 |
| I11 | 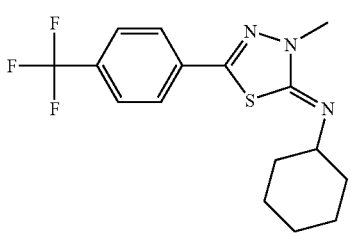 |
| I12 | 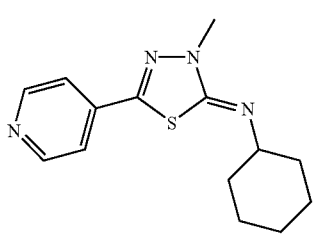 |

-continued
| Example | Structure |
|---|---|
| I13 | 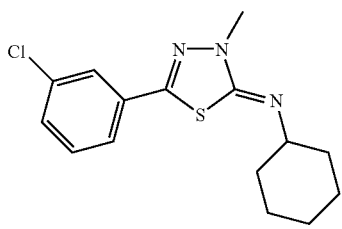 |
| I14 | 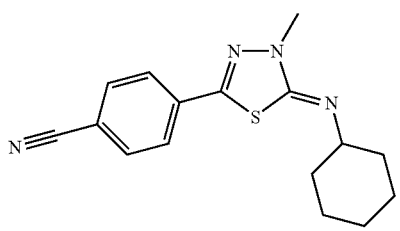 |
| I15 | 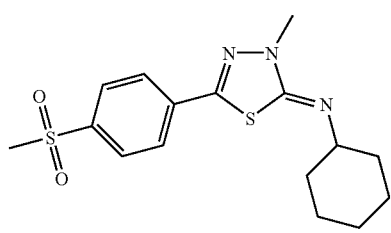 |
| I15,1 | 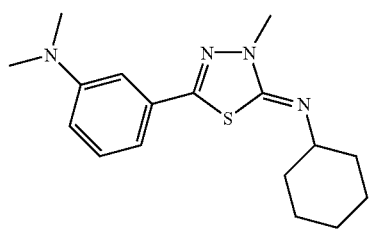 |
| I15,2 | 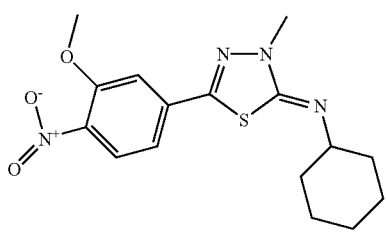 |
| I16 | 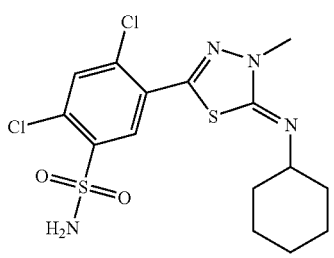 |

-continued
| Example | Structure |
|---|---|
| I17 | 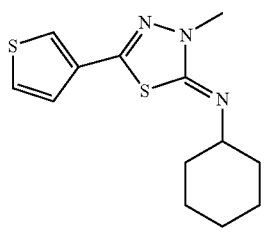 |
| I17,1 | 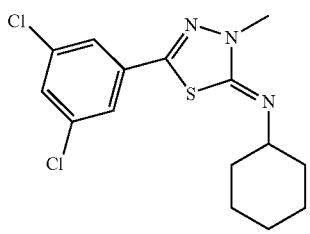 |
| I17,2 | 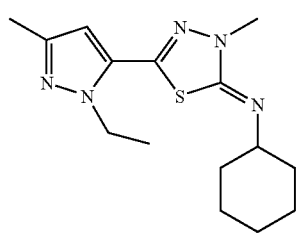 |
| I18 | 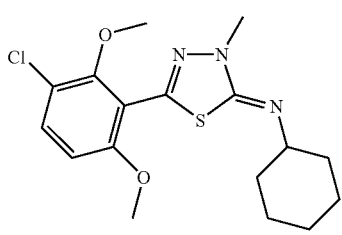 |
| I18,1 | 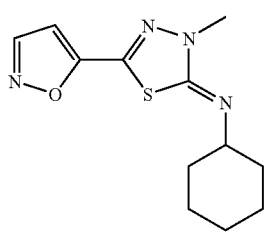 |
| I18,2 | 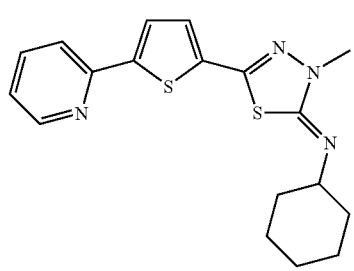 |

-continued
| Example | Structure |
|---|---|
| I18,3 | 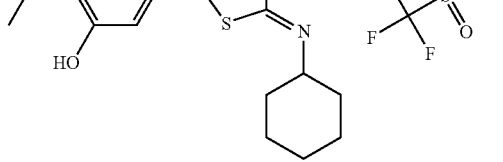 |
| I18,4 | 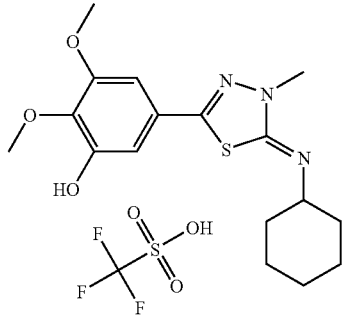 |
| I18,5 | 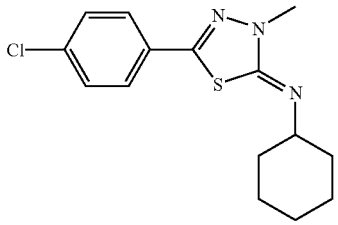 |
| I18,6 | 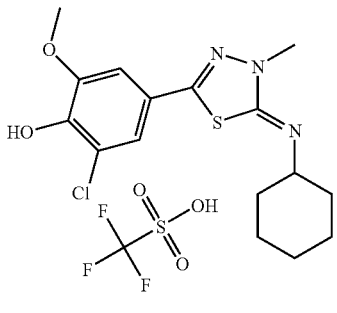 |
| I19 | 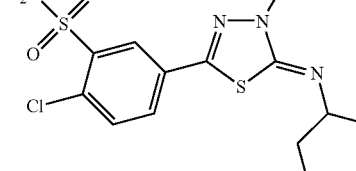 |

| Example | Structure |
|---|---|
| I19,1 | 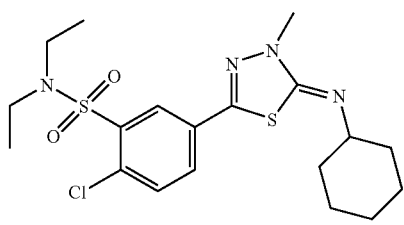 |
| I19,2 | 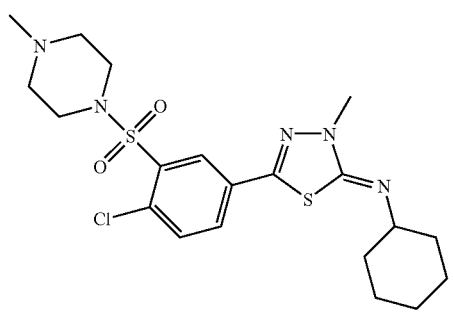 |
| I19,3 | 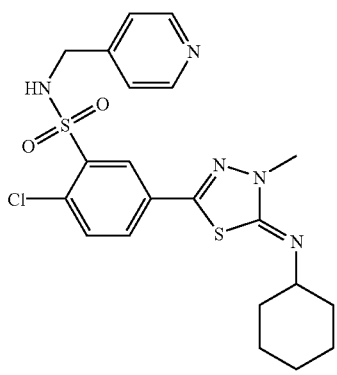 |
| I19,4 | 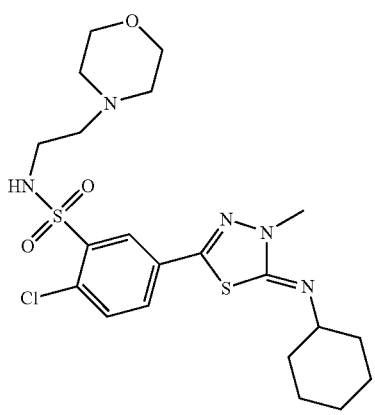 |

-continued
| Example | Structure |
|---|---|
| I19,5 | 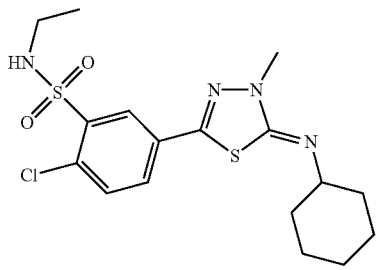 |
| I19,6 | 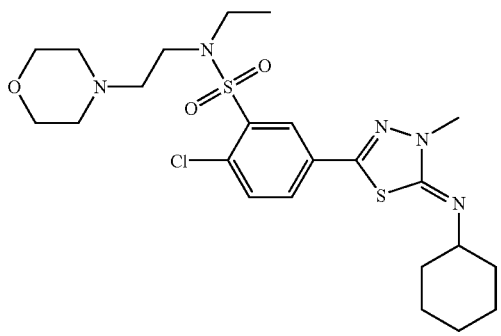 |
| I19,7 | 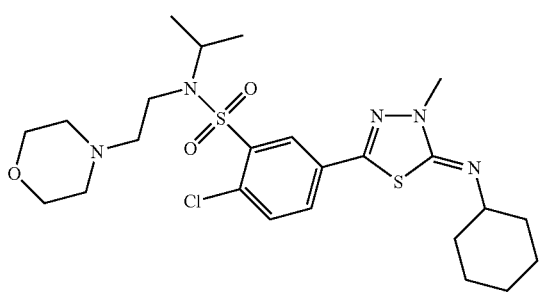 |
| I19,8 | 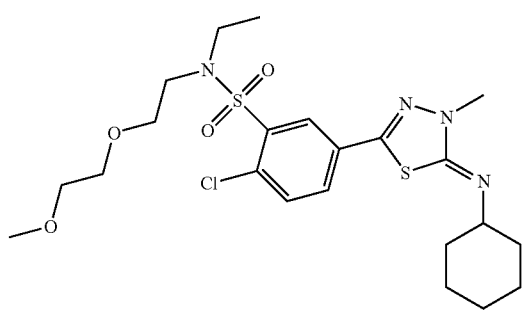 |
| I19,9 | 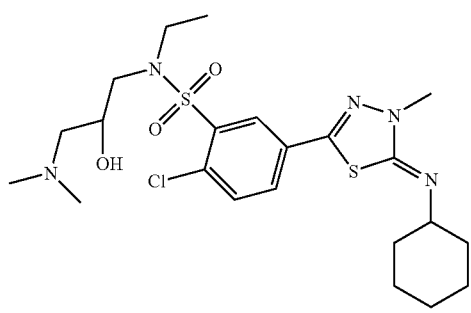 |

| Example | Structure |
|---|---|
| I19,10 | 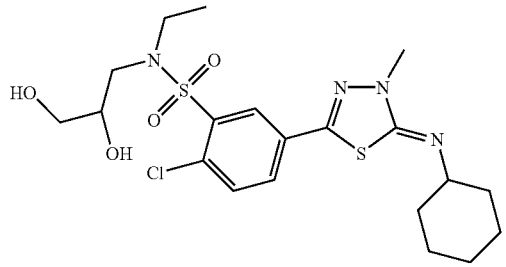 |
| I19,11 | 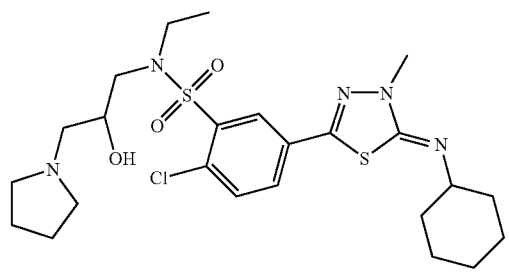 |
| I19,12 | 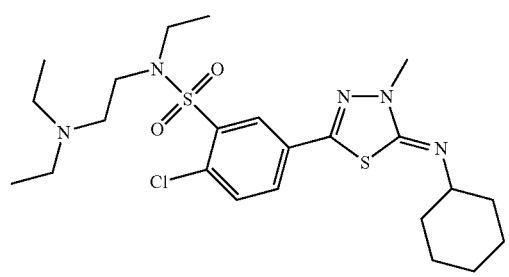 |
| I19,13 | 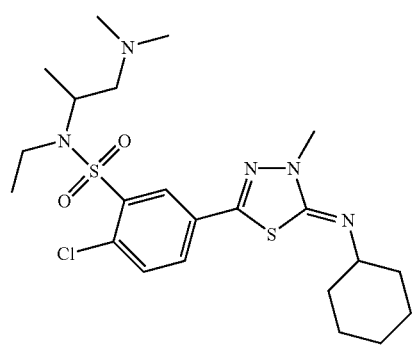 |
| I19,14 | 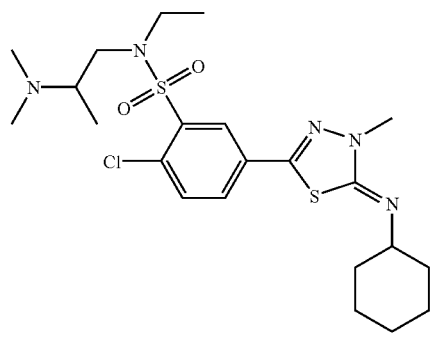 |

-continued
| Example | Structure |
|---------|-----------|
| I20 | 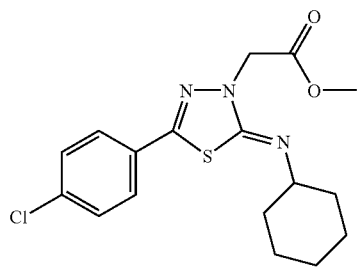 |
| I20.1 | 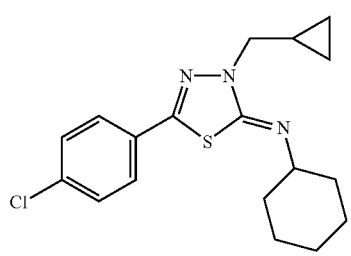 |
| I20.2 | 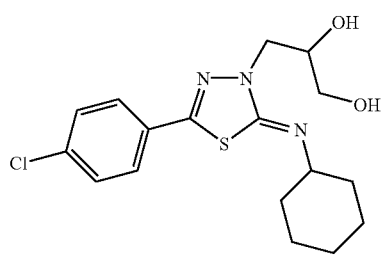 |
| I20.3 | 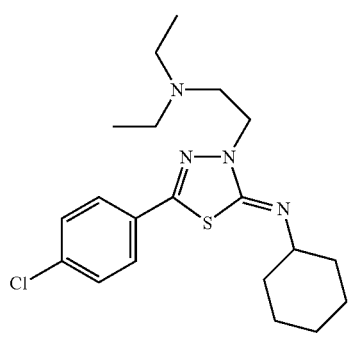 |
| I21 | 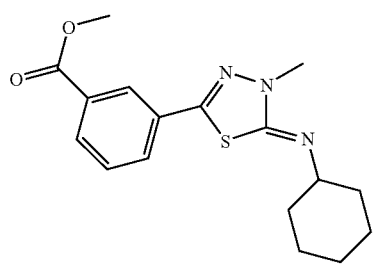 |

-continued

| Example | Structure |
|---------|-----------|
| I21,1 | 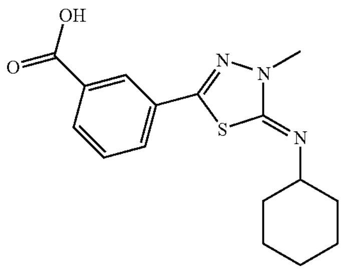 |
| I21,2 | 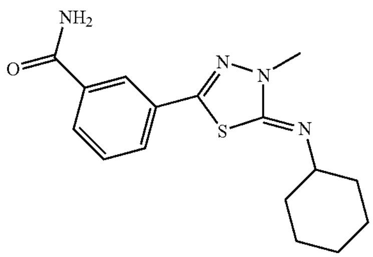 |
| I21,3 | 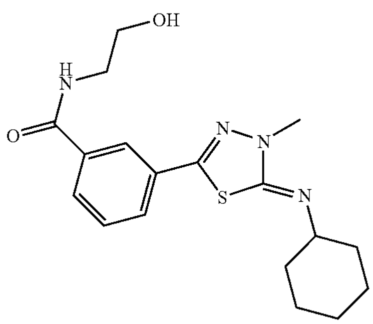 |
| I21,4 | 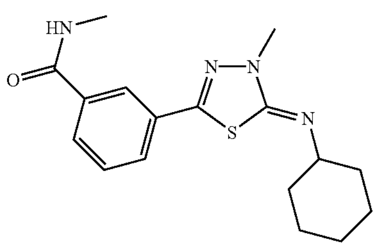 |
| I22 | 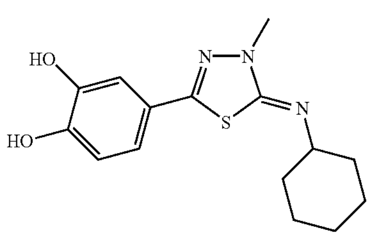 |
| I23 | 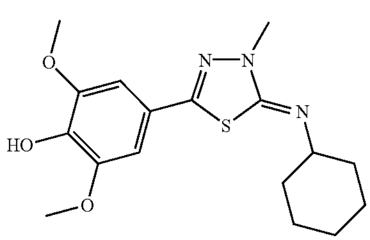 |

-continued
| Example | Structure |
|---------|-----------|
| I23,1 | 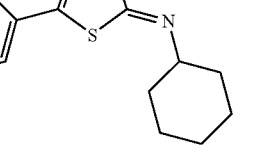 |
| I23,2 | 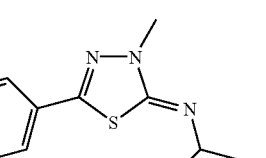 |
| I24 | 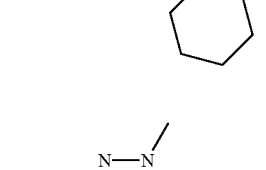 |
| I25 | 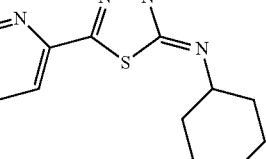 |
| I26 | 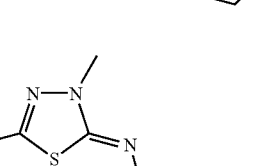 |
| I27 | 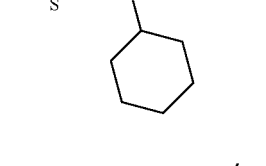 |

-continued
| Example | Structure |
|---|---|
| I28 | 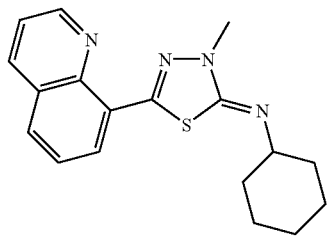 |
| I29 | 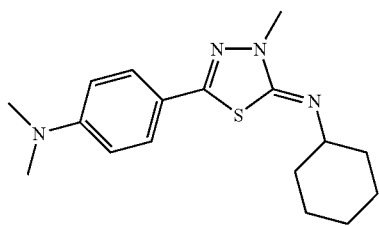 |
| I30 | 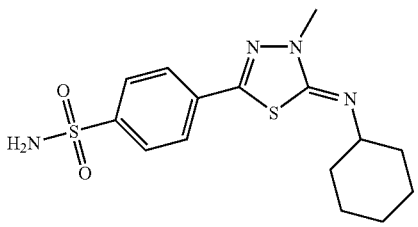 |
| I31 | 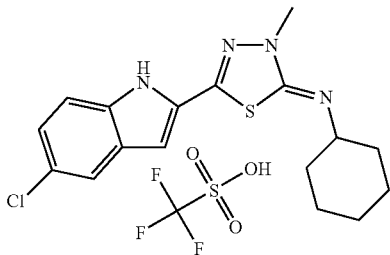 |
| I31,1 | 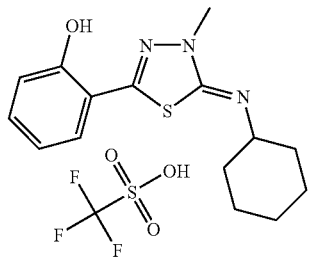 |
| I32 | 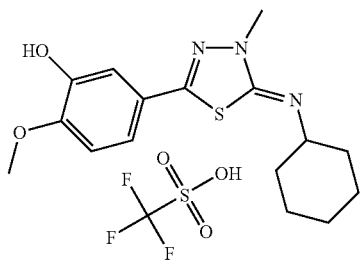 |

-continued
| Example | Structure |
|---|---|
| I33 | 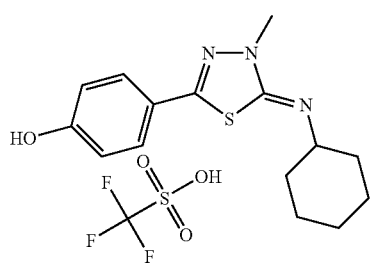 |
| I34 | 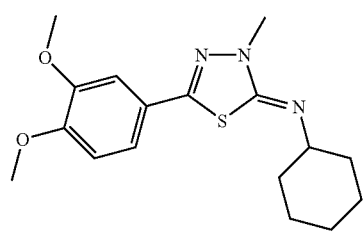 |
| I35 | 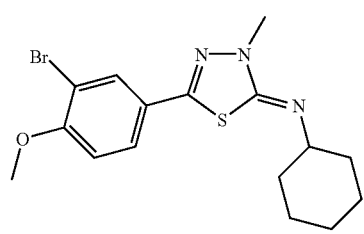 |
| I35,1 | 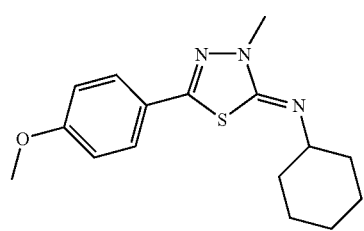 |
| I35,2 | 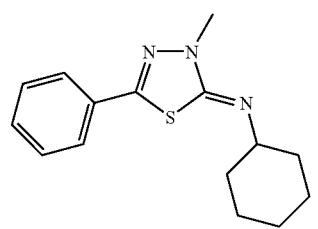 |
| I36 | 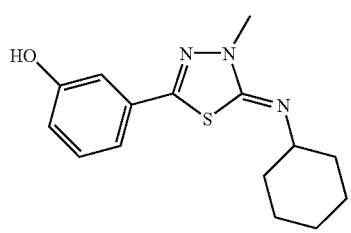 |

| Example | Structure |
|---|---|
| I37 | 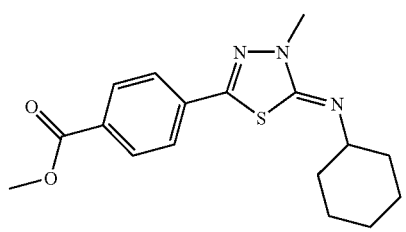 |
| I37,1 | 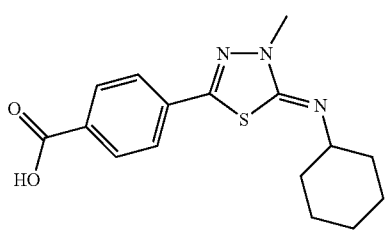 |
| I37,2 | 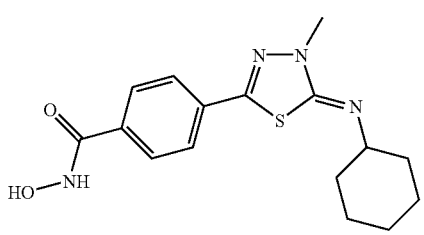 |
| I37,3 | 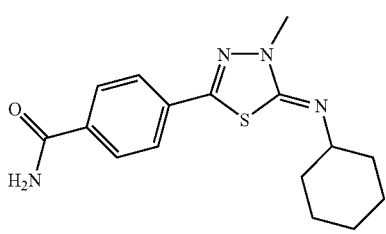 |
| I37,4 | 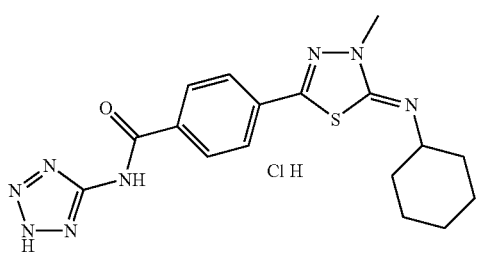 Cl H |
| I37,5 | 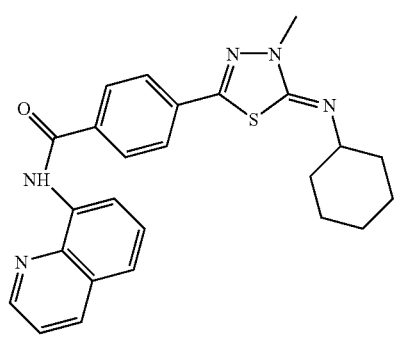 |

-continued
| Example | Structure |
|---------|-----------|
| I37,6 | 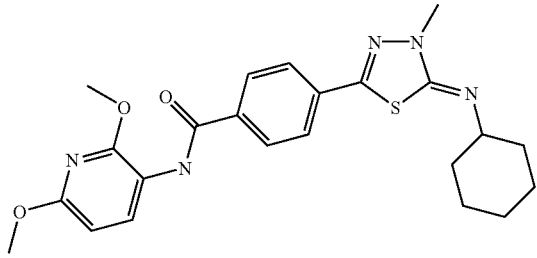 |
| I37,7 | 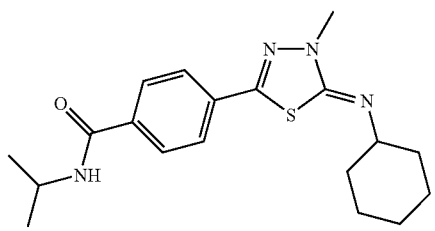 |
| I37,8 | 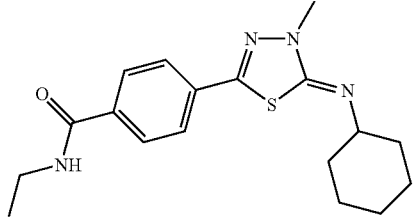 |
| I37.8-1 | 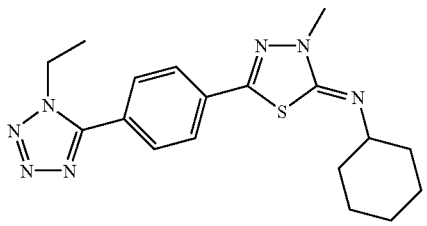 |
| I37,9 | 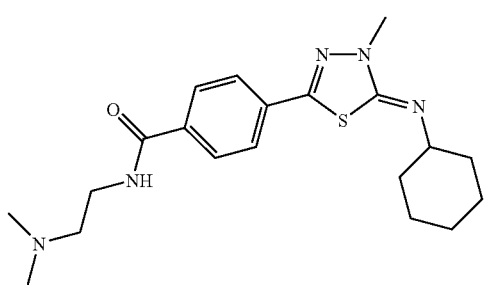 |
| I37,10 | 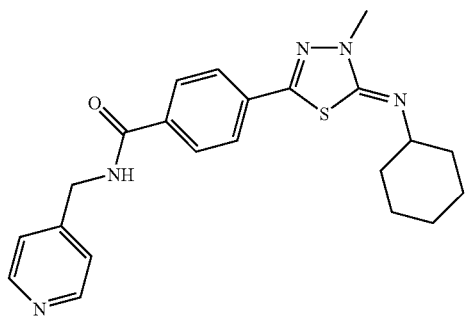 |

| Example | Structure |
|---------|-----------|
| I37,11 | 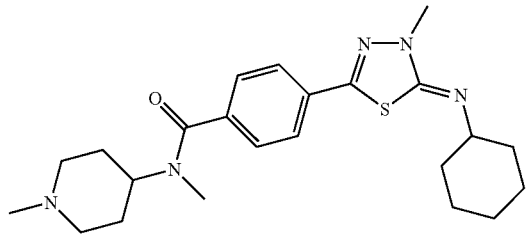 |
| I37,12 | 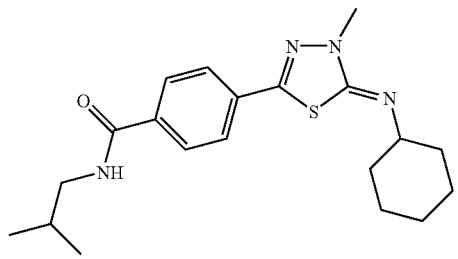 |
| I37,13 | 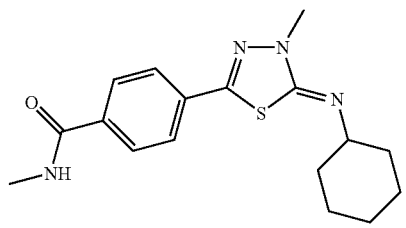 |
| I37,13-1 | 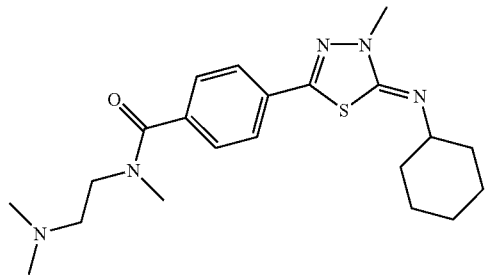 |
| I37,14 | 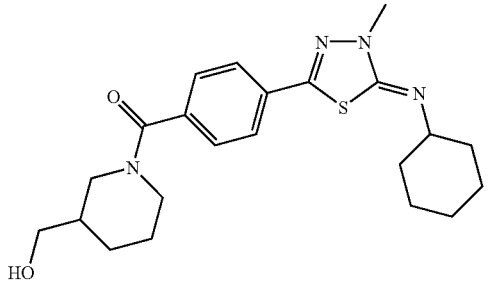 |

| Example | Structure |
|---|---|
| I37,15 | 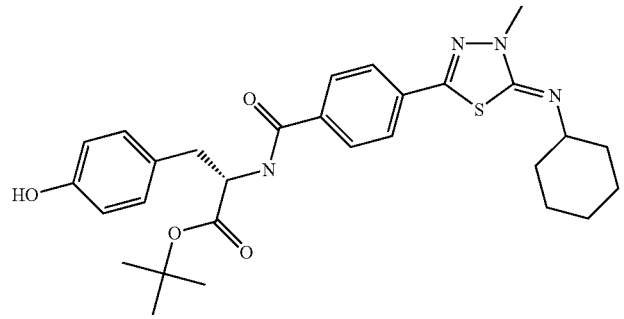 |
| I37,15-a | 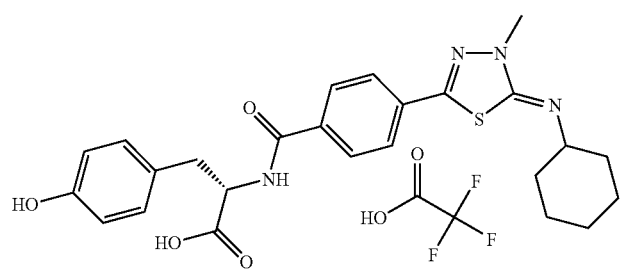 |
| I37,16 | 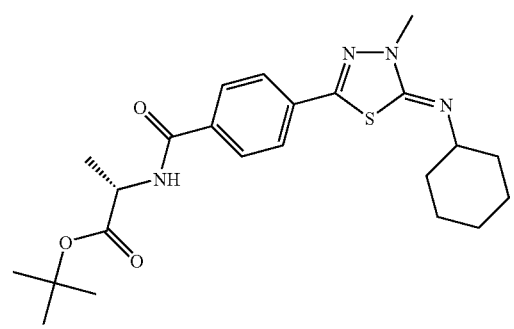 |
| I37,16-a | 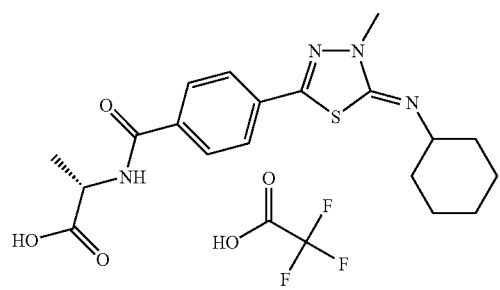 |

-continued
| Example | Structure |
|---------|-----------|
| I37,17 | 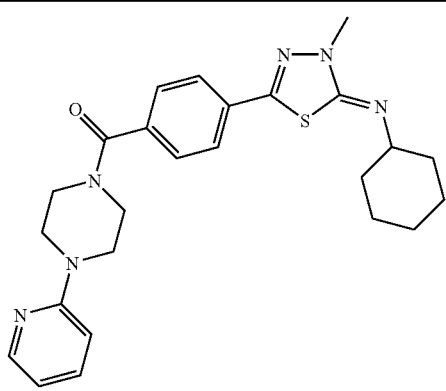 |
| I37,18 | 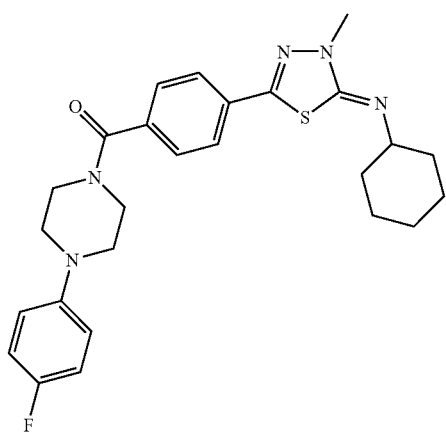 |
| I37,19 | 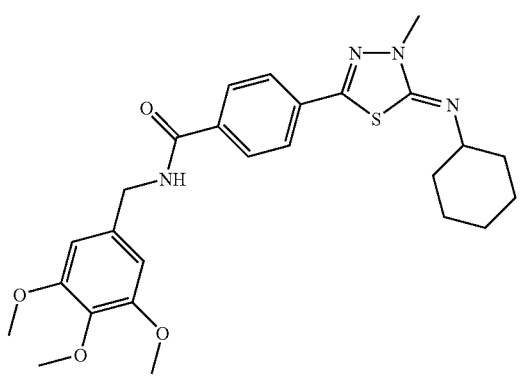 |
| I37,20 | 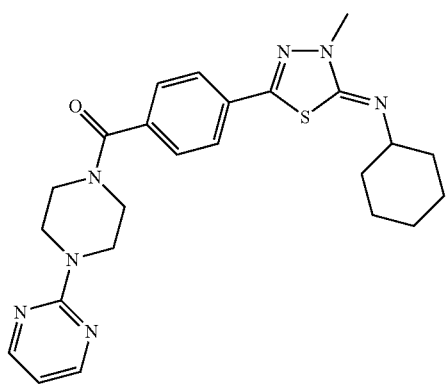 |

-continued
| Example | Structure |
|---|---|
| I37,21 | 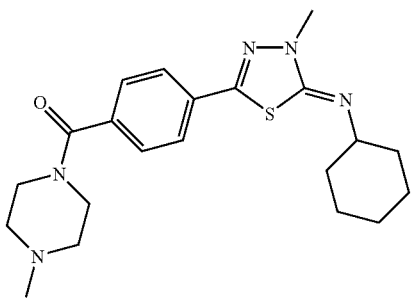 |
| I37,22 | 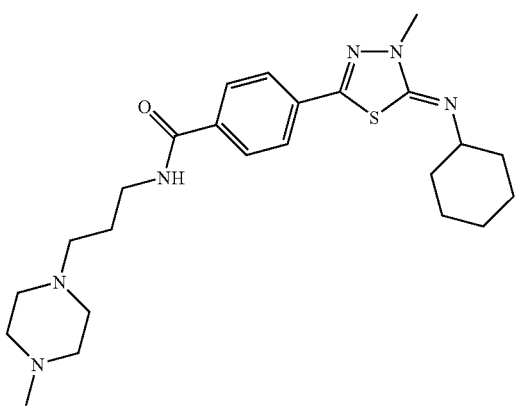 |
| I37,23 | 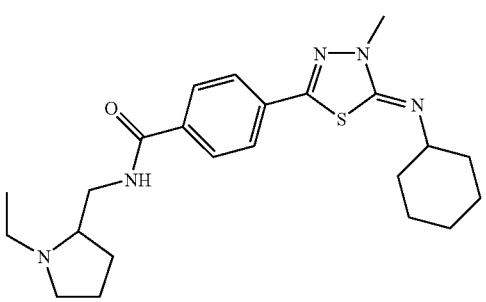 |
| I37,24 | 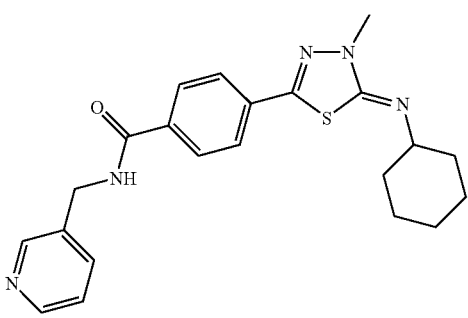 |

-continued
| Example | Structure |
|---|---|
| I37,25 | 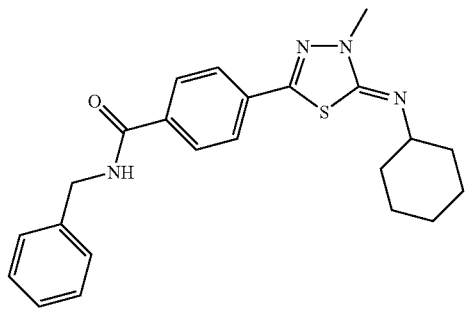 |
| I37,26 | 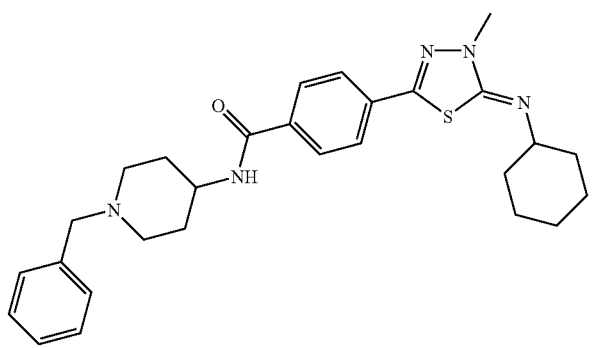 |
| I37,27 | 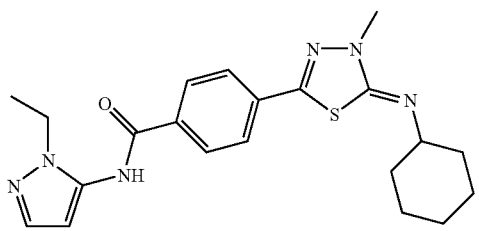 |
| I37,28 | 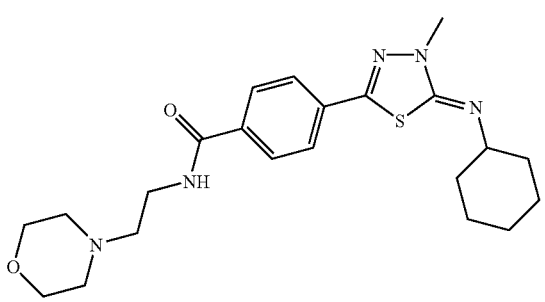 |
| I37,28-1 | 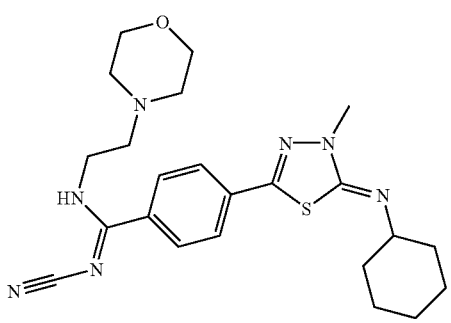 |

-continued
| Example | Structure |
|---|---|
| I37,29 | 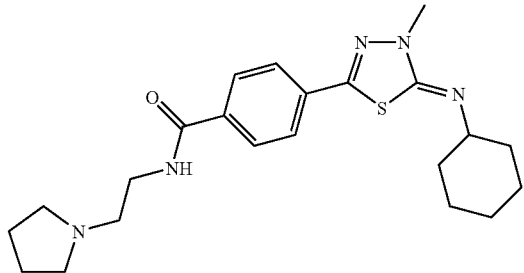 |
| I38 | 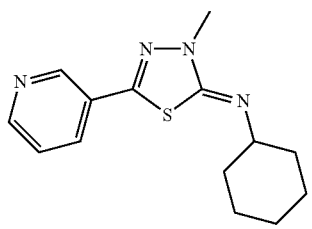 |
| I39 | 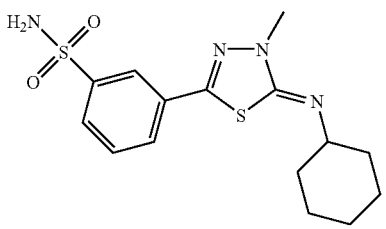 |
| I40 | 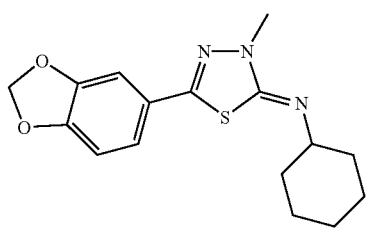 |
| I41 | 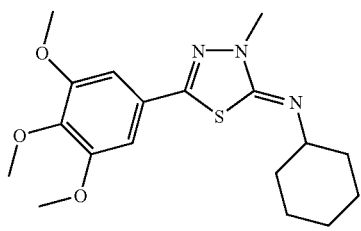 |
| I42 | 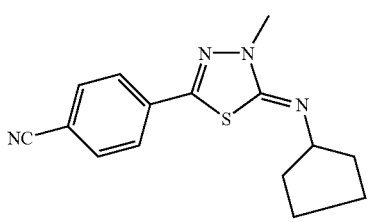 |

-continued
| Example | Structure |
|---|---|
| I43 | 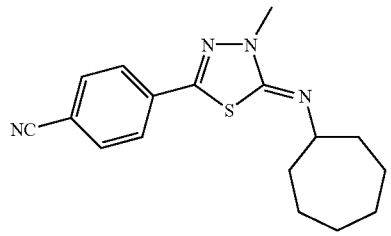 |
| I44 | 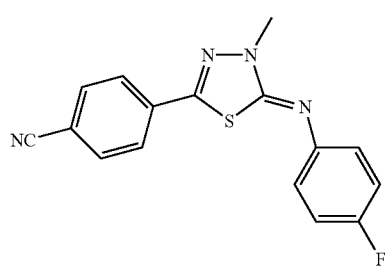 |
| I45 | 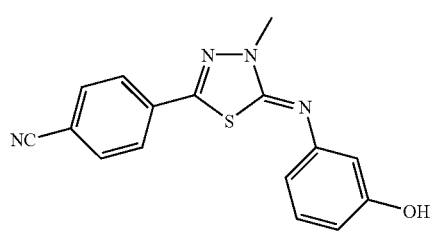 |
| I46 | 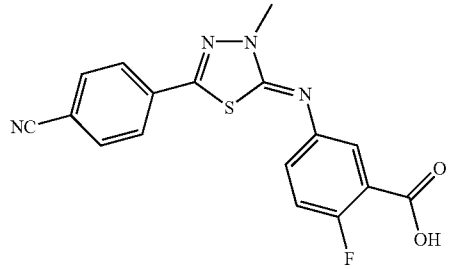 |
| I47-a | 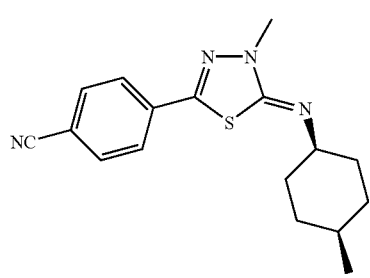 |
| I47-b | 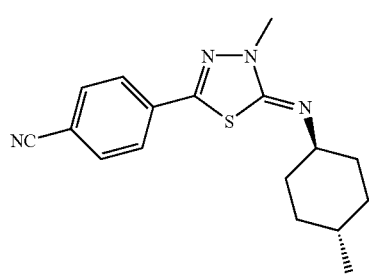 |

-continued
| Example | Structure |
|---|---|
| I48 | 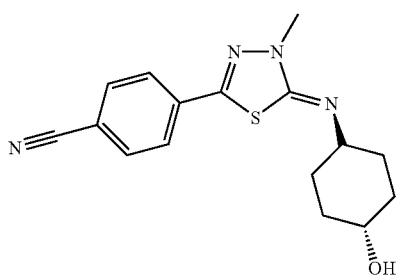 |
| I49 | 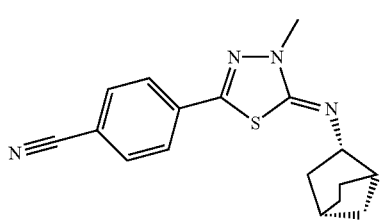 |
| I50 | 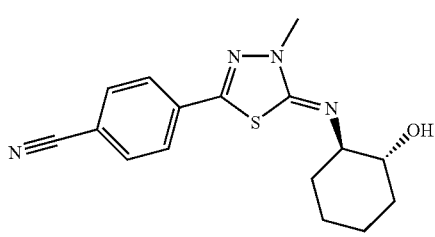 |
| I51 | 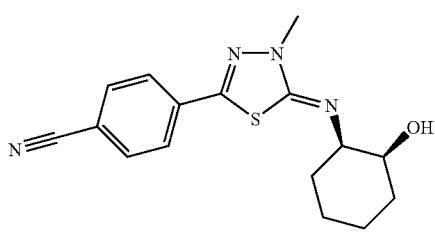 |
| I52-a | 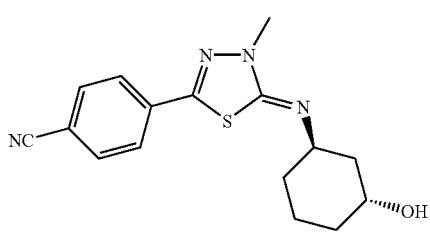 |
| I52-b | 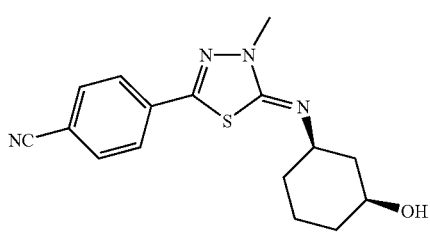 |

-continued

| Example | Structure |
|---|---|
| I53 | 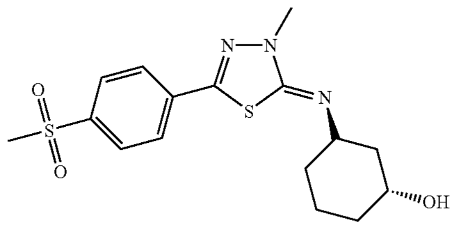 |
| I54 | 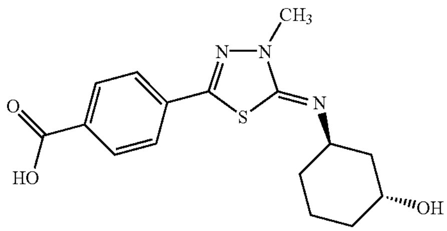 |
| I55 | 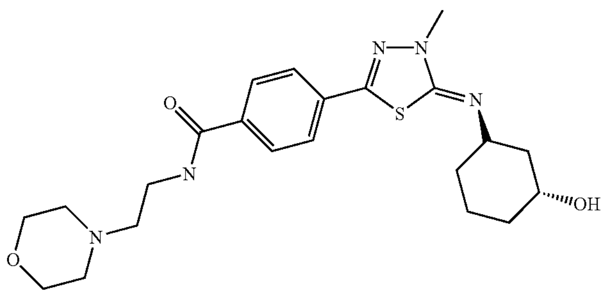 |
| I56 | 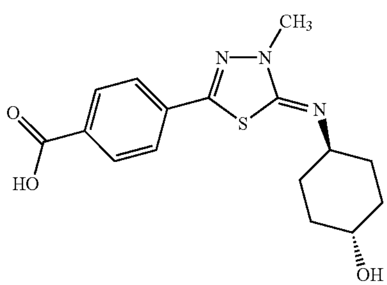 |
| I57 | 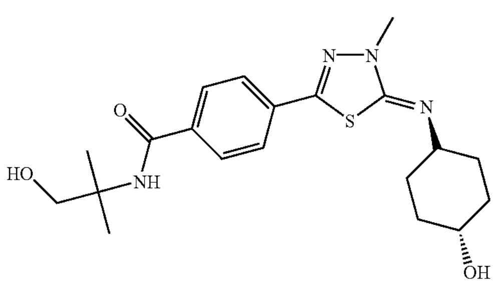 |
| I58 | 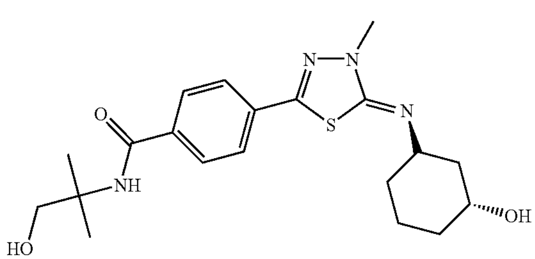 |

-continued
| Example | Structure |
|---------|-----------|
| I59 | 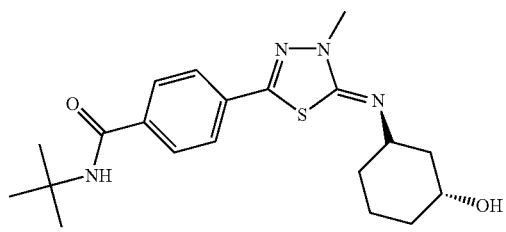 |
| I60 | 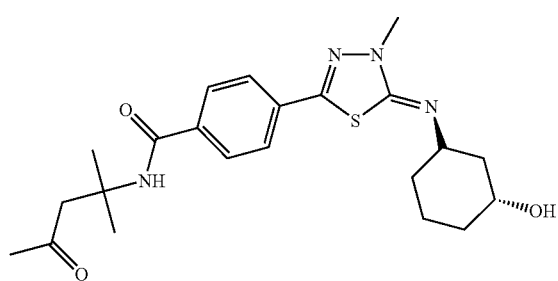 |
| I61 | 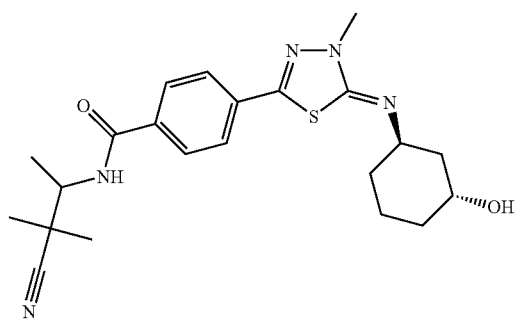 |
| I62 | 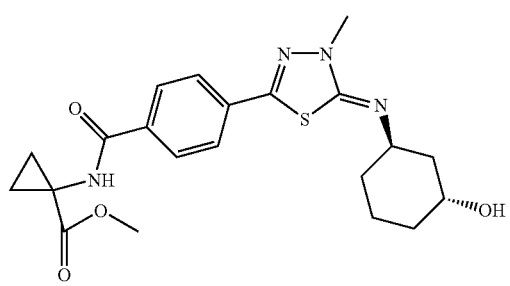 |
| I63 | 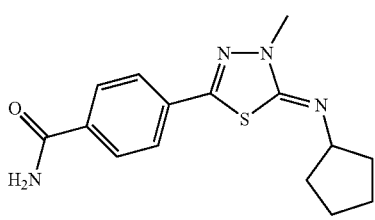 |

-continued
| Example | Structure |
|---|---|
| I64 | 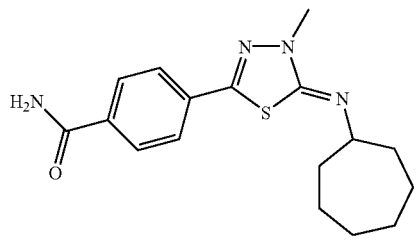 |
| I65 | 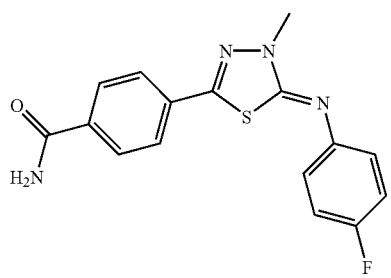 |
| I66 | 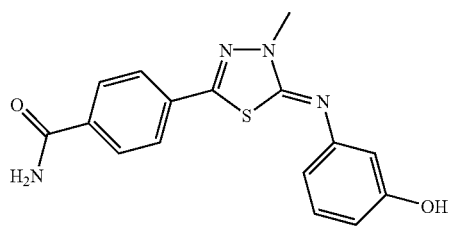 |
| I67 | 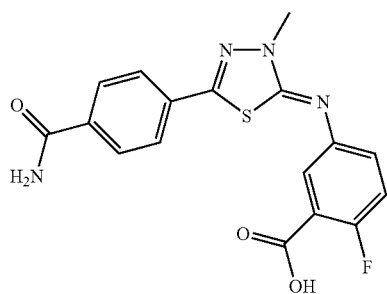 |
| I68 | 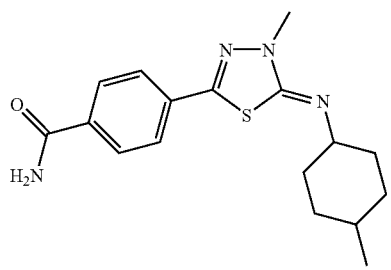 |

-continued
| Example | Structure |
|---------|-----------|
| I69 | 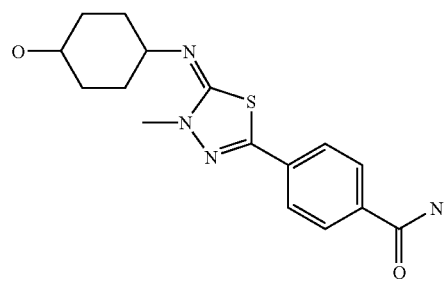 |
| I70 | 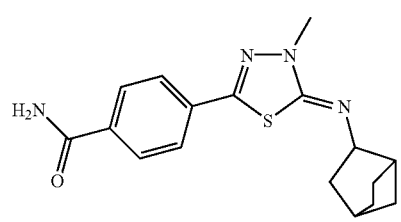 |
| I71 | 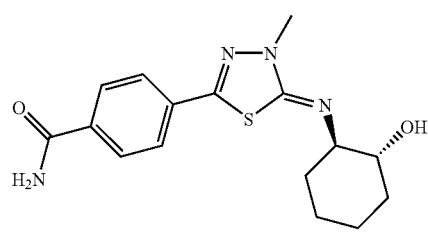 |
| I72 | 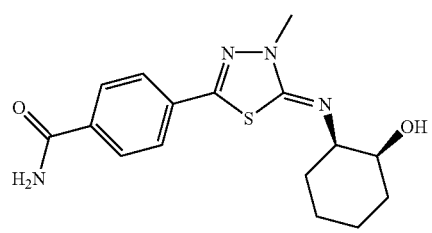 |
| I73 | 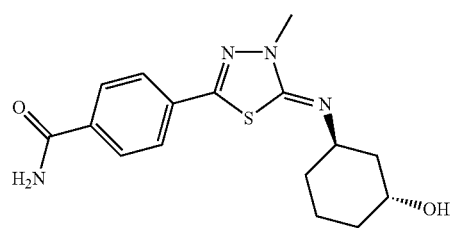 |
| I74 | 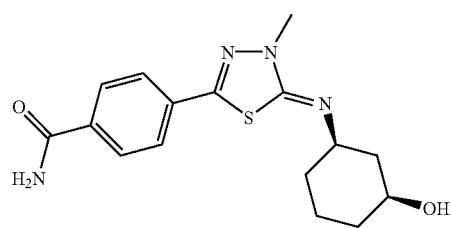 |

-continued
| Example | Structure |
|---------|-----------|
| I74,1 | 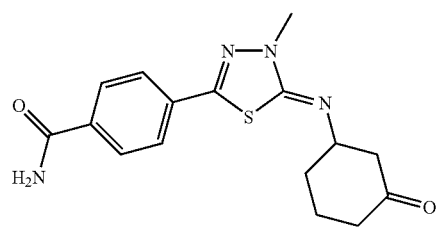 |
| I75 | 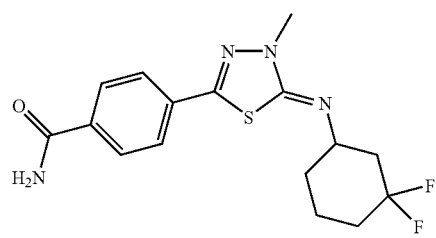 |
| I76 | 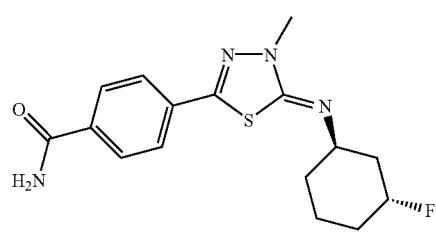 |
| I77 | 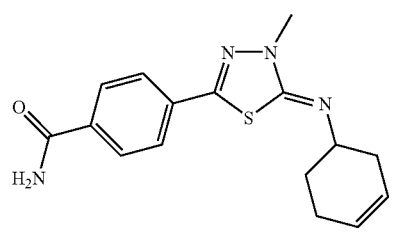 |
| I78 | 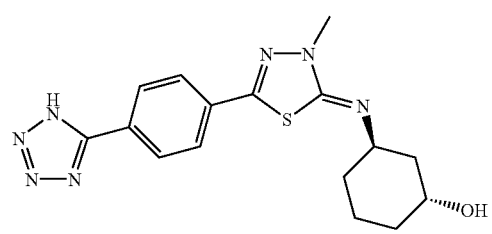 |
| I79 | 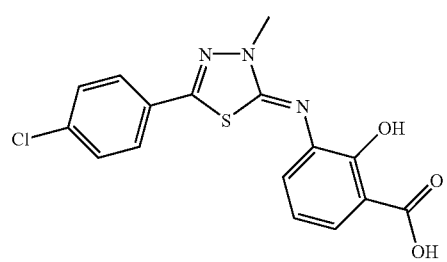 |

| Example | Structure |
|---|---|
| I80 | 3-({[5-(4-cyanophenyl)-4-methyl-1,3,4-thiadiazol-2(3H)-ylidene]amino})benzoic acid |
| I80,1 | 3-({[5-(4-carbamoylphenyl)-4-methyl-1,3,4-thiadiazol-2(3H)-ylidene]amino})benzoic acid |
| I81 | 2-fluoro-5-({[4-methyl-5-(4-methylsulfonylphenyl)-1,3,4-thiadiazol-2(3H)-ylidene]amino})benzoic acid |
| I82 | 3-({[4-methyl-5-(4-methylsulfonylphenyl)-1,3,4-thiadiazol-2(3H)-ylidene]amino})cyclohexanecarboxylic acid |
| I83 | 4-methyl-5-(4-methylsulfonylphenyl)-2-(piperidin-1-ylimino)-1,3,4-thiadiazol |
| I84 | 4-methyl-5-(4-methylsulfonylphenyl)-2-(tetrahydropyran-4-ylimino)-1,3,4-thiadiazol |

-continued
| Example | Structure |
|---------|-----------|
| I85 | 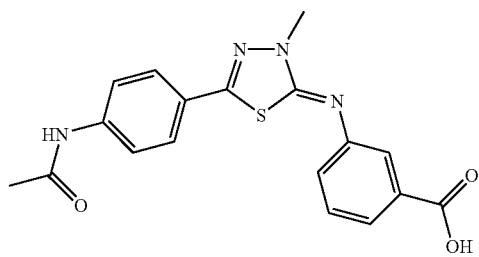 |
| I86 | 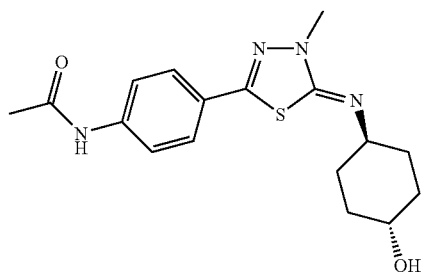 |
| I87 | 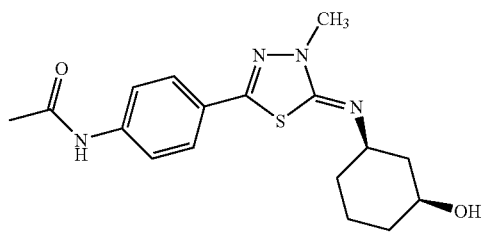 |
| I88 | 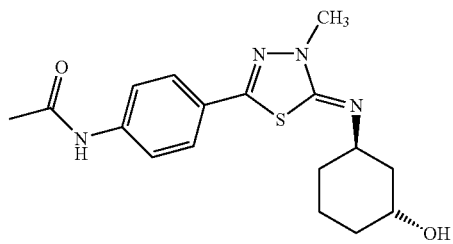 |
| I89 | 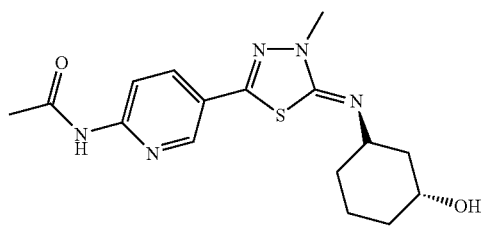 |
| I90 | 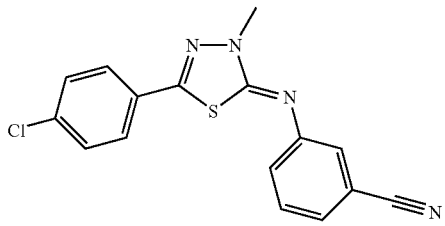 |

-continued
| Example | Structure |
|---|---|
| I90,1 | 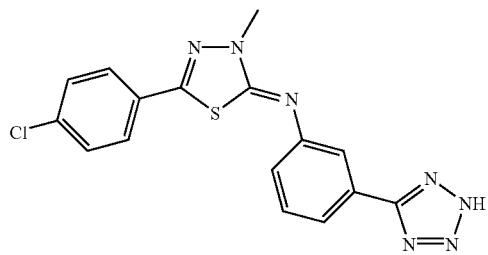 |
| I90,2 | 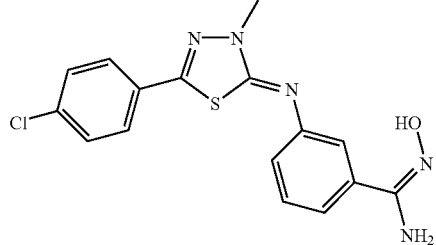 |
| I90,3 | 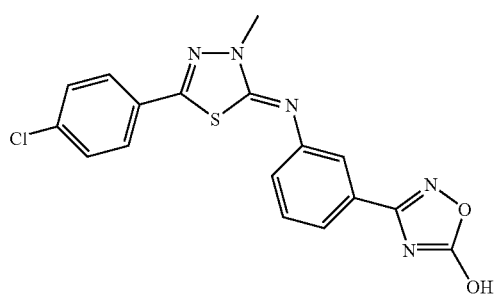 |
| I91 | 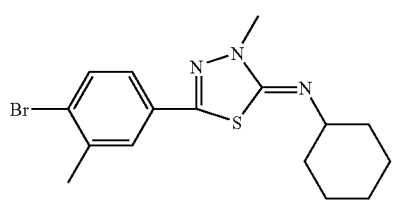 |
| I91,1 | 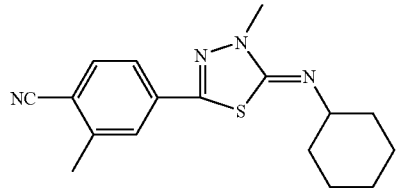 |
| I91,2 | 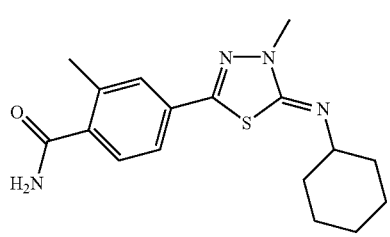 |

-continued
| Example | Structure |
|---|---|
| I92 | 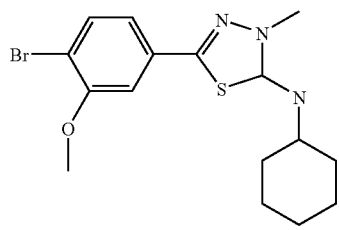 |
| I92,1 | 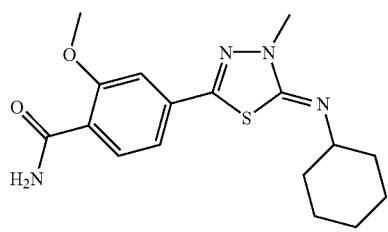 |
| I92,2 | 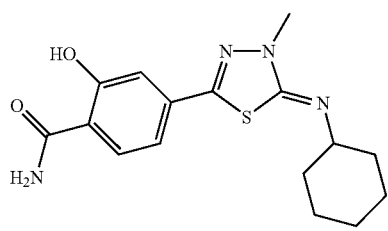 |
| I93 | 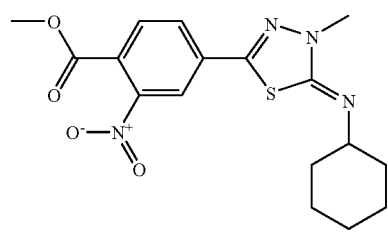 |
| I93,1 | 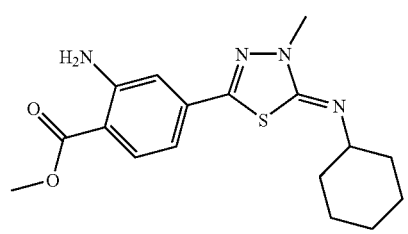 |
| I93,2 | 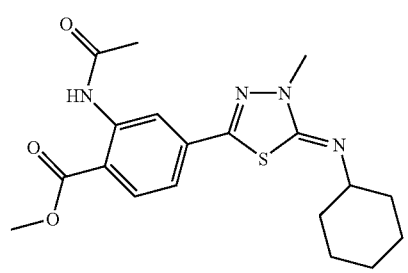 |

-continued
| Example | Structure |
|---|---|
| I93,3 | 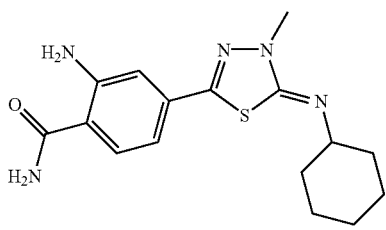 |
| I93,4 | 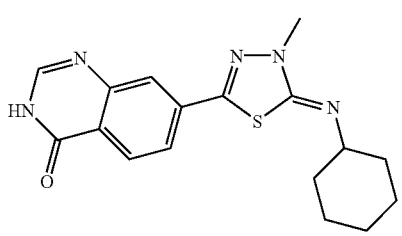 |
| I93,5 | 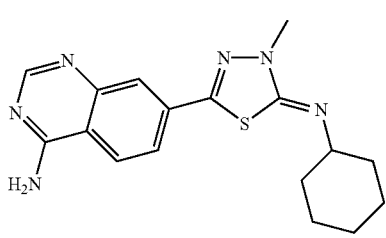 |
| I93,6 | 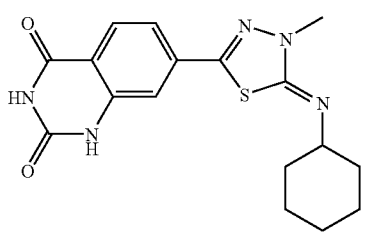 |
| I94 | 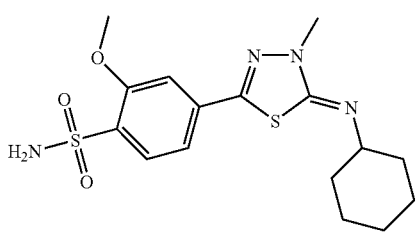 |
| I95 | 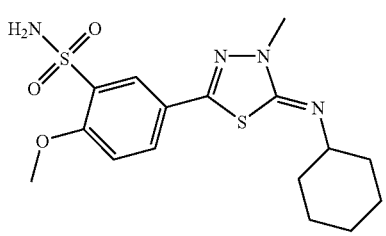 |

-continued
| Example | Structure |
|---|---|
| I96 | 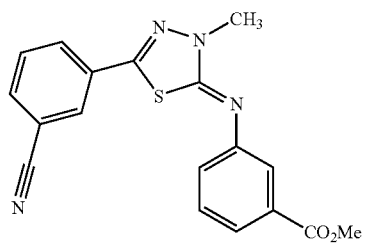 |
| I96,1 | 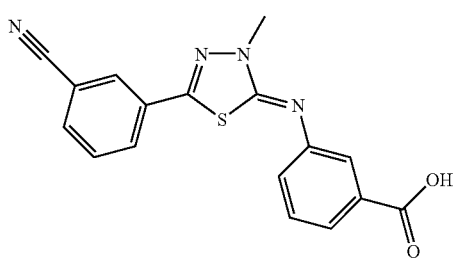 |
| I97 | 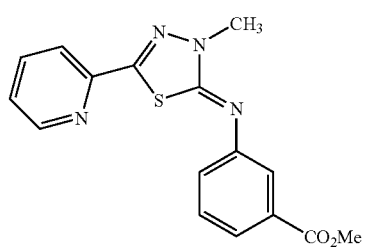 |
| I97,1 | 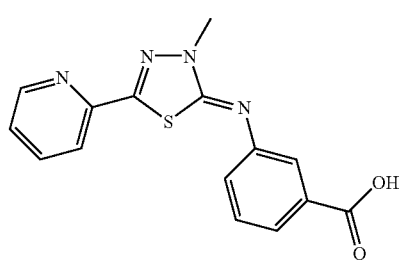 |
| I98 | 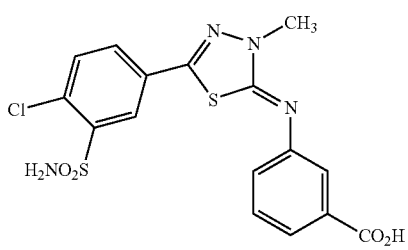 |
| I99 | 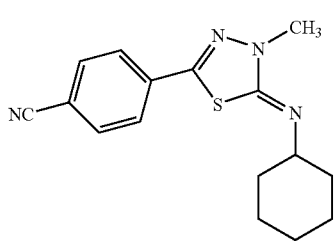 |

| Example | Structure |
|---|---|
| I99,1 | 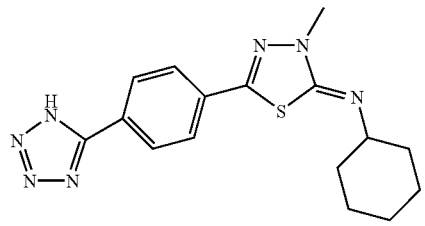 |
| I100 | 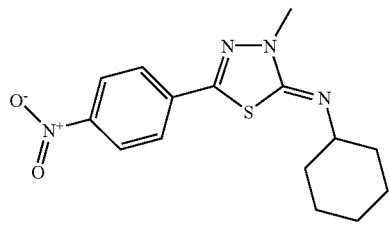 |
| I100,1 | 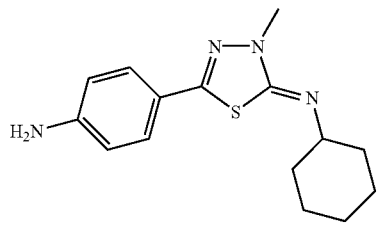 |
| I100,2 | 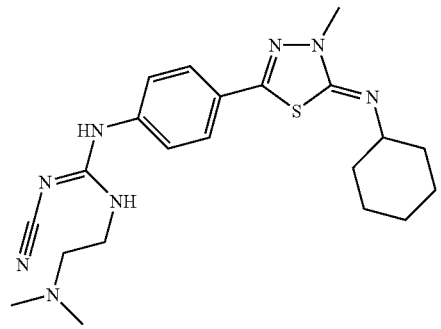 |
| I100,3 | 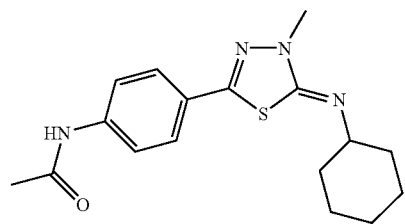 |
| I100,4 | 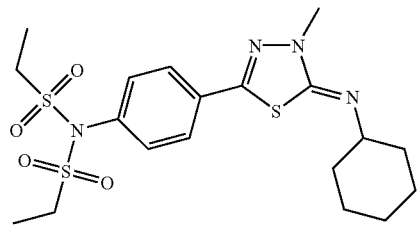 |

-continued
| Example | Structure |
|---|---|
| I100,5 | 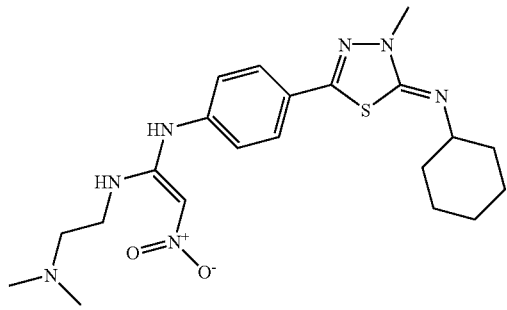 |
| I100,6 | 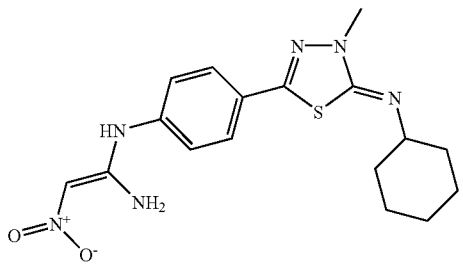 |
| I100,7 | 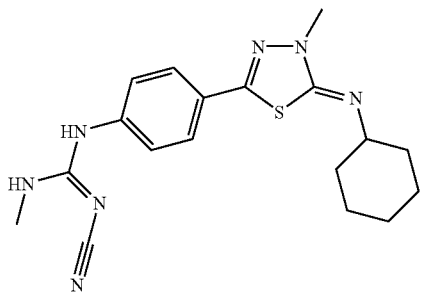 |
| I100,8 | 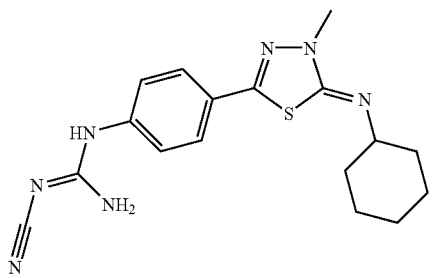 |
| I100,9 | 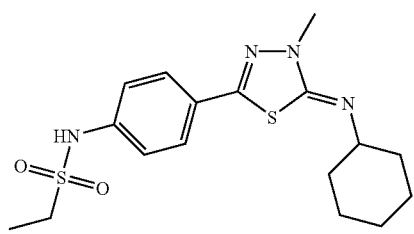 |

-continued
| Example | Structure |
|---|---|
| I100,10 | 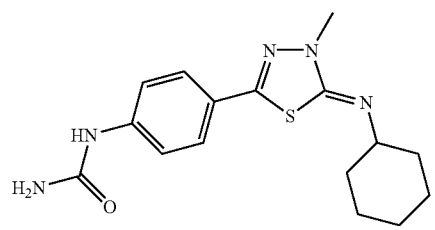 |
| I100,11 | 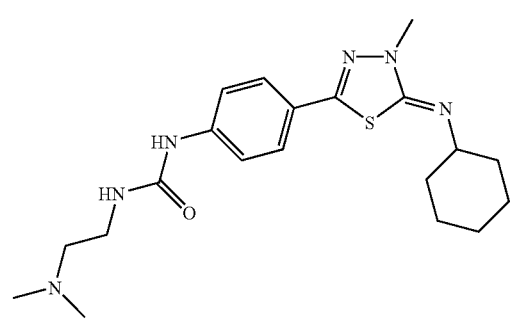 |
| I101 | 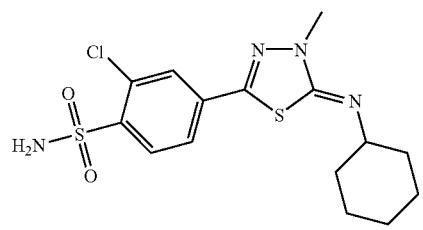 |
| I102 | 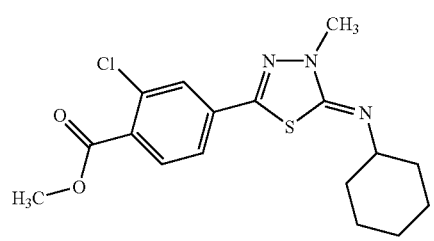 |
| I102,1 | 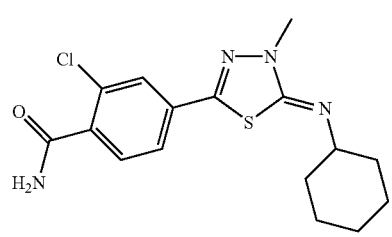 |

-continued

| Example | Structure |
|---|---|
| I103 | (structure) |
| I104 | (structure) |
| I104,1 | (structure) |

Biological Results

In vitro Inhibition of the Phosphodiesterase 7 and of Other Phosphodiesterases

The capacity of the compounds of the invention to inhibit cyclic nucleotide phosphodiesterases was evaluated by measuring their $IC_{50}$ (concentration necessary to inhibit the enzymatic activity by 50%).

PDE3A3, PDE4D3, and PDE7A1 were cloned and expressed in insect cells Sf 21 using the baculovirus expression system. The source of PDE103 and of PDE503 were human cell lines (respectively TPH1 human monocytes and MCF7 human Caucasian breast adenocarcinoma). The various types of phosphodiesterases were obtained partially purified on an anion exchange column (Mono Q) according to a method adapted from Lavan B. E., Lakey T., Houslay M. D., *Biochemical Pharmacology*, 1989;38(22):4123–4136.

Measurement of the enzymatic activity for the various types of PDE was then made according to a method adapted from Thompson W. J. et al., Advances in Cyclic Nucleotide Research, ed. G. Brooker et al. New York: Raven Press, 1979;10:69–92.

The substrate used was cGMP for PDE1 and PDE5 and cAMP for PDE3, PDE4, and PDE7. The substrate concentration was 0.2 µM for PDE1, PDE3, and PDE5, 0.25 µM for PDE4, and 50 nM for PDE7.

The enzymatic reaction was stopped after 1 hour for PDE1, PDE3, and PDE5 and 10 minutes for PDE4 and PDE7.

In order to determine their $IC_{50}$, compounds of the invention were assayed at eight concentrations ranging from 0.03 nM to 100 µM for PDE4 and PDE7, and at six concentrations ranging from 0.1 µM to 30 µM for PDE1, PDE3, and PDE5.

The $IC_{50}$ (µM) were determined for some of the compounds of the invention, and the results are summarized in the following table:

| Compounds | $IC_{50}$ (PDE7) |
|---|---|
| I1 | 0.15 |
| I2,1 | 0.13 |
| I3,25 | 1.20 |
| I4 | 0.15 |
| I7 | 1.05 |
| I8 | 0.45 |
| I9 | 0.28 |
| I10,1 | 1.30 |
| I11 | 0.98 |
| I12 | 0.29 |
| I13 | 0.70 |
| I14 | 0.27 |
| I15 | 0.14 |
| I17,1 | 1.30 |
| I18,2 | 0.32 |
| I18,3 | 0.061 |
| I18,4 | 0.092 |
| I18,5 | 1.20 |
| I19 | 0.07 |
| I21 | 0.15 |
| I21,1 | 0.87 |
| I22 | 1 |
| I23 | 0.85 |
| I24 | 0.36 |
| I25 | 0.47 |
| I26 | 0.4 |
| I27 | 0.46 |
| I28 | 0.23 |
| I29 | 0.30 |
| I30 | 0.14 |
| I31 | 0.23 |

-continued

| Compounds | IC$_{50}$ (PDE7) |
|---|---|
| I32 | 0.23 |
| I33 | 0.24 |
| I34 | 0.63 |
| I35 | 0.58 |
| I36 | 0.29 |
| I37 | 0.23 |
| I37,1 | 0.55 |
| I37,2 | 1.2 |
| I37,3 | 0.062 |
| I37,4 | 0.15 |
| I37,5 | 0.093 |
| I37,6 | 0.097 |
| I37,7 | 0.086 |
| I37,8 | 0.064 |
| I37,9 | 0.075 |
| I37,10 | 0.044 |
| I37,11 | 0.072 |
| I38 | 0.34 |
| I39 | 0.2 |
| I40 | 0.45 |
| I41 | 1.3 |

These results show that the compounds of the invention inhibit PDE7 at very low concentrations, with some IC$_{50}$ values lower than 100 nM. The results of the assays with other PDE (1, 3, 4, and 5) show IC$_{50}$ values often superior to 10 μM.

It demonstrates that compounds of the invention are strong and selective PDE7 inhibitors.

References

M. Akbar Ali, S. E. Livingston, and D. J. Philipps, *Inorganica Chimica Acta,* 1972;6:11
P. Molina, A. Tarraga, A. Espinosa, *Synthesis,* 1988:690
P. Molina, A. Tarraga, A. Espinosa; *Heterocycles,* 1989:29 (12)
R. Noto, P. Lo Meo, M. Gruttadauria, G. Werber; *J. Heterocyclic Chem.,* 1996;33:863
patent: Gulf Oil Corporation, WO 77 12352
patent: Bayer AG, DE 44 18 066 A1
patent: Gulf Oil Corporation, WO 80 1507

All references cited herein are hereby incorporated by reference.

What is claimed is:

1. A compound of Formula 1:

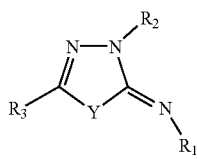

I wherein:
Y is S;
R$_1$ is:
C$_4$–C$_{10}$ alkyl
C$_2$–C$_{10}$ alkenyl,
C$_2$–C$_{10}$ alkynyl,
cycloalkyl,
cycloalkenyl,
heterocyclyl,
aryl,
or a bicyclic group;
each optionally substituted with one or several groups of the formula X$_1$—R$_4$, identical or different, wherein:
X$_1$ is:
a single bond, lower alkylenyl, C$_2$–C$_6$ alkenylenyl, cycloalkylenyl, arylenyl or divalent heterocyclyl, and,
R$_4$ is:
1) H, =O, NO$_2$, CN, halogen, lower haloalkyl, lower alkyl, carboxylic acid bioisostere,
2) COOR$_5$, C(=O)R$_5$, SO$_2$R$_5$, SOR$_5$, SO$_3$R$_5$, SR$_5$, OR$_5$,
3) C(=O)NR$_7$R$_8$, C(=S)NR$_7$R$_8$, C(=CN—NO$_2$)NR$_7$R$_8$, C(=N—CH)NR$_7$R$_8$, C(=N—SO$_2$NH$_2$)NR$_7$R$_8$, C(=NR$_7$)NHR$_8$, C(=NR$_7$)R$_8$, C(=NR$_9$)NHR$_8$, C(=NR$_9$)R$_8$, SO$_2$NR$_7$R$_8$ $_l$ $_{or}$ $_{NR_7R_8}$ in which R$_7$ and R$_8$ are the same or different and are OH, R$_5$, R$_6$, C(=O)NR$_5$R$_6$, C(=O)R$_5$, C(=NR$_9$)NHR$_{10}$, C(=NR$_9$)R$_{10}$, C(=CH—NO$_2$)NR$_9$R$_{10}$, C)=N—SO$_2$NH$_2$)NR$_9$R$_{10}$, C(=N—CN)NR$_9$R$_{10}$ or C(=S)NR$_9$R$_{10}$;

R$_2$ is:
lower alkyl,
C$_2$–C$_{10}$ alkenyl,
C$_4$–C$_{10}$ alkynyl,
cycloalkyl,
cycloalkenyl,
heterocyclyl, or
aryl;
each optionally substituted with one or several groups which are the same or different and which are:
1) H, carboxylic acid bioisostere, lower haloalkyl, halogen,
2) COOR$_5$, OR$_5$, SO$_2$R$_5$,
3) SO$_2$NR$_{11}$R$_{12}$, C(=O)NR$_{11}$R$_{12}$ or NR$_{11}$R$_{12}$ in which R$_{11}$ and R$_{12}$ are the same or different and are OH, R$_5$, R$_6$, C(=O)NR$_5$R$_6$, C(=O)R$_5$, SO$_2$R$_5$, C(=S)NR$_9$R$_{10}$, C(=CH—NO$_2$)NR$_9$R$_{10}$, C(=N—CN)NR$_9$R$_{10}$, C(=N—SO$_2$NH$_2$)NR$_9$R$_{10}$, C(=NR$_9$)NHR$_{10}$, or C(=NR$_9$)R$_{10}$;

R$_3$ is X$_2$—R'$_3$ wherein:
X$_2$ is a single bond,
R'$_3$ is:
cycloalkyl,
cycloalkenyl,
aryl,
heterocyclyl,
or a polycyclic group;
each optionally substituted with one or several groups of the formula X$_3$—R$_{17}$, identical or different, in which:
X$_3$ is:
a single bond, lower alkylenyl, C$_2$–C$_6$ alkenylenyl, C$_2$–C$_6$ alkynylenyl, cycloalkylenyl, arylenyl, divalent heterocyclyl, or a divalent polycyclic group, and,
R$_{17}$ is:
1) H, =O, NO$_2$, CN, lower haloalkyl, halogen, cycloalkyl,
2) COOR$_5$, C(=O)R$_5$, C(=S)R$_5$, SO$_2$R$_5$, SOR$_5$, SO$_3$R$_5$, SR$_5$, OR$_5$,
3) C(=O)NR$_{15}$R$_{16}$, C(=S)NR$_{15}$R$_{16}$, C(=N—CN)NR$_{15}$R$_{16}$, C(=N—SO$_2$NH$_2$)NR$_{15}$R$_{16}$, C(=CH—NO$_2$)NR$_{15}$R$_{16}$, SO$_2$NR$_{15}$R$_{16}$, C(=NR$_{15}$)NHR$_{16}$, C(=NR$_{15}$)R$_{16}$, C(=NR$_9$)NHR$_{16}$, C(=NR$_9$)R$_{16}$ or NR$_{15}$R$_{16}$ in which R$_{15}$ and R$_{16}$ are the same or different and are OH, R$_5$, R$_6$, C(=O)NR$_5$R$_6$, C(=O)R$_5$, SO$_2$R$_5$, C(=S)NR$_9$R$_{10}$, C(=CH—NO$_2$)NR$_9$R$_{10}$, C(=N—CN)NR$_9$R$_{10}$, C(=N—SO$_2$NH$_2$)NR$_9$R$_{10}$, C(=NR$_9$)NHR$_{10}$, or C(=NR$_9$)R$_{10}$; or 4) heterocyclyl optionally substituted with one or several R$_5$ groups;

R$_5$ and R$_6$ are the same or different and are:
H,
lower alkyl, C$_2$–C$_6$ alkenyl, C$_2$–C$_6$ alkynyl;
X$_4$-cycloalkyl, X$_4$-cycloalkenyl, X$_4$-aryl, X$_4$-heterocyclyl or a X$_4$-polycyclic group, in which X$_4$ is a single bond, lower alkylenyl or C$_2$–C$_6$ alkenylenyl;

each optionally substituted with one or several groups which are the same or different and which are:
halogen, =O, COOR$_{20}$, CH, OR$_{20}$, lower alkyl optionally substituted with OR$_{20}$, O-lower alkyl optionally substituted with OR$_{20}$,
C(=O)-lower alkyl, lower haloalkyl,

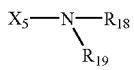

in which X$_5$ is a single bond or lower alkylenyl and R$_{18}$, R$_{19}$, and R$_{20}$ are the same or different and are selected from H or lower alkyl;
X$_6$-heterocyclyl, X$_6$-aryl, X$_6$-cycloalkyl, X$_6$-cycloalkenyl, or an X$_6$-polycyclic group in which X$_6$ is a single bond or lower alkylenyl, these groups being optionally substituted with one or several groups, identical or different, selected from halogens, COOR$_{21}$, OR$_{21}$, and (CH$_2$)$_n$NR$_{21}$R$_{22}$ in which n is 0, 1, or 2 and R$_{21}$ and R$_{22}$ are the same or different and are H or lower alkyl;

R$_9$ is H, CN, OH, lower alkyl, O-lower alkyl, aryl, heterocyclyl, SO$_2$NH$_2$ or

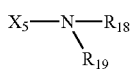

in which X$_5$ is a single bond or lower alkylenyl and R$_{18}$ and R$_{19}$ are the same or different and are selected from H or lower alkyl;

R$_{10}$ is selected from hydrogen, lower alkyl, cyclopropyl or heterocyclyl; or a pharmaceutically acceptable derivative thereof, with the provisos that,
a) the substituent group "=O" is not bonded to a single bond, a carbon atom of a carbon-carbon double bond or a carbon-carbon triple bond, a carbon atom of a trisubstituted carbon, an arylenyl, or a heteroatom of a divalent heterocyclyl,
b) when R$_1$ is phenyl, it bears at least one substituent other than H,
c) when both R$_1$ and R'$_3$ are phenyl, each of R$_1$ and R'$_3$ bear at least one substituent other than H,
d) when R'$_3$ is phenyl, R'$_3$ is not substituted by an ester or a carboxylic acid in the ortho position,
e) the atom of R$_3$ which is linked to the thiadiazole group is a carbon atom, and excluding the following compounds, 1-Phenyl-1-[4-phenyl-5-(5-trifluoromethyl-2H-[1,2,4]triazol-3-ylimino)-4,5-dihydro-[1,3,4]thiadiazol-2-yl]-methanone,
1-[4-Phenyl5-(5-trifluoromethyl-2H-[1,2,4]triazol-3-ylimino)-4,5-dihydro-[1,3,4]thiadiazol-2-yl]-1-thiophen-2-yl-methanone,
1-Phenyl-1-(4-phenyl-5-p-tolylimino-4,5-dihydro-[1,3,4]thiadiazol-2-yl)-methanone,
Cyclohexyl-[3-(2,4,6-trichloro-phenyl)-5-(2,3,3-trimethyl-cyclopent-1-enylmethyl)-3H-[1,3,4]thiadiazol-2-ylidene]-amine,
2-(3,5-Diphenyl-3H-[1,3,4]thiadiazol-2-ylideneamino)-1,4-diphenyl-but-2-ene-1,4-dione,
2-[3-Phenyl-5-(1-phenyl-methanoyl)-3H-[1,3,4]thiadiazol-2-ylideneamino]-but-2-enedioic acid dimethyl ester,
2-[5-(1-Phenyl-methanoyl)-3-p-tolyl-3H-[1,3,4]thiadiazol-2-ylideneamino]-but-2-enedioic acid dimethyl ester, and
2-[3-(4-Chloro-phenyl)-5-(1-phenyl-methanoyl)-3H-[1,3,4]thiadiazol-2-ylideneamino]-but-2-enedioic acid dimethyl ester.

2. A compound of claim 1 wherein when R$_2$ is a phenyl, unsubstituted or substituted with 1 to 3 chlorine or with a methyl, then R$_3$ does not represent C(=O)-phenyl, C(=O)-thienyl, phenyl, or CH$_2$-(2,3,3-trimethyl-cyclopent-1-enyl).

3. A compound of claim 1, wherein
R$_1$ is:
C$_4$–C$_6$ alkyl,
cycloalkyl,
cycloalkenyl,
heterocyclyl,
aryl,
or a bicyclic group;
each optionally sustituted with one or several groups of the formula X$_1$—R$_4$, identical or different, wherein:
X$_1$ is a single bond, a divalent heterocyclyl or a lower alkylenyl, and
R$_4$ is:
1) H, =O, halogen, CN, lower haloalkyl, preferably CF$_3$, lower alkyl, carboxylic acid bioisostere,
2) COOR$_5$, SO$_2$R$_5$, OR$_5$, C(=)R$_5$,
3) C(=O)NR$_7$R$_8$, SO$_2$NR$_7$R$_8$, or NR$_7$R$_8$ in which R$_7$ and R$_8$ are the same or different and are R$_5$, R$_6$, C(=O)NR$_5$R$_6$, C(=O)R$_5$, SO$_2$R$_5$, C(=NR$_9$)NHR$_{10}$, C(=NR$_9$)R$_{10}$, or C(=S)NR$_9$R$_{10}$,
wherein R$_5$ is hydrogen or lower alkyl, optionally substituted with OH, and R$_6$, R$_9$, and R$_{10}$ are identical or different and are hydrogen or lower alkyl.

4. A compound of claim 1 wherein R$_2$ is lower alkyl.

5. A compound of claim 1 wherein
R'$_3$ is:
cycloalkyl,
cycloalkenyl,
aryl,
heterocyclyl,
or a polycyclic group;
each optionally substituted with one or several groups of the formula X$_3$—R$_{17}$, identical or different, wherein:
X$_3$ is a single bond or lower alkylenyl, and
R$_{17}$ is:
1) H, =O, NO$_2$, CN, lower haloalkyl, halogen, cycloalkyl,
2) COOR$_5$, C(=O)R$_5$, C(=S)R$_5$, SO$_2$R$_5$, SOR$_5$, SO$_3$R$_5$, SR$_5$, OR$_5$,
3) C(=O)NR$_{15}$R$_{16}$, C(=S)NR$_{15}$R$_{16}$, C(=N—CN)NR$_{15}$R$_{16}$, C(=CH—NO$_2$)NR$_{15}$R$_{16}$, SO$_2$NR$_{15}$R$_{16}$, C(=NR$_{15}$)NHR$_{16}$, C(=NR$_{15}$)R$_{16}$, C(=NR$_9$)NHR$_{16}$, C(=NR$_9$)R$_{16}$, or NR$_{15}$R$_{16}$ in which R$_{15}$ and R$_{16}$ are the same or different and are OH, R$_5$, R$_6$, C(=O)NR$_5$R$_6$, C(=O)R$_5$, SO$_2$R$_5$, C(=S)NR$_9$R$_{10}$, C(=CH—NO$_2$)NR$_9$R$_{10}$, C(=N—CN)NR$_9$R$_{10}$, C(=NR$_9$)NHR$_{10}$, or C(=NR$_9$)R$_{10}$, 4) heterocyclyl optionally substituted with one or several $R_5$ groups.

6. A compound of claim 1 wherein
$R_1$ is:
cycloalkyl,
cycloalkenyl,
aryl,
or a bicyclic group;
each optionally substituted with one or several groups $X_1$—$R_4$, identical or different, wherein:
$X_1$ is a single bond or a divalent heterocyclyl, and,
$R_4$ is:
1) H, halogen, $CF_3$, =O,
2) $COOR_5$, $OR_5$, or
3) $C(=O)NR_5R_6$;
wherein $R_5$ and $R_6$ are identical or different and are hydrogen or methyl.

7. A compound of claim 1, wherein $R_2$ is $CH_3$.

8. A compound of claim 1 wherein
$R'_3$ is:
cycloalkyl,
aryl,
heterocyclyl,
or a polycyclic group;
each optionally substituted with one or several groups of the formula $X_3$—$R_{17}$, identical or different, wherein:
$X_3$ is a single bond or —$CH_2$—, and,
$R_{17}$ is:
1) H, CN, $CF_3$, halogen, $NO_2$,
2) $COOR_5$, $SO_2R_5$, $OR_5$, $C(=O)R_5$,
3) $C(=O)NR_{15}R_{16}$, $SO_2NR_{15}R_{16}$, or $NR_{15}R_{16}$ in which $R_{15}$ and $R_{16}$ are the same or different and are OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, $C(=NR_9)R_{10}$, or $C(=N-CN)NR_9R_{10}$,
4) heterocyclyl optionally substituted with one or several $R_5$ groups.

9. A compound of Formula I,

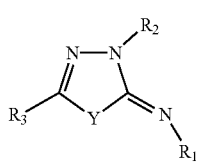

wherein
Y is S;
$R_1$ is
$C_4$–$C_6$ alkyl,
cycloalkyl,
cycloalkenyl,
heterocyclyl,
aryl,
or a bicyclic group;
each optionally substituted with one or several groups of the formula $X_1$—$R_4$, identical or different, wherein:
$X_1$ is a single bond, a divalent heterocyclyl or a lower alkylenyl, and,
$R_4$ is:
1) H, =O, halogen, CN, lower haloalkyl, lower alkyl, carboxylic acid bioisostere,
2) $COOR_5$, $SO_2R_5$, $OR_5$, $C(=O)R_5$,
3) $C(=O)NR_7R_8$, $SO_2NR_7R_8$, or $NR_7R_8$ in which $R_7$ and $R_8$ are the same or different and are $R_5$, $R_6$, $C(=O)NR_5R_6$, $C(=O)R_5$, $SO_2R_5$, $C(=NR_9)NHR_{10}$, $C(=NR_9)R_{10}$, or $C(=S)NR_9R_{10}$,
wherein $R_5$ is hydrogen or lower alkyl, optionally substituted with OH, and $R_6$, $R_9$ and $R_{10}$ are identical or different and are hydrogen or lower alkyl;

$R_2$ is lower alkyl;
$R_3$ is $X_2$—$R'_3$;
$X_2$ is a single bond;
$R'_3$ is:
cycloalkyl,
cycloalkenyl,
aryl,
heterocyclyl,
or a polycyclic group;
each optionally substituted with one or several groups of the formula $X_3$—$R_{17}$, identical or different, in which:
$X_3$ is a single bond or lower alkylenyl, and
$R_{17}$ is:
1) H, =O, $NO_2$, CN, lower haloalkyl, halogen, cycloalkyl,
2) $COOR_5$, $C(=O)R_5$, $C(=S)R_5$, $SO_2R_5$, $SOR_5$, $SO_3R_5$, $SR_5$, $OR_5$,
3) $C(=O)NR_{15}R_{16}$, $C(=S)NR_{15}R_{16}$, $C(=N-CN)NR_{15}R_{16}$, $C(=CH-NO_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ in which $R_{15}$ and $R_{16}$ are the same or different and are OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=NR_9)NHR_{10}$, or $C(=NR_9)R_{10}$, or
4) heterocyclyl optionally substituted with one or several $R_5$ groups;
wherein
$R_5$ and $R_6$ are the same or different and are:
H,
lower alkyl, $C_2$–$C_6$ alkenyl, $C_2$–$C_6$ alkynyl,
$X_4$-cycloalkyl, $X_4$-cycloalkenyl, $X_4$-aryl, $X_4$-heterocyclyl or $X_4$-polycyclic group, in which $X_4$ is a single bond, lower alkylenyl, or $C_2$–$C_6$ alkenylenyl;
each optionally substituted with one or several groups which are the same or different and which are:
halogen, =O, $COOR_{20}$, CN, $OR_{20}$, lower alkyl optionally substituted with $OR_{20}$, O-lower alkyl optionally substituted with $OR_{20}$, C(=O)-lower alkyl, lower haloalkyl,

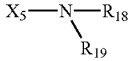

in which $X_5$ is a single bond or lower alkylenyl and $R_{18}$, $R_{19}$, and $R_{20}$ are the same or different and are H or lower alkyl;
$X_6$-heterocyclyl, $X_6$-aryl, $X_6$-cycloalkyl, $X_6$-cycloalkenyl, or an $X_6$-polycyclic group in which $X_6$ is a single bond or lower alkylenyl, these groups being optionally substituted with one or several groups, identical or different, selected from halogens, $COOR_{21}$, $OR_{21}$, and $(CH_2)_nNR_{21}R_{22}$ in which n is 0, 1, or 2 and $R_{21}$ and $R_{22}$ are the same or different and are H or lower alkyl;

$R_9$ is H, CN, OH, lower alkyl, O-lower alkyl, aryl, heterocyclyl, SO$_2$NH$_2$, or

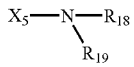

in which $X_5$ is a single bond or lower alkylenyl and $R_{18}$ and $R_{19}$ are the same or different and are H or lower alkyl;

$R_{10}$ is selected from hydrogen, lower alkyl, cyclopropyl or heterocyclyl;

or a pharmaceutically acceptable derivative thereof, with the provisos that,
a) the substituent group "=O" is not bonded to a single bond, a carbon atom of a carbon-carbon double bond or a carbon-carbon triple bond, a carbon atom of a trisubstituted carbon, an arylenyl, or a heteroatom of a divalent heterocyclyl,
b) when $R_1$ is phenyl, it bears at least one substituent other than H,
c) when both $R_1$ and $R'_3$ are phenyl, each of $R_1$ and $R'_3$ bear at least one substituent other than H,
d) when $R'_3$ is phenyl, $R'_3$ is not substituted by an ester or a carboxylic acid in the ortho position, and
e) the atom of $R_3$ which is linked to the thiadiazole group is a carbon atom.

10. A compound of Formula I,

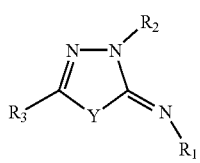

wherein

Y is S;

$R_1$ is
cycloalkyl,
cycloalkenyl,
aryl,
or a bicyclic group;
each optionally substituted with one or several groups of the formula $X_1$—$R_4$, identical or different, wherein:
$X_1$ is a single bond or a divalent heterocyclyl, and
$R_4$ is:
1) H, halogen, CF$_3$, =O
2) COOR$_5$, OR$_5$,
3) C(=O)NR$_5$R$_6$, or
wherein R$_5$ and R$_6$ are identical or different and are hydrogen or methyl;

$R_2$ is CH$_3$;

$R_3$ is $X_2$—$R'_3$;
$X_2$ is a single bond;
$R'_3$ is:
cycloalkyl,
aryl,
heterocyclyl,
or a polycyclic group;
each optionally substituted with one or several groups of the formula $X_3$—$R_{17}$, identical or different, wherein:
$X_3$ is a single bond or —CH$_2$—, and
$R_{17}$ is:
1) H, CN, CF$_3$, halogen, NO$_2$,
2) COOR$_5$, SO$_2$R$_5$, OR$_5$, C(=O)R$_5$,
3) C(=O)NR$_{15}$R$_{16}$, SO$_2$NR$_{15}$R$_{16}$, or NR$_{15}$R$_{16}$ in which $R_{15}$ and
$R_{16}$ are the same or different and are OH, R$_5$, R$_6$, C(=O)NR$_5$R$_6$,
C(=O)R$_5$, SO$_2$R$_5$, C(=S)NR$_9$R$_{10}$, C(=CH—NO$_2$)NR$_9$R$_{10}$,
C(=NR$_9$)NHR$_{10}$, C(=NR$_9$)R$_{10}$, or C(=N—CN)NR$_9$R$_{10}$; or
4) heterocyclyl optionally substituted with one or several R$_5$ groups;

wherein

R$_5$ and R$_6$ are the same or different and are:
H,
lower alkyl, C$_2$–C$_6$ alkenyl, C$_2$–C$_6$ alkynyl;
X$_4$-cycloalkyl, X$_4$-cycloalkenyl, X$_4$-aryl, X$_4$-heterocyclyl or a X$_4$-polycyclic group, in which X$_4$ is a single bond, lower alkylenyl, or C$_2$–C$_6$ alkenylenyl;

each optionally substituted with one or several groups which are the same or different and which are:
halogen, =O, COOR$_{20}$, CN, OR$_{20}$, lower alkyl optionally substituted with OR$_{20}$, O-lower alkyl optionally substituted with OR$_{20}$, C(=O)-lower alkyl, lower haloalkyl,

in which $X_5$ is a single bond or lower alkylenyl and $R_{18}$, $R_{19}$, and $R_{20}$ are the same or different and are H or lower alkyl;

$X_6$-heterocyclyl, $X_6$-aryl, $X_6$-cycloalkyl, $X_6$-cycloalkenyl, or an $X_6$-polycyclic group in which $X_6$ is a single bond or lower alkylenyl, these groups being optionally substituted with one or several groups, identical or different, selected from halogens, COOR$_{21}$, OR$_{21}$, and (CH$_2$)$_n$NR$_{21}$R$_{22}$ in which n is 0, 1, or 2 and R$_{21}$ and R$_{22}$ are the same or different and are H or lower alkyl;

$R_9$ is H, CN, OH, lower alkyl, O-lower alkyl, aryl, heterocyclyl, SO$_2$NH$_2$, or

in which $X_5$ is a single bond or lower alkylenyl and $R_{18}$ and $R_{19}$ are the same or different and are H or lower alkyl;

$R_{10}$ is hydrogen, lower alkyl, cyclopropyl, or heterocyclyl;

or a pharmaceutically acceptable derivative thereof, with the provisos that
a) the substituent group "=O" is not bonded ot a single bond, a carbon atom of a carbon-carbon double bond or a carbon-carbon triple bond, a carbon atom of a trisubstituted carbon, an arylenyl, or a heteroatom of a divalent heterocyclyl,
b) when $R_1$ is phenyl, it bears at least one substituent other than H,
c) when both $R_1$ and $R'_3$ are phenyl, each of $R_1$ and $R'_3$ bear at least one substituent other than H,
d) when $R'_3$ is phenyl, $R'_3$ is not substituted by an ester or a carboxylic acid in the ortho position, and
e) the atom of $R_3$ which is linked to the thiadiazole group is a carbon atom.

11. A compound of Formula I

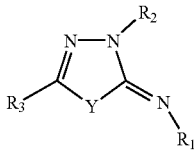

wherein
Y is S;
$R_1$ is:
  cyclohexyl,
  phenyl,
  or a bicyclic group
  each optionally substituted with one or several groups of the formula $X_1$—$R_4$, identical or different, wherein:
  $X_1$ is a single bond or a divalent heterocyclyl, and
  $R_4$ is:
    1) H, halogen, $CF_3$,
    2) COOH, OH, or
    3) C(=O)$NR_7R_8$ in which $R_7$ and $R_8$ are the same or different and are H or lower alkyl,
$R_2$ is $CH_3$, and
$R_3$ is $X_2$—$R'_3$;
  $X_2$ is a single bond;
  $R'_3$ is:
    phenyl,
    heterocyclyl,
    or a polycyclic group;
  each optionally substituted with one or several groups of the formula $X_3$—$R_{17}$, identical or different, wherein:
  $X_3$ is a single bond, and
  $R_{17}$ is:
    1) CN, OH, $C_3$, =O, $C_1$–$C_6$ alkoxy, halogen,
    2) $COOR_5$, $SO_2R_5$,
    3) C(=O)$NR_{15}R_{16}$, $SO_2NR_{15}R_{16}$, or $NR_{15}R_{16}$ in which $R_{15}$ and $R_{16}$ are the same or different and are selected from OH, C(=O)$R_5$, C(=O)$NR_5N_6$, $R_5$, or $R_6$; or
    4) heterocyclyl optionally substituted with one or several $R_5$ groups;
    wherein,
  $R_5$ and $R_6$ are the same or different and are:
    H,
    lower alkyl, $C_2$–$C_6$ alkenyl, $C_2$–$C_6$ alkynyl;
    $X_4$-cycloalkyl, $X_4$-cycloalkenyl, $X_4$-aryl, $X_4$-heterocyclyl or a $X_4$-polycyclic group, in which $X_4$ is a single bond, lower alkylenyl, or $C_2$–$C_6$ alkenylenyl;
  each optionally substituted with one or several groups which are the same or different and which are:
    halogen, =O, $COOR_{20}$, CN, $OR_{20}$, lower alkyl optionally substituted with $OR_{20}$, O-lower alkyl optionally substituted with $OR_{20}$, C(=O)-lower alkyl, lower haloalkyl,

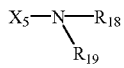

in which $X_5$ is a single bond or lower alkylenyl and $R_{18}$, $R_{19}$, and $R_{20}$ are the same or different and are H or lower alkyl;
$X_6$-heterocyclyl, $X_6$-aryl, $X_6$-cycloalkyl, $X_6$-cycloalkenyl, or an $X_6$-polycyclic group in which $X_6$ is a single bond or lower alkylenyl, these groups being optionally substituted with one or several groups, identical or different, selected from halogens, $COOR_{21}$, $OR_{21}$, and $(CH_2)_nNR_{21}R_{22}$ in which n is 0, 1, or 2 and $R_{21}$ and $R_{22}$ are the same or different and are H or lower alkyl;
$R_9$ is H, CN, OH, lower alkyl, O-lower alkyl, aryl, heterocyclyl, $SO_2NR_2$, or

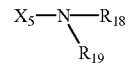

in which $X_5$ is a single bond or lower alkylenyl and $R_{18}$ and $R_{19}$ are the same or different and are H or lower alkyl;
$R_{10}$ is hydrogen, lower alkyl, cyclopropyl, or heterocyclyl;
or a pharmaceutically acceptable derivative thereof,
with the provisos that,
  a) the substituent group "=O" is not bonded to a single bond, a carbon atom of a carbon-carbon double bond or a carbon-carbon triple bond, a carbon atom of a trisubstituted carbon, an arylenyl, or a heteroatom of a divalent heterocyclyl,
  b) when $R_1$ is phenyl, it bears at least one substituent other than H,
  c) when both $R_1$ and $R'_3$ are phenyl, each of $R_1$ and $R'_3$ bear at least one substituent other than H,
  d) when $R'_3$ is phenyl, $R'_3$ is not substituted by an ester or a carboxylic acid in the ortho position, and
  e) the atom of $R_3$ which is linked to the thiadiazole group is a carbon atom.

12. A compound selected from the group consisting of:
3-[5-(4-Chloro-phenyl)-3-methyl-3H-[1,3,4]thiadiazol-2-ylideneamino]-benzoic acid,
(1R*,2R*)-2-[5-(4-Chloro-phenyl)-3-methyl-3H-[1,3,4]thiadiazol-2-ylideneamino]-cyclohexanecarboxylic acid,
(S)-2-[5-(4-Chloro-phenyl)-3-methyl-3H-[1,3,4]thiadiazol-2-ylideneamino]-2-phenyl-ethanol,
2-{2-[5-(4-Chloro-phenyl)-3-methyl-3H-[1,3,4]thiadiazol-2-ylideneamino]-phenyl}-ethanol,
{1-[5-(4-Chloro-phenyl)-3-methyl-3H-[1,3,4]thiadiazol-2-ylideneamino]-cyclopentyl}-methanol,
3-[5-(4-Chloro-phenyl)-3-methyl-3H-[1,3,4]thiadiazol-2-ylidenamino]-cyclohexanecarboxylic acid,
5-[5-(4-Chloro-phenyl)-3-methyl-3H[1,3,4]thiadiazol-2-ylideneamino]-2-fluoro-benzoic acid,
3-[5-(4-Chloro-phenyl)-3-methyl-3H-[1,3,4]thiadiazol-2-ylideneamino]-2,5,6-trifluoro-benzoic acid,
[5-(4-Chloro-phenyl)-3-methyl-3H-[1,3,4]thiadiazol-2-ylidene]-propyl-amine,
(S)-2-[5-(4-Chloro-phenyl)-3-methyl-3H-[1,3,4]thiadiazol-2-ylideneamino]-butan-1-ol,
[5-(4-Chloro-phenyl)-3-methyl-3H-[1,3,4]thiadiazol-2-ylidene]-cyclobutyl-amine,
3-[5-(4-Chloro-phenyl)-3-methyl-3H-[1,3,4]thiadiazol-2-ylideneamino]-azepan-2-one,
[5-(4-Chloro-phenyl)-3-methyl-3H-[1,3,4]thiadiazol-2-ylidene]-cyclopentyl-amine,
[5-(4-Chloro-phenyl)-3-methyl-3H-[1,3,4]thiadiazol-2-ylidene]-cycloheptyl-amine,
(S)-2-[5-(4-Chloro-phenyl)-3-methyl-3H-[1,3,4]thiadiazol-2-ylideneamino]-3-methyl-butan-1-ol,
2-[5-(4-Chloro-phenyl)-3-methyl-3H-[1,3,4]thiadiazol-2-ylideneamino]-2-methyl-propan-1-ol,
tert-Butyl-[5-(4-chloro-phenyl)-3-methyl-3H-[1,3,4]thiadiazol-2-ylidene]-amine,

[5-(4-Chloro-phenyl)-3-methyl-3H-[1,3,4]thiadiazol-2-ylidene]-isopropyl-amine,
4-[5-(4-Chloro-phenyl)-3-methyl-3H-[1,3,4]thiadiazol-2-ylideneamino]-benzoic acid,
[5-(4-Chloro-phenyl)-3-methyl-3H-[1,3,4]thiadiazol-2-ylidene]-(1-ethyl-propyl)-amine,
4-[5-(4-Chloro-phenyl)-3-methyl-3H-[1,3,4]thiadiazol-2-ylideneamino]-phenol,
N-[5-(4-Chloro-phenyl)-3-methyl-3H-[1,3,4]thiadiazol-2-ylidene]-cyclohexane-1,2-diamine,
[5-(4-Chloro-phenyl)-3-methyl-3H-[1,3,4]thiadiazol-2-ylidene]-(4-fluoro-phenyl)-amine,
N-[5-(4-Chloro-phenyl)-3-methyl-3H-[1,3,4]thiadiazol-2-ylidene]-cyclohexane-1,4-diamine,
(1R*,2S*)-2-[5-(4-Chloro-phenyl)-3-methyl-3H-[1,3,4]thiadiazol-2-ylideneamino]-cyclohexanol,
[5-(4-Chloro-phenyl)-3-methyl-3H-[1,3,4]thiadiazol-2-ylidene]-(4-trifluoromethyl-phenyl)-amine,
3-[5-(4-Methanesulfonyl-phenyl)-3-methyl-3H-[1,3,4]thiadiazol-2-ylideneamino]-benzoic acid,
3-[5-(4-Chloro-phenyl)-3-methyl-3H-[1,3,4]thiadiazol-2-ylideneamino]-phenol,
5-[5-(4-Chloro-phenyl)-3-methyl-3H-[1,3,4]thiadiazol-2-ylideneamino]-2-hydroxy-benzoic acid,
(1-Aza-bicyclo[2.2.2]oct-3-yl)-[5-(4-chloro-phenyl)-3-methyl-3H-[1,3,4]thiadiazol-2-ylidene]-amine,
2-[5-(4-Chloro-phenyl)-3-methyl-3H-[1,3,4]thiadiazol-2-ylideneamino]-phenol,
(R)-2-[5-(4-Chloro-phenyl)-3-methyl-3H-[1,3,4]thiadiazol-2-ylideneamino]-butan-1-ol,
[5-(4-Chloro-phenyl)-3-methyl-3H-[1,3,4]thiadiazol-2-ylidene]-(3-fluoro-phenyl)-amine,
(3-Chloro-phenyl)-[5-(4-chloro-phenyl)-3-methyl-3H-[1,3,4]thiadiazol-2-ylidene]-amine,
{3-[5-(4-Chloro-phenyl)-3-methyl-3H-[1,3,4]thiadiazol-2-ylideneamino]-phenyl}-acetic acid,
3-[5-(4-Chloro-phenyl)-3-methyl-3H-[1,3,4]thiadiazol-2-ylideneamino]-benzamide,
Bicyclo[2.2.1]hept-2-yl-[5-(4-chloro-phenyl)-3-methyl-3H-[1,3,4]thiadiazol-2-ylidene]-amine,
(1R*,2R*)-2-[5-(4-Chloro-phenyl)-3-methyl-3H-[1,3,4]thiadiazol-2-ylideneamino]-cyclohexanol,
5-(5-Cyclohexyl-3-methyl-3H-[1,3,4]thiadiazol-2-ylideneamino)-2-methoxy-phenol,
3-(5-Cyclohexyl-3-methyl-3H-[1,3,4]thiadiazol-2-ylideneamino)-benzoic acid,
3-[5-(4-Chloro-phenyl)-3-methyl-3H-[1,3,4]thiadiazol-2-ylideneamino]-4-hydroxy-benzoic acid,
(5-Cyclohexyl-3-methyl-3H-[1,3,4]thiadiazol-2-ylidene)-(3-methanesulfonyl-phenyl)-amine,
(1R*,2*)-2-[5-(4-Methanesulfonyl-phenyl)-3-methyl-3H-[1,3,4]thiadiazol-2-ylideneamino]-cyclohexanol,
Cyclohexyl-[5-(2,4-dichloro-phenyl)-3-methyl-3H-[1,3,4]thiadiazol-2-ylidene]-amine,
[5-(2-Chloro-phenyl)-3-methyl-3H-[1,3,4]thiadiazol-2-ylidene]-cyclohexyl-amine,
Cyclohexyl-[3-methyl-5-(4-trifluoromethyl-phenyl)-3H-[1,3,4]thiadiazol-2-ylidene]-amine,
Cyclohexyl-(3-methyl-5-pyridin-4-yl-3H-[1,3,4]thiadiazol-2-ylidene)-amine,
[5-(3-Chloro-phenyl)-3-methyl-3H-[1,3,4]thiadiazol-2-ylidene]-cyclohexyl-amine,
4-(5-Cyclohexylimino-4-methyl-4,5-dihydro-[1,3,4]thiadiazol-2-yl)-benzonitrile,
Cyclohexyl-[5-(4-methanesulfonyl-phenyl)-3-methyl-3H-[1,3,4]thiadiazol-2-ylidene]-amine,
[3-(5-Cyclohexylimino-4-methyl-4,5-dihydro-[1,3,4]thiadiazol-2-yl)-phenyl]-dimethyl-amine,
Cyclohexyl-[5-(3-methoxy-4-nitro-phenyl)-3-methyl-3H-[1,3,4]thiadiazol-2-ylidene]-amine,
2,4-Dichloro-5-(5-cyclohexylimino-4-methyl-4,5-dihydro-[1,3,4]thiadiazol-2-yl)-benzenesulfonamide,
Cyclohexyl-(3-methyl-5-thiophen-3-yl-3H-[1,3,4]thiadiazol-2-ylidene)-amine,
Cyclohexyl-[5-(3,5-dichloro-phenyl)-3-methyl-3H-[1,3,4]thiadiazol-2-ylidene]-amine,
CYclohexyl-[5-(2-ethyl-5-methyl-2H-pyrazol-3-yl)-3-methyl-3H-[1,3,4]thiadiazol-2-ylidene]-amine,
[5-(3-Chloro-2,6-dimethoxy-phenyl)-3-methyl-3H-[1,3,4]thiadiazol-2-ylidene]-cyclohexyl-amine,
Cyclohexyl-(5-isoxazol-5-yl-3-methyl-3H-[1,3,4]thiadiazol-2-ylidene)-amine,
Cyclohexyl-[3-methyl-5-(5-pyridin-2-yl-thiophen-2-yl)-3H-[1,3,4]thiadiazol-2-ylidene]-amine,
5-(5-Cyclohexylimino-4-methyl-4,5-dihydro[1,3,4]thiadiazol-2-yl)-2-methoxy-benzene-1,3-diol; compound with trifluoro-methanesulfonic acid,
5-(5-Cyclohexylimino-4-methyl-4,5-dihydro[1,3,4]thiadiazol-2-yl)-2,3-dimethoxy-phenol, compound with trifluoro-methanesulfonic acid
[5-(4-Chloro-phenyl)-3-methyl-3H-[1,3,4]thiadiazol-2-ylidene]-cyclohexyl-amine,
2-Chloro-4-(5-cyclohexylimino-4-methyl-4,5-dihydro-[1,3,4]thiadiazol-2-yl)-6-methoxy-phenol; compound with 1,1,1-trifluoro-methanesulfonic acid,
2-Chloro-5-(5-cyclohexylimino-4-methyl-4,5-dihydro-[1,3,4]thiadiazol-2-yl)-benzenesulfonamide,
2-Chloro-5-(5-cyclohexylimino-4-methyl-4,5-dihydro[1,3,4]thiadiazol-2-yl)-N,N-diethyl-benzenesulfonamide,
{5-[4-Chloro-3-(4-methyl-piperazine-1-sulfonyl)-phenyl]-3-methyl-3H-[1,3,4]thiadiazol-2-ylidene}-cyclohexyl-amine,
2-Chloro-5-(5-cyclohexylimino-4-methyl-4,5-dihydro-[1,3,4]thiadiazol-2-yl)-N-pyridin-4-ylmethyl-benzenesulfonamide,
2-Chloro-5-(5-cyclohexylimino-4-methyl-4,5-dihydro-[1,3,4]thiadiazol-2-yl)-N-(2-morpholin-4-yl-ethyl)-benzenesulfonamide,
2-Chloro-5-(5-cyclohexylimino-4-methyl-4,5-dihydro-[1,3,4]thiadiazol-2-yl)-N-ethyl-benzenesulfonamide,
2-Chloro-5-(5-cyclohexylimino-4-methyl-4,5-dihydro-[1,3,4]thiadiazol-2-yl)-N-ethyl-N-(2-morpholin-4-yl-ethyl)-benzenesulfonamide,
2-Chloro-5-(5-cyclohexylimino-4-methyl-4,5-dihydro-[1,3,4]thiadiazol-2-yl)-N-isopropyl-N-(2-morpholin-4-yl-ethyl)-benzenesulfonamide,
2-Chloro-5-(5-cyclohexylimino-4-methyl-4,5-dihydro-[1,3,4]thiadiazol-2-yl)-N-ethyl-N-[2-(2-methoxy-ethoxy)-ethyl]-benzenesulfonamide,
C-Chloro-(cyclohexylimino-methyl-4,5-dihydro-[1,3,4]thiadiazol-2-yl)-N-(dimethylamino-hydroxy-propyl)-N-ethyl-benzenesulfonamide,
2-Chloro-5-(5-cyclohexylimino-4-methyl-4,5-dihydro-[1,3,4]thiadiazol-2-yl)-N-(2,3-dihydroxy-propyl)-N-ethyl-benzenesulfonamide,
2-Chloro-5-(5-cyclohexylimino-4-methyl-4,5-dihydro-[1,3,4]thiadiazol-2-yl)-N-ethyl-N-(2-hydroxy-3-pyrrolidin-1-yl-propyl)-benzenesulfonamide,
2-Chloro-5-(cyclohexylimino-methyl-4,5-dihydro-[1,3,4]thiadiazol-2-yl)-N-(2-diethylamino-ethyl)-N-ethyl-benzenesulfonamide,
2-Chloro-5-(5-cyclohexylimino-4-methyl-4,5-dihydro-[1,3,4]thiadiazol-2-yl)-N-(2-dimethylamino-propyl)-N-ethyl-benzenesulfonamide,
[5-(4-Chloro-phenyl)-2-cyclohexylimino-[1,3,4]thiadiazol-3-yl]-acetic acid methyl ester, 3-(5-Cyclohexylimino-4-methyl-4,5-dihydro-[1,3,4]thiadiazol-2-yl)-benzoic acid methyl ester,
3-(5-Cyclohexylimino-4-methyl-4,5-dihydro-[1,3,4]thiadiazol-2-yl)-benzoid acid,
3-(5-Cyclohexylimino-4-methyl-4,5-dihydro-[1,3,4]thiadiazol-2-yl)-benzamide,
3-(5-Cyclohexylimino-4-methyl-4,5-dihydro-[1,3,4]thiadiazol-2-yl)-N-(2-hydroxy-ethyl)-benzamide,
3-(5-Cyclohexylimino-4-methyl-4,5-dihydro-[1,3,4]thiadiazol-2-yl)-N-methyl-benzamide,
4-(5-Cyclohexylimino-4-methyl-4,5-dihydro-[1,3,4]thiadiazol-2-yl)-benzene-1,2-diol,
4-(5-Cyclohexylimino-4-methyl-4,5-dihydro-[1,3,4]thiadiazol-2-yl)-2,6-dimethoxy-phenol,
6-(5-Cyclohexylimino-4-methyl-4,5-dihydro-[1,3,4]thiadiazol-2-yl)-pyridin-2-ol,
5-(5-Cyclohexylimino-4-methyl-4,5-dihydro-[1,3,4]thiadiazol-2-yl)-benzene-1,2,3-triol,
2-(5-Cyclohexylimino-4-methyl-4,5-dihydro-[1,3,4]thiadiazol-2-yl)quinolin-8-ol,
Cyclohexyl-(3-methyl-5-pyrazin-2-yl-3H-[1,3,4]thiadiazol-2-ylidene)-amine,
4-(5-Cyclohexylimino-4-methyl-4,5-dihydro-[1,3,4]thiadiazol-2-yl)-2-methoxy-phenol,
Cyclohexyl-(3-methyl-5-quinolin-8-yl-3H-[1,3,4]thiadiazol-2-ylidene)-amine,
[4-(5-Cyclohexylimino-4-methyl-4,5-dihydro-[1,3,4]thiadiazol-2-yl)-phenyl]-dimethyl-amine,
4-(5-Cyclohexylimino-4-methyl-4,5-dihydro-[1,3,4]thiadiazol-2-yl)-benzenesulfonamide,
[5-(5-Chloro-1H-indol-2-yl)-3-methyl-3H-[1,3,4]thiadiazol-2-ylidene]-cyclohexyl-amine; compound with trifluoro-methanesulfonic acid,
2-(5-Cyclohexylimino-4-methyl-4,5-dihydro-[1,3,4]thiadiazol-2-yl)-phenol; compound with 1,1,1-trifluoro-methanesulfonic acid,
5-(5-Cyclohexylimino-4-methyl-4,5-dihydro-[1,3,4]thiadiazol-2-yl)-2-methoxy-phenol, compound with 1,1,1-trifluoro-methanesulfonic acid,
4-(5-Cyclohexylimino-4-methyl-4,5-dihydro-[1,3,4]thiadiazol-2-yl)-phenol, compound with 1,1,1-trifluoro-methanesulfonic acid,
Cyclohexyl-[5-(3,4-dimethoxy-phenyl)-3-methyl-3H-[1,3,4]thiadiazol-2-ylidene]-amine,
[5-(3-Bromo-4-methoxy-phenyl)-3-methyl-3H-[1,3,4]thiadiazol-2-ylidene]-cyclohexyl-amine,
Cyclohexyl-[5-(4-methoxy-phenyl)-3-methyl-3H-[1,3,4]thiadiazol-2-ylidene]-amine,
Cyclohexyl-(3-methyl-5-phenyl-3H-[1,3,4]thiadiazol-2-ylidene)-amine,
3-(5-Cyclohexylimino-4-methyl-4,5-dihydro-[1,3,4]thiadiazol-2-yl)-phenol,
4-(5-Cyclohexylimino-4-methyl-4,5-dihydro-[1,3,4]thiadiazol-2-yl)-benzoic acid methyl ester,
4-(5-Cyclohexylimino-4-methyl-4,5-dihydro-[1,3,4]thiadiazol-2-yl)-benzoic acid,
4-(5-Cyclohexylimino-4-methyl-4,5-dihydro-[1,3,4]thiadiazol-2-yl)-N-hydroxy-benzamide,
4-(5-Cyclohexylimino-4-methyl-4,5-dihydro-[1,3,4]thiadiazol-2-yl)-benzamide,
4-(5-Cyclohexylimino-4-methyl-4,5-dihydro-[1,3,4]thiadiazol-2-yl)-N-(2H-tetrazol-5-yl)-benzamide hydrochloride salt,
4-(5-Cyclohexylimino-4-methyl-4,5-dihydro[1,3,4]thiadiazol-2-yl)-N-quinolin-8-yl-benzamide,
4-(5-Cyclohexylimino-4-methyl-4,5-dihydro[1,3,4]thiadiazol-2-yl)-N-(2,6-dimethoxy-pyridin-3-yl)-benzamide,
4-(5-Cyclohexylimino-4-methyl-4,5-dihydro[1,3,4]thiadiazol-2-yl)-N-isopropyl-benzamide,
4-(5-Cyclohexylimino-4-methyl-4,5-dihydro[1,3,4]thiadiazol-2-yl)-N-ethyl-benzamide,
Cyclohexyl-{5-[4-(1-ethyl-1H-tetrazol-5-yl)-phenyl]-3-methyl-3H-[1,3,4]thiadiazol-2-ylidene}-amine,
4-(5-Cyclohexylimino-4-methyl-4,5-dihydro[1,3,4]thiadiazol-2-yl)-N-(2-dimethylamino-ethyl)-benzamide,
4-(5-Cyclohexylimino-4-methyl-4,5-dihydro[1,3,4]thiadiazol-2-yl)-N-pyridin-4-ylmethyl-benzamide,
4-(5-Cyclohexylimino-4-methyl-4,5-dihydro[1,3,4]thiadiazol-2-yl)-N-methyl-N-(1-methyl-piperidin-4-yl)-benzamide,
4-(5-Cyclohexylimino-4-methyl-4,5-dihydro-[1,3,4]thiadiazol-2-yl)-N-isobutyl-benzamide,
4-(5-Cyclohexylimino-4-methyl-4,5-dihydro-[1,3,4]thiadiazol-2-yl)-N-methyl-benzamide,
4-(Cyclohexylimino-methyl-4,5-dihydro-[1,3,4]thiadiazol-2-yl)-N-(2-dimethylamino-ethyl)-N-methyl-benzamide,
[4-(5-Cyclohexylimino-4-methyl-4,5-dihydro-[1,3,4]thiadiazol-2-yl)-phenyl]-1-(3-hydroxymethyl-piperidin-1-yl)-methanone,
2-[4-(5-Cyclohexylimino-4-methyl-4,5-dihydro-[1,3,4]thiadiazol-2-yl)-benzoylamino]-3-(4-hydroxy-phenyl)-propionic acid tert-butyl ester,
2-({1-[4-(5-Cyclohexylimino-4-methyl-4,5-dihydro-[1,3,4]thiadiazol-2-yl)-phenyl]-methanoyl}-amino)-3-(4-hydroxy-phenyl)-propionic acid, compound with 2,2,2-trifluoro-acetic acid,
(S)-2-[4-(5-Cyclohexylimino-4-methyl-4,5-dihydro-[1,3,4]thiadiazol-2-yl)-benzoylamino]-propionic acid tert-butyl ester,
(S)-2-[4-(5-Cyclohexylimino-4-methyl-4,5-dihydro-[1,3,4]thiadiazol-2-yl)-benzoylamino]-propionic acid; compound with 2,2,2-trifluoro-acetic acid,
[4-(5-Cyclohexylimino-4-methyl-4,5-dihydro-[1,3,4]thiadiazol-2-yl)-phenyl]-(4-pyridin-2-yl-piperazin-1-yl)-methanone,
[4-(5-Cyclohexylimino-4-methyl-4,5-dihydro-[1,3,4]thiadiazol-2-yl)-phenyl]-[4-(4-fluoro-phenyl)-piperazin-1-yl]-methanone,
4-(5-Cyclohexylimino-4-methyl-4,5-dihydro-[1,3,4]thiadiazol-2-yl)-N-(3,4,5-trimethoxy-benzyl)-benzamide,
[4-(5-Cyclohexylimino-4-methyl-4,5-dihydro-[1,3,4]thiadiazol-2-yl)-phenyl]-(4-pyrimidin-2-yl-piperazin-1-yl)-methanone,
[4-(5-Cyclohexylimino-4-methyl-4,5-dihydro-[1,3,4]thiadiazol-2-yl)-phenyl]-(4-methyl-piperazin-1-yl)-methanone,
4-(5-Cyclohexylimino-4-methyl-4,5-dihydro-[1,3,4]thiadiazol-2-yl)-N-[3-(4-methyl-piperazin-1-yl)-propyl]-benzamide,
4-(5-Cyclohexylimino-4-methyl-4,5-dihydro-[1,3,4]thiadiazol-2-yl)-N-(1-ethyl-pyrrolidin-2-ylmethyl)-benzamide,
4-(5-Cyclohexylimino-4-methyl-4,5-dihydro-[1,3,4]thiadiazol-2-yl)-N-pyridin-3-ylmethyl-benzamide,
N-Benzyl-4-(5-cyclohexylimino-4-methyl-4,5-dihydro-[1,3,4]thiadiazol-2-yl)-benzamide,
N-(1-Benzyl-piperidin-4-yl)-4-(5-cyclohexylimino-4-methyl-4,5-dihydro-[1,3,4]thiadiazol-2-yl)-benzamide,
4-(5-Cyclohexylimino-4-methyl-4,5-dihydro-[1,3,4]thiadiazol-2-yl)-N-(2-ethyl-2H-pyrazol-2-yl)-benzamide,
4-(5-Cyclohexylimino-4-methyl-4,5-dihydro-[1,3,4]thiadiazol-2-yl)-N-(2-morpholin-4-yl-ethyl)-benzamide,
[5-(4-((N-cyano-N'-ethylmorpholine)-carboximidamide)-phenyl)-3-methyl-3H-[1,3,4]thiadiazol-2-ylidene]-cyclohexyl-amine, 4-(5-Cyclohexylimino-4-methyl-4,5-dihydro-[1,3,4] thiadiazol-2-yl)-N-(2-pyrrolidin-1-yl-ethyl)-benzamide,
Cyclohexyl-(3-methyl-5-pyridin-3-yl-3H-[1,3,4]thiadiazol-2-ylidene)-amine,
3-(5-Cyclohexylimino-4-methyl-4,5-dihydro-[1,3,4] thiadiazol-2-yl)-benzenesulfonamide,
(5-Benzo[1,3]dioxol-5-yl-3-methyl-3H-[1,3,4]thiadiazol-2-ylidene)-cyclohexyl-amine,
Cyclohexyl-[3-methyl-5-(3,4,5-trimethoxy-phenyl)-3H-[1,3,4]thiadiazol-2-ylidene]-amine,
4-(5-Cyclopentylimino-4-methyl-4,5-dihydro-[1,3,4] thiadiazol-2-yl)-benzonitrile,
4-(5-Cycloheptylimino-4-methyl-4,5-dihydro-[1,3,4] thiadiazol-2-yl)-benzonitrile,
4-[5-(4-Fluoro-phenylimino)-4-methyl-4,5-dihydro-[1,3,4] thiadiazol-2-yl]-benzonitrile,
4-[5-(3-Hydroxy-phenylimino)-4-methyl-4,5-dihydro-[1,3,4]thiadiazol-2-yl]-benzonitrile,
5-[5-(4-Cyano-phenyl)-3-methyl-3H-[1,3,4]thiadiazol-2-ylideneamino]-2-fluoro-benzoic acid,
4-[4-Methyl-5-(cis-4-methyl-cyclohexylimino)-4,5-dihydro-[1,3,4]thiadiazol-2-yl]-benzonitrile,
4-[4-Methyl-5-(trans-4-methyl-cyclohexylimino)-4,5-dihydro-[1,3,4]thiadiazol-2-yl]-benzonitrile,
4-[5-(trans-4-Hydroxy-cyclohexylimino)-4-methyl-4,5-dihydro-[1,3,4]thiadiazol-2-yl]-benzonitrile,
4-[5-(Bicyclo[2,2,1]hept-2-ylimino)-4-methyl-4,5-dihydro-[1,3,4]thiadiazol-2-yl]-benzonitrile,
4-[5-((1R*,2R*)-2-Hydroxy-cyclohexylimino)-4-methyl-4,5-dihydro-[1,3,4]thiadiazol-2-yl]-benzonitrile,
4-[5-((1R*,2S*)-2-Hydroxy-cyclohexylimino)-4-methyl-4,5-dihydro-[1,3,4]thiadiazol-2-yl]-benzonitrile,
4-[5-((1R*,3R*)-3-Hydroxy-cyclohexylimino)-4-methyl-4,5-dihydro-[1,3,4]thiadiazol-2-yl]-benzonitrile,
4-[5-((1R*,3S*)-3-Hydroxy-cyclohexylimino)-4-methyl-4,5-dihydro-[1,3,4]thiadiazol-2-yl]-benzonitrile,
(1R*,3R*))-3-[5-(4-Methanesulfonyl-phenyl)-3-methyl-3H-[1,3,4]thiadiazol-2-ylideneamino]-cyclohexanol,
4-[5-(1R*,3R*)-3-Hydroxy-cyclohexylimino)-4-methyl-4,5-dihydro-[1,3,4]thiadiazol-2-yl]-benzoic acid,
4-[5-((1R*,3R*)-3-hydroxy-cyclohexylimino)-4-methyl-4,5-dihydro-[1,3,4]thiadiazol-2-yl]-N-(2-morpholin-4-yl-ethyl)-benzamide,
4-[5-(trans-4-Hydroxy-cyclohexylimino)-4-methyl-4,5-dihydro-[1,3,4]thiadiazol-2-yl]-benzoic acid,
4-[5-(trans-4-Hydroxy-cyclohexylimino)-4-methyl-4,5-dihydro-[1,3,4]thiadiazol-2-yl]-N-(2-hydroxy-1,1-dimethyl-ethyl)-benzamide,
4-[5-((1R*,3R*)-3-Hydroxy-cyclohexylimino)-4-methyl-4,5-dihydro-[1,3,4]thiadiazol-2-yl]-N-(2-hydroxy-1,1-dimethyl-ethyl)-benzamide,
N-tert-Butyl-4-[5-((1R*,3R*)-3-hydroxy-cyclohexylimino)-4-methyl-4,5-dihydro-[1,3,4] thiadiazol-2-yl]-benzamide,
N-(1,1-dimethyl-3-oxo-butyl)-4-[5-(1R*,3R*)-3-hydroxy-cyclohexylimino)-4-methyl-4,5-dihydro-[1,3,4] thiadiazol-2-yl]-benzamide,
N-(2-Cyano-1,2,2-trimethyl-ethyl)-4-[5-(1R*,3R*)-3-hydroxy-cyclohexylimino)-4-methyl-4,5-dihydro-[1,3,4] thiadiazol-2-yl]-benzamide,
1-{4-[5-((1R*,3R*)-3-Hydroxy-cyclohexylimino)-4-methyl-4,5-dihydro-[1,3,4]thiadiazol-2-yl]-benzoylamino}-cyclopropanecarboxylic acid methyl ester,
4-(5-Cyclopentylimino-4-methyl-4,5-dihydro-[1,3,4] thiadiazol-2-yl)-benzamide,
4-(5-Cyclopentylimino-4-methyl-4,5-dihydro-[1,3,4] thiadiazol-2-yl)-benzamide,
4-[5-(4-Fluoro-phenylimino)-4-methyl-4,5-dihydro-[1,3,4] thiadiazol-2-yl]-benzamide,
4-[5-(3-Hydroxy-phenylimino)-4-methyl-4,5-dihydro-[1,3,4]thiadiazol-2-yl]-benzamide,
5-[5-(4-Carbamoyl-phenyl)-3-methyl-3H-[1,3,4]thiadiazol-2-ylideneamino]-2-fluoro-benzoic acid,
4-[4-Methyl-5-(4-methyl-cyclohexylimino)-4,5-dihydro-[1,3,4]thiadiazol-2-yl]-benzamide,
4-[5-(4-Hydroxy-cyclohexylimino)-4-methyl-4,5-dihydro-[1,3,4]thiadiazol-2-yl]-benzamide,
4-[5-(Bicyclo[2.2.1]hept-2-ylimino)-4-methyl-4,5-dihydro-[1,3,4]thiadiazol-2-yl]-benzamide,
4-[5-((1R*,2R*)-2-Hydroxy-cyclohexylimino)-4-methyl-4,5-dihydro-[1,3,4]thiadiazol-2-yl]-benzamide,
4-[5-((1R*,2R*)-2-Hydroxy-cyclohexylimino)-4-methyl-4,5-dihydro-[1,3,4]thiadiazol-2-yl]-benzamide,
4-[5-((1R*,3R*)-3-Hydroxy-cyclohexylimino)-4-methyl-4,5-dihydro-[1,3,4]thiadiazol-2-yl]-benzamide,
4-[5-((1R*,3S*)-3-Hydroxy-cyclohexylimino)-4-methyl-4,5-dihydro-[1,3,4]thiadiazol-2-yl]-benzamide,
4-[4-Methyl-5-(3-oxo-cyclohexylimino)-4,5-dihydro-[1,3,4]thiadiazol-2-yl]-benzamide,
4-[5-(3,3-Difluoro-cyclohexylimino)-4-methyl-4,5-dihydro-[1,3,4]thiadiazol-2-yl]-benzamide,
4-[5-((1R*,3R*)-3-Fluoro-cyclohexylimino)-4-methyl-4,5-dihydro-[1,3,4]thiadiazol-2-yl]-benzamide,
4-[5-(Cyclohex-3-enylimino)-4-methyl-4,5-dihydro-[1,3,4] thiadiazol-2-yl]-benzamide,
(1R*,3R*)-3-{3-Methyl-5-[4-(1H-tetrazol-5-yl)-phenyl]-3H-[1,3,4]thiadiazol-2-ylideneamino}-cyclohexanol,
3-[5-(4-Chloro-phenyl)-3-methyl-3H-[1,3,4]thiadiazol-2-ylideneamino]-2-hydroxy-benzoic acid,
3-[5-(4-Cyano-phenyl)-3-methyl-3H-[1,3,4]thiadiazol-2-ylideneamino]-benzoic acid,
3-[5-(4-carbamoyl-phenyl)-3-methyl-3H-[1,3,4]thiadiazol-2-ylideneamino]-benzoic acid,
2-Fluoro-5-[5-(4-methanesulfonyl-phenyl)-3-methyl-3H-[1,3,4]thiadiazol-2-ylideneamino]-benzoic acid,
3-[5-(4-methanesulfonyl-phenyl)-3-methyl-3H-[1,3,4] thiadiazol-2-ylideneamino]-cyclohexanecarboxylic acid,
[5-(4-methanesulfonyl-phenyl)-3-methyl-3H-[1,3,4] thiadiazol-2-ylidene]-piperidin-1-yl amine,
[5-(4-Methanesulfonyl-phenyl)-3-methyl-3H-[1,3,4] thiadiazol-2-ylidene]-(tetrahydro-pyran-4-yl)-amine,
3-[5-(4-Acetylamino-phenyl)-3-methyl-3H-[1,3,4] thiadiazol-2-ylideneamino]-benzoic acid,
N-{4-[5-(trans-4-Hydroxy-cyclohexylimino)-4-methyl-4,5-dihydro-[1,3,4]thiadiazol-2-yl]-phenyl}-acetamide,
N-{4-[5-((1R*,3S*)-3-Hydroxy-cyclohexylimino)-4-methyl-4,5-dihydro-[1,3,4]thiadiazol-2-yl]-phenyl}-acetamide,
N-{4-[5-((1R*,3R*)-3-Hydroxy-cyclohexylimino)-4-methyl-4,5-dihydro-[1,3,4]thiadiazol-2-yl]-phenyl}-acetamide,
N-{5-[5-((1R*,3R*)-3-Hydroxy-cyclohexylimino)-4-methyl-4,5-dihydro-[1,3,4]thiadiazol-2-yl]-pyridin-2-yl}-acetamide,
3-[5-(4-Chloro-phenyl)-3-methyl-3H/-[1,3,4]thiadiazol-2-ylideneamino]-benzonitrile,
[5-(4-Chloro-phenyl)-3-methyl-3H-[1,3,4]thiadiazol-2-ylidene]-[3-(1H-tetrazol-5-yl)-phenyl]-amine,
3-[5-(4-Chloro-phenyl)-3-methyl-3H-[1,3,4]thiadiazol-2-ylideneamino]-N-hydroxy-benzamidine,
3-{3-[5-(4-Chloro-phenyl)-3-methyl-3H-[1,3,4]thiadiazol-2-ylideneamino]-phenyl}-[1,2,4]oxadiazol-5-ol,
[5-(4-Bromo-3-methyl-phenyl)-3-methyl-3H-[1,3,4] thiadiazol-2-ylidene]-cyclohexyl-amine, 4-(5-Cyclohexylimino-4-methyl-4,5-dihydro-[1,3,4]thiadiazol-2-yl)-2-methyl-benzonitrile,
4-(5-Cyclohexylimino-4-methyl-4,5-dihydro-[1,3,4]thiadiazol-2-yl)-2-methyl-benzamide,
[5-(4-Bromo-3-methoxy-phenyl)-3-methyl-2,3-dihydro-[1,3,4]thiadiazol-2-yl]-cyclohexyl-amine,
4-(5-Cyclohexylimino-4-methyl-4,5-dihydro-[1,3,4]thiadiazol-2-yl)-2-methoxy-benzamide,
4-(5-Cyclohexylimino-4-methyl-4,5-dihydro-[1,3,4]thiadiazol-2-yl)-2-hydroxy-benzamide,
4-(5-Cyclohexylimino-4-methyl-4,5-dihydro-[1,3,4]thiadiazol-2-yl)-2-nitro-benzoic acid methyl ester,
2-Amino-4-(5-cyclohexylimino-4-methyl-4,5-dihydro-[1,3,4]thiadiazol-2-yl)-benzoic acid methyl ester,
2-Acetylamino-4-(5-cyclohexylimino-4-methyl-4,5-dihydro-[1,3,4]thiadiazol-2-yl)-benzoic acid methyl ester,
2-Amino-4-(5-cyclohexylimino-4-methyl-4,5-dihydro-[1,3,4]thiadiazol-2-yl)-benzamide,
7-(5-Cyclohexylimino-4-methyl-4,5-dihydro-[1,3,4]thiadiazol-2-yl)-3H-quinazolin-4-one,
7-(5-Cyclohexylimino-4-methyl-4,5-dihydro-[1,3,4]thiadiazol-2-yl)-quinazolin-4-ylamine,
7-(5-Cyclohexylimino-4-methyl-4,5-dihydro-[1,3,4]thiadiazol-2-yl)-1H-quinazoline-2,4-dione,
4-(5-Cyclohexylimino-4-methyl-4,5-dihydro-[1,3,4]thiadiazol-2-yl)-2-methoxy-benzenesulfonamide,
5-(5-Cyclohexylimino-4-methyl-4,5-dihydro-[1,3,4]thiadiazol-2-yl)-2-methoxy-benzenesulfonamide,
3-[5-(3-Cyano-phenyl)-3-methyl-3H-[1,3,4]thiadiazol-2-ylideneamino]-benzoic acid methyl ester,
3-[5-(3-Cyano-phenyl)-3-methyl-3H-[1,3,4]thiadiazol-2-ylideneamino]-benzoic acid,
3-[3-Methyl-5-pyridin-2-yl-3H-[1,3,4]thiadiazol-2-ylideneamino]-benzoic acid,
3-[5-(4-Chloro-3-methyl-3H-[1,3,4]thiadiazol-2-ylideneamino]-benzoic acid,
4-(5-Cyclohexylimino-4-methyl-4,5-dihydro-[1,3,4]thiadiazol-2-yl)-benzonitrile,
Cyclohexyl-{3-methyl-5-[4-(1H-tetrazol-5-yl)-phenyl]3H-[1,3,4]thiadiazol-2-ylidene}-amine,
Cyclohexyl-[3-methyl-5-(4-nitro-phenyl)-3H-[1,3,4]thiadiazol-2-ylidene]-amine,
4-(5-Cyclohexylimino-4-methyl-4,5-dihydro-[1,3,4]thiadiazol-2-yl)-phenylamine,
[5-(4-(N-cyano-N'-(2-dimethylaminoethyl)-carboximidamide)-phenyl)-3-methyl-3H-[1,3,4]thiadiazol-2-ylidene]-cyclohexyl-amine,
N-[4-(5-Cyclohexylimino-4-methyl-4,5-dihydro-[1,3,4]thiadiazol-2-yl)-phenyl]-acetamide,
[5-(4-(bis-ethylsulfonylamino)-phenyl)-3-methyl-3H-[1,3,4]thiadiazol-2-ylidene]-cyclohexyl-amine,
[5-(4-(1-(2-dimethylaminoethyl)amino-2-nitro-vinylamino)-phenyl)-3-methyl-3H-[1,3,4]thiadiazol-2-ylidene]-cyclohexyl-amine,
(E)-N'-[4-(5-Cyclohexylimino-4-methyl-4,5-dihydro-[1,3,4]thiadiazol-2-yl)-phenyl]-2-nitro-ethene-1,1-diamine,
[5-(N-cyano-N'-methyl-4-carboximidamide-phenyl)-3-methyl-3H-[1,3,4]thiadiazol-2-ylidene]-cyclohexyl-amine,
[5-(4-(N-cyano-N'-amino-carboximidamide)-phenyl)-3-methyl-3H-[1,3,4]thiadiazol-2-ylidene]-cyclohexyl-amine,
Ethanesulfonic acid[4-(5-cyclohexylimino-4-methyl-4,5-dihydro-[1,3,4]thiadiazol-2-yl)-phenyl]-amide,
[4-(5-Cyclohexylimino-4-methyl-4,5-dihydro-[1,3,4]thiadiazol-2-yl)-phenyl]-urea,
1-[4-(Cyclohexylimino-methyl-4,5-dihydro-[1,3,4]thiadiazol-2-yl)-phenyl]-3-(2-dimethylamino-ethyl)-urea,
2-Chloro-4-(5-cyclohexylimino-4-methyl-4,5-dihydro-[1,3,4]thiadiazol-2-yl)-benzenesulfonamide,
2-Chloro-4-(5-cyclohexylimino-4-methyl-4,5-dihydro-[1,3,4]thiadiazol-2-yl)-benzoic acid methyl ester,
2-Chloro-4-(5-cyclohexylimino-4-methyl-4,5-dihydro-[1,3,4]thiadiazol-2-yl)-benzamide and
2-Chloro-5-(5-cyclohexylimino-4-methyl-4,5-dihydro-[1,3,4]thiadiazol-2-yl)-benzamide.

13. A compound according to claim 11, selected from the group consisting of:
5-(5-Cyclohexylimino-4-methyl-4,5-dihydro[1,3,4]thiadiazol-2-yl)-2-methoxy-benzene-1,3-diol; compound with trifluoro-methanesulfonic acid,
5-(5-Cyclohexylimino-4-methyl-4,5-dihydro[1,3,4]thiadiazol-2-yl)-2,3-dimethoxy-phenol; compound with trifluoro-methanesulfonic acid,
2-Chloro-5-(5-cyclohexylimino-4-methyl-4,5-dihydro-[1,3,4]thiadiazol-2-yl)-benzenesulfonamide,
2-Chloro-5-(5-cyclohexylimino-4-methyl-4,5-dihydro[1,3,4]thiadiazol-2-yl)-N,N-diethyl-benzenesulfonamide,
{5-[4-Chloro-3-(4-methyl-piperazine-1-sulfonyl)-phenyl]-3-methyl-3H-[1,3,4]thiadiazol-2-ylidene}-cyclohexyl-amine,
2-Chloro-5-(5-cyclohexylimino-4-methyl-4,5-dihydro-[1,3,4]thiadiazol-2-yl)-N-pyridin-4-ylmethyl-benzenesulfonamide,
2-Chloro-5-(5-cyclohexylimino-4-methyl-4,5-dihydro-[1,3,4]thiadiazol-2-yl)-N-(2-morpholin-4-yl-ethyl)-benzenesulfonamide,
2-Chloro-5-(5-cyclohexylimino-4-methyl-4,5-dihydro-[1,3,4]thiadiazol-2-yl)-N-ethyl-benzenesulfonamide,
2-Chloro-5-(5-cyclohexylimino-4-methyl-4,5-dihydro-[1,3,4]thiadiazol-2-yl)-N-ethyl-N-(2-morpholin-4-yl-ethyl)-benzenesulfonamide,
2-Chloro-5-(5-cyclohexylimino-4-methyl-4,5-dihydro-[1,3,4]thiadiazol-2-yl)-N-isopropyl-N-(2-morpholin-4-yl-ethyl)-benzenesulfonamide,
2-Chloro-5-(5-cyclohexylimino-4-methyl-4,5-dihydro-[1,3,4]thiadiazol-2-yl)-N-ethyl-N-[2-(2-methoxy-ethoxy)-ethyl]-benzenesulfonamide,
2-Chloro-(cyclohexylimino-methyl-4,5-dihydro-[1,3,4]thiadiazol-2-yl)-N-(3-dimethylamino-2-hydroxy-propyl)-N-ethyl-benzenesulfonamide,
2-Chloro-5-(5-cyclohexylimino-4-methyl-4,5-dihydro-[1,3,4]thiadiazol-2-yl)-N-(2,3-dihydroxy-propyl)-N-ethyl-benzenesulfonamide,
2-Chloro-5-(5-cyclohexylimino-4-methyl-4,5-dihydro-[1,3,4]thiadiazol-2-yl)-N-ethyl-N-(2-hydroxy-3-pyrrolidin-1-yl-propyl)-benzenesulfonamide,
3-(5-Cyclohexylimino-4-methyl-4,5-dihydro-[1,3,4]thiadiazol-2-yl)-benzamide,
4-(5-Cyclohexylimino-4-methyl-4,5-dihydro-[1,3,4]thiadiazol-2-yl)-benzamide,
4-(5-Cyclohexylimino-4-methyl-4,5-dihydro[1,3,4]thiadiazol-2-yl)-N-quinolin-8-yl-benzamide,
4-(5-Cyclohexylimino-4-methyl-4,5-dihydro[1,3,4]thiadiazol-2-yl)-N-(2,6-dimethoxy-pyridin-3-yl)-benzamide,
4-(5-Cyclohexylimino-4-methyl-4,5-dihydro[1,3,4]thiadiazol-2-yl)-N-isopropyl-benzamide,
4-(5-Cyclohexylimino-4-methyl-4,5-dihydro[1,3,4]thiadiazol-2-yl)-N-ethyl-benzamide,
4-(5-Cyclohexylimino-4-methyl-4,5-dihydro[1,3,4]thiadiazol-2-yl)-N-(2-dimethylamino-ethyl)-benzamide,
4-(5-Cyclohexylimino-4-methyl-4,5-dihydro[1,3,4]thiadiazol-2-yl)-N-pyridin-4-ylmethyl-benzamide,
4-(5-Cyclohexylimino-4-methyl-4,5-dihydro[1,3,4]thiadiazol-2-yl)-N-methyl-N-(1-methyl-piperidin-4-yl)-benzamide, 4-(5-Cyclohexylimino-4-methyl-4,5-dihydro-[1,3,4]
thiadiazol-2-yl)-N-methyl-benzamide,
2-[4-(5-Cyclohexylimino-4-methyl-4,5-dihydro-[1,3,4]
thiadiazol-2-yl)-benzoylamino]-3-(4-hydroxy-phenyl)-
propionic acid tert-butyl ester,
(S)-2-[4-(5-Cyclohexylimino-4-methyl-4,5-dihydro-[1,3,4]
thiadiazol-2-yl)-benzoylamino]-3-(4-hydroxy-phenyl)-
propionic acid, compound with 2,2,2-trifluoro-acetic acid,
4-(5-Cyclohexylimino-4-methyl-4,5-dihydro-[1,3,4]
thiadiazol-2-yl)-N-(3,4,5-trimethoxy-benzyl)-benzamide,
4-(5-Cyclohexylimino-4-methyl-4,5-dihydro-[1,3,4]
thiadiazol-2-yl)-N-[3-(4-methyl-piperazin-1-yl)-propyl]-
benzamide,
4-(5-Cyclohexylimino-4-methyl-4,5-dihydro-[1,3,4]
thiadiazol-2-yl)-N-pyridin-3-ylmethyl-benzamide,
N-(1-Benzyl-piperidin-4-yl)-4-(5-cyclohexylimino-4-
methyl-4,5-dihydro-[1,3,4]thiadiazol-2-yl)-benzamide,
4-(5-Cyclohexylimino-4-methyl-4,5-dihydro-[1,3,4]
thiadiazol-2-yl)-N-(2-ethyl-2H-pyrazol-3-yl)-benzamide,
4-(5-Cyclohexylimino-4-methyl-4,5-dihydro-[1,3,4]
thiadiazol-2-yl)-N-(2-morpholin-4-yl-ethyl)-benzamide,
4-(5-Cyclohexylimino-4-methyl-4,5-dihydro-[1,3,4]
thiadiazol-2-yl)-N-(2-pyrrolidin-1-yl-ethyl)-benzamide,
3-[5-(4-carbamoyl-phenyl)-3-methyl-3H-[1,3,4]thiadiazol-
2-ylideneamino]-benzoic acid,
[5-(4-Chloro-phenyl)-3-methyl-3H-[1,3,4]thiadiazol-2-
ylidene]-[3-(1H-tetrazol-5-yl)-phenyl]-amine,
2-Amino-4-(5-cyclohexylimino-4-methyl-4,5-dihydro-[1,3,
4]thiadiazol-2-yl)-benzoic acid methyl ester,
2-Amino-4-(5-cyclohexylimino-4-methyl-4,5-dihydro-[1,3,
4]thiadiazol-2-yl)-benzamide,
7-(5-Cyclohexylimino-4-methyl-4,5-dihydro-[1,3,4]
thiadiazol-2-yl)-3H-quinazolin-4-one,
7-(5-Cyclohexylimino-4-methyl-4,5-dihydro-[1,3,4]
thiadiazol-2-yl)-quinazolin-4-ylamine,
N-[4-(5-Cyclohexylimino-4-methyl-4,5-dihydro-[1,3,4]
thiadiazol-2-yl)-phenyl]-acetamide, and,
1-[4-(Cyclohexylimino-methyl-4,5-dihydro-[1,3,4]
thiadiazol-2-yl)-phenyl]-3-(2-dimethylamino-ethyl)-urea.

14. A pharmaceutical composition comprising a compound of Formula I,

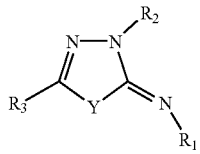

I wherein
Y is S;
$R_1$ is:
  $C_1$–$C_{10}$ alkyl,
  $C_2$–$C_{10}$ alkenyl,
  $C_2$–$C_{10}$ alkynyl,
  cycloalkyl,
  cycloalkenyl,
  heterocycle,
  aryl,
  or a polycyclic group;
  each optionally substituted with one or several groups $X_1$—$R_4$, identical or different, wherein:
    $X_1$ is a single bond, lower alkylene, $C_2$–$C_6$ alkenylene, cycloalkylene, arylene or a divalent heterocycle, and
    $R_4$ is:
      1) H, =O, $NO_2$, CN, halogen, lower haloalkyl, lower alkyl, carboxylic acid bioisostere,
      2) $COOR_5$, $C(=O)R_5$, $C(=S)R_5$, $SO_2R_5$, $SOR_5$, $SO_3R_5$, $SR_5$, $OR_5$,
      3) $C(=O)NR_7R_8$, $C(=S)NR_7R_8$, $C(=N-CN)NR_7R_8$, $C(=N-SO_2NH_2)NR_7R_8$, $C(=CH-O_2)NR_7R_8$, $C(=NR_7)NHR_8$, $C(=NR_7)R_8$, $C(=NR_9)NHR_8$, $C(=NR_9)R_8$, $SO_2NR_7R_8$, or $NR_7R_8$ in which $R_7$ and $R_8$ are the same or different and are OH, $R_5$, $R_6$, $C(=O)NR_5R_6$, $C(=O)R_5$, $SO_2R_5$, $C(=NR_9)NHR_{10}$, $C(=NR_9)R_{10}$, $C(=CH-NO_2)NR_9R_{10}$, $C(=N-SO_2NH_2)NR_9R_{10}$, $C(=N-CN)NR_9R_{10}$, or $C(=S)NR_9R_{10}$;
$R_2$ is:
  lower alkyl,
  $C_2$–$C_{10}$ alkenyl,
  $C_2$–$C_{10}$ alynyl,
  cycloalkyl,
  cycloalkenyl,
  heterocycle,
  aryl;
  each optionally substituted with one or several groups which are the same or different and which are:
    1) H, carboxylic acid bioisostere, lower haloalkyl, halogen,
    2) $COOR_5$, $OR_5$, $SO_2R_5$,
    3) $SO_2NR_{11}R_{12}$, $C(=O)NR_{11}R_{12}$, or $NR_{11}R_{12}$ in which $R_{11}$ and $R_{12}$ are the same or different and are OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$;
$R_3$ is $X_2$—$R'_3$;
  $X_2$ is a single bond;
  $R'_3$ is:
    cycloalkyl,
    cycloalkenyl,
    aryl,
    heterocycle,
    or a polycyclic group;
  each optionally substituted with one or several groups or the formula $X_3$—$R_{17}$, identical or different, wherein:
    $X_3$ is a single bond, lower alkylene, $C_2$–$C_6$ alkenylene, cycloalkylenyl, arlenyl, a divalent heterocycle or a divalent polycyclic group, and
    $R_{17}$ is:
      1) H, =O, $NO_2$, CN, lower haloalkyl, halogen, carboxylic acid bioisostere, cycloalkyl,
      2) $COOR_5$, $C(=O)R_5$, $C(=S)R_5$, $SO_2R_5$, $SOR_5$, $SO_3R_5$, $SR_5$, $OR_5$,
      3) $C(=O)NR_{15}R_{16}$, $C(=S)NR_{15}R_{16}$, $C(=N-CN)NR_{15}R_{16}$, $C(=N-SO_2NH_2)NR_{15}R_{16}$, $C(=CH-NO_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ in which $R_{15}$ and $R_{16}$ are the same or different and are OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$, or
      4) heterocycle optionally substituted with one or several $R_5$ groups;
    wherein,
$R_5$ and $R_6$ are the same or different and are:
  H,
  lower alkyl, $C_2$–$C_6$ alkenyl, $C_2$–$C_6$ alkynyl;

$X_4$-cycloalkyl, $X_4$-cycloalkenyl, $X_4$-aryl, $X_4$-heterocycle or a $X_4$-polycyclic group, in which $X_4$ is a single bond, lower alkylene, or $C_2$–$C_6$ alkenylenyl;

each optionally substituted with one or several groups which are the same or different and which are:

halogen, =O, COOR$_{20}$, CN, OR$_{20}$, lower alkyl optionally substituted with OR$_{20}$, O-lower alkyl optionally substituted with OR$_{20}$, C(=O)-lower alkyl, lower haloalkyl,

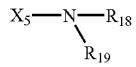

in which $X_5$ is a single bond or lower alkyl and $R_{18}$, $R_{19}$, and $R_{20}$ are the same or different and are H or lower alkyl;

$X_6$-heterocycle, $X_6$-aryl, $X_6$-cycloalkyl, $X_6$-cycloalkenyl, or an $X_6$-polycyclic group in which $X_6$ is a single bond or lower alkylenyl, these groups being optinally substituted with one or several groups, identical or different, selected from halogens, COOR$_{21}$, OR$_{21}$, and (CH$_2$)$_n$NR$_{21}$R$_{22}$ in which n is 0, 1, or 2 and $R_{21}$ and $R_{22}$ are the same or different and are H or lower alkyl;

$R_9$ is selected from H, CN, OH, lower alkyl, O-lower alkyl, aryl, heterocycle, SO$_2$NH$_2$, or

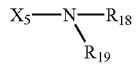

in which $X_5$ is a single bond or lower alkylene and $R_{18}$ and $R_{19}$ are the same or different and are H or lower alkyl;

$R_{10}$ is hydrogen, lower alkyl, cyclopropyl, or heterocycle;

or a pharmaceutically acceptable derivative thereof, together with a pharmaceutically acceptable carrier, with the proviso that the substituent group "=O" is not bonded to a single bond, a carbon atom of a carbon-carbon double bond or a carbon-carbon triple bond, a carbon atom of a trisubstituted carbon, an arylenyl, or a heteroatom of a divalent heterocycle, and with the proviso that the compound of Formula I is not 4-[2-Formylimino-5-(4-methoxy-phenyl)-[1,3,4]thiadiazol-3-yl]-butyric acid ethyl ester, or 4-[5-(4-Chloro-phenyl)-2-formylimino-[1,3,4]thiadiazol-3-yl]-butyric acid ethyl ester.

15. A pharmaceutical composition of claim 14, wherein in said compound, when $R_1$ is C(=O)—H, then $R_2$ does not represent (CH$_2$)$_3$—C(=O)OCH$_2$CH$_3$.

16. A pharmaceutical composition comprising a compound of Formula I of any one of claims 1 to 9, 10, 11, 12 or 13, together with a pharmaceutically acceptable carrier.

17. A method for treating a disease for which treatment by a PDE7 inhibitor is indicated, comprising administering to a mammal in need thereof, an effective amount of compound of Formula I of any one of claims 1 to 9, 10, 11, 12 or 13.

18. A method of claim 17, in which the disease being treated is selected from T-cell-related diseases, autoimmune diseases, inflammatory diseases, respiratory diseases, CNS diseases, allergic diseases, endocrine or exocrine pancreas diseases, and gastrointestinal diseases.

19. A method claim 17, in which the disease being treated is selected from visceral pain, inflammatory bowel disease, osteoarthritis, multiple sclerosis, chronic obstructive pulmonary disease (COPD), asthma, cancer, acquired immune deficiency syndrome (AIDS), and graft rejection.

20. A compound of claim 6 wherein $R_1$ is cyclohexyl or phenyl.

21. A compound of claim 8 wherein R'$_3$ is phenyl.

22. A compound of claim 9 wherein $R_4$ is trifluoromethyl.

23. A compound of claim 10 wherein $R_1$ is cyclohexyl or phenyl; and R'$_3$ is phenyl.

* * * * *

UNITED STATES PATENT AND TRADEMARK OFFICE
CERTIFICATE OF CORRECTION

| | | |
|---|---|---|
| PATENT NO. | : 7,122,565 B2 | Page 1 of 1 |
| APPLICATION NO. | : 09/968371 | |
| DATED | : October 17, 2006 | |
| INVENTOR(S) | : Vergne et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (912) days Delete the phrase "by 676 days" and insert -- by 912 days--

Signed and Sealed this

Twenty-sixth Day of June, 2007

JON W. DUDAS
*Director of the United States Patent and Trademark Office*